US011420974B2

(12) United States Patent
Gutierrez et al.

(10) Patent No.: US 11,420,974 B2
(45) Date of Patent: *Aug. 23, 2022

(54) SUBSTITUTED PYRROLIZINE COMPOUNDS AND USES THEREOF

(71) Applicant: GILEAD SCIENCES, INC., Foster City, CA (US)

(72) Inventors: David Alan Gutierrez, San Jose, CA (US); Tetsuya Kobayashi, Pleasanton, CA (US); Scott E. Lazerwith, Burlingame, CA (US); Rick Andrew Lee, Livermore, CA (US); Philip Anthony Morganelli, Oakland, CA (US); Hyung-Jung Pyun, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/070,236

(22) Filed: Oct. 14, 2020

(65) Prior Publication Data

US 2021/0147429 A1 May 20, 2021

Related U.S. Application Data

(63) Continuation of application No. 16/284,812, filed on Feb. 25, 2019, now Pat. No. 10,836,769.

(60) Provisional application No. 62/635,262, filed on Feb. 26, 2018.

(51) Int. Cl.
C07D 487/04 (2006.01)
A61P 31/20 (2006.01)
(52) U.S. Cl.
CPC ............ C07D 487/04 (2013.01); A61P 31/20 (2018.01)
(58) Field of Classification Search
CPC .............................. C07D 487/04; A61P 31/20
See application file for complete search history.

(56) References Cited

U.S. PATENT DOCUMENTS

| | | | |
|---|---|---|---|
| 5,733,912 A | 3/1998 | Wasicak et al. | |
| 6,232,320 B1 | 5/2001 | Stewart et al. | |
| 8,629,274 B2 | 1/2014 | Hartman et al. | |
| 8,653,115 B2 | 2/2014 | Nan et al. | |
| 9,181,288 B2 | 11/2015 | Hartman et al. | |
| 10,328,053 B2 | 6/2019 | Du et al. | |
| 10,836,769 B2 | 11/2020 | Gutierrez et al. | |
| 10,874,640 B2 | 12/2020 | Du et al. | |
| 2005/0054850 A1 | 3/2005 | Wu et al. | |
| 2005/0137187 A1 | 6/2005 | Souers et al. | |
| 2005/0137243 A1 | 6/2005 | Souers et al. | |
| 2005/0187279 A1 | 8/2005 | Souers et al. | |
| 2005/0277638 A1 | 12/2005 | Souers et al. | |
| 2005/0288233 A1 | 12/2005 | Venkatraman et al. | |
| 2006/0100204 A1 | 5/2006 | Cogan et al. | |
| 2007/0135461 A1 | 6/2007 | Rodgers et al. | |
| 2009/0209533 A1 | 8/2009 | Zablocki et al. | |
| 2009/0326019 A1 | 12/2009 | Or et al. | |
| 2010/0113549 A1 | 5/2010 | Block et al. | |
| 2012/0184572 A1 | 7/2012 | Song et al. | |
| 2014/0178337 A1 | 6/2014 | Hartman et al. | |
| 2014/0194386 A1 | 7/2014 | Burns et al. | |
| 2014/0275167 A1 | 9/2014 | Hartman | |
| 2015/0132258 A1 | 5/2015 | Hartman | |
| 2015/0197533 A1 | 7/2015 | Hartman et al. | |
| 2015/0216938 A1 | 8/2015 | Hartman | |
| 2015/0225355 A1 | 8/2015 | Hartman | |
| 2015/0259324 A1 | 9/2015 | Hartman et al. | |
| 2015/0274652 A1 | 10/2015 | Hartman | |
| 2015/0307443 A1 | 10/2015 | Xu et al. | |
| 2015/0315159 A1 | 11/2015 | Hartman | |
| 2017/0355701 A1 | 12/2017 | Qiu et al. | |
| 2018/0001207 A1 | 1/2018 | Wei et al. | |
| 2018/0370976 A1 | 12/2018 | Ding et al. | |
| 2019/0292187 A1 | 9/2019 | Gutierrez et al. | |
| 2021/0251957 A1 | 8/2021 | Du et al. | |

FOREIGN PATENT DOCUMENTS

| | | |
|---|---|---|
| AU | 2012204508 A1 | 7/2012 |
| EP | 274867 A2 | 7/1988 |
| EP | 498723 A1 | 8/1992 |
| EP | 1217000 A1 | 6/2002 |
| EP | 1479676 A1 | 11/2004 |
| EP | 1867647 A1 | 12/2007 |
| EP | 1867648 A1 | 12/2007 |
| EP | 1932845 A1 | 6/2008 |
| EP | 3381918 A1 | 5/2017 |
| JP | 2014133739 A | 12/2013 |
| KR | 2015025531 A | 12/2017 |
| WO | WO-1997048697 A1 | 12/1997 |
| WO | WO-1999018951 A1 | 4/1999 |
| WO | WO-1999062908 A2 | 12/1999 |

(Continued)

OTHER PUBLICATIONS

Abbas et al., Novel substituted and fused pyrrolizine derivatives: Synthesis, antiinflammatory and ulcerogenecity studies, European Journal of Medicinal Chemistry, Oct. 2009, pp. 482-491, vol. 45, No. 2.

Campagna et al., Sulfamoylbenzamide Derivatives Inhibit the Assembly of Hepatitis B Virus Nucleocapsids, Journal of Virology, 2013, p. 6931, vol. 87, No. 12.

(Continued)

*Primary Examiner* — Golam M Shameem
(74) *Attorney, Agent, or Firm* — Mintz, Levin, Cohn, Ferris, Glovsky and Popeo, P.C.

(57) ABSTRACT

This application relates generally to certain substituted pyrrolizine compounds, and pharmaceutical compositions which inhibit HBV replication, and methods of making and using them.

33 Claims, No Drawings

(56) References Cited

FOREIGN PATENT DOCUMENTS

| | | |
|---|---|---|
| WO | WO-2000075145 A1 | 12/2000 |
| WO | WO-2001009097 A1 | 2/2001 |
| WO | WO-2001014336 A1 | 3/2001 |
| WO | WO-2001098301 A | 12/2001 |
| WO | WO-2002020016 A1 | 3/2002 |
| WO | WO-2002022586 A1 | 3/2002 |
| WO | WO-2002066034 A1 | 8/2002 |
| WO | WO-2002066035 A2 | 8/2002 |
| WO | WO-2002070491 A1 | 9/2002 |
| WO | WO-2002083628 A1 | 10/2002 |
| WO | WO-2002096426 A1 | 12/2002 |
| WO | WO-2003007888 A2 | 1/2003 |
| WO | WO-2003053941 A2 | 7/2003 |
| WO | WO-2003068221 A1 | 8/2003 |
| WO | WO-2003084948 A1 | 10/2003 |
| WO | WO-2003091202 A1 | 11/2003 |
| WO | WO-2004024705 A1 | 3/2004 |
| WO | WO-2004024727 A2 | 3/2004 |
| WO | WO-2004026873 A1 | 4/2004 |
| WO | WO-2004035581 A1 | 4/2004 |
| WO | WO-2004050613 A2 | 6/2004 |
| WO | WO-2004082606 A2 | 9/2004 |
| WO | WO-2005023761 A2 | 3/2005 |
| WO | WO-2005033072 A2 | 4/2005 |
| WO | WO-2005039506 A2 | 5/2005 |
| WO | WO-2005040133 A1 | 5/2005 |
| WO | WO-2005090333 A1 | 9/2005 |
| WO | WO-2005099824 A1 | 10/2005 |
| WO | WO-2006077401 A1 | 7/2006 |
| WO | WO-2006085111 A1 | 8/2006 |
| WO | WO-2006091862 A2 | 8/2006 |
| WO | WO-2007019098 A2 | 2/2007 |
| WO | WO-2007085136 A1 | 2/2007 |
| WO | WO-2007031791 A1 | 3/2007 |
| WO | WO-2007058990 A2 | 5/2007 |
| WO | WO-2007119889 A1 | 10/2007 |
| WO | WO-2007144202 A1 | 12/2007 |
| WO | WO-2007144203 A1 | 12/2007 |
| WO | WO-2007144204 A1 | 12/2007 |
| WO | WO-2007147336 A1 | 12/2007 |
| WO | WO-2008025822 A1 | 3/2008 |
| WO | WO-2008071456 A2 | 6/2008 |
| WO | WO-2008091349 A1 | 7/2008 |
| WO | WO-2008091681 A2 | 7/2008 |
| WO | WO-2008115369 A2 | 9/2008 |
| WO | WO-2008119792 A1 | 10/2008 |
| WO | WO-2008124848 A1 | 10/2008 |
| WO | WO-2008102381 A | 11/2008 |
| WO | WO-2009014910 A2 | 1/2009 |
| WO | WO-2009019295 A2 | 2/2009 |
| WO | WO-2009033281 A1 | 3/2009 |
| WO | WO-2009034433 A2 | 3/2009 |
| WO | WO-2009055437 A2 | 4/2009 |
| WO | WO-2009074260 A1 | 6/2009 |
| WO | WO-2009094668 A1 | 7/2009 |
| WO | WO-2009105782 A1 | 8/2009 |
| WO | WO-2009126691 A | 10/2009 |
| WO | WO-2009133834 A1 | 11/2009 |
| WO | WO-2009146539 A2 | 12/2009 |
| WO | WO-2010008739 A1 | 1/2010 |
| WO | WO-2010010191 A1 | 1/2010 |
| WO | WO-2010012761 A1 | 2/2010 |
| WO | WO-2010022300 A1 | 2/2010 |
| WO | WO-2010029299 A1 | 3/2010 |
| WO | WO-2010034740 A1 | 4/2010 |
| WO | WO-2010045542 A2 | 4/2010 |
| WO | WO-2010053998 A1 | 5/2010 |
| WO | WO-2010068287 A2 | 6/2010 |
| WO | WO-2010092181 A1 | 8/2010 |
| WO | WO-2010099938 A1 | 9/2010 |
| WO | WO-2010112124 A1 | 10/2010 |
| WO | WO-2010115491 A2 | 10/2010 |
| WO | WO-2010003418 A1 | 1/2011 |
| WO | WO-2011035231 A1 | 3/2011 |
| WO | WO-2011048611 A1 | 4/2011 |
| WO | WO-2011084970 A1 | 7/2011 |
| WO | WO-2011087051 A1 | 7/2011 |
| WO | WO-2011113606 A1 | 9/2011 |
| WO | WO-2011133707 A2 | 10/2011 |
| WO | WO-2011133722 A2 | 10/2011 |
| WO | WO-2011143645 A1 | 11/2011 |
| WO | WO-2011145669 A1 | 11/2011 |
| WO | WO-2011146401 A1 | 11/2011 |
| WO | WO-2012014114 A1 | 2/2012 |
| WO | WO-2012016186 A1 | 2/2012 |
| WO | WO-2012020567 A1 | 2/2012 |
| WO | WO-2012028243 A1 | 3/2012 |
| WO | WO-2012038942 A1 | 3/2012 |
| WO | WO-2012050868 A1 | 4/2012 |
| WO | WO-2012058645 A1 | 5/2012 |
| WO | WO-2012112743 A1 | 8/2012 |
| WO | WO-2012116135 A2 | 8/2012 |
| WO | WO-2012123938 A1 | 9/2012 |
| WO | WO-2012129562 A2 | 9/2012 |
| WO | WO-2012158672 A2 | 11/2012 |
| WO | WO-2012158844 A1 | 11/2012 |
| WO | WO-2012159047 A1 | 11/2012 |
| WO | WO-2012169649 A1 | 12/2012 |
| WO | WO-2013006394 A1 | 1/2013 |
| WO | WO-2013017189 A1 | 2/2013 |
| WO | WO-2013042139 A1 | 3/2013 |
| WO | WO-2013059278 A2 | 4/2013 |
| WO | WO-2013085877 A1 | 6/2013 |
| WO | WO-2013087162 A1 | 6/2013 |
| WO | WO-2013096744 A1 | 6/2013 |
| WO | WO-2013113841 A1 | 8/2013 |
| WO | WO-2013/144228 A1 | 10/2013 |
| WO | WO-2013161871 A1 | 10/2013 |
| WO | WO-2014031872 A2 | 2/2014 |
| WO | WO-2014033167 A1 | 3/2014 |
| WO | WO-2014033170 A1 | 3/2014 |
| WO | WO-2014033176 A1 | 3/2014 |
| WO | WO-2014039595 A1 | 3/2014 |
| WO | WO-2014045305 A1 | 3/2014 |
| WO | WO-2014096965 A2 | 6/2014 |
| WO | WO-2014102818 A1 | 7/2014 |
| WO | WO-2014106019 A2 | 7/2014 |
| WO | WO-2014118133 A1 | 8/2014 |
| WO | WO-2014128486 A1 | 8/2014 |
| WO | WO-2014131847 A1 | 9/2014 |
| WO | WO-2014151958 A1 | 9/2014 |
| WO | WO-2014161888 A1 | 10/2014 |
| WO | WO-2014179144 A1 | 11/2014 |
| WO | WO-2014184350 A1 | 11/2014 |
| WO | WO-2014184365 A1 | 11/2014 |
| WO | WO-2014206344 A1 | 12/2014 |
| WO | WO-2015002894 A1 | 1/2015 |
| WO | WO-2015011281 A1 | 1/2015 |
| WO | WO-2015026935 A2 | 2/2015 |
| WO | WO-2015051230 A1 | 4/2015 |
| WO | WO-2015057945 A1 | 4/2015 |
| WO | WO-2015058140 A1 | 4/2015 |
| WO | WO-2015059212 A1 | 4/2015 |
| WO | WO-2015085238 A1 | 6/2015 |
| WO | WO-2015118057 A1 | 8/2015 |
| WO | WO-2015148854 A1 | 10/2015 |
| WO | WO-2015180631 A1 | 12/2015 |
| WO | WO-2016008011 A1 | 1/2016 |
| WO | WO-2016023511 A1 | 2/2016 |
| WO | WO-2016110821 A1 | 7/2016 |
| WO | WO-2016113273 A1 | 7/2016 |
| WO | WO-2016128908 A1 | 8/2016 |
| WO | WO-2016189129 A1 | 12/2016 |
| WO | WO-2016201370 A1 | 12/2016 |
| WO | WO-2016201440 A1 | 12/2016 |
| WO | WO-2017001655 A1 | 1/2017 |
| WO | WO-2017012379 A1 | 1/2017 |
| WO | WO-2017015451 A1 | 1/2017 |
| WO | WO-2017040963 A1 | 3/2017 |
| WO | WO-2017046605 A1 | 3/2017 |
| WO | WO-2017076346 A1 | 5/2017 |
| WO | WO-2017083304 A1 | 5/2017 |
| WO | WO-2017114512 A1 | 7/2017 |

(56) References Cited

FOREIGN PATENT DOCUMENTS

| WO | WO-2017156255 A1 | 9/2017 |
| WO | WO-2017161028 A1 | 9/2017 |
| WO | WO-2017161524 A1 | 9/2017 |
| WO | WO-2017162007 A1 | 9/2017 |
| WO | WO-2017173274 A1 | 10/2017 |
| WO | WO-2017193063 A1 | 11/2017 |
| WO | WO-2017209265 A1 | 12/2017 |
| WO | WO-2018039531 A | 3/2018 |
| WO | WO-2019165374 A1 | 8/2019 |

OTHER PUBLICATIONS

Chang et al., Prevention of Hepatitis B, Cold Spring Harb. Perspect. Med., 2015, 12 pages, vol. 5.

Cho et al., 2-Amino-N-(2-6-dichloropyridin-3-yl) acetamide derivatives as a novel class of HBV capsid assembly inhibitor, Journal of Viral Hapatitis, 2014, pp. 843-852, vol. 21.

Cho et al., Structure-based design and biochemical evaluation of sulfanilamide derivatives as hepatitis B virus capsid assembly inhibitors, Journal of Enzyme Inhibition and Medicinal Chemistry, 2012, 10 pages.

Gane et al., Phase 1a Safety and Pharmacokinetics of NVR 3-778, a potential First-In-Class HBV Core Inhibitor, Novira Therapeutics Post Aasld LB-19, 2014, 1 page.

Journal of Vascular and Interventional Radiology, Supplementary Data, No Date Given, 8 pages.

Katen et al., Assembly-Directed Antivirals Differentially Bind Quasiequivalent Pockets to Modify Hepatitis B Virus Capsid Tertiary and Quaternary Structure, Structure Article, 2013, pp. 1406-1416.

Ray et al., Tenofovir alafenamide: A novel prodrug of tenofovir for the treatment of human immunodeficiency virus, Antiviral Res. Jan. 2016, pp. 63-70, vol. 125.

International Searching Authority of the European Patent Office, International Search Report and Written Opinion for PCT International Application No. PCT/US2019/019428, Apr. 23, 2019, 20 pages.

The International Bureau of WIPO, International Preliminary Report on Patentability for PCT International Application No. PCT/US2017/048565, Mar. 7, 2019, 8 pages.

SUBSTITUTED PYRROLIZINE COMPOUNDS AND USES THEREOF

CROSS-REFERENCES TO RELATED APPLICATIONS

This application is a continuation of U.S. patent application Ser. No. 16/284,812, filed Feb. 25, 2019, which claims priority to U.S. Provisional Patent Application No. 62/635,262, filed Feb. 26, 2018, each of which is incorporated herein in its entirety for all purposes.

BACKGROUND OF THE INVENTION

The hepatitis B virus (HBV) is an enveloped, partially double-stranded DNA virus. HBV is an infectious disease that affects the liver. Initial symptoms of infection may include vomiting, jaundice, lethargy, dark urine, and abdominal pain. Chronic HBV infection can result in cirrhosis and liver cancer. Currently available therapies can inhibit replication of the virus and minimize liver damage; however, there are no currently available therapies that can reliably clear an HBV infection.

In view of the continued prevalence of HBV infection, there is a need for new therapeutic options, including new inhibitors of HBV replication. Additionally, compounds capable of inhibiting HBV replication while having low predicted metabolic clearance are of particular interest.

BRIEF SUMMARY OF THE INVENTION

In one embodiment, the present disclosure provides a compound of Formula (I):

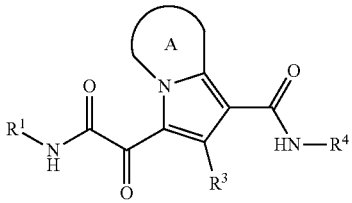

Formula I or a pharmaceutically acceptable salt thereof, wherein:
$R^1$ is $C_{1-6}$ alkyl optionally substituted with 1 to 3 $R^{1A}$, $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$;
each $R^{1A}$ is independently halogen, —OH, —CN, $C_{1-2}$ haloalkyl, —C(O)NR$^X$R$^Y$, $C_{6-10}$ aryl optionally substituted with 1 to 3 $R^{1D}$, or a 5 to 8 membered heteroaryl having 1 to 3 heteroatoms selected from N, O, and S, optionally substituted with 1 to 3 $R^{1D}$, provided no more than 1 $R^{1A}$ is $C_{6-10}$ aryl optionally substituted with 1 to 3 $R^{1D}$ or 5 to 8 membered heteroaryl having 1 to 3 heteroatoms selected from N, O, and S;
each $R^{1B}$ is independently —CN, halogen, $C_{1-6}$ alkyl optionally substituted with 1 to 3 —OH or —NR$^a$R$^b$, $C_{2-4}$ alkynyl, $C_{1-4}$ alkoxy, $C_{1-2}$ haloalkyl, $C_{3-6}$ cycloalkyl, —C(O)NR$^X$R$^Y$, or a 5 to 8 membered heteroaryl having 1 to 3 heteroatoms selected from N, O, and S optionally substituted with 1 to 3 $R^{1D}$, provided no more than 1 $R^{1B}$ is $C_{3-6}$ cycloalkyl or 5 to 8 membered heteroaryl having 1 to 3 heteroatoms selected from N, O, and S;
each $R^{1C}$ is independently $C_{1-6}$ alkyl, oxo, $C_{1-4}$ haloalkyl, —C(O)H, —C(O)C$_{1-4}$ alkyl, —C(O)OC$_{1-4}$ alkyl, —C(O)NR$^X$R$^Y$, or a 5 to 12 membered heteroaryl having 1 to 3 heteroatoms selected from N, O, and S optionally substituted with 1 to 3 $R^{1D}$, provided no more than 1 $R^{1C}$ is a 5 to 12 membered heteroaryl having 1 to 3 heteroatoms selected from N, O, and S;
each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;
each $R^Y$ is independently —H or $C_{1-6}$ alkyl optionally substituted with 1 to 3 $R^Z$;
or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$;
wherein each $R^Z$ is independently halogen, methyl, ethyl, oxo, —OH, —S(O)$_2$C$_{1-3}$ alkyl, or 3 to 8 membered monocyclic or bicyclic heterocyclyl having 1 to 3 heteroatoms selected from N, O, and S;
each $R^a$ is —H, $C_{1-3}$ alkyl, or a 3 to 8 membered monocyclic or bicyclic heterocyclyl having 1 to 3 heteroatoms selected from N, O, and S, optionally substituted with 1 to 3 $R^Z$;
each $R^b$ is —H or $C_{1-3}$ alkyl; or
$R^a$ and $R^b$ taken together form a 3 to 8 membered monocyclic or bicyclic heterocycle optionally substituted with 1 to 3 $R^Z$;
the moiety

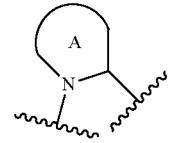

is a pyrrolidine or a 5-7 membered bicyclic heterocycle having one nitrogen, optionally substituted with 1 to 6 $R^2$ groups;
wherein each $R^2$ is independently halogen, $C_{1-3}$ alkyl, —OH, or —OC$_{1-3}$ alkyl;
$R^3$ is —H, halogen, or $C_{1-4}$ alkyl;
$R^4$ is $C_{6-10}$ aryl optionally substituted with 1 to 5 $R^{4A}$, or 5 to 12 membered heteroaryl having 1 to 3 heteroatoms selected from N, O, and S, optionally substituted with 1 to 4 $R^{4B}$; and
each $R^{1D}$, $R^{4A}$, and $R^{4B}$ are independently —CN, halogen, $C_{1-4}$ alkyl optionally substituted with —Si(C$_{1-4}$ alkyl)$_3$, —OC$_{1-4}$ alkyl, —OC$_{1-4}$ haloalkyl, or $C_{1-4}$ haloalkyl.

In another embodiment, the present invention provides a compound of Formula (II):

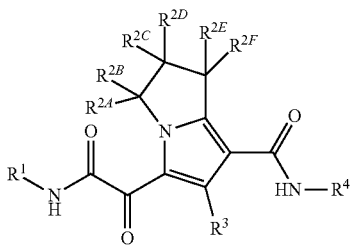

Formula II or a pharmaceutically acceptable salt thereof,
wherein
- $R^1$ is $C_{3-6}$ cycloalkyl optionally substituted with 1 to 4 $R^{1B}$, or 3 to 6 membered monocyclic heterocyclyl having 1 to 3 heteroatoms selected from N, O, and S, optionally substituted with 1 to 3 $R^{1C}$;
- each $R^{1B}$ is independently halogen, $C_{1-6}$ alkyl optionally substituted with 1 —OH, $C_{2-6}$ alkyne, —C(O)NR$^X$R$^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$;
- each $R^{1C}$ is independently —C(O)NR$^X$R$^Y$, or 5 to 8 membered heteroaryl having 1 to 3 heteroatoms selected from N, O, and S optionally substituted with 1 to 3 $R^{1D}$;
- each $R^{1D}$ is independently $C_{1-4}$ alkyl optionally substituted with —Si($C_{1-4}$ alkyl)$_3$;
- each $R^X$ is independently —H, or $C_{1-6}$ alkyl;
- each $R^Y$ is independently —H or $C_{1-6}$ alkyl;
- each of $R^{2A}$, $R^{2B}$, $R^{2C}$, $R^{2D}$, $R^{2E}$, and $R^{2F}$ are —H, or $R^{2C}$ or $R^{2D}$ may be taken together with $R^{2A}$ or $R^{2B}$ or with $R^{2E}$ or $R^{2F}$ to form a cyclopropyl group;
- $R^3$ is methyl;
- $R^4$ is phenyl substituted with 1 to 5 $R^{4A}$, or pyridinyl, substituted with 1 to 4 $R^{4B}$;
- each $R^{4A}$ is independently —CN, halogen, or $C_{1-4}$ haloalkyl; and
- each $R^{4B}$ is independently halogen, or $C_{1-4}$ haloalkyl.

In certain embodiments, the present disclosure provides a pharmaceutical composition comprising a compound of the present disclosure, or a pharmaceutically acceptable salt thereof, and a pharmaceutically acceptable excipient. In certain embodiments, the pharmaceutical composition comprises one or more additional therapeutic agents.

In certain embodiments, a method of inhibiting HBV replication is provided, comprising administering a compound of the present disclosure, or a pharmaceutically acceptable salt thereof, to an individual (e.g. a human).

In certain embodiments, a method of treating or preventing a HBV infection is provided, comprising administering to an individual (e.g. a human) in need thereof a therapeutically effective amount of a compound of the present disclosure, or a pharmaceutically acceptable salt thereof. In certain embodiments, the method of treating or preventing a HBV infection comprises administering one or more additional therapeutic agents.

In certain embodiments, a compound of the present disclosure, or a pharmaceutically acceptable salt thereof, for use in medical therapy is provided.

In certain embodiments, the use of a compound of the present disclosure, or a pharmaceutically acceptable salt thereof, for treating or preventing a HBV infection, is provided.

In certain embodiments, the use of a compound of the present disclosure, or a pharmaceutically acceptable salt thereof, for the manufacture of a medicament for treating or preventing a HBV infection, is provided.

Kits comprising the compounds, or pharmaceutically acceptable salts thereof, or pharmaceutical compositions of the foregoing are also provided. Articles of manufacture comprising a unit dose of the compounds, or pharmaceutically acceptable salts thereof, of the foregoing are also provided. Methods of preparing compounds of the present disclosure are also provided.

DETAILED DESCRIPTION OF THE INVENTION

I. General

The compounds of the present invention include certain 5-oxoacetyl-6-methyl-2,3-dihydro-1H-pyrrolizine-7-carboxamides that have improved kinetic solubility compared to other substituted pyrrolizines in the art, such as 7-oxoacetyl-6-methyl-2,3-dihydro-1H-pyrrolizine-5-carboxamides. The compounds can be combined with a pharmaceutically acceptable excipient and one or more additional therapeutic agents to form a pharmaceutical composition. The compounds and pharmaceutical compositions are useful for treating or preventing a Hepatitis B viral infection.

II. Definitions

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or ($C_u$-$C_v$) indicates that the following group has from u to v carbon atoms, where u and v are integers. For example, "$C_{1-6}$ alkyl" indicates that the alkyl group has from 1 to 6 carbon atoms.

"Alkyl" is a linear or branched saturated monovalent hydrocarbon. For example, an alkyl group can have 1 to 10 carbon atoms (i.e., ($C_{1-10}$)alkyl) or 1 to 8 carbon atoms (i.e., ($C_{1-8}$)alkyl) or 1 to 6 carbon atoms (i.e., ($C_{1-6}$ alkyl) or 1 to 4 carbon atoms (i.e., ($C_{1-4}$)alkyl). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH (CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

"Alkoxy" refers to the group —O-alkyl, where alkyl is as defined above. For example, C$_{1-4}$alkoxy refers to an —O-alkyl group having 1 to 4 carbons.

"Alkynyl" is a linear or branched monovalent hydrocarbon radical with at least one carbon-carbon triple bond. For example, an alkynyl group can have 2 to 8 carbon atoms (i.e., C$_{2-8}$ alkyne) or 2 to 6 carbon atoms (i.e., C$_{2-6}$ alkynyl) or 2 to 4 carbon atoms (i.e., C$_{2-4}$ alkynyl). Examples of alkynyl groups include, but are not limited to, acetylenyl (—C≡CH), propargyl (—CH$_2$C≡CH), and —CH$_2$—C≡C—CH$_3$.

"Halo" or "halogen" as used herein refers to fluoro (—F), chloro (—Cl), bromo (—Br) and iodo (—I).

"Haloalkyl" as used herein refers to an alkyl as defined herein, wherein one or more hydrogen atoms of the alkyl are independently replaced by a halo substituent, which may be the same or different. For example, C$_{1-4}$ haloalkyl is a C$_{1-4}$ alkyl wherein one or more of the hydrogen atoms of the C$_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, and triazolyl.

"Cycloalkyl" refers to a single saturated or partially unsaturated all carbon ring having 3 to 20 annular carbon atoms (i.e., C$_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocyles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Heterocyclyl" or "heterocycle" or "heterocycloalkyl" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 3 to about 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine-2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like.

"Oxo" as used herein refers to =O.

A "compound of the present disclosure" includes compounds disclosed herein, for example a compound of the present disclosure includes compounds of Formula (I), (II), (IIa), (IIb), (III), (IIIa), (IIIb), (IV), (V), (Va) or (Vb), including the compounds of the Examples.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Delaying" as used herein refers to development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

"Prevent" or "prevention" or "preventing" as used herein refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, in certain embodiments, the term "preventing HBV infection" refers to administering to a subject who does not have a detectable HBV infection an anti-HBV therapeutic substance. It is understood that the subject for anti-HBV preventative therapy may be an individual at risk of contracting the HBV virus. It is also understood that prevention does not require a 100% success rate. In some instances, prevention may be understood as a reduction of the risk of infection, but not a complete elimination the occurrence of an infection.

"At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Stereoisomer" as used herein refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Tautomer" as used herein refers to a proton shift from one atom of a molecule to another atom of the same molecule. The present disclosure includes tautomers of any said compounds.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the parent drug according to some chemical or enzymatic pathway.

III. Compounds

The present disclosure provides compounds for treating HBV. In some embodiments, the present disclosure provides a compound of Formula (I):

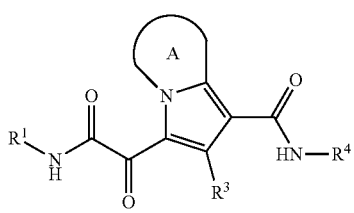

Formula I or a pharmaceutically acceptable salt thereof,
wherein:
- $R^1$ is $C_{1-6}$ alkyl optionally substituted with 1 to 3 $R^{1A}$, $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$;
- each $R^{1A}$ is independently halogen, —OH, —CN, $C_{1-2}$ haloalkyl, —C(O)NR$^X$R$^Y$, $C_{6-10}$ aryl optionally substituted with 1 to 3 $R^{1D}$, or a 5 to 8 membered heteroaryl having 1 to 3 heteroatoms selected from N, O, and S, optionally substituted with 1 to 3 $R^{1D}$, provided no more than 1 $R^{1A}$ is $C_{6-10}$ aryl optionally substituted with 1 to 3 $R^{1D}$ or 5 to 8 membered heteroaryl having 1 to 3 heteroatoms selected from N, O, and S;
- each $R^{1B}$ is independently —CN, halogen, $C_{1-6}$ alkyl optionally substituted with 1 to 3 —OH or —NR$^a$R$^b$, $C_{2-4}$ alkynyl, $C_{1-4}$ alkoxy, $C_{1-2}$ haloalkyl, $C_{3-6}$ cycloalkyl, —C(O)NR$^X$R$^Y$, or a 5 to 8 membered heteroaryl having 1 to 3 heteroatoms selected from N, O, and S optionally substituted with 1 to 3 $R^{1D}$, provided no more than 1 $R^{1B}$ is $C_{3-6}$ cycloalkyl or 5 to 8 membered heteroaryl having 1 to 3 heteroatoms selected from N, O, and S;
- each $R^{1C}$ is independently $C_{1-6}$ alkyl, oxo, $C_{1-4}$ haloalkyl, —C(O)H, —C(O)$C_{1-4}$ alkyl, —C(O)O$C_{1-4}$ alkyl, —C(O)NR$^X$R$^Y$, or a 5 to 12 membered heteroaryl having 1 to 3 heteroatoms selected from N, O, and S optionally substituted with 1 to 3 $R^{1D}$, provided no more than 1 $R^{1C}$ is a 5 to 12 membered heteroaryl having 1 to 3 heteroatoms selected from N, O, and S;
- each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;
- each $R^Y$ is independently —H or $C_{1-6}$ alkyl optionally substituted with 1 to 3 $R^Z$;
- or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$;
- wherein each $R^Z$ is independently halogen, methyl, ethyl, oxo, —OH, —S(O)$_2$$C_{1-3}$ alkyl, or 3 to 8 membered monocyclic or bicyclic heterocyclyl having 1 to 3 heteroatoms selected from N, O, and S;
- each $R^a$ is —H, $C_{1-3}$ alkyl, or a 3 to 8 membered monocyclic or bicyclic heterocyclyl having 1 to 3 heteroatoms selected from N, O, and S, optionally substituted with 1 to 3 $R^Z$;
- each $R^b$ is —H or $C_{1-3}$ alkyl; or
- $R^a$ and $R^b$ taken together form a 3 to 8 membered monocyclic or bicyclic heterocycle optionally substituted with 1 to 3 $R^Z$;

the moiety

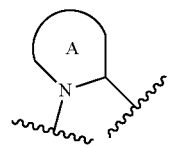

is a pyrrolidine or a 5-7 membered bicyclic heterocycle having one nitrogen, optionally substituted with 1 to 6 $R^2$ groups;
- wherein each $R^2$ is independently halogen, $C_{1-3}$ alkyl, —OH, or —O$C_{1-3}$ alkyl;
- $R^3$ is —H, halogen, or $C_{1-4}$ alkyl;
- $R^4$ is $C_{6-10}$ aryl optionally substituted with 1 to 5 $R^{4A}$, or 5 to 12 membered heteroaryl having 1 to 3 heteroatoms selected from N, O, and S, optionally substituted with 1 to 4 $R^{4B}$; and
- each $R^{1D}$, $R^{4A}$, and $R^{4B}$ are independently —CN, halogen, $C_{1-4}$ alkyl optionally substituted with —Si($C_{1-4}$ alkyl)$_3$, —O$C_{1-4}$ alkyl, —O$C_{1-4}$ haloalkyl, or $C_{1-4}$ haloalkyl.

In certain embodiments of a compound of Formula (I), the moiety

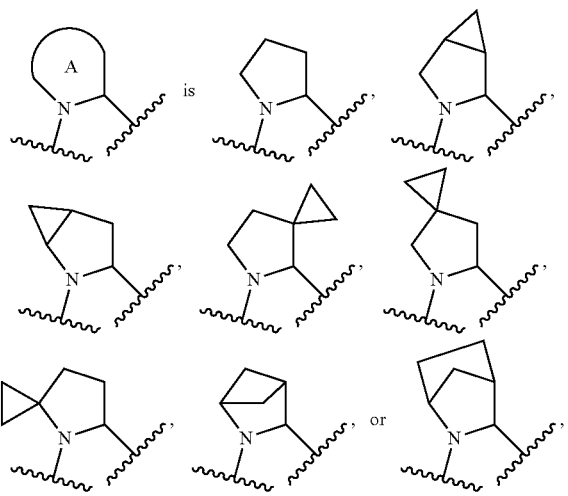

each of which is optionally substituted with 1 to 6 $R^2$.

In certain embodiments of a compound of Formula (I), the moiety

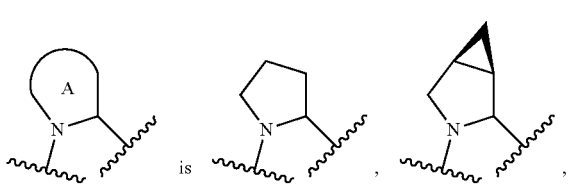

-continued

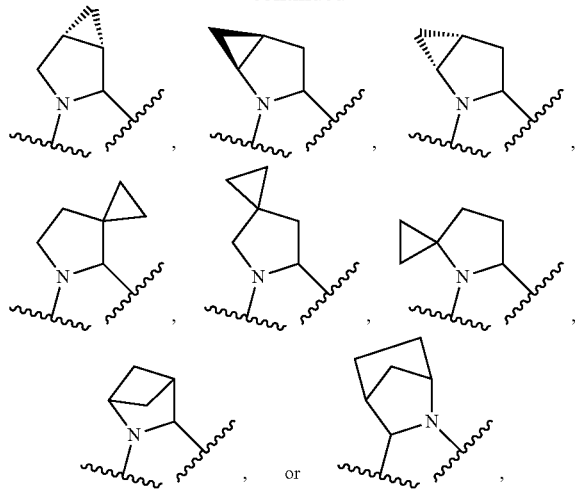

each of which is optionally substituted with 1 to 6 $R^2$.

In certain embodiments of a compound of Formula (I), the moiety

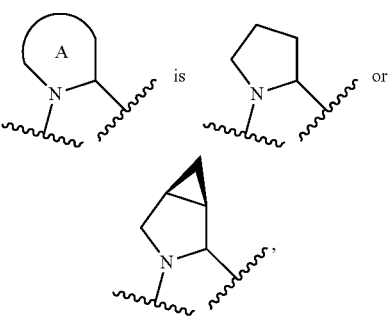

each of which is optionally substituted with 1 to 6 $R^2$.

In certain embodiments of a compound of Formula (I), the moiety

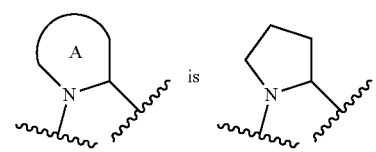

which is optionally substituted with 1 to 6 $R^2$.

In certain embodiments of a compound of Formula (I), the moiety

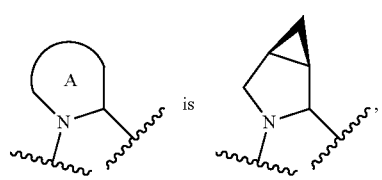

which is optionally substituted with 1 to 6 $R^2$.

In certain embodiments of a compound of Formula (I), the moiety

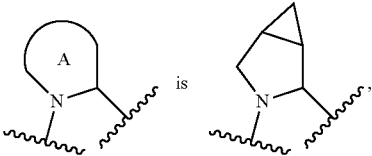

which is optionally substituted with 1 to 6 $R^2$.

In some embodiments, when the moiety

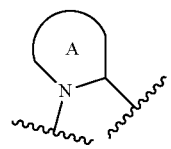

is a pyrrolidine or a 5-7 membered bicyclic heterocycle having one nitrogen, the one nitrogen refers to the nitrogen depicted in the structure

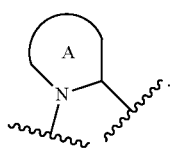

In certain embodiments of a compound of Formula (I), the moiety

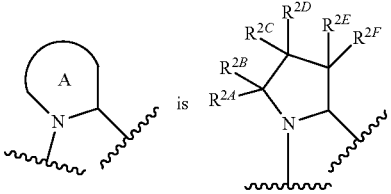

wherein each of $R^{2A}$, $R^{2B}$, $R^{2C}$, $R^{2D}$, $R^{2E}$, and $R^{2F}$ is independently —H, halogen, $C_{1-3}$ alkyl, —OH, or —$OC_{1-3}$ alkyl, or $R^{2C}$ or $R^{2D}$ may be taken together with $R^{2A}$ or $R^{2B}$ or with $R^{2E}$ or $R^{2F}$ to form a cyclopropyl group. In certain embodiments of a compound of Formula (I) or (II), each of $R^{2A}$, $R^{2B}$, $R^{2C}$, $R^{2D}$, $R^{2E}$, and $R^{2F}$ is independently —H, or $C_{1-3}$ alkyl, or $R^{2C}$ or $R^{2D}$ may be taken together with $R^{2A}$ or $R^{2B}$ or with $R^{2E}$ or $R^{2F}$ to form a cyclopropyl group. In certain embodiments of a compound of Formula (I) or (II), each of $R^{2A}$, $R^{2B}$, $R^{2C}$, $R^{2D}$, $R^{2E}$, and $R^{2F}$ is —H, or $R^{2C}$ or $R^{2D}$ may be taken together with $R^{2A}$ or $R^{2B}$ or with $R^{2E}$ or $R^{2F}$ to form a cyclopropyl group.

In some embodiments, the compound of Formula (I) can be a compound of Formula (II):

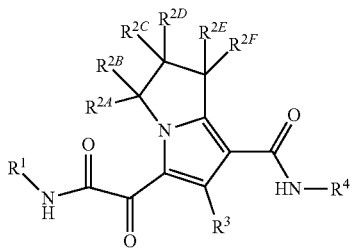

Formula II wherein

R$^1$ is C$_{1-6}$ alkyl optionally substituted with 1 to 3 R$^{1A}$, C$_{3-8}$ cycloalkyl optionally substituted with 1 to 4 R$^{1B}$, or 3 to 8 membered monocyclic or bicyclic heterocyclyl having 1 to 3 heteroatoms selected from N, O, and S, optionally substituted with 1 to 3 R$^{1C}$;

each R$^{1A}$ is independently halogen, —OH, —CN, C$_{1-2}$ haloalkyl, —C(O)NR$^X$R$^Y$, C$_{6-10}$ aryl optionally substituted with 1 to 3 R$^{1D}$, or a 5 to 12 membered heteroaryl having 1 to 3 heteroatoms selected from N, O, and S, optionally substituted with 1 to 3 R$^{1D}$, provided no more than 1 R$^{1A}$ is C$_{6-10}$ aryl optionally substituted with 1 to 3 R$^{1D}$ or 5 to 12 membered heteroaryl having 1 to 3 heteroatoms selected from N, O, and S, optionally substituted with 1 to 3 R$^{1D}$;

each R$^{1B}$ is independently halogen, C$_{1-6}$ alkyl optionally substituted with 1 to 3 —OH or —NR$^a$R$^b$, C$_{1-4}$ alkoxy, C$_{1-2}$ haloalkyl, C$_{2-6}$ alkyne, —C(O)NR$^X$R$^Y$, or 5 to 8 membered heteroaryl having 1 to 3 heteroatoms selected from N, O, and S optionally substituted with 1 to 3 R$^{1D}$, provided no more than 1 R$^{1B}$ is 5 to 8 membered heteroaryl having 1 to 3 heteroatoms selected from N, O, and S optionally substituted with 1 to 3 R$^{1D}$;

each R$^{1C}$ is independently C$_{1-6}$ alkyl, oxo, C$_{1-4}$ haloalkyl, —C(O)H, —C(O)C$_{1-4}$alkyl, —C(O)OC$_{1-4}$ alkyl, —C(O)NR$^X$R$^Y$, or 5 to 8 membered heteroaryl having 1 to 3 heteroatoms selected from N, O, and S optionally substituted with 1 to 3 R$^{1D}$;

each R$^X$ is independently —H, C$_{3-6}$ cycloalkyl, C$_{1-6}$ alkyl optionally substituted with 1 to 3 R$^Z$, 3 to 8 membered monocyclic or bicyclic heterocyclyl having 1 to 3 heteroatoms selected from N, O, and S, optionally substituted with 1 to 3 R$^Z$;

each R$^Y$ is independently —H or C$_{1-6}$ alkyl optionally substituted with 1 to 3 R$^Z$;

or R$^X$ and R$^Y$ are taken together to form a 3 to 8 membered monocyclic or bicyclic heterocyclyl having 1 to 3 heteroatoms selected from N, O, and S, optionally substituted with 1 to 3 R$^Z$;

wherein each R$^Z$ is independently halogen, methyl, ethyl, oxo, —OH, —S(O)$_2$C$_{1-3}$ alkyl, or 3 to 8 membered monocyclic or bicyclic heterocyclyl having 1 to 3 heteroatoms selected from N, O, and S;

each R$^a$ is —H, C$_{1-3}$ alkyl, or a 3 to 8 membered monocyclic or bicyclic heterocyclyl having 1 to 3 heteroatoms selected from N, O, and S, optionally substituted with 1 to 3 R$^Z$;

each R$^b$ is —H or C$_{1-3}$ alkyl; or

R$^a$ and R$^b$ taken together form a 3 to 8 membered monocyclic or bicyclic heterocyclyl optionally substituted with 1 to 3 R$^Z$;

each of R$^{2A}$, R$^{2B}$, R$^{2C}$, R$^{2D}$, R$^{2E}$, and R$^{2F}$ are independently —H, halogen, C$_{1-3}$ alkyl, —OH, or —OC$_{1-3}$ alkyl, or R$^{2C}$ or R$^{2D}$ may be taken together with R$^{2A}$ or R$^{2B}$ or with R$^{2E}$ or R$^{2F}$ to form a cyclopropyl group;

R$^3$ is halogen or methyl;

R$^4$ is phenyl optionally substituted with 1 to 5 R$^{4A}$, or pyridinyl, optionally substituted with 1 to 4 R$^{4B}$; and each R$^{1D}$, R$^{4A}$, and R$^{4B}$ are independently —CN, halogen, C$_{1-4}$ alkyl optionally substituted with —Si(C$_{1-4}$ alkyl)$_3$, —OC$_{1-4}$ alkyl, —OC$_{1-4}$ haloalkyl, or C$_{1-4}$ haloalkyl.

In some embodiments of a compound of Formula (I) or (II), IV is C$_{1-6}$ alkyl optionally substituted with 1 to 3 R$^{1A}$, C$_{3-8}$ cycloalkyl optionally substituted with 1 to 4 R$^{1B}$, or 3 to 8 membered monocyclic or bicyclic heterocyclyl having 1 to 3 heteroatoms selected from N, O, and S, optionally substituted with 1 to 3 R$^{1C}$. In some embodiments, R$^1$ is C$_{1-6}$ alkyl optionally substituted with 1 to 3 R$^{1A}$. In some embodiments, R$^1$ is C$_{3-8}$ cycloalkyl optionally substituted with 1 to 4 R$^{1B}$, or 3 to 8 membered monocyclic or bicyclic heterocyclyl having 1 to 3 heteroatoms selected from N, O, and S, optionally substituted with 1 to 3 R$^{1C}$. In some embodiments, R$^1$ is C$_{3-8}$ cycloalkyl optionally substituted with 1 to 4 R$^{1B}$. In some embodiments, R$^1$ is a 3 to 8 membered monocyclic or bicyclic heterocyclyl having 1 to 3 heteroatoms selected from N, O, and S, optionally substituted with 1 to 3 R$^{1C}$.

In some embodiments of a compound of Formula (I) or (II), R$^1$ is C$_{1-6}$ alkyl optionally substituted with 1 to 3 R$^{1A}$, wherein each R$^{1A}$ is independently halogen, —OH, —CN, C$_{1-2}$ haloalkyl, —C(O)NR$^X$R$^Y$, C$_{6-10}$ aryl optionally substituted with 1 to 3 R$^{1D}$, or a 5 to 12 membered heteroaryl having 1 to 3 heteroatoms selected from N, O, and S, optionally substituted with 1 to 3 R$^{1D}$, provided no more than 1 R$^{1A}$ is C$_{6-10}$ aryl optionally substituted with 1 to 3 R$^{1D}$ or 5 to 12 membered heteroaryl having 1 to 3 heteroatoms selected from N, O, and S optionally substituted with 1 to 3 R$^{1D}$.

In some embodiments of the compound of Formula (I) or (II), R$^1$ is C$_{1-6}$ alkyl optionally substituted with 1 to 3 R$^{1A}$, wherein each R$^{1A}$ is independently halogen, —OH, —CN, C$_{1-2}$ haloalkyl, or —C(O)NR$^X$R$^Y$. In some embodiments, R$^1$ is C$_{1-6}$ alkyl optionally substituted with 1 to 3 R$^{1A}$, wherein each R$^{1A}$ is independently C$_{1-2}$ haloalkyl, or —C(O)NR$^X$R$^Y$. In some embodiments, R$^1$ is C$_{1-6}$ alkyl optionally substituted with 1 to 3 R$^{1A}$, wherein each R$^{1A}$ is independently C$_{1-2}$ haloalkyl or —C(O)NH$_2$. In some embodiments, R$^1$ is C$_{1-6}$ alkyl optionally substituted with 1 to 3 R$^{1A}$, wherein each R$^{1A}$ is independently CF$_3$ or —C(O)NH$_2$.

In some embodiments of the compound of Formula (I) or (II), R$^1$ is

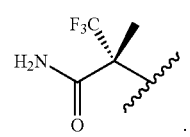

In some embodiments of the compound of Formula (I) or (II), $R^1$ is

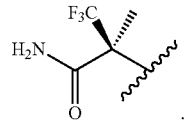

In some embodiments of the compound of Formula (I) or (II), $R^3$ is a halogen. In some embodiments $R^3$ is Cl.

In some embodiments of a compound of Formula (I) or (II), $R^1$ is $C_{3-8}$ cycloalkyl optionally substituted with 1 to 4 $R^{1B}$, or 3 to 8 membered monocyclic or bicyclic heterocyclyl having 1 to 3 heteroatoms selected from N, O, and S, optionally substituted with 1 to 3 $R^{1C}$;

- each $R^{1B}$ is independently halogen, $C_{1-6}$ alkyl optionally substituted with 1 to 3 —OH or —$NR^aR^b$, $C_{1-4}$ alkoxy, $C_{1-2}$ haloalkyl, $C_{2-6}$ alkyne, —$C(O)NR^XR^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$;
- each $R^{1C}$ is independently $C_{1-6}$ alkyl, oxo, $C_{1-4}$ haloalkyl, —C(O)H, —$C(O)C_{1-4}$ alkyl, —$C(O)OC_{1-4}$ alkyl, —$C(O)NR^XR^Y$, or 5 to 8 membered heteroaryl having 1 to 3 heteroatoms selected from N, O, and S optionally substituted with 1 to 3 $R^{1D}$;
- each $R^X$ is independently —H, $C_{3-6}$ cycloalkyl, $C_{1-6}$ alkyl optionally substituted with 1 to 3 $R^Z$, 3 to 8 membered monocyclic or bicyclic heterocyclyl having 1 to 3 heteroatoms selected from N, O, and S, optionally substituted with 1 to 3 $R^Z$;
- each $R^Y$ is independently —H or $C_{1-6}$ alkyl optionally substituted with 1 to 3 $R^Z$;
- or $R^X$ and $R^Y$ are taken together to form a 3 to 8 membered monocyclic or bicyclic heterocyclyl having 1 to 3 heteroatoms selected from N, O, and S, optionally substituted with 1 to 3 $R^Z$;
- wherein each $R^Z$ is independently halogen, methyl, ethyl, oxo, —OH, —$S(O)_2C_{1-3}$ alkyl, or 3 to 8 membered monocyclic or bicyclic heterocyclyl having 1 to 3 heteroatoms selected from N, O, and S;
- each $R^a$ is —H, $C_{1-3}$ alkyl, or a 3 to 8 membered monocyclic or bicyclic heterocyclyl having 1 to 3 heteroatoms selected from N, O, and S, optionally substituted with 1 to 3 $R^Z$;
- each $R^b$ is —H or $C_{1-3}$ alkyl; or
- $R^a$ and $R^b$ taken together form a 3 to 8 membered monocyclic or bicyclic heterocyclyl optionally substituted with 1 to 3 $R^Z$; and
- each $R^{1D}$ is independently —CN, halogen, $C_{1-4}$ alkyl optionally substituted with —$Si(C_{1-4} \text{alkyl})_3$, —$OC_{1-4}$ alkyl, —$OC_{1-4}$ haloalkyl, or $C_{1-4}$ haloalkyl.

In some embodiments, a compound of Formula (I) can be a compound of Formula (II):

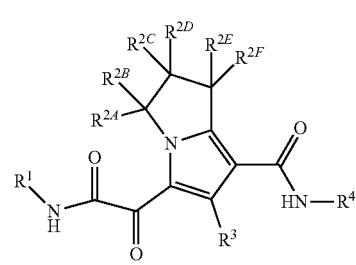

Formula II wherein $R^1$ is $C_{3-6}$ cycloalkyl optionally substituted with 1 to 4 $R^{1B}$, or 3 to 6 membered monocyclic heterocyclyl having 1 to 3 heteroatoms selected from N, O, and S, optionally substituted with 1 to 3 $R^{1C}$;

each $R^{1B}$ is independently halogen, $C_{1-6}$ alkyl optionally substituted with 1 —OH, $C_{2-6}$ alkyne, —$C(O)NR^XR^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$;

each $R^{1C}$ is independently —$C(O)NR^XR^Y$, or 5 to 8 membered heteroaryl having 1 to 3 heteroatoms selected from N, O, and S optionally substituted with 1 to 3 $R^{1D}$; each $R^{1D}$ is independently $C_{1-4}$ alkyl optionally substituted with —$Si(C_{1-4} \text{alkyl})_3$;

each $R^X$ is independently —H, or $C_{1-6}$ alkyl;

each $R^Y$ is independently —H or $C_{1-6}$ alkyl;

each of $R^{2A}$, $R^{2B}$, $R^{2C}$, $R^{2D}$, $R^{2E}$, and $R^{2F}$ are —H, or $R^{2C}$ or $R^{2D}$ may be taken together with $R^{2A}$ or $R^{2B}$ or with $R^{2E}$ or $R^{2F}$ to form a cyclopropyl group;

$R^3$ is methyl;

$R^4$ is phenyl substituted with 1 to 5 $R^{4A}$, or pyridinyl, substituted with 1 to 4 $R^{4B}$;

each $R^{4A}$ is independently —CN, halogen, or $C_{1-4}$ haloalkyl; and each $R^{4B}$ is independently halogen, or $C_{1-4}$ haloalkyl.

In some embodiments of the compound of Formula (II), each of $R^{2A}$, $R^{2B}$, $R^{2C}$, $R^{2D}$, $R^{2E}$, and $R^{2F}$ are —H, or $R^{2C}$ or $R^{2D}$ may be taken together with $R^{2A}$ or $R^{2B}$ or with $R^{2E}$ or $R^{2F}$ to form a cyclopropyl group. In some embodiments of the compound of Formula (II), each of $R^{2A}$, $R^{2B}$, $R^{2C}$, $R^{2D}$, $R^{2E}$, and $R^{2F}$ are —H. In some embodiments of the compound of Formula (II), each of $R^{2A}$ and $R^{2B}$ is H, and $R^{2C}$ or $R^{2D}$ is taken together with $R^{2E}$ or $R^{2F}$ to form a cyclopropyl group. In some embodiments of the compound of Formula (II), each of $R^{2E}$ and $R^{2F}$ are —H, and $R^{2C}$ or $R^{2D}$ is taken together with $R^{2A}$ or $R^{2B}$ to form a cyclopropyl group.

In certain embodiments, a compound of Formula (I) or (II) is a compound of Formula (IIa):

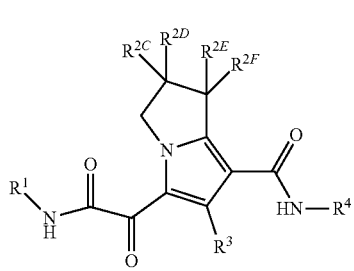

Formula IIa wherein $R^1$, $R^{2C}$, $R^{2D}$, $R^{2E}$, $R^{2F}$, $R^3$ and $R^4$, are as defined above or below for Formula (I) and (II), or any combination thereof.

In certain embodiments, a compound of Formula (I), (II) or (IIa) is a compound of Formula (IIb):

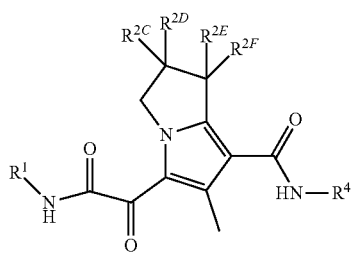

Formula IIb wherein $R^1$, $R^{2C}$, $R^{2D}$, $R^{2E}$, $R^{2F}$ and $R^4$, are as defined above or below for Formula (I) and (II), or any combination thereof.

In certain embodiments, a compound of Formula (I) or (II) is a compound of Formula (III):

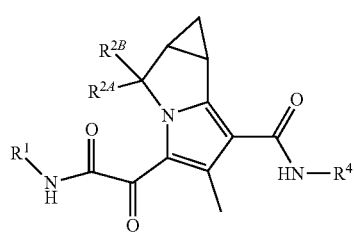

Formula III wherein $R^1$, $R^{2A}$, $R^{2B}$, and $R^4$, are as defined above or below for Formula (I) and (II), or any combination thereof. In some embodiments of a compound of Formula (I), (II) or (III), $R^{2A}$ and $R^{2B}$ are each independently —H, halogen, $C_{1-3}$ alkyl, —OH, or —$OC_{1-3}$ alkyl. In some embodiments of a compound of Formula (I), (II) or (III), $R^{2A}$ and $R^{2B}$ are each independently —H and $C_{1-3}$ alkyl. In some embodiments of a compound of Formula (I), (II) or (III), $R^{2A}$ and $R^{2B}$ are each —H.

In certain embodiments of a compound of Formula (I), (II) or (III), the compound is a compound of Formula (IIIa):

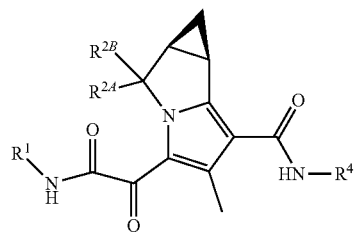

Formula IIIa wherein $R^1$, $R^{2A}$, $R^{2B}$, and $R^4$, are as defined above or below for Formula (I), (II) and (III), or any combination thereof.

In certain embodiments of a compound of Formula (I), (II) or (III), the compound is a compound of Formula (IIIb):

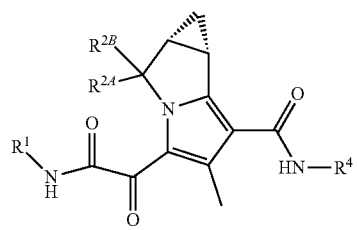

Formula IIIb wherein $R^1$, $R^{2A}$, $R^{2B}$, and $R^4$, are as defined above or below for Formula (I), (II) and (III), or any combination thereof.

In some embodiments of a compound of Formula (I), (II), (III), (IIIa) or (IIIb), $R^{2A}$ and $R^{2B}$ are each independently —H, halogen, $C_{1-3}$ alkyl, —OH, or —$OC_{1-3}$ alkyl. In some embodiments of a compound of Formula (I), (II), (III), (IIIa) or (IIIb), $R^{2A}$ and $R^{2B}$ are each independently —H and $C_{1-3}$ alkyl. In some embodiments of a compound of Formula (I), (II), (III), (IIIa) or (IIIb), $R^{2A}$ and $R^{2B}$ are each —H.

In certain embodiments, a compound of Formula (I) or (II) is a compound of Formula (IV):

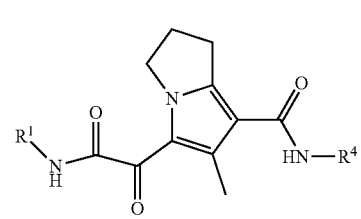

Formula IV wherein $R^1$, $R^{2A}$, $R^{2B}$, and $R^4$, are as defined above or below for Formula (I) and (II), or any combination thereof.

In certain embodiments, a compound of Formula (I) or (II) is a compound of Formula (V):

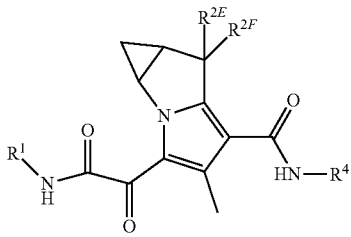

Formula V wherein $R^1$, $R^{2E}$, $R^{2F}$, and $R^4$, are as defined above or below for Formula (I) and (II), or any combination thereof.

In certain embodiments of a compound of Formula (I), (II) or (V), the compound is a compound of Formula (Va):

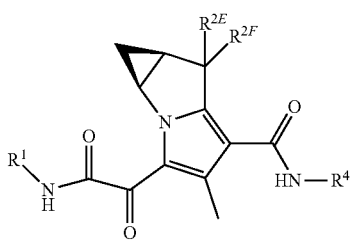

Formula Va wherein $R^1$, $R^{2E}$, $R^{2F}$, and $R^4$, are as defined above or below for Formula (I), (II) and (V), or any combination thereof.

In certain embodiments of a compound of Formula (I), (II) or (V), the compound is a compound of Formula (Vb):

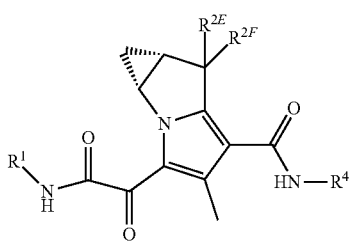

Formula Vb wherein $R^1$, $R^{2E}$, $R^{2F}$, and $R^4$, are as defined above or below for Formula (I), (II) and (V), or any combination thereof.

In some embodiments of a compound of Formula (I), (II), (V), (Va) or (Vb), $R^{2E}$ and $R^{2F}$ are each independently —H, halogen, $C_{1-3}$ alkyl, —OH, or —$OC_{1-3}$ alkyl. In some embodiments of a compound of Formula (I), (II), (V), (Va) or (Vb), $R^{2E}$ and $R^{2F}$ are each independently —H and $C_{1-3}$ alkyl. In some embodiments of a compound of Formula (I), (II), (V), (Va) or (Vb), $R^{2E}$ and $R^{2F}$ are each —H.

In some embodiments of a compound of Formula (I), (II), (IIa), (IIb), (III), (IIIa), (IIIb), (IV), (V), (Va) or (Vb), $R^1$ is $C_{3-6}$ cycloalkyl optionally substituted with 1 to 4 $R^{1B}$, or 3 to 6 membered monocyclic heterocyclyl having 1 to 3 heteroatoms selected from N, O, and S, optionally substituted with 1 to 3 $R^{1C}$.

In some embodiments of a compound of Formula (I), (II), (IIa), (IIb), (III), (IIIa), (IIIb), (IV), (V), (Va) or (Vb), $R^1$ is $C_{3-6}$ cycloalkyl optionally substituted with 1 to 4 $R^{1B}$. In some embodiments of a compound of Formula (I), (II), (IIa), (IIb), (III), (IIIa), (IIIb), (IV), (V), (Va) or (Vb), $R^1$ is $C_{3-5}$ cycloalkyl optionally substituted with 1 to 4 $R^{1B}$. In some embodiments of a compound of Formula (I), (II), (IIa), (IIb), (III), (IIIa), (IIIb), (IV), (V), (Va) or (Vb), $R^1$ is cyclopropyl, cyclobutyl, or cyclopentyl, optionally substituted with 1 to 3 $R^{1B}$. In some embodiments of a compound of Formula (I), (II), (IIa), (IIb), (III), (IIIa), (IIIb), (IV), (V), (Va) or (Vb), $R^1$ is cyclopropyl or cyclobutyl, optionally substituted with 1 to 3 $R^{1B}$. In some embodiments of a compound of Formula (I), (II), (IIa), (IIb), (III), (IIIa), (IIIb), (IV), (V), (Va) or (Vb), $R^1$ is cyclopropyl, optionally substituted with 1 to 3 $R^{1B}$. In some embodiments of a compound of Formula (I), (II), (IIa), (IIb), (III), (IIIa), (IIIb), (IV), (V), (Va) or (Vb), $R^1$ is cyclopropyl, substituted with 1 $R^{1B}$. In some embodiments of a compound of Formula (I), (II), (IIa), (IIb), (III), (IIIa), (IIIb), (IV), (V), (Va) or (Vb), $R^1$ is cyclobutyl, optionally substituted with 1 to 3 $R^{1B}$. In some embodiments of a compound of Formula (I), (II), (IIa), (IIb), (III), (IIIa), (IIIb), (IV), (V), (Va) or (Vb), $R^1$ is cyclobutyl, substituted with 3 $R^{1B}$. In some embodiments of a compound of Formula (I), (II), (IIa), (IIb), (III), (IIIa), (IIIb), (IV), (V), (Va) or (Vb), $R^1$ is cyclopentyl, optionally substituted with 1 to 3 $R^{1B}$.

In some embodiments of a compound of Formula (I), (II), (IIa), (IIb), (III), (IIIa), (IIIb), (IV), (V), (Va) or (Vb), each $R^{1B}$ is independently halogen, $C_{1-6}$ alkyl optionally substituted with 1 —OH, $C_{2-6}$ alkyne, —C(O)$NR^XR^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$. In some embodiments of a compound of Formula (I), (II), (IIa), (IIb), (III), (IIIa), (IIIb), (IV), (V), (Va) or (Vb), each $R^{1B}$ is independently halogen, $C_{1-3}$ alkyl optionally substituted with —OH, $C_{2-4}$ alkynyl, —C(O)$NR^XR^Y$ or 5 to 6 membered heteroaryl having 1 to 3 heteroatoms selected from N, O, and S optionally substituted with 1 to 3 $R^{1D}$. In some embodiments of a compound of Formula (I), (II), (IIa), (IIb), (III), (IIIa), (IIIb), (IV), (V), (Va) or (Vb), each $R^{1B}$ is independently halogen, $C_{1-3}$ alkyl optionally substituted with —OH, $C_{2-4}$ alkynyl, —C(O)$NR^XR^Y$ or 5 membered heteroaryl having 1 to 3 heteroatoms selected from N, O, and S optionally substituted with 1 to 3 $R^{1D}$. In some embodiments of a compound of Formula (I), (II), (IIa), (IIb), (III), (IIIa), (IIIb), (IV), (V), (Va) or (Vb), when $R^{1B}$ is independently —C(O)$NR^XR^Y$, $R^{1B}$ is —C(O)$NH_2$, —C(O)NHMe or —C(O)$NMe_2$. In some embodiments of a compound of Formula (I), (II), (IIa), (IIb), (III), (IIIa), (IIIb), (IV), (V), (Va) or (Vb), when $R^{1B}$ is 5 or 6 membered heteroaryl having 1 to 3 heteroatoms selected from N, O, and S optionally substituted with 1 to 3 $R^{1D}$, the heteroaryl can be pyrrolyl, pyridinyl, imidazolyl, pyrazolyl, triazolyl, pyrazinyl, pyrimidinyl, pyridazinyl, triazolyl, thiophenyl, furanyl, pyranyl, thiazolyl, isothiazolyl, thiadiazolyl, oxazolyl, isoxazolyl, or oxadiazolyl. In some embodiments of a compound of Formula (I), (II), (IIa), (IIb), (III), (IIIa), (IIIb), (IV), (V), (Va) or (Vb), when $R^{1B}$ is 5 membered heteroaryl having 1 to 3 heteroatoms selected from N, O, and S optionally substituted with 1 to 3 $R^{1D}$, the heteroaryl can be pyrrolyl, imidazolyl, pyrazolyl, triazolyl, thiazolyl, isothiazolyl, thiadiazolyl, oxazolyl, isoxazolyl, or oxadiazolyl. In some embodiments of a compound of Formula (I), (II), (IIa), (IIb), (III), (IIIa), (IIIb), (IV), (V), (Va) or (Vb), $R^{1B}$ is triazolyl, thiadiazolyl, oxazolyl, isoxazolyl, or oxadiazolyl. In some embodiments of a compound of Formula (I), (II), (IIa), (IIb), (III), (IIIa), (IIIb), (IV), (V), (Va) or (Vb), $R^{1B}$ is triazolyl, thiadiazolyl, or oxadiazolyl. In some embodiments of a compound of Formula (I), (II), (IIa), (IIb), (III), (IIIa), (IIIb), (IV), (V), (Va) or (Vb), $R^{1B}$ is triazolyl, or thiadiazolyl. In some embodiments of a compound of Formula (I), (II), (IIa), (IIb), (III), (IIIa), (IIIb), (IV), (V), (Va) or (Vb), $R^{1B}$ is triazolyl. In some embodiments of a compound of Formula (I), (II), (IIa), (IIb), (III), (IIIa), (IIIb), (IV), (V), (Va) or (Vb), $R^{1B}$ is thiadiazolyl. In some embodiments of a compound of Formula (I), (II), (IIa), (IIb), (III), (IIIa), (IIIb), (IV), (V), (Va) or (Vb), each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$. In some embodiments of a compound of Formula (I), (II), (IIa), (IIb), (III), (IIIa), (IIIb), (IV), (V), (Va) or (Vb), wherein 2 $R^{1B}$ are optionally F, and 1 $R^{1B}$ is —CH$_2$OH, —C≡CH, —C(O)NH$_2$, —C(O)NHMe, —C≡CH, triazolyl or thiadiazolyl, wherein the triazolyl and thiadiazolyl are optionally substituted with Me or —CH$_2$Si(Me)$_3$. In some embodiments of a compound of Formula (I), (II), (IIa), (IIb), (III), (IIIa), (IIIb), (IV), (V), (Va) or (Vb), wherein 2 $R^{1B}$ are optionally F, and 1 $R^{1B}$ is —C(O)NH$_2$, or —C(O)NHMe. In some embodiments of a compound of Formula (I), (II), (IIa), (IIb), (III), (IIIa), (IIIb), (IV), (V), (Va) or (Vb), wherein 2 $R^{1B}$ are optionally F, and 1 $R^{1B}$ is thiadiazolyl.

In some embodiments of a compound of Formula (I), (II), (IIa), (IIb), (III), (IIIa), (IIIb), (IV), (V), (Va) or (Vb), each $R^{1B}$ is independently halogen, $C_{1-3}$ alkyl optionally substituted with —OH, $C_{2-4}$ alkynyl, —C(O)NR$^X$R$^Y$ or 5 to 6 membered heteroaryl having 1 to 3 heteroatoms selected from N, O, and S optionally substituted with 1 to 3 $R^{1D}$; each $R^{1D}$ is independently $C_{1-3}$ alkyl optionally substituted with —Si(C$_{1-2}$ alkyl)$_3$; $R^X$ is $C_{1-2}$ alkyl; and $R^Y$ is —H.

In some embodiments of a compound of Formula (I), (II), (IIa), (IIb), (III), (IIIa), (IIIb), (IV), (V), (Va) or (Vb), each $R^{1D}$ is independently $C_{1-4}$ alkyl optionally substituted with —Si(C$_{1-4}$ alkyl)$_3$. In some embodiments of a compound of Formula (I), (II), (IIa), (IIb), (III), (IIIa), (IIIb), (IV), (V), (Va) or (Vb), each $R^{1D}$ is independently $C_{1-3}$ alkyl optionally substituted with —Si(C$_{1-2}$ alkyl)$_3$. In some embodiments of a compound of Formula (I), (II), (IIa), (IIb), (III), (IIIa), (IIIb), (IV), (V), (Va) or (Vb), each $R^{1D}$ is independently Me or —CH$_2$Si(Me)$_3$.

In some embodiments of a compound of Formula (I), (II), (IIa), (IIb), (III), (IIIa), (IIIb), (IV), (V), (Va) or (Vb), each $R^X$ is independently —H, or $C_{1-6}$ alkyl; and each $R^Y$ is independently —H or $C_{1-6}$ alkyl. In some embodiments of a compound of Formula (I), (II), (IIa), (IIb), (III), (IIIa), (IIIb), (IV), (V), (Va) or (Vb), $R^X$ is $C_{1-2}$ alkyl; and $R^Y$ is —H. In some embodiments of a compound of Formula (I), (II), (IIa), (IIb), (III), (IIIa), (IIIb), (IV), (V), (Va) or (Vb), $R^X$ is Me; and $R^Y$ is —H.

In some embodiments of a compound of Formula (I), (II), (IIa), (IIb), (III), (IIIa), (IIIb), (IV), (V), (Va) or (Vb), $R^1$ is $C_{3-5}$ cycloalkyl optionally substituted with 1 to 4 $R^{1B}$, wherein each $R^{1B}$ is independently halogen, $C_{1-6}$ alkyl optionally substituted with 1 —OH, $C_{2-6}$ alkyne, —C(O)NR$^X$R$^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$. In some embodiments of a compound of Formula (I), (II), (IIa), (IIb), (III), (IIIa), (IIIb), (IV), (V), (Va) or (Vb), $R^1$ is $C_{3-5}$ cycloalkyl optionally substituted with 1 to 4 $R^{1B}$, wherein each $R^{1B}$ is independently halogen, $C_{1-3}$ alkyl optionally substituted with —OH, $C_{2-4}$ alkynyl, —C(O)NR$^X$R$^Y$ or 5 membered heteroaryl having 1 to 3 heteroatoms selected from N, O, and S optionally substituted with 1 to 3 $R^{1D}$. In some embodiments of a compound of Formula (I), (II), (IIa), (IIb), (III), (IIIa), (IIIb), (IV), (V), (Va) or (Vb), $R^1$ is $C_{3-5}$ cycloalkyl optionally substituted with 1 to 4 $R^{1B}$, wherein each $R^{1B}$ is independently F, —CH$_2$OH, —C(O)NH$_2$, —C(O)NHMe, triazolyl or thiadiazolyl, wherein the triazolyl and thiadiazolyl are each optionally substituted with Me or —CH$_2$Si(Me)$_3$.

In some embodiments of a compound of Formula (I), (II), (IIa), (IIb), (III), (IIIa), (IIIb), (IV), (V), (Va) or (Vb), $R^1$ is $C_{3-5}$ cycloalkyl substituted with 1 to 4 $R^{1B}$, wherein each $R^{1B}$ is independently halogen, $C_{1-6}$ alkyl optionally substituted with 1 —OH, $C_{2-6}$ alkyne, —C(O)NR$^X$R$^Y$, or 5 to 8 membered heteroaryl having 1 to 3 heteroatoms selected from N, O, and S optionally substituted with 1 to 3 $R^{1D}$. In some embodiments of a compound of Formula (I), (II), (IIa), (IIb), (III), (IIIa), (IIIb), (IV), (V), (Va) or (Vb), $R^1$ is cyclopropyl or cyclobutyl, substituted with 1 to 3 $R^{1B}$, wherein each $R^{1B}$ is independently halogen, $C_{1-3}$ alkyl optionally substituted with —OH, $C_{2-4}$ alkynyl, —C(O)NR$^X$R$^Y$ or 5 membered heteroaryl having 1 to 3 heteroatoms selected from N, O, and S optionally substituted with 1 to 3 $R^{1D}$. In some embodiments of a compound of Formula (I), (II), (IIa), (IIb), (III), (IIIa), (IIIb), (IV), (V), (Va) or (Vb), $R^1$ is cyclopropyl or cyclobutyl, substituted with 1 to 3 $R^{1B}$, wherein each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$. In some embodiments of a compound of Formula (I), (II), (IIa), (IIb), (III), (IIIa), (IIIb), (IV), (V), (Va) or (Vb), $R^1$ is cyclopropyl substituted with F, —CH$_2$OH, —C(O)NH$_2$, —C(O)NHMe, triazolyl or thiadiazolyl, wherein the triazolyl and thiadiazolyl are each optionally substituted with Me or —CH$_2$Si(Me)$_3$. In some embodiments of a compound of Formula (I), (II), (IIa), (IIb), (III), (IIIa), (IIIb), (IV), (V), (Va) or (Vb), $R^1$ is cyclopropyl or cyclobutyl, substituted with 1 to 3 $R^{1B}$, wherein 2 $R^{1B}$ are optionally F, and 1 $R^{1B}$ is thiadiazolyl.

In some embodiments of a compound of Formula (I), (II), (IIa), (IIb), (III), (IIIa), (IIIb), (IV), (V), (Va) or (Vb), $R^1$ is cyclopropyl substituted with —C≡CH, triazolyl or thiadiazolyl, wherein the triazolyl is optionally substituted with Me or —CH$_2$Si(Me)$_3$. In some embodiments of a compound of Formula (I), (II), (IIa), (IIb), (III), (IIIa), (IIIb), (IV), (V), (Va) or (Vb), $R^1$ is cyclopropyl substituted with thiadiazolyl. In some embodiments of a compound of Formula (I), (II), (IIa), (IIb), (III), (IIIa), (IIIb), (IV), (V), (Va) or (Vb), $R^1$ is cyclobutyl substituted with 1 to 3 $R^{1B}$, wherein each $R^{1B}$ is independently F, —CH$_2$OH, —C(O)NH$_2$, —C(O)NHMe, triazolyl or thiadiazolyl, wherein the triazolyl and thiadiazolyl are each optionally substituted with Me or —CH$_2$Si(Me)$_3$. In some embodiments of a compound of Formula (I), (II), (IIa), (IIb), (III), (IIIa), (IIIb), (IV), (V), (Va) or (Vb), $R^1$ is cyclobutyl substituted with 2 fluoro and 1 —CH$_2$OH, —C≡CH, —C(O)NH$_2$, —C(O)NHMe, triazolyl or thiadiazolyl, wherein the triazolyl is optionally substituted with Me. In some embodiments of a compound of Formula (I), (II), (IIa), (IIb), (III), (IIIa), (IIIb), (IV), (V), (Va) or (Vb), $R^1$ is cyclobutyl substituted with 2 fluoro and 1 —C(O)NH$_2$, or —C(O)NHMe. In some embodiments of a compound of Formula (I), (II), (IIa), (IIb), (III), (IIIa), (IIIb), (IV), (V), (Va) or (Vb), is cyclobutyl substituted with 2 fluoro and 1 thiadiazolyl.

In some embodiments of a compound of Formula (I), (II), (IIa), (IIb), (III), (IIIa), (IIIb), (IV), (V), (Va) or (Vb), $R^1$ is

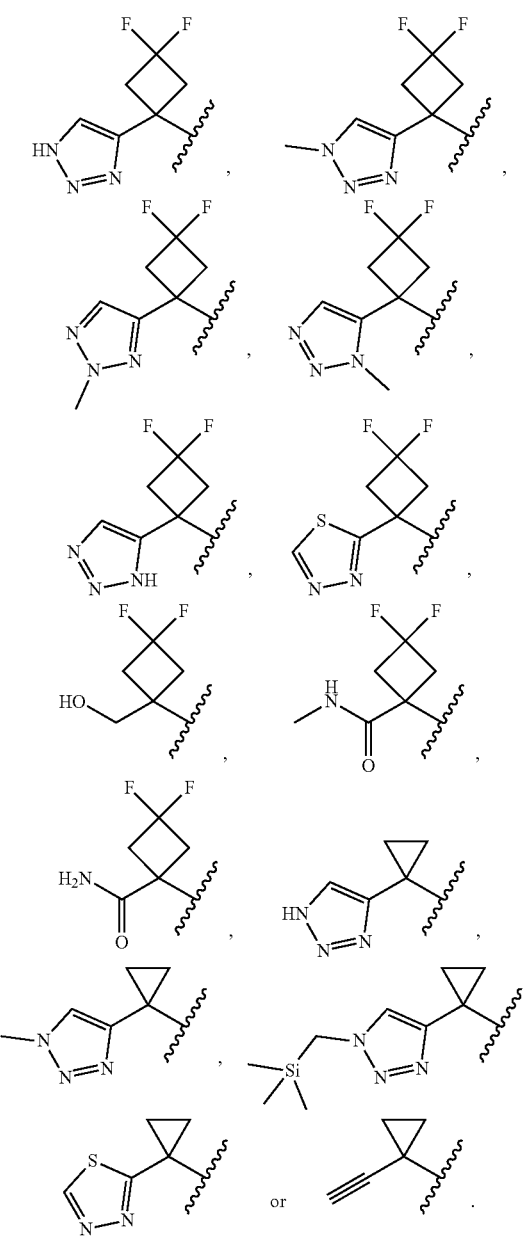
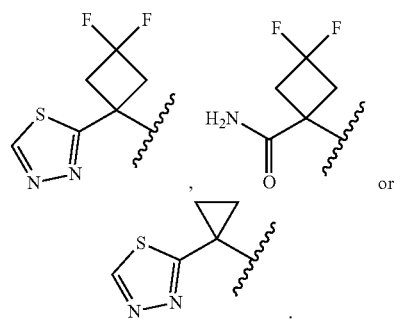
In some embodiments of a compound of Formula (I), (II), (IIa), (IIb), (III), (IIIa), (IIIb), (IV), (V), (Va) or (Vb), R¹ is
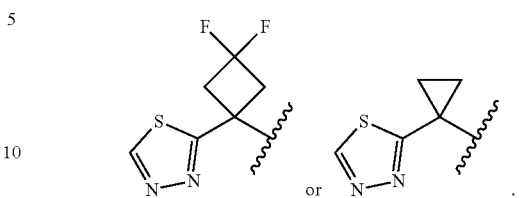
In some embodiments of a compound of Formula (I), (II), (IIa), (IIb), (III), (IIIa), (IIIb), (IV), (V), (Va) or (Vb), R¹ is
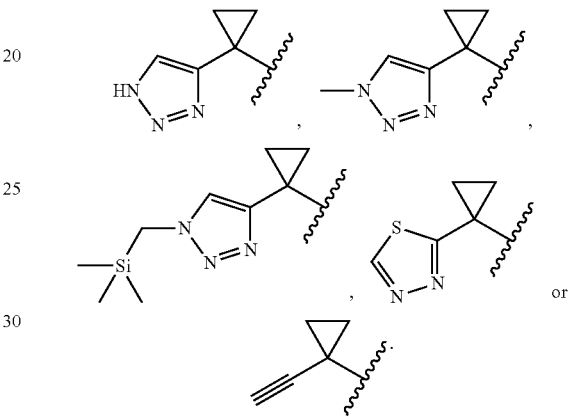
In some embodiments of a compound of Formula (I), (II), (IIa), (IIb), (III), (IIIa), (IIIb), (IV), (V), (Va) or (Vb), R¹ is
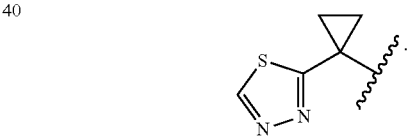
In some embodiments of a compound of Formula (I), (II), (IIa), (IIb), (III), (IIIa), (IIIb), (IV), (V), (Va) or (Vb), R¹ is
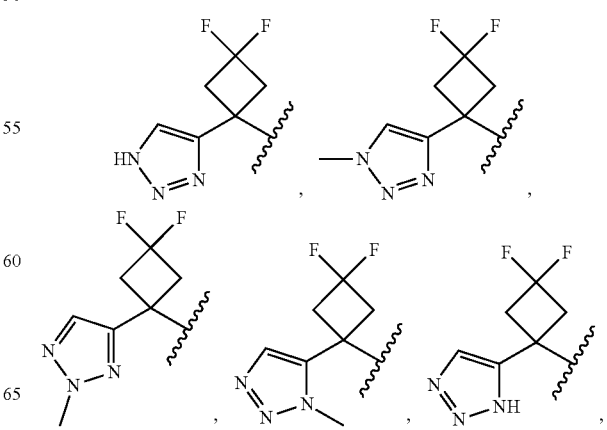

-continued

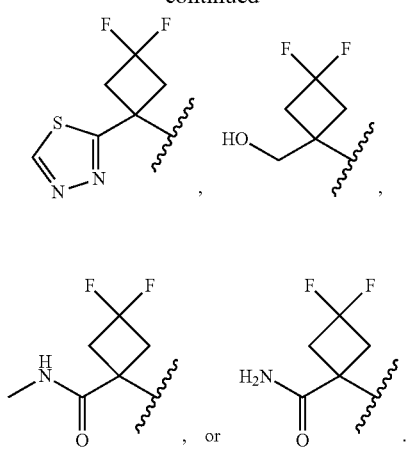

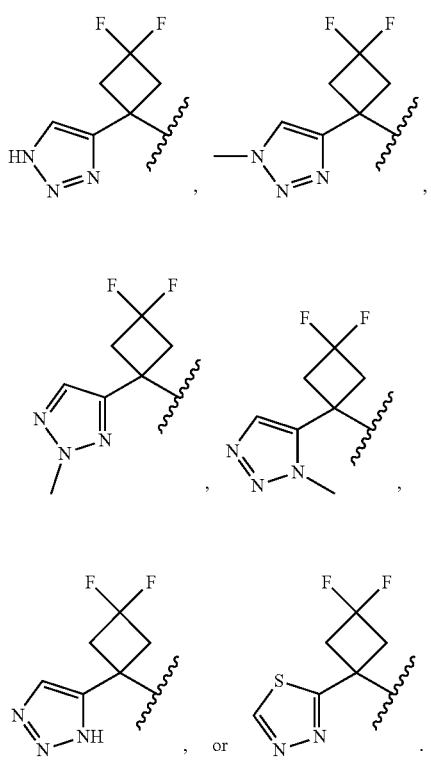

In some embodiments of a compound of Formula (I), (II), (IIa), (IIb), (III), (IIIa), (IIIb), (IV), (V), (Va) or (Vb), R¹ is

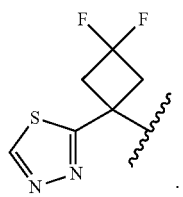 [SMILES: *C1(c2nncs2)CC(F)(F)C1]

In some embodiments of a compound of Formula (I), (II), (IIa), (IIb), (III), (IIIa), (IIIb), (IV), (V), (Va) or (Vb), R¹ is

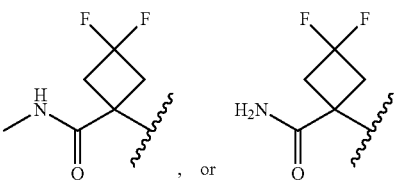

In some embodiments of a compound of Formula (I), (II), (IIa), (IIb), (III), (IIIa), (IIIb), (IV), (V), (Va) or (Vb), R¹ is

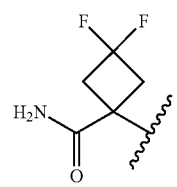

In some embodiments of a compound of Formula (I), (II), (IIa), (IIb), (III), (IIIa), (IIIb), (IV), (V), (Va) or (Vb), R¹ is

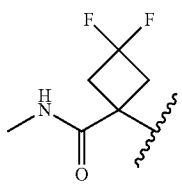

In some embodiments of a compound of Formula (I), (II), (IIa), (IIb), (III), (IIIa), (IIIb), (IV), (V), (Va) or (Vb), R¹ is 3 to 6 membered monocyclic heterocyclyl having 1 to 3 heteroatoms selected from N, O, and S, optionally substituted with 1 to 3 $R^{1C}$. In some embodiments of a compound of Formula (I), (II), (IIa), (IIb), (III), (IIIa), (IIIb), (IV), (V), (Va) or (Vb), R¹ is 3 to 6 membered monocyclic heterocyclyl having 1 heteroatom that is O, optionally substituted with 1 to 3 $R^{1C}$. In some embodiments of a compound of Formula (I), (II), (IIa), (IIb), (III), (IIIa), (IIIb), (IV), (V), (Va) or (Vb), R¹ is oxiranyl, oxetanyl, tetrahydrofuranyl or tetrahydropyranyl, optionally substituted with 1 to 3 $R^{1C}$. In some embodiments of a compound of Formula (I), (II), (IIa), (IIb), (III), (IIIa), (IIIb), (IV), (V), (Va) or (Vb), R¹ is oxiranyl or oxetanyl, optionally substituted with 1 to 3 $R^{1C}$. In some embodiments of a compound of Formula (I), (II), (IIa), (IIb), (III), (IIIa), (IIIb), (IV), (V), (Va) or (Vb), R¹ is oxetanyl substituted with 1 $R^{1C}$. In some embodiments of a compound of Formula (I), (II), (IIa), (IIb), (III), (IIIa), (IIIb), (IV), (V), (Va) or (Vb), R¹ is oxetan-2-yl, oxetan-3-yl or oxetan-4-yl, optionally substituted with 1 to 3 $R^{1C}$. In some embodiments of a compound of Formula (I), (II), (IIa), (IIb), (III), (IIIa), (IIIb), (IV), (V), (Va) or (Vb), R¹ is oxetan-3-yl substituted with 1 $R^{1C}$.

In some embodiments of a compound of Formula (I), (II), (IIa), (IIb), (III), (IIIa), (IIIb), (IV), (V), (Va) or (Vb), each $R^{1C}$ is independently —C(O)NR$^X$R$^Y$, or 5 to 6 membered heteroaryl having 1 to 3 heteroatoms selected from N, O, and S optionally substituted with 1 to 3 $C_{1-2}$ alkyl; R$^X$ is $C_{1-2}$ alkyl; and R$^Y$ is —H. In some embodiments of a compound of Formula (I), (II), (IIa), (IIb), (III), (IIIa), (IIIb), (IV), (V), (Va) or (Vb), when $R^{1C}$ is independently —C(O)NR$^X$R$^Y$, $R^{1C}$ is —C(O)NH$_2$, —C(O)NHMe or —C(O)NMe$_2$. In some embodiments of a compound of Formula (I), (II), (IIa), (IIb), (III), (IIIa), (IIIb), (IV), (V), (Va) or (Vb), when $R^{1C}$ is 5 or 6 membered heteroaryl having 1 to 3 heteroatoms selected from N, O, and S optionally substituted with 1 to 3 $R^{1D}$, the heteroaryl can be pyrrolyl, pyridinyl, imidazolyl, pyrazolyl, triazolyl, pyrazinyl, pyrimidinyl, pyridazinyl, triazolyl, thiophenyl, furanyl, pyranyl, thiazolyl, isothiazolyl, thiadiazolyl, oxazolyl, isoxazolyl, or oxadiazolyl. In some embodiments of a compound of Formula (I), (II), (IIa), (IIb), (III), (IIIa), (IIIb), (IV), (V), (Va) or (Vb), when $R^{1C}$ is 5 membered heteroaryl having 1 to 3 heteroatoms selected from N, O, and S optionally substituted with 1 to 3 $R^{1D}$, the heteroaryl can be pyrrolyl, imidazolyl, pyrazolyl, triazolyl, thiazolyl, isothiazolyl, thiadiazolyl, oxazolyl, isoxazolyl, or oxadiazolyl. In some embodiments of a compound of Formula (I), (II), (IIa), (IIb), (III), (IIIa), (IIIb), (IV), (V), (Va) or (Vb), each $R^{1C}$ is independently —C(O)NHMe or triazolyl.

In some embodiments of a compound of Formula (I), (II), (IIa), (IIb), (III), (IIIa), (IIIb), (IV), (V), (Va) or (Vb), $R^1$ is 3 to 6 membered monocyclic heterocyclyl having 1 to 3 heteroatoms selected from N, O, and S, optionally substituted with 1 to 3 $R^{1C}$, wherein each $R^{1C}$ is independently —C(O)NR$^X$R$^Y$, or 5 to 6 membered heteroaryl having 1 to 3 heteroatoms selected from N, O, and S optionally substituted with 1 to 3 C$_{1-2}$ alkyl, R$^X$ is C$_{1-2}$ alkyl, and R$^Y$ is —H. In some embodiments of a compound of Formula (I), (II), (IIa), (IIb), (III), (IIIa), (IIIb), (IV), (V), (Va) or (Vb), $R^1$ is 3 to 6 membered monocyclic heterocyclyl having 1 heteroatom that is O, optionally substituted with 1 to 3 $R^{1C}$, wherein each $R^{1C}$ is independently —C(O)NR$^X$R$^Y$, or 5 to 6 membered heteroaryl having 1 to 3 heteroatoms selected from N, O, and S optionally substituted with 1 to 3 C$_{1-2}$ alkyl, R$^X$ is C$_{1-2}$ alkyl, and R$^Y$ is —H. In some embodiments of a compound of Formula (I), (II), (IIa), (IIb), (III), (IIIa), (IIIb), (IV), (V), (Va) or (Vb), $R^1$ is 3 to 6 membered monocyclic heterocyclyl having 1 heteroatom that is O, optionally substituted with 1 to 3 $R^{1C}$, wherein each $R^{1C}$ is independently —C(O)NH$_2$, —C(O)NHMe, —C(O)NMe$_2$, pyrrolyl, imidazolyl, pyrazolyl, triazolyl, thiazolyl, isothiazolyl, thiadiazolyl, oxazolyl, isoxazolyl, or oxadiazolyl.

In some embodiments of a compound of Formula (I), (II), (IIa), (IIb), (III), (IIIa), (IIIb), (IV), (V), (Va) or (Vb), $R^1$ is oxiranyl, oxetanyl, tetrahydrofuranyl or tetrahydropyranyl, substituted with —C(O)NH$_2$, —C(O)NHMe, —C(O)NMe$_2$, pyrrolyl, imidazolyl, pyrazolyl, triazolyl, thiazolyl, isothiazolyl, thiadiazolyl, oxazolyl, isoxazolyl, or oxadiazolyl. In some embodiments of a compound of Formula (I), (II), (IIa), (IIb), (III), (IIIa), (IIIb), (IV), (V), (Va) or (Vb), $R^1$ is oxiranyl, oxetanyl, tetrahydrofuranyl or tetrahydropyranyl, substituted with —C(O)NH$_2$, —C(O)NHMe, —C(O)NMe$_2$, pyrrolyl, imidazolyl, pyrazolyl, triazolyl, thiazolyl, isothiazolyl, thiadiazolyl, oxazolyl, isoxazolyl, or oxadiazolyl. In some embodiments of a compound of Formula (I), (II), (IIa), (IIb), (III), (IIIa), (IIIb), (IV), (V), (Va) or (Vb), $R^1$ is oxiranyl or oxetanyl, substituted with —C(O)NHMe or triazolyl. In some embodiments of a compound of Formula (I), (II), (IIa), (IIb), (III), (IIIa), (IIIb), (IV), (V), (Va) or (Vb), $R^1$ is oxetanyl substituted with —C(O)NHMe or triazolyl. In some embodiments of a compound of Formula (I), (II), (IIa), (IIb), (III), (IIIa), (IIIb), (IV), (V), (Va) or (Vb), $R^1$ is oxetan-2-yl, oxetan-3-yl or oxetan-4-yl, substituted with —C(O)NHMe or triazolyl.

In some embodiments of a compound of Formula (I), (II), (IIa), (IIb), (III), (IIIa), (IIIb), (IV), (V), (Va) or (Vb), $R^1$ is oxetan-3-yl substituted with —C(O)NHMe or triazolyl. In some embodiments of a compound of Formula (I), (II), (IIa), (IIb), (III), (IIIa), (IIIb), (IV), (V), (Va) or (Vb), $R^1$ is

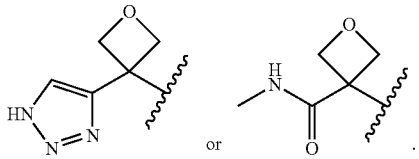

In some embodiments of a compound of Formula (I), (II), (IIa), (IIb), (III), (IIIa), (IIIb), (IV), (V), (Va) or (Vb), $R^1$ is C$_{3-5}$ cycloalkyl optionally substituted with 1 to 4 $R^{1B}$, or $R^1$ is 3 to 6 membered monocyclic heterocyclyl having 1 heteroatom that is O, optionally substituted with 1 to 3 $R^{1C}$, wherein each $R^{1B}$ is independently halogen, C$_{1-6}$ alkyl optionally substituted with 1 —OH, C$_{2-6}$ alkyne, —C(O)NR$^X$R$^Y$, or 5 to 8 membered heteroaryl having 1 to 3 heteroatoms selected from N, O, and S optionally substituted with 1 to 3 Rip, provided no more than 1 $R^{1B}$ is 5 to 8 membered heteroaryl having 1 to 3 heteroatoms selected from N, O, and S optionally substituted with 1 to 3 $R^{1D}$, wherein each $R^{1C}$ is independently —C(O)NR$^X$R$^Y$, or 5 to 6 membered heteroaryl having 1 to 3 heteroatoms selected from N, O, and S optionally substituted with 1 to 3 C$_{1-2}$ alkyl, R$^X$ is C$_{1-2}$ alkyl, and R$^Y$ is —H. In some embodiments of a compound of Formula (I), (II), (IIa), (IIb), (III), (IIIa), (IIIb), (IV), (V), (Va) or (Vb), $R^1$ is C$_{3-5}$ cycloalkyl optionally substituted with 1 to 4 $R^{1B}$, or 3 to 6 membered monocyclic heterocyclyl having 1 heteroatom that is O, optionally substituted with 1 to 3 $R^{1C}$, wherein each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$, and wherein each $R^{1C}$ is independently —C(O)NHMe or triazolyl. In some embodiments of a compound of Formula (I), (II), (IIa), (IIb), (III), (IIIa), (IIIb), (IV), (V), (Va) or (Vb), $R^1$ is cyclopropyl or cyclobutyl, substituted with 1 to 3 $R^{1B}$, wherein each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$, or $R^1$ is oxetanyl substituted with —C(O)NHMe or triazolyl.

In some embodiments of a compound of Formula (I), (II), (IIa), (IIb), (III), (IIIa), (IIIb), (IV), (V), (Va) or (Vb), $R^4$ is phenyl substituted with 1 to 5 $R^{4A}$, or pyridinyl substituted with 1 to 4 $R^{4B}$. In some embodiments of a compound of Formula (I), (II), (IIa), (IIb), (III), (IIIa), (IIIb), (IV), (V), (Va) or (Vb), $R^4$ is phenyl optionally substituted with 1 to 3 $R^{4A}$ groups, or pyridinyl optionally substituted with 1 to 2 $R^{4B}$ groups. In some embodiments of a compound of Formula (I), (II), (IIa), (IIb), (III), (IIIa), (IIIb), (IV), (V), (Va) or (Vb), when $R^4$ is pyridinyl, the pyridinyl can be pyridin-2-yl, pyridin-3-yl or pyridin-4-yl, each substituted with 1 to 2 $R^{4B}$ groups. In some embodiments of a compound of Formula (I), (II), (IIa), (IIb), (III), (IIIa), (IIIb), (IV), (V), (Va) or (Vb), $R^4$ is 4-F-phenyl optionally substituted with 1 to 2 $R^{4A}$ groups, or pyridin-4-yl substituted with 1 to 2 $R^{4B}$ groups.

In some embodiments of a compound of Formula (I), (II), (IIa), (IIb), (III), (IIIa), (IIIb), (IV), (V), (Va) or (Vb), each $R^{4A}$ is independently —CN, halogen, or C$_{1-4}$ haloalkyl. In some embodiments of a compound of Formula (I), (II), (IIa), (IIb), (III), (IIIa), (IIIb), (IV), (V), (Va) or (Vb), each $R^{4A}$ group is independently F, Cl, CN, $CH_2F$, $CHF_2$, $CF_3$, or $CH_2CF_3$. In some embodiments of a compound of Formula (I), (II), (IIa), (IIb), (III), (IIIa), (IIIb), (IV), (V), (Va) or (Vb), each $R^{4A}$ group is independently F, Cl, CN or $CHF_2$. In some embodiments of a compound of Formula (I), (II), (IIa), (IIb), (III), (IIIa), (IIIb), (IV), (V), (Va) or (Vb), each $R^{4A}$ group is F.

In some embodiments of the compound of Formula (I), (II), (IIa), (IIb), (III), (IIIa), (IIIb), (IV), (V), (Va) or (Vb), each $R^{4A}$ is independently —CN, halogen, $C_{1-4}$ alkyl substituted with —$OC_{1-4}$ alkyl or $C_{1-4}$ haloalkyl. In some embodiments of the compound of Formula (I), (II), (IIa), (IIb), (III), (IIIa), (IIIb), (IV), (V), (Va) or (Vb), each $R^{4A}$ group is independently F, Cl, CN, $CH_2F$, $CHF_2$, $CF_3$, $CH_2OCH_3$, or $CH_2CF_3$. In some embodiments of the compound of Formula (I), (II), (IIa), (IIb), (III), (IIIa), (IIIb), (IV), (V), (Va) or (Vb), each $R^{4A}$ group is independently F, Cl, CN, $CH_2OCH_3$ or $CHF_2$. In some embodiments of the compound of Formula (I), (II), (IIa), (IIb), (III), (IIIa), (IIIb), (IV), (V), (Va) or (Vb), each $R^{4A}$ group is independently F or $CH_2OCH_3$.

In some embodiments of a compound of Formula (I), (II), (IIa), (IIb), (III), (IIIa), (IIIb), (IV), (V), (Va) or (Vb), each $R^{4B}$ is independently halogen, or $C_{1-4}$ haloalkyl. In some embodiments of a compound of Formula (I), (II), (IIa), (IIb), (III), (IIIa), (IIIb), (IV), (V), (Va) or (Vb), each $R^{4B}$ group is independently F, Cl, $CH_2F$, $CHF_2$, $CF_3$, or $CH_2CF_3$. In some embodiments of a compound of Formula (I), (II), (IIa), (IIb), (III), (IIIa), (IIIb), (IV), (V), (Va) or (Vb), each $R^{4B}$ group is independently F, Cl or $CHF_2$. In some embodiments of a compound of Formula (I), (II), (IIa), (IIb), (III), (IIIa), (IIIb), (IV), (V), (Va) or (Vb), each $R^{4B}$ group is independently F or $CHF_2$.

In some embodiments of a compound of Formula (I), (II), (IIa), (IIb), (III), (IIIa), (IIIb), (IV), (V), (Va) or (Vb), each $R^{4A}$ is independently —CN, halogen, or $C_{1-4}$ haloalkyl, and each $R^{4B}$ is independently halogen, or $C_{1-4}$ haloalkyl. In some embodiments of a compound of Formula (I), (II), (IIa), (IIb), (III), (IIIa), (IIIb), (IV), (V), (Va) or (Vb), each $R^{4A}$ is independently —CN, F, Cl, $CH_2F$, $CHF_2$, $CF_3$, or $CH_2CF_3$, and each $R^{4B}$ is independently F, Cl, $CH_2F$, $CHF_2$, $CF_3$, or $CH_2CF_3$. In some embodiments of a compound of Formula (I), (II), (IIa), (IIb), (III), (IIIa), (IIIb), (IV), (V), (Va) or (Vb), each $R^{4A}$ group is independently F, Cl, CN or $CHF_2$; and each $R^{4B}$ group is independently F, Cl or $CHF_2$. In some embodiments of a compound of Formula (I), (II), (IIa), (IIb), (III), (IIIa), (IIIb), (IV), (V), (Va) or (Vb), each $R^{4A}$ group is independently F, Cl, CN or $CHF_2$; and each $R^{4B}$ group is independently F or $CHF_2$.

In some embodiments of a compound of Formula (I), (II), (IIa), (IIb), (III), (IIIa), (IIIb), (IV), (V), (Va) or (Vb), $R^4$ is phenyl substituted with 1 to 5 $R^{4A}$, or pyridinyl substituted with 1 to 4 $R^{4B}$, wherein each $R^{4A}$ is independently —CN, halogen, or $C_{1-4}$ haloalkyl, and each $R^{4B}$ is independently halogen, or $C_{1-4}$ haloalkyl. In some embodiments of a compound of Formula (I), (II), (IIa), (IIb), (III), (IIIa), (IIIb), (IV), (V), (Va) or (Vb), $R^4$ is phenyl optionally substituted with 1 to 3 $R^{4A}$ groups, or pyridinyl optionally substituted with 1 to 2 $R^{4B}$ groups, wherein each $R^{4A}$ group is independently F, Cl, CN or $CHF_2$; and each $R^{4B}$ group is independently F, Cl or $CHF_2$. In some embodiments of a compound of Formula (I), (II), (IIa), (IIb), (III), (IIIa), (IIIb), (IV), (V), (Va) or (Vb), $R^4$ is 4-F-phenyl optionally substituted with 1 to 2 $R^{4A}$ groups, or pyridin-4-yl substituted with 1 to 2 $R^{4B}$ groups, wherein each $R^{4A}$ group is independently F, Cl, CN or $CHF_2$; and each $R^{4B}$ group is independently F or $CHF_2$.

In some embodiments of a compound of Formula (I), (II), (IIa), (IIb), (III), (IIIa), (IIIb), (IV), (V), (Va) or (Vb), $R^4$ is 4-F-phenyl optionally substituted with 1 to 2 $R^{4A}$ groups wherein each is independently F, Cl, CN or $CHF_2$. In some embodiments of a compound of Formula (I), (II), (IIa), (IIb), (III), (IIIa), (IIIb), (IV), (V), (Va) or (Vb), $R^4$ is 4-F-phenyl optionally substituted with 1 F, Cl, CN or $CHF_2$. In some embodiments of a compound of Formula (I), (II), (IIa), (IIb), (III), (IIIa), (IIIb), (IV), (V), (Va) or (Vb), $R^4$ is 4-F-phenyl optionally substituted with 2 $R^{4A}$ groups wherein each is independently F, Cl, CN or $CHF_2$. In some embodiments of a compound of Formula (I), (II), (IIa), (IIb), (III), (IIIa), (IIIb), (IV), (V), (Va) or (Vb), $R^4$ is 4-F-phenyl optionally substituted with 1 to 2 $R^{4A}$ groups wherein each is F.

In some embodiments of a compound of Formula (I), (II), (IIa), (IIb), (III), (IIIa), (IIIb), (IV), (V), (Va) or (Vb), $R^4$ is pyridin-4-yl substituted with 1 to 2 $R^{4B}$ groups wherein each is independently F, Cl or $CHF_2$. In some embodiments of a compound of Formula (I), (II), (IIa), (IIb), (III), (IIIa), (IIIb), (IV), (V), (Va) or (Vb), $R^4$ is pyridin-4-yl substituted with 1 to 2 $R^{4B}$ groups wherein each is independently F or $CHF_2$.

In some embodiments of a compound of Formula (I), (II), (IIa), (IIb), (III), (IIIa), (IIIb), (IV), (V), (Va) or (Vb), wherein $R^4$ is

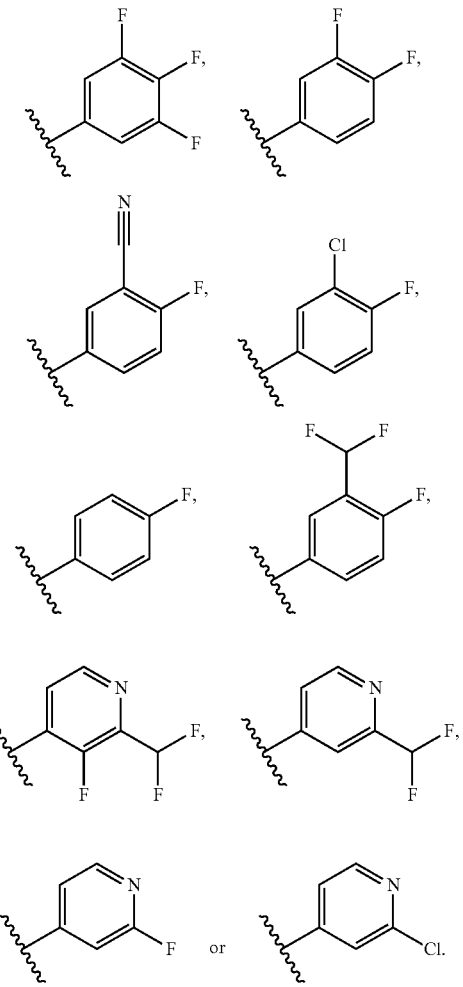

In some embodiments of a compound of Formula (I), (II), (IIa), (IIb), (III), (IIIa), (IIIb), (IV), (V), (Va) or (Vb), wherein R⁴ is

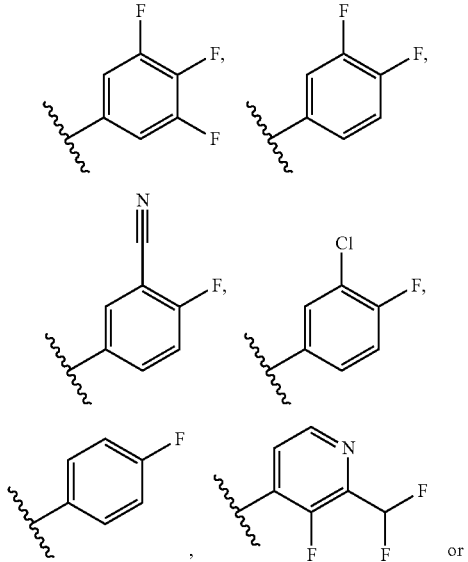

In some embodiments of a compound of Formula (I), (II), (IIa), (IIb), (III), (IIIa), (IIIb), (IV), (V), (Va) or (Vb), wherein R⁴ is

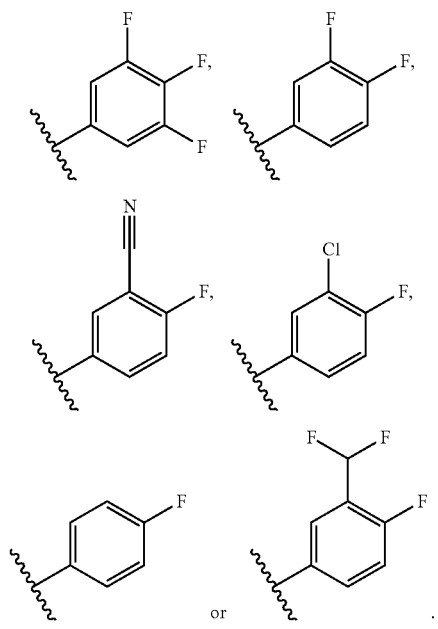

In some embodiments of a compound of Formula (I), (II), (IIa), (IIb), (III), (IIIa), (IIIb), (IV), (V), (Va) or (Vb), wherein R⁴ is

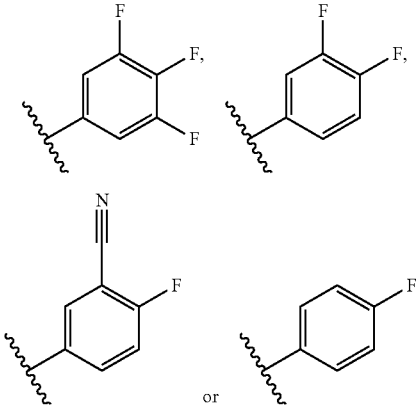

In some embodiments of a compound of Formula (I), (II), (IIa), (IIb), (III), (IIIa), (IIIb), (IV), (V), (Va) or (Vb), wherein R⁴ is In some embodiments of a compound of Formula (I), (II), (IIa), (IIb), (III), (IIIa), (IIIb), (IV), (V), (Va) or (Vb), wherein R⁴ is

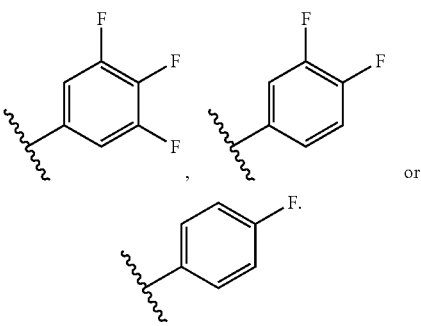

In some embodiments of a compound of Formula (I), (II), (IIa), (IIb), (III), (IIIa), (IIIb), (IV), (V), (Va) or (Vb), wherein R⁴ is

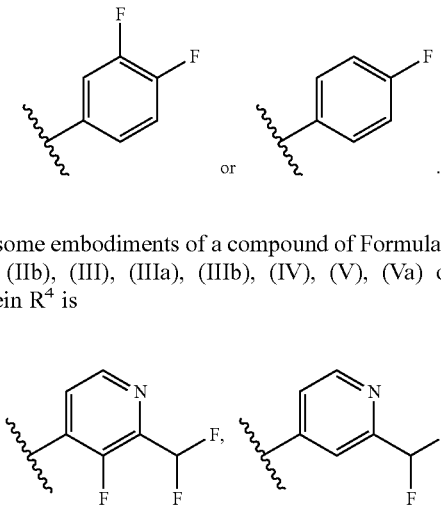

-continued

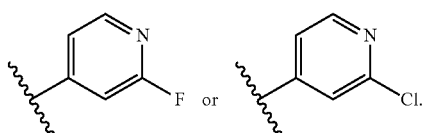

In some embodiments of a compound of Formula (I), (II), (IIa), (IIb), (III), (IIIa), (IIIb), (IV), (V), (Va) or (Vb), wherein $R^4$ is

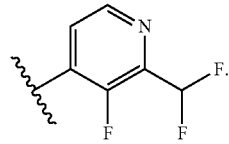 [SMILES: *c1ccnc(C(F)F)c1F]

In some embodiments of a compound of Formula (I), (II), (IIa), (IIb), (III), (IIIa), (IIIb), (IV), (V), (Va) or (Vb), wherein $R^4$ is

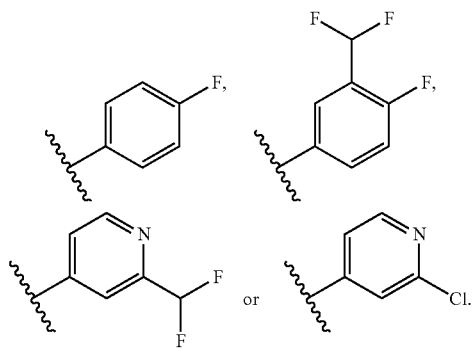

In some embodiments of a compound of Formula (I), (II), (IIa), (IIb), (III), (IIIa), (IIIb), (IV), (V), (Va) or (Vb), $R^4$ is selected from the group consisting of

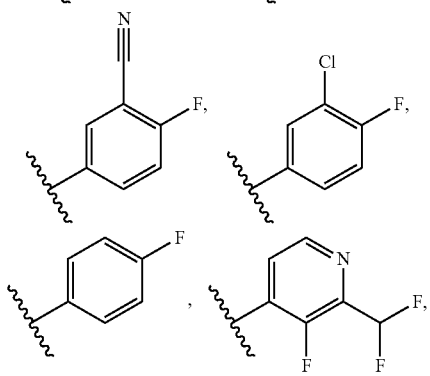

-continued

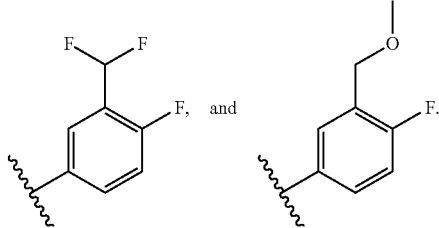

In some embodiments, $R^4$ is selected from the group consisting of

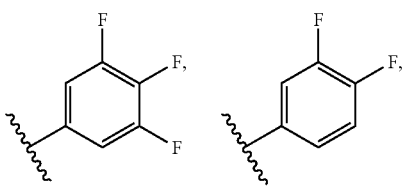

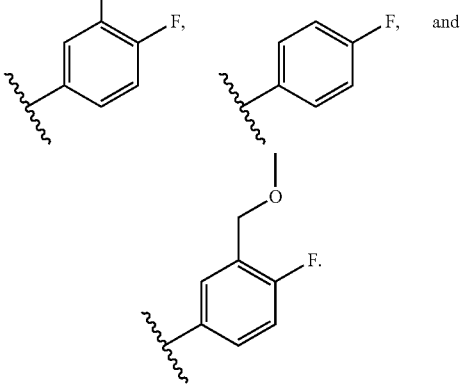

In some embodiments, $R^4$ is

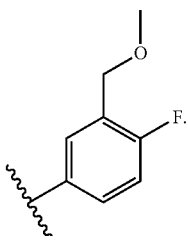 [SMILES: *c1ccc(F)c(COC)c1]

In some embodiments of a compound of Formula (I), (II), (IIa), (IIb), (III), (IIIa), (IIIb), (IV), (V), (Va) or (Vb), $R^1$ is $C_{3-5}$ cycloalkyl optionally substituted with 1 to 4 $R^{1B}$, or $R^1$ is 3 to 6 membered monocyclic heterocyclyl having 1 heteroatom that is O, optionally substituted with 1 to 3 $R^{1C}$, wherein each $R^{1B}$ is independently halogen, $C_{1-6}$ alkyl optionally substituted with 1 —OH, $C_{2-6}$ alkyne, —C(O)NR$^X$R$^Y$, or 5 to 8 membered heteroaryl having 1 to 3 heteroatoms selected from N, O, and S optionally substituted with 1 to 3 Rip, provided no more than 1 $R^{1B}$ is 5 to 8 membered heteroaryl having 1 to 3 heteroatoms selected from N, O, and S optionally substituted with 1 to 3 $R^{1D}$, wherein each $R^{1C}$ is independently —C(O)NR$^X$R$^Y$, or 5 to 6 membered heteroaryl having 1 to 3 heteroatoms selected from N, O, and S optionally substituted with 1 to 3 $C_{1-2}$ alkyl, $R^X$ is $C_{1-2}$ alkyl, $R^Y$ is —H, $R^4$ is phenyl substituted with 1 to 3 $R^{4A}$, or pyridinyl substituted with 1 to 2 $R^{4B}$, wherein each $R^{4A}$ is independently —CN, halogen, or $C_{1-4}$ haloalkyl, and wherein each $R^{4B}$ is independently halogen, or $C_{1-4}$ haloalkyl. In some embodiments of a compound of Formula (I), (II), (IIa), (IIb), (III), (IIIa), (IIIb), (IV), (V), (Va) or (Vb), $R^1$ is $C_{3-5}$ cycloalkyl optionally substituted with 1 to 4 $R^{1B}$, or 3 to 6 membered monocyclic heterocyclyl having 1 heteroatom that is O, optionally substituted with 1 to 3 $R^{1C}$, wherein each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$, and wherein each $R^{1C}$ is independently —C(O)NHMe or triazolyl, $R^4$ is phenyl substituted with 1 to 3 $R^{4A}$, or pyridinyl substituted with 1 to 2 $R^{4B}$, wherein each $R^{4A}$ group is independently F, Cl, CN or CHF$_2$, and wherein each $R^{4B}$ group is independently F, Cl or CHF$_2$. In some embodiments of a compound of Formula (I), (II), (IIa), (IIb), (III), (IIIa), (IIIb), (IV), (V), (Va) or (Vb), $R^1$ is cyclopropyl or cyclobutyl, substituted with 1 to 3 $R^{1B}$, wherein each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$, or $R^1$ is oxetanyl substituted with —C(O)NHMe or triazolyl, $R^4$ is 4-F-phenyl optionally substituted with 1 to 2 $R^{4A}$ groups, or pyridin-4-yl substituted with 1 to 2 $R^{4B}$ groups wherein each $R^{4A}$ group is independently F, Cl, CN or CHF$_2$, and wherein each $R^{4B}$ group is independently F, Cl or CHF$_2$.

In some embodiments of a compound of Formula (I), (II), (IIa), (IIb), (III), (IIIa), (IIIb), (IV), (V), (Va) or (Vb), $R^1$ is $C_{3-5}$ cycloalkyl optionally substituted with 1 to 4 $R^{1B}$, wherein each $R^{1B}$ is independently halogen, $C_{1-6}$ alkyl optionally substituted with 1 —OH, $C_{2-6}$ alkyne, —C(O)NR$^X$R$^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$, $R^X$ is $C_{1-2}$ alkyl, $R^Y$ is —H, $R^4$ is phenyl substituted with 1 to 3 $R^{4A}$, and each $R^{4A}$ is independently —CN, halogen, or $C_{1-4}$ haloalkyl. In some embodiments of a compound of Formula (I), (II), (IIa), (IIb), (III), (IIIa), (IIIb), (IV), (V), (Va) or (Vb), is $C_{3-5}$ cycloalkyl optionally substituted with 1 to 4 $R^{1B}$, wherein each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$, $R^4$ is phenyl substituted with 1 to 3 $R^{4A}$, and each $R^{4A}$ group is independently F, Cl, CN or CHF$_2$. In some embodiments of a compound of Formula (I), (II), (IIa), (IIb), (III), (IIIa), (IIIb), (IV), (V), (Va) or (Vb), $R^1$ is cyclopropyl or cyclobutyl, substituted with 1 to 3 $R^{1B}$, wherein each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$, $R^4$ is 4-F-phenyl optionally substituted with 1 to 2 $R^{4A}$ groups, wherein each $R^{4A}$ group is independently F, Cl, CN or CHF$_2$. In some embodiments of a compound of Formula (I), (II), (IIa), (IIb), (III), (IIIa), (IIIb), (IV), (V), (Va) or (Vb), $R^1$ is cyclobutyl substituted with 1 to 3 $R^{1B}$, wherein each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$, $R^4$ is 4-F-phenyl optionally substituted with 1 to 2 $R^{4A}$ groups, wherein each $R^{4A}$ group is independently F, Cl, CN or CHF$_2$. In some embodiments of a compound of Formula (I), (II), (IIa), (IIb), (III), (IIIa), (IIIb), (IV), (V), (Va) or (Vb), $R^1$ is cyclobutyl substituted with 2 fluoro and 1 —CH$_2$OH, —C≡CH, —C(O)NH$_2$, —C(O)NHMe, triazolyl or thiadiazolyl, wherein the triazolyl is optionally substituted with Me, $R^4$ is 4-F-phenyl optionally substituted with 1 to 2 $R^{4A}$ groups, wherein each $R^{4A}$ group is independently F, Cl, CN or CHF$_2$. In some embodiments of a compound of Formula (I), (II), (IIa), (IIb), (III), (IIIa), (IIIb), (IV), (V), (Va) or (Vb), $R^1$ is cyclobutyl substituted with 2 fluoro and 1 —C(O)NH$_2$, or —C(O)NHMe, $R^4$ is 4-F-phenyl optionally substituted with 1 to 2 $R^{4A}$ groups, wherein each $R^{4A}$ group is independently F, Cl, CN or CHF$_2$. In some embodiments of a compound of Formula (I), (II), (IIa), (IIb), (III), (IIIa), (IIIb), (IV), (V), (Va) or (Vb), $R^1$ is cyclobutyl substituted with 2 fluoro and 1 —C(O)NH$_2$, or —C(O)NHMe, $R^4$ is 4-F-phenyl optionally substituted with 1 to 2 $R^{4A}$ groups, wherein each $R^{4A}$ group is F.

In some embodiments of a compound of Formula (I), (II), (IIa), (IIb), (III), (IIIa), (IIIb), (IV), (V), (Va) or (Vb), $R^1$ is

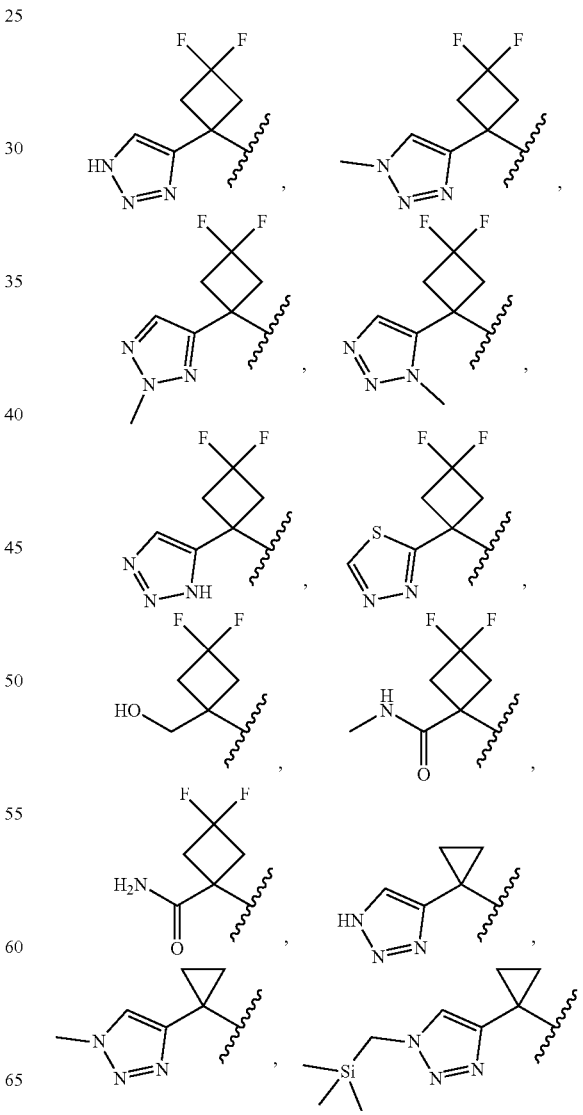

-continued
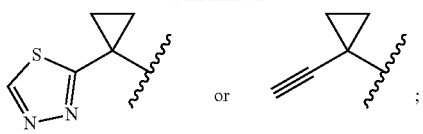 or 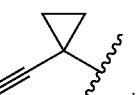;
and
R⁴ is
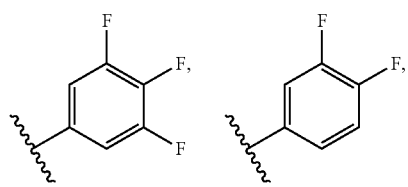
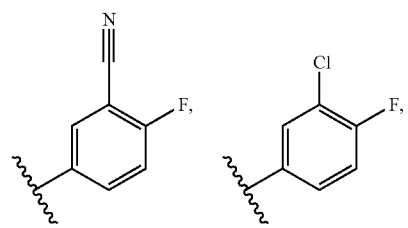
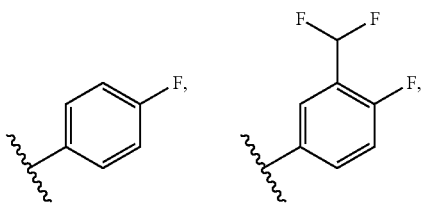
In some embodiments of a compound of Formula (I), (II), (IIa), (IIb), (III), (IIIa), (IIIb), (IV), (V), (Va) or (Vb), R¹ is
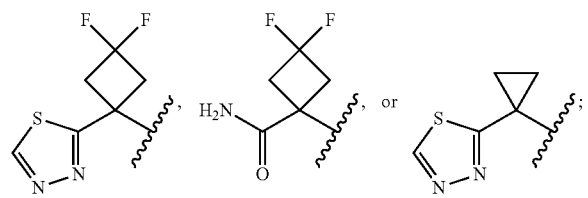 [SMILES: *C1(c2nncs2)CC(F)(F)C1 ; *C1(C(N)=O)CC(F)(F)C1 ; *C1(c2nncs2)CC1]
and
R⁴ is
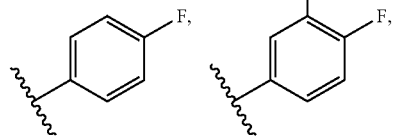
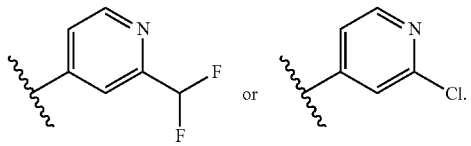
In some embodiments of a compound of Formula (I), (II), (IIa), (IIb), (III), (IIIa), (IIIb), (IV), (V), (Va) or (Vb), R¹ is
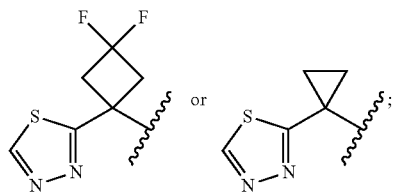 [SMILES: *C1(c2nncs2)CC(F)(F)C1 ; *C1(c2nncs2)CC1]
and
R⁴ is
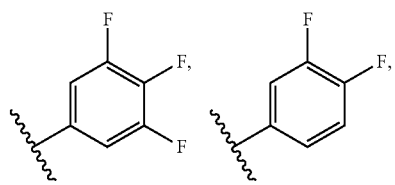
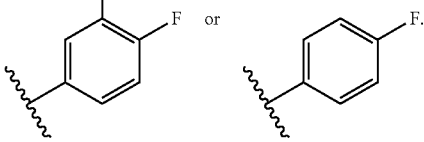
In some embodiments, a compound of Formula (I) can be a compound of Formula (II):
Formula II
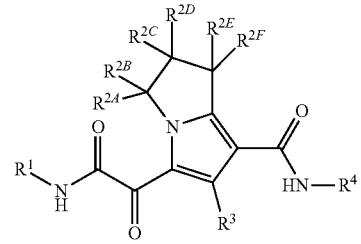

wherein
- $R^1$ is $C_{3-5}$ cycloalkyl optionally substituted with 1 to 4 $R^{1B}$, or $R^1$ is 3 to 6 membered monocyclic heterocyclyl having 1 heteroatom that is O, optionally substituted with 1 to 3 $R^{1C}$;
- each $R^{1B}$ is independently halogen, $C_{1-6}$ alkyl optionally substituted with 1 —OH, $C_{2-6}$ alkyne, —C(O)NR$^X$R$^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$, wherein each $R^{1C}$ is independently —C(O)NR$^X$R$^Y$, or 5 to 6 membered heteroaryl having 1 to 3 heteroatoms selected from N, O, and S optionally substituted with 1 to 3 $C_{1-2}$ alkyl;
- $R^X$ is $C_{1-2}$ alkyl;
- $R^Y$ is —H;
- each of $R^{2A}$, $R^{2B}$, $R^{2C}$, $R^{2D}$, $R^{2E}$, and $R^{2F}$ are —H, or $R^{2C}$ or $R^{2D}$ may be taken together with $R^{2A}$ or $R^{2B}$ or with $R^{2E}$ or $R^{2F}$ to form a cyclopropyl group;
- $R^4$ is phenyl substituted with 1 to 3 $R^{4A}$, or pyridinyl substituted with 1 to 2 $R^{4B}$;
- each $R^{4A}$ is independently —CN, halogen, or $C_{1-4}$ haloalkyl; and
- each $R^{4B}$ is independently halogen, or $C_{1-4}$ haloalkyl.

In some embodiments, a compound of Formula (I) can be a compound of Formula (II):

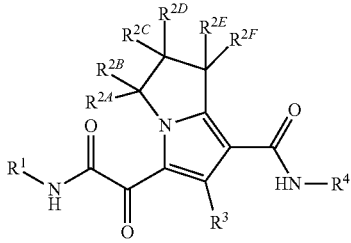

Formula II wherein
- $R^1$ is $C_{3-5}$ cycloalkyl optionally substituted with 1 to 4 $R^{1B}$, or 3 to 6 membered monocyclic heterocyclyl having 1 heteroatom that is O, optionally substituted with 1 to 3 $R^{1C}$;
- each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$;
- each $R^{1C}$ is independently —C(O)NHMe or triazolyl;
- each of $R^{2A}$, $R^{2B}$, $R^{2C}$, $R^{2D}$, $R^{2E}$, and $R^{2F}$ are —H, or $R^{2C}$ or $R^{2D}$ may be taken together with $R^{2A}$ or $R^{2B}$ or with $R^{2E}$ or $R^{2F}$ to form a cyclopropyl group;
- $R^4$ is phenyl substituted with 1 to 3 $R^{4A}$, or pyridinyl substituted with 1 to 2 $R^{4B}$;
- each $R^{4A}$ group is independently F, Cl, CN or CHF$_2$; and
- each $R^{4B}$ group is independently F or CHF$_2$.

In some embodiments, a compound of Formula (I) can be a compound of Formula (II):

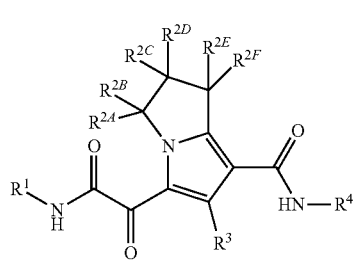

Formula II wherein
- $R^1$ is cyclopropyl or cyclobutyl, substituted with 1 to 3 $R^{1B}$, wherein each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$;
- or $R^1$ is oxetanyl substituted with —C(O)NHMe or triazolyl;
- each of $R^{2A}$, $R^{2B}$, $R^{2C}$, $R^{2D}$, $R^{2E}$, and $R^{2F}$ are —H, or $R^{2C}$ or $R^{2D}$ may be taken together with $R^{2A}$ or $R^{2B}$ or with $R^{2E}$ or $R^{2F}$ to form a cyclopropyl group;
- $R^4$ is 4-F-phenyl optionally substituted with 1 to 2 $R^{4A}$ groups, or pyridin-4-yl substituted with 1 to 2 $R^{4B}$ groups;
- each $R^{4A}$ group is independently F, Cl, CN or CHF$_2$; and
- each $R^{4B}$ group is independently F or CHF$_2$.

In certain embodiments, a compound of Formula (I), (II) or (III) has the structure:

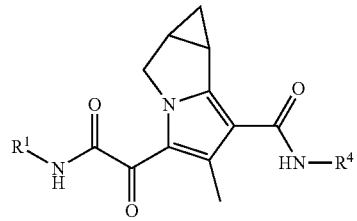

wherein
- $R^1$ is $C_{3-6}$ cycloalkyl optionally substituted with 1 to 4 $R^{1B}$, or 3 to 6 membered monocyclic heterocyclyl having 1 to 3 heteroatoms selected from N, O, and S, optionally substituted with 1 to 3 $R^{1C}$;
- each $R^{1B}$ is independently halogen, $C_{1-6}$ alkyl optionally substituted with 1 —OH, $C_{2-6}$ alkyne, —C(O)NR$^X$R$^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$;
- each $R^{1C}$ is independently —C(O)NR$^X$R$^Y$, or 5 to 8 membered heteroaryl having 1 to 3 heteroatoms selected from N, O, and S optionally substituted with 1 to 3 $R^{1D}$;

each $R^{1D}$ is independently $C_{1-4}$ alkyl optionally substituted with —Si($C_{1-4}$ alkyl)$_3$; each $R^X$ is independently —H, or $C_{1-6}$ alkyl;
each $R^Y$ is independently —H or $C_{1-6}$ alkyl;
$R^4$ is phenyl substituted with 1 to 5 $R^{4A}$, or pyridinyl, substituted with 1 to 4 $R^{4B}$;
each $R^{4A}$ is independently —CN, halogen, or $C_{1-4}$ haloalkyl; and
each $R^{4B}$ is independently halogen, or $C_{1-4}$ haloalkyl.

In certain embodiments, a compound of Formula (I), (II), (IIa), (IIb) or (III) has the structure:

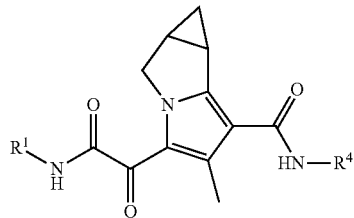

wherein
$R^1$ is

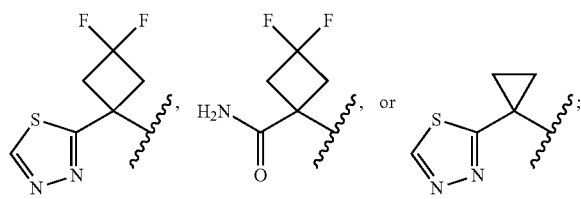 [SMILES: *C1(c2nncs2)CC(F)(F)C1 ; *C1(C(N)=O)CC(F)(F)C1 ; *C1(c2nncs2)CC1]

and
$R^4$ is

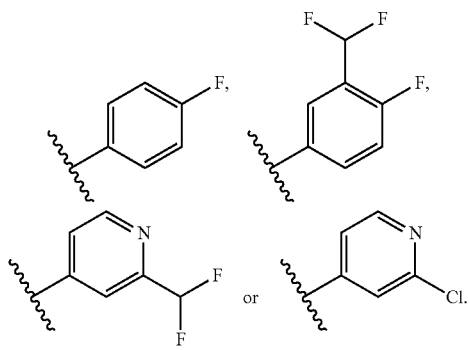

In certain embodiments, a compound of Formula (I) or (II) is a compound of Formula (IV):

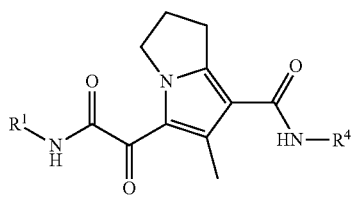

Formula IV wherein
$R^1$ is $C_{3-6}$ cycloalkyl optionally substituted with 1 to 4 $R^{1B}$, or 3 to 6 membered monocyclic heterocyclyl having 1 to 3 heteroatoms selected from N, O, and S, optionally substituted with 1 to 3 $R^{1C}$;
each $R^{1B}$ is independently halogen, $C_{1-6}$ alkyl optionally substituted with 1 —OH, $C_{2-6}$ alkyne, —C(O)NR$^X$R$^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 $R^{1D}$;
each $R^{1C}$ is independently —C(O)NR$^X$R$^Y$, or 5 to 8 membered heteroaryl having 1 to 3 heteroatoms selected from N, O, and S optionally substituted with 1 to 3 $R^{1D}$;
each $R^{1D}$ is independently $C_{1-4}$ alkyl optionally substituted with —Si($C_{1-4}$ alkyl)$_3$;
each $R^X$ is independently —H, or $C_{1-6}$ alkyl;
each $R^Y$ is independently —H or $C_{1-6}$ alkyl;
$R^4$ is phenyl substituted with 1 to 5 $R^{4A}$, or pyridinyl, substituted with 1 to 4 $R^{4B}$;
each $R^{4A}$ is independently —CN, halogen, or $C_{1-4}$ haloalkyl; and
each $R^{4B}$ is independently halogen, or $C_{1-4}$ haloalkyl.

In certain embodiments, a compound of Formula (I) or (II) is a compound of Formula (IV):

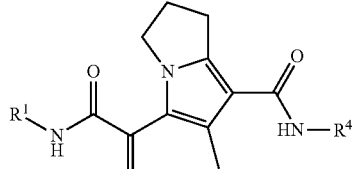

Formula IV wherein
$R^1$ is $C_{3-5}$ cycloalkyl optionally substituted with 1 to 4 $R^{1B}$, or $R^1$ is 3 to 6 membered monocyclic heterocyclyl having 1 heteroatom that is O, optionally substituted with 1 to 3 $R^{1C}$;
each $R^{1B}$ is independently halogen, $C_{1-6}$ alkyl optionally substituted with 1 —OH, $C_{2-6}$ alkyne, —C(O)NR$^X$R$^Y$, or 5 to 8 membered heteroaryl having 1 to 3 heteroatoms selected from N, O, and S optionally substituted with 1 to 3 $R^{1D}$, provided no more than 1 $R^{1B}$ is 5 to 8 membered heteroaryl having 1 to 3 heteroatoms selected from N, O, and S optionally substituted with 1 to 3 Rip;
each $R^{1C}$ is independently —C(O)NR$^X$R$^Y$, or 5 to 6 membered heteroaryl having 1 to 3 heteroatoms selected from N, O, and S optionally substituted with 1 to 3 $C_{1-2}$ alkyl;
$R^X$ is $C_{1-2}$ alkyl;
$R^Y$ is —H;
$R^4$ is phenyl substituted with 1 to 3 $R^{4A}$, or pyridinyl substituted with 1 to 2 $R^{4B}$;
each $R^{4A}$ is independently —CN, halogen, or $C_{1-4}$ haloalkyl; and
each $R^{4B}$ is independently halogen, or $C_{1-4}$ haloalkyl.

In certain embodiments, a compound of Formula (I) or (II) is a compound of Formula (IV):

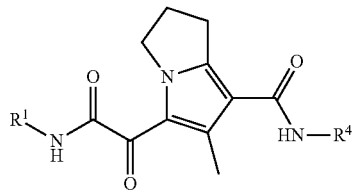

Formula IV wherein
R¹ is C$_{3-5}$ cycloalkyl optionally substituted with 1 to 4 R$^{1B}$, or 3 to 6 membered monocyclic heterocyclyl having 1 heteroatom that is O, optionally substituted with 1 to 3 R$^{1C}$;
each R$^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$;
each R$^{1C}$ is independently —C(O)NHMe or triazolyl;
R⁴ is phenyl substituted with 1 to 3 R$^{4A}$, or pyridinyl substituted with 1 to 2 R$^{4B}$;
each R$^{4A}$ group is independently F, Cl, CN or CHF$_2$; and
each R$^{4B}$ group is independently F, Cl or CHF$_2$.

In certain embodiments, a compound of Formula (I) or (II) is a compound of Formula (IV):

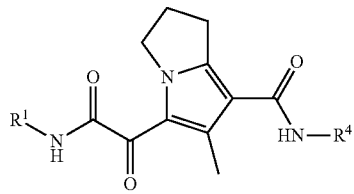

Formula IV wherein
R¹ is cyclopropyl or cyclobutyl, substituted with 1 to 3 R$^{1B}$;
or R¹ is oxetanyl substituted with —C(O)NHMe or triazolyl;
each R$^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$;
R⁴ is 4-F-phenyl optionally substituted with 1 to 2 R$^{4A}$ groups, or pyridin-4-yl substituted with 1 to 2 R$^{4B}$ groups;
each R$^{4A}$ group is independently F, Cl, CN or CHF$_2$; and
each R$^{4B}$ group is independently F, Cl or CHF$_2$.

In certain embodiments, a compound of Formula (I) or (II) is a compound of Formula (IV):

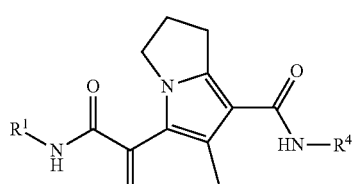

Formula IV wherein
R¹ is

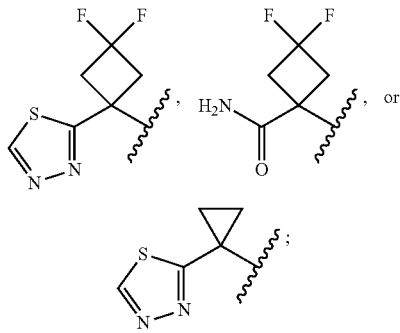

and
R⁴ is

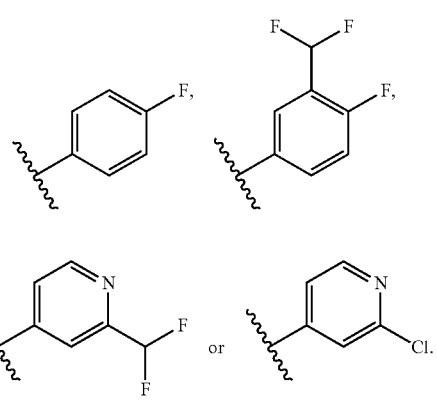

In certain embodiments, a compound of Formula (I) or (II) is a compound of Formula (IV):

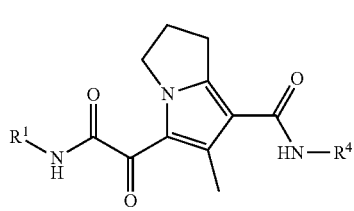

Formula IV wherein
R¹ is

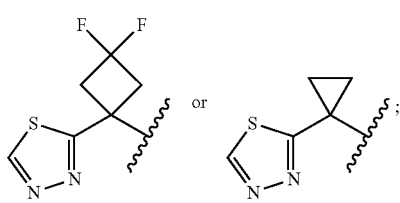 [SMILES: *C1(c2nncs2)CC(F)(F)C1 ; *C1(c2nncs2)CC1]

and
R⁴ is

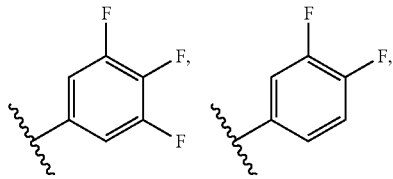

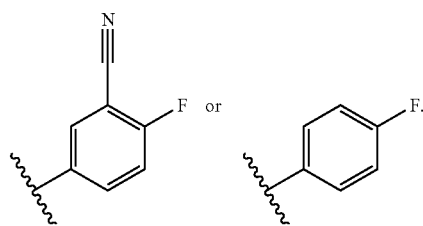

In certain embodiments, a compound of Formula (I), (II), or (V) has the structure:

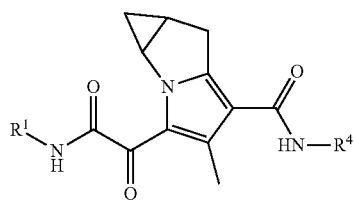

wherein

- R¹ is C₃₋₆ cycloalkyl optionally substituted with 1 to 4 R$^{1B}$, or 3 to 6 membered monocyclic heterocyclyl having 1 to 3 heteroatoms selected from N, O, and S, optionally substituted with 1 to 3 R$^{1C}$;
- each R$^{1B}$ is independently halogen, C₁₋₆ alkyl optionally substituted with 1 —OH, C₂₋₆ alkyne, —C(O)NR$^X$R$^Y$, or 5 to 8 membered heteroaryl having 1 to 3 heteroatoms selected from N, O, and S optionally substituted with 1 to 3 R$^{1D}$, provided no more than 1 R$^{1B}$ is 5 to 8 membered heteroaryl having 1 to 3 heteroatoms selected from N, O, and S optionally substituted with 1 to 3 R$^{1D}$;
- each R$^{1C}$ is independently —C(O)NR$^X$R$^Y$, or 5 to 8 membered heteroaryl having 1 to 3 heteroatoms selected from N, O, and S optionally substituted with 1 to 3 R$^{1D}$;
- each R$^{1D}$ is independently C₁₋₄ alkyl optionally substituted with —Si(C₁₋₄ alkyl)₃;
- each R$^X$ is independently —H, or C₁₋₆ alkyl;
- each R$^Y$ is independently —H or C₁₋₆ alkyl;
- R⁴ is phenyl substituted with 1 to 5 R$^{4A}$, or pyridinyl, substituted with 1 to 4 R$^{4B}$;
- each R$^{4A}$ is independently —CN, halogen, or C₁₋₄ haloalkyl; and
- each R$^{4B}$ is independently halogen, or C₁₋₄ haloalkyl.

In certain embodiments a compound of Formula (I) or (II), is:

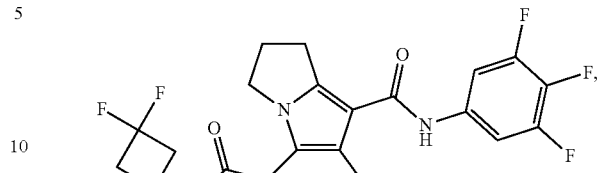

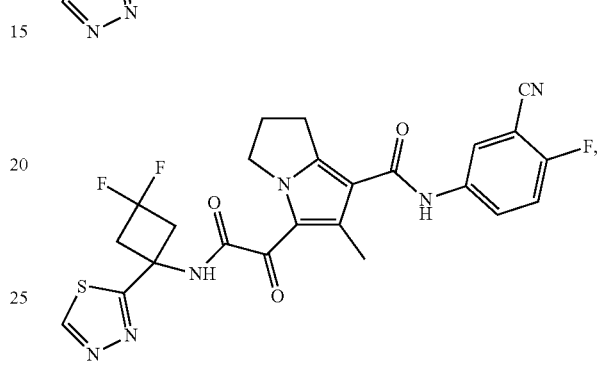

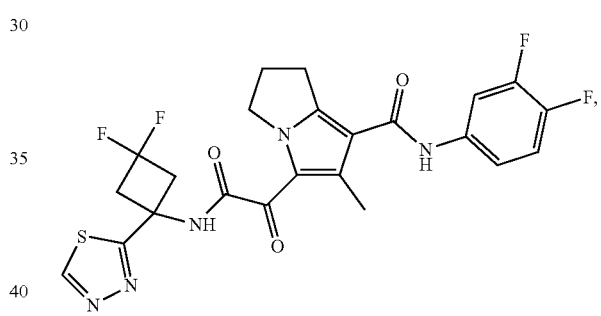

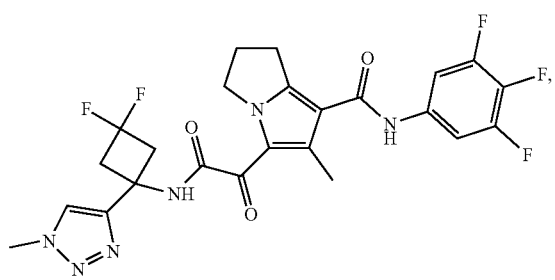

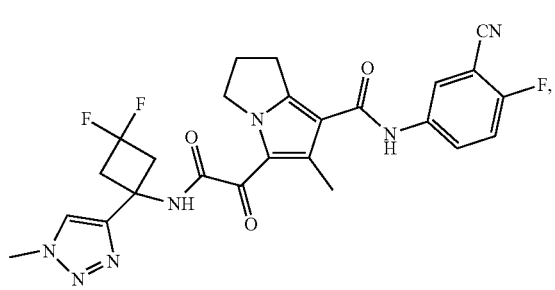

49
-continued
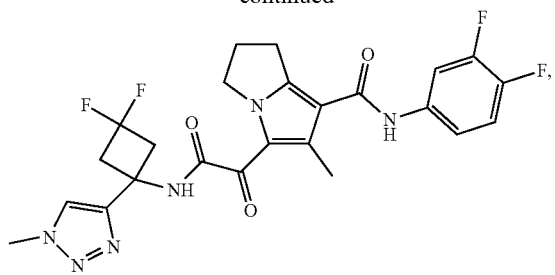
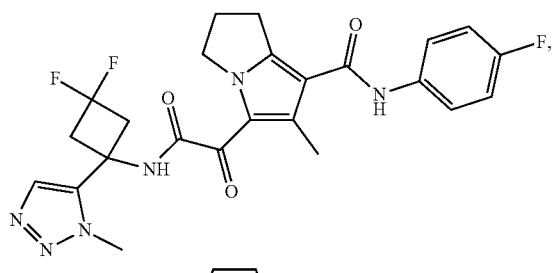
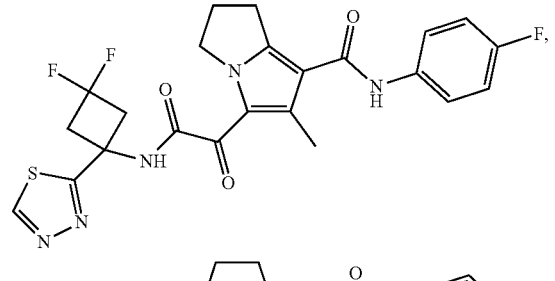
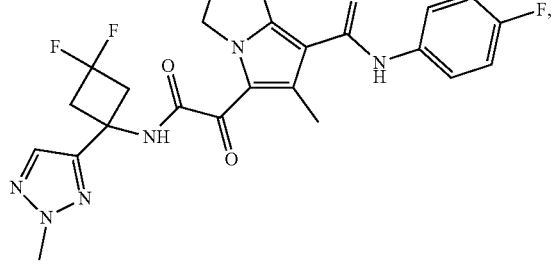
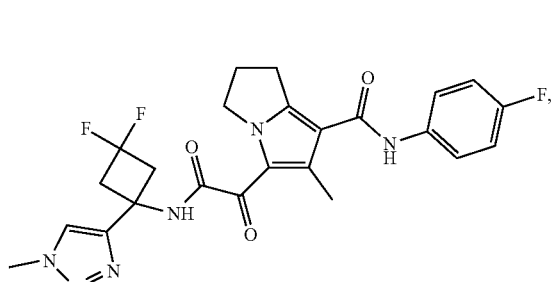
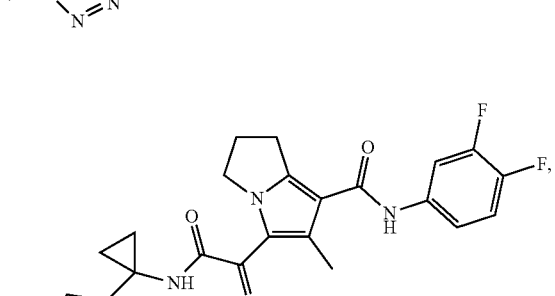
50
-continued
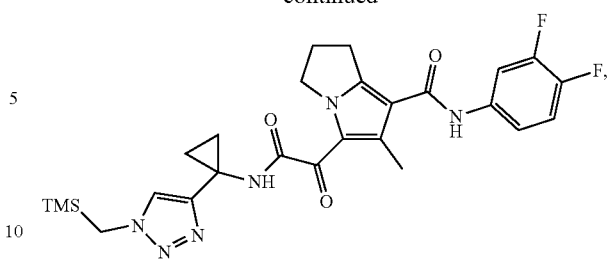
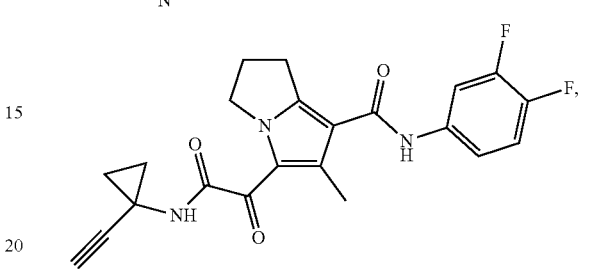
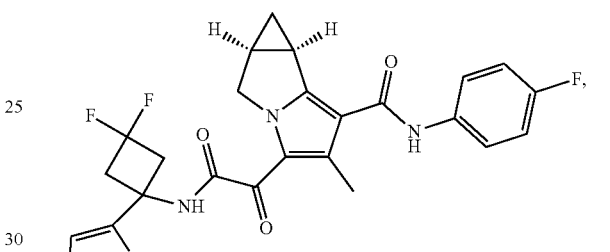
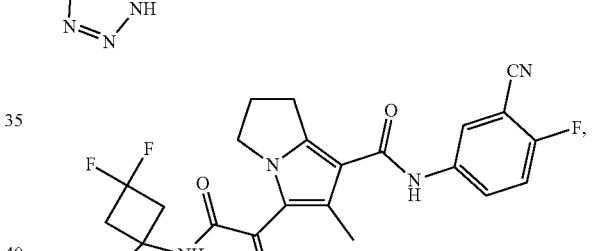
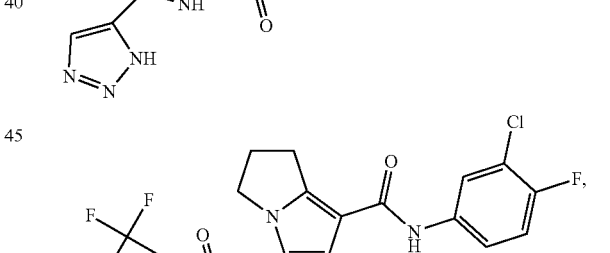
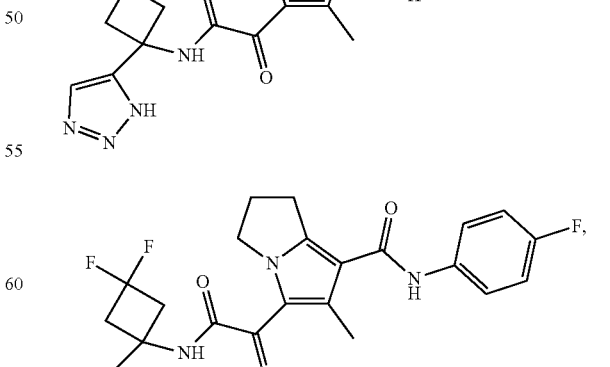

51
-continued
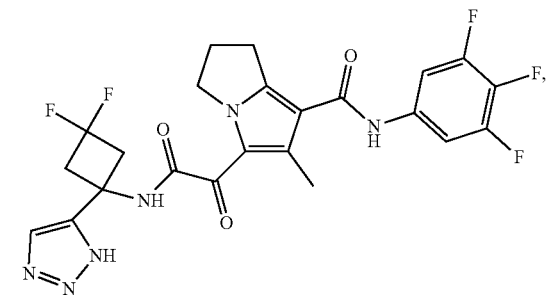
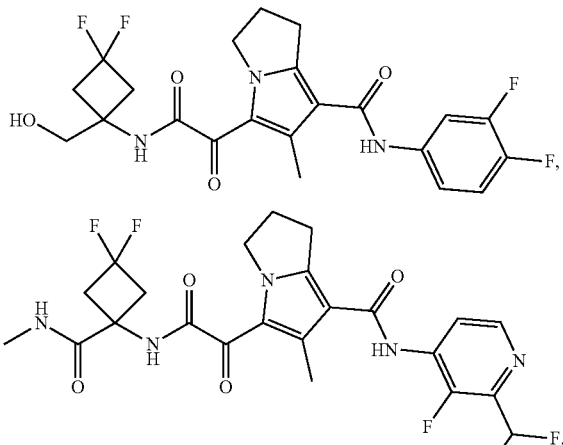
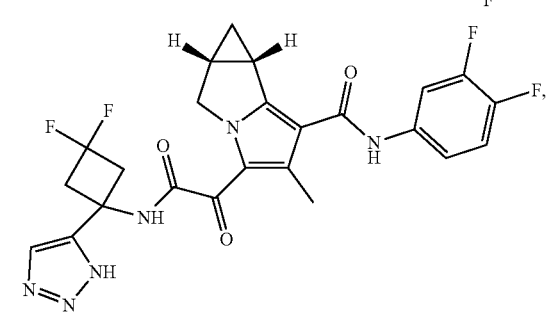
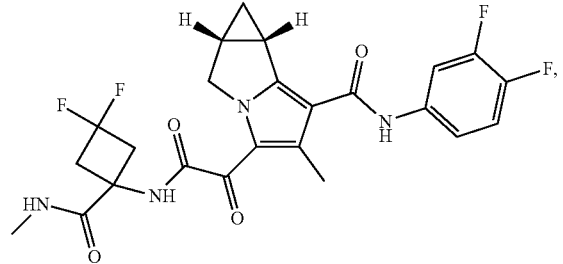
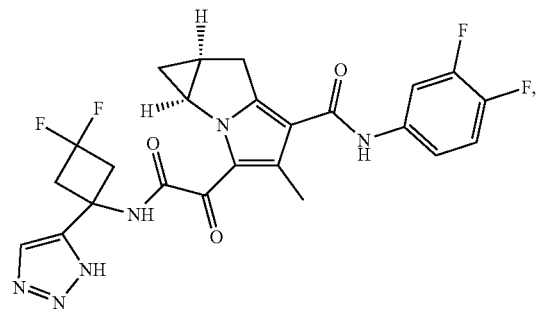
52
-continued
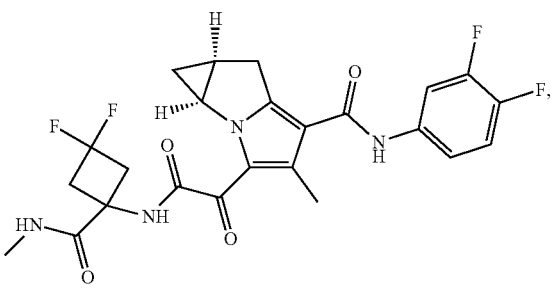
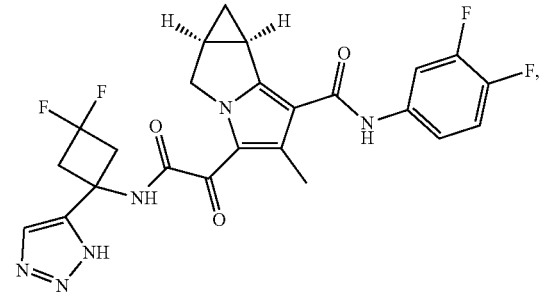
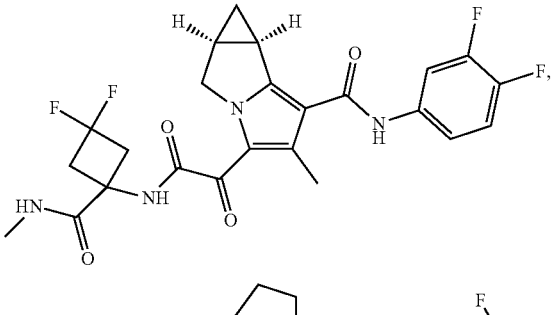
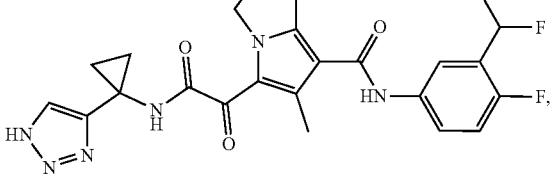
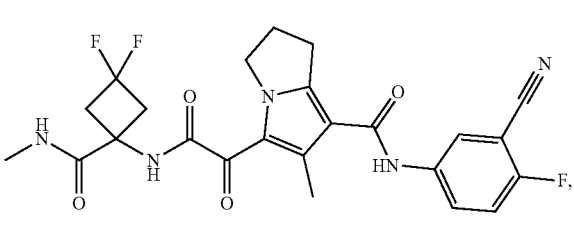
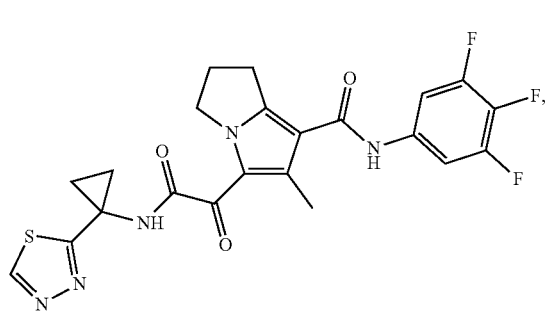

53
-continued
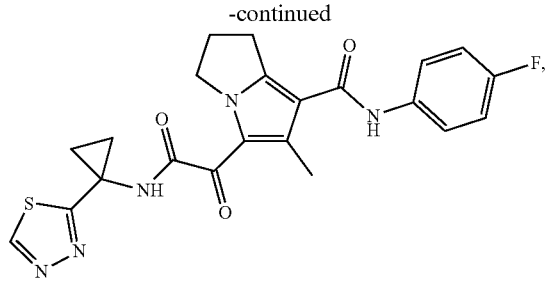
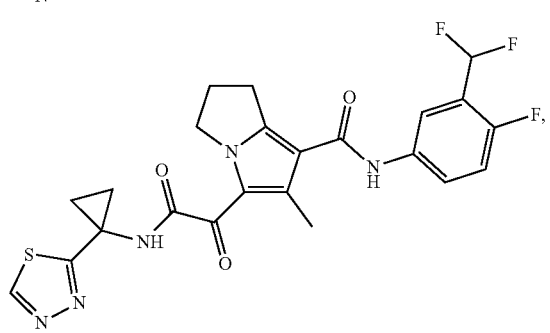
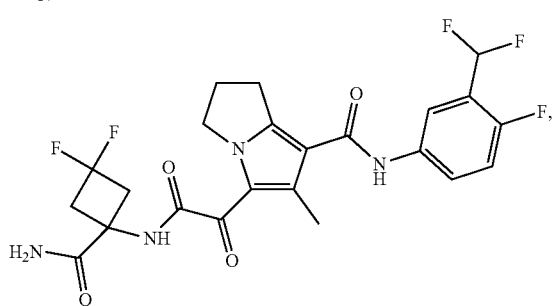
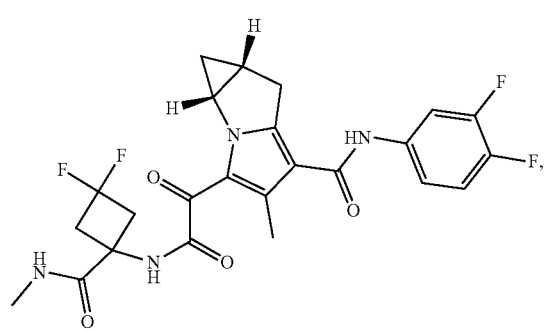
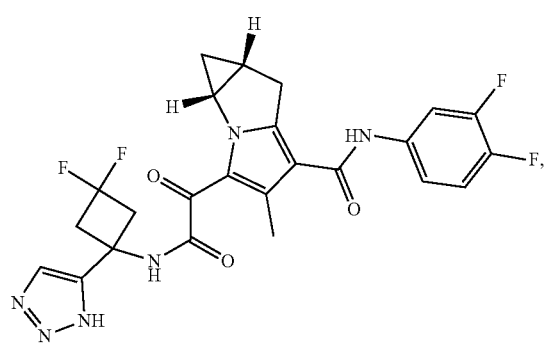
54
-continued
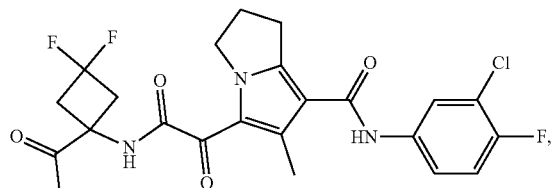
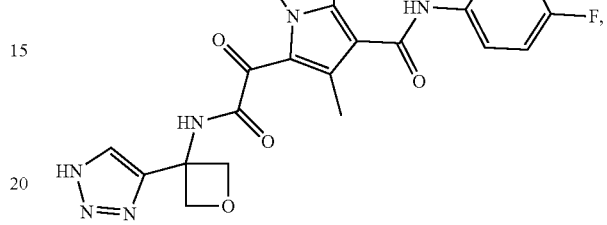
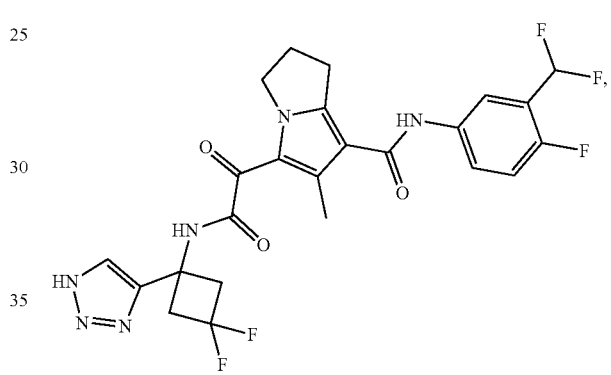
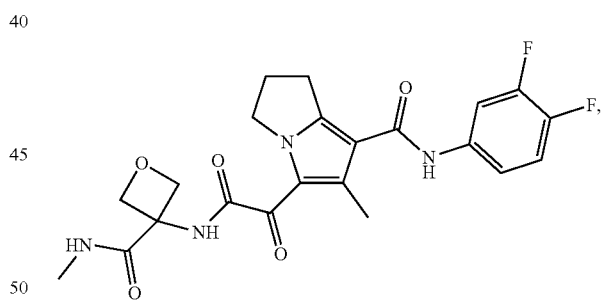
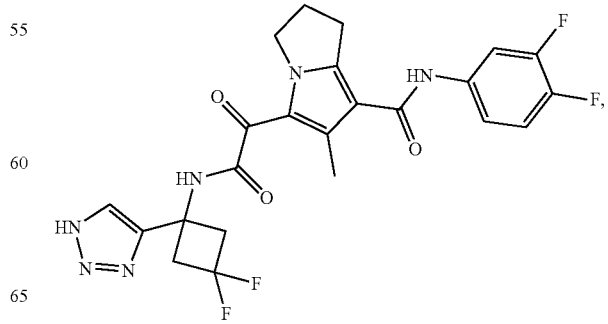

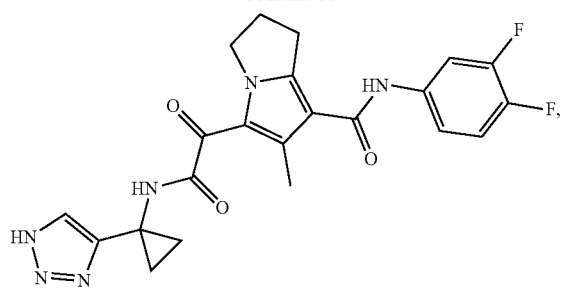
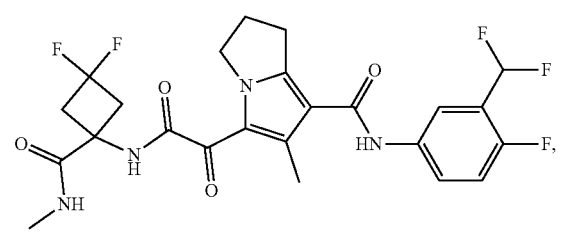
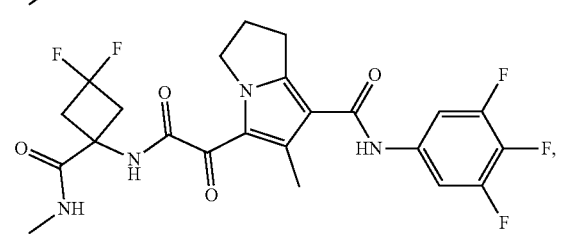
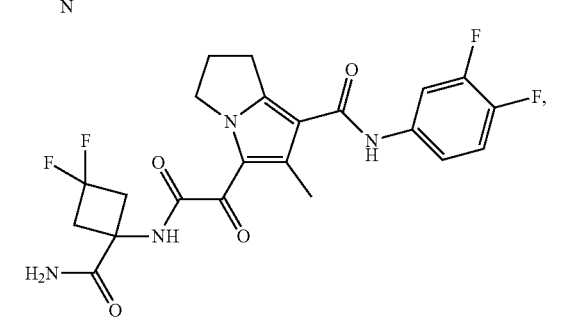
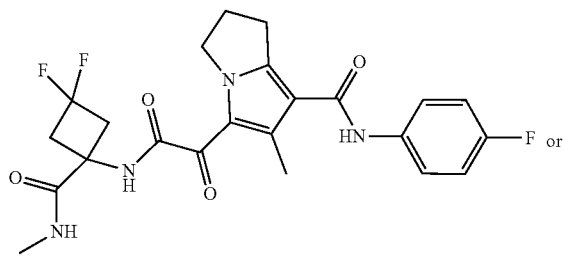
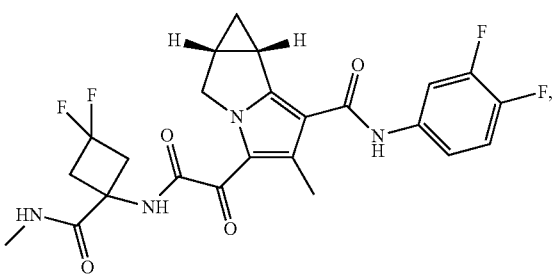
In certain embodiments a compound of Formula (I) or (II), is:
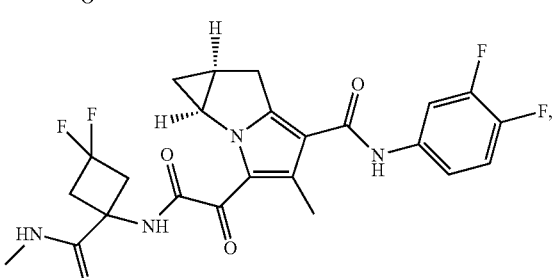
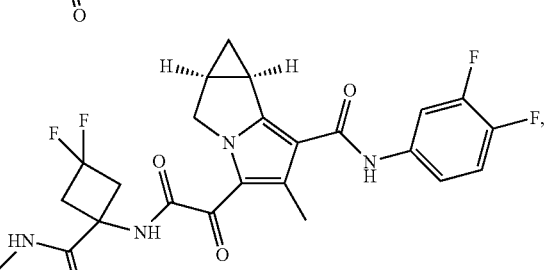
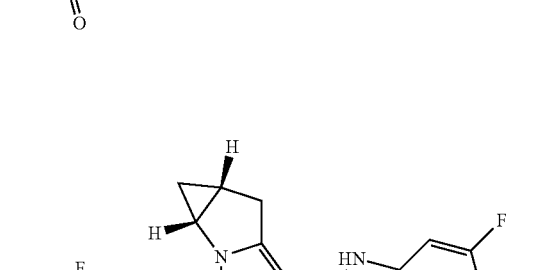
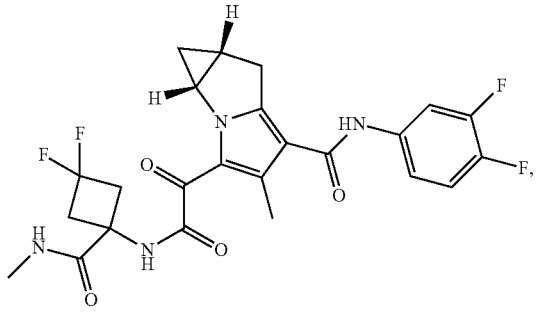

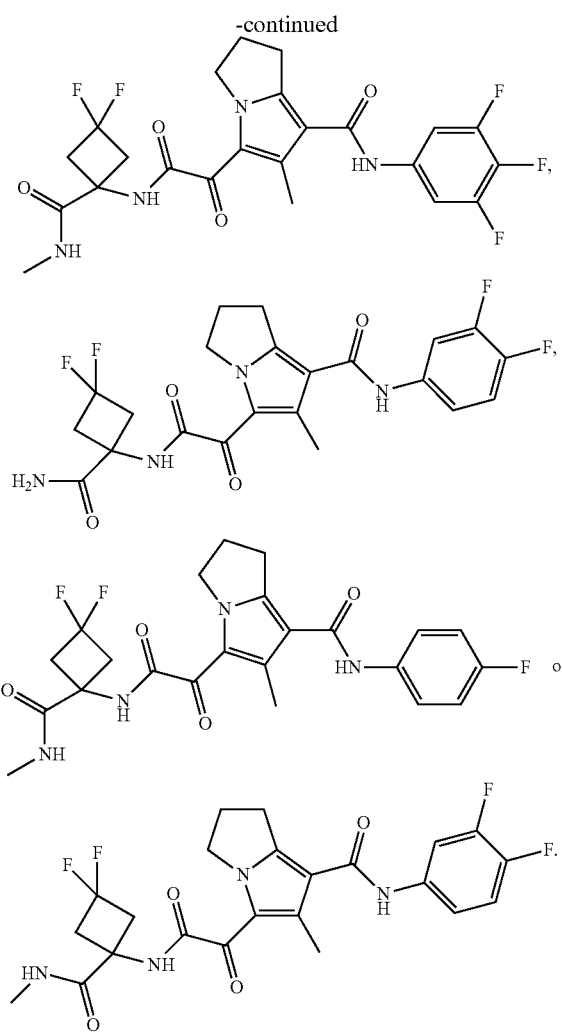
In certain embodiments a compound of Formula (I), (II) or (III), is:
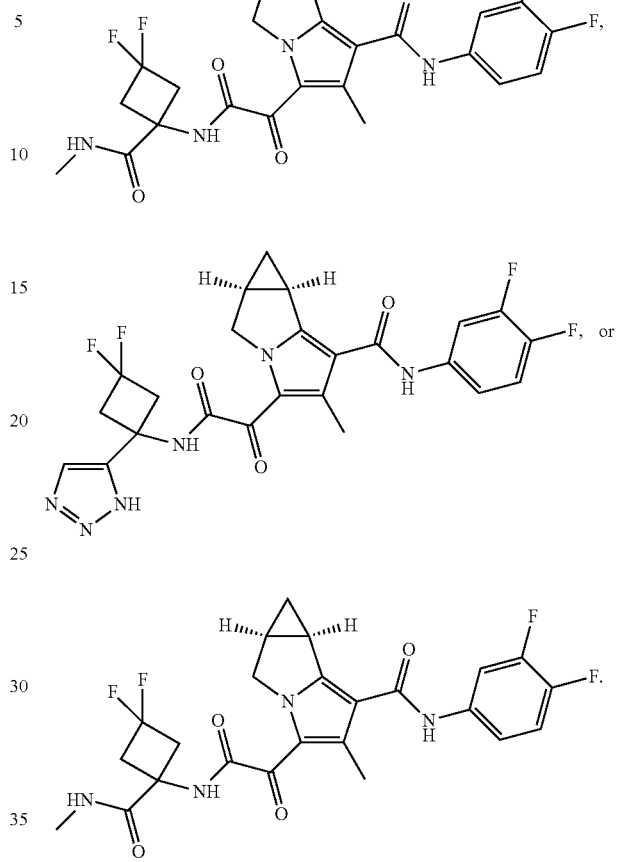
In certain embodiments a compound of Formula (I), (II) or (IV), is:
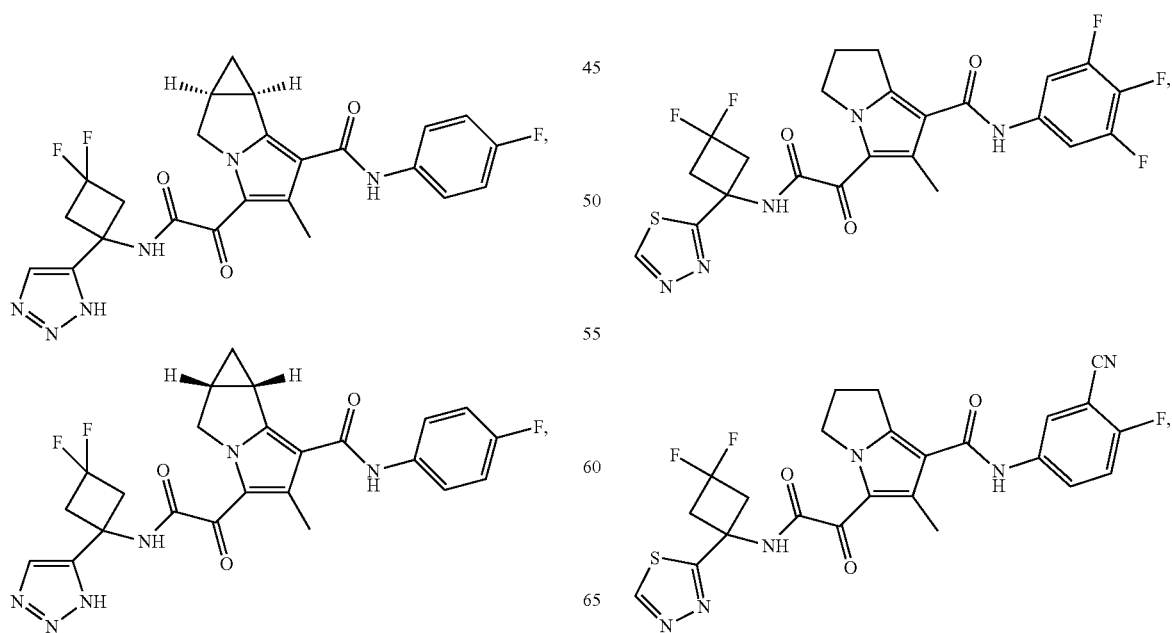

-continued
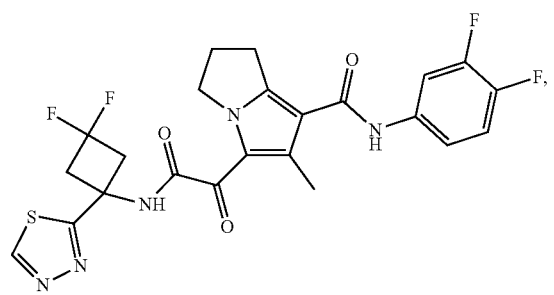
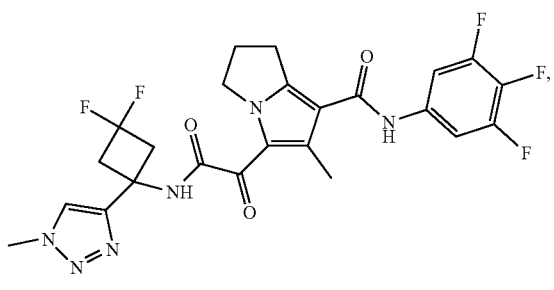
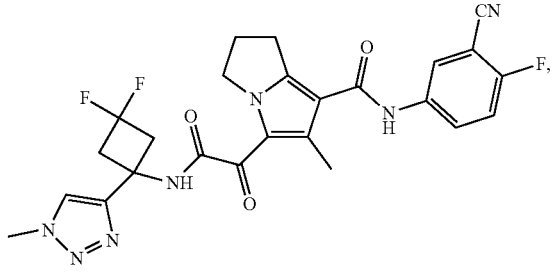
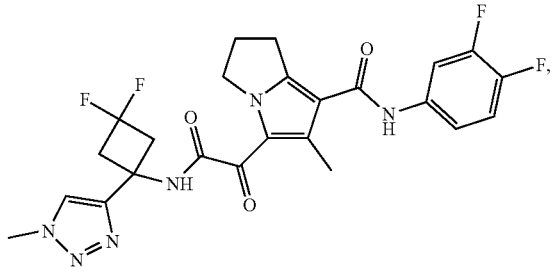
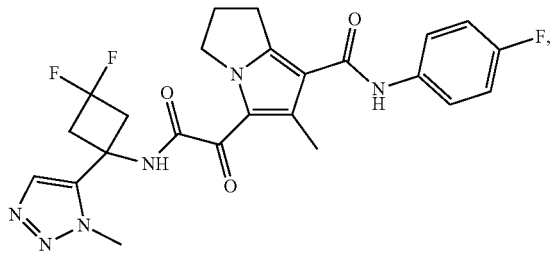
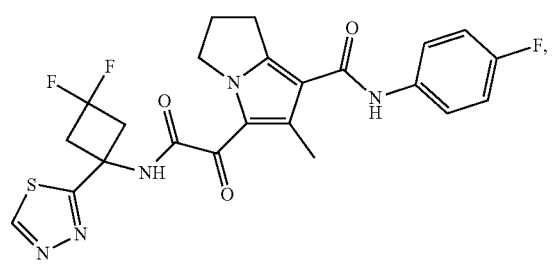
-continued
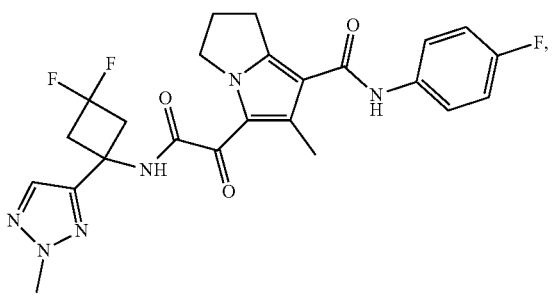
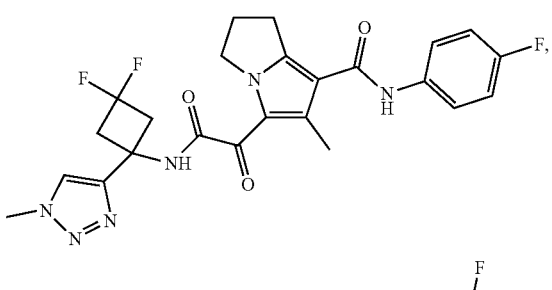
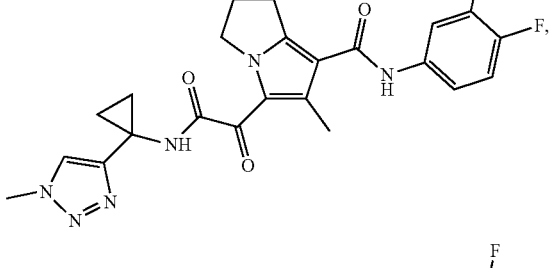
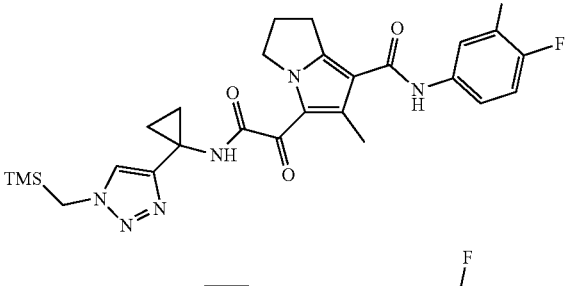
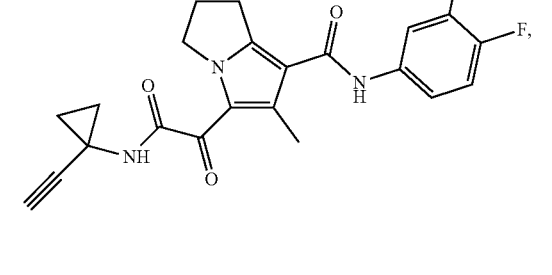
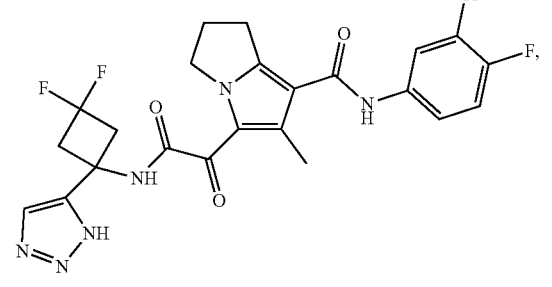

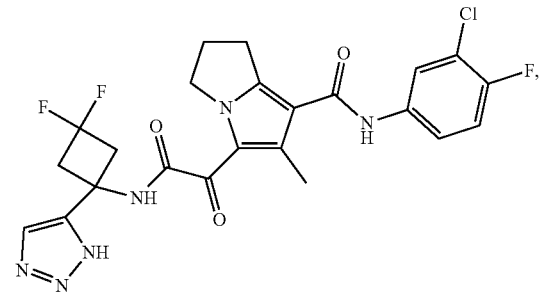
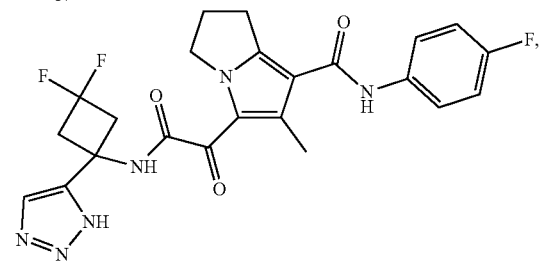
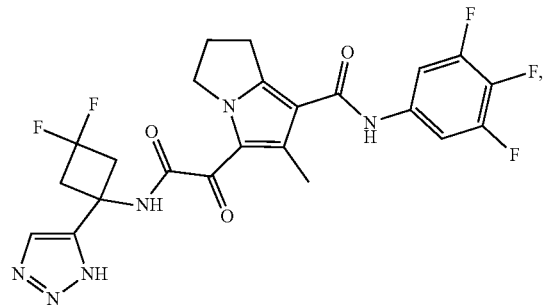
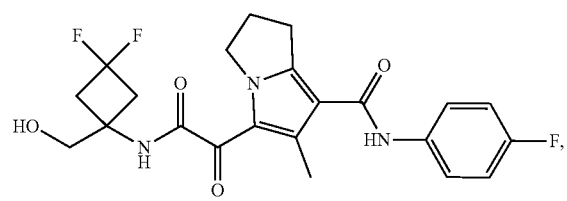
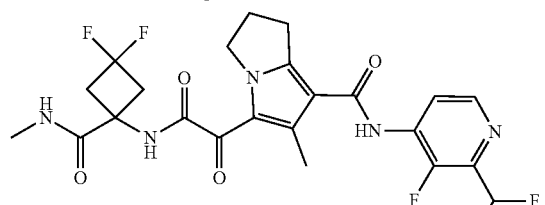
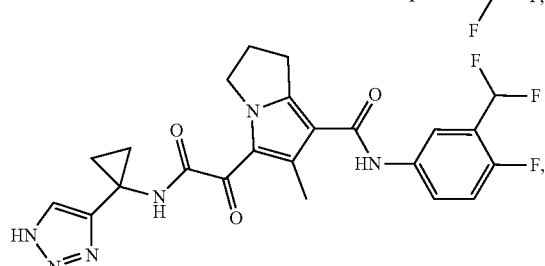
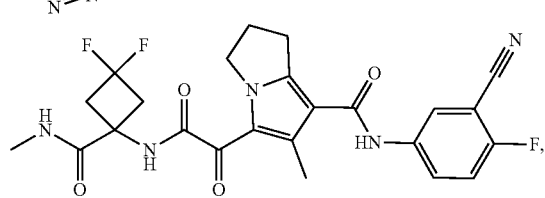
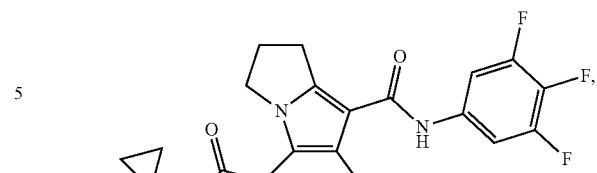
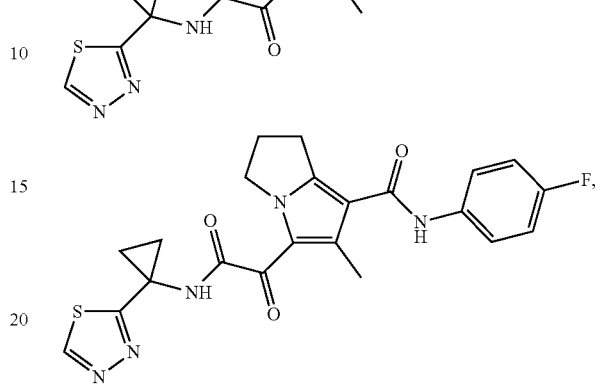
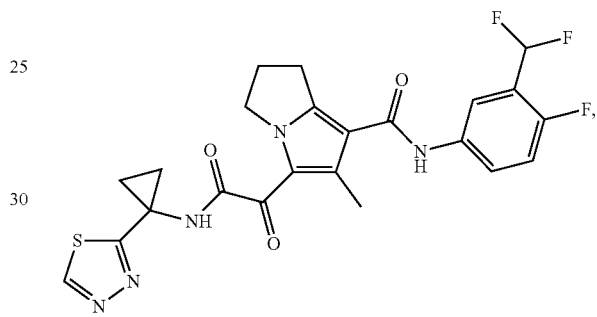
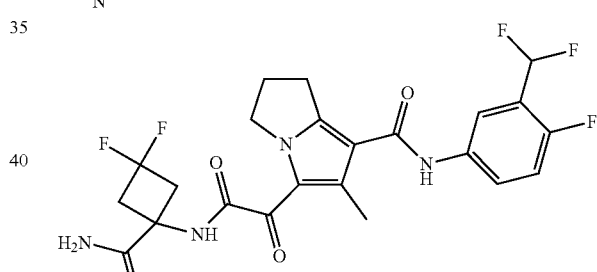
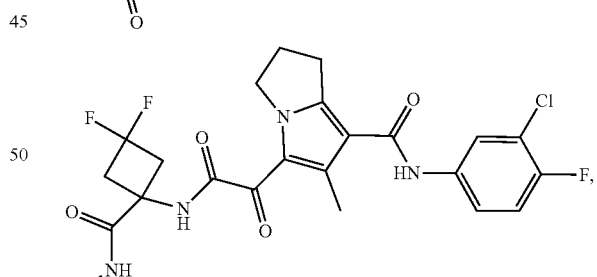
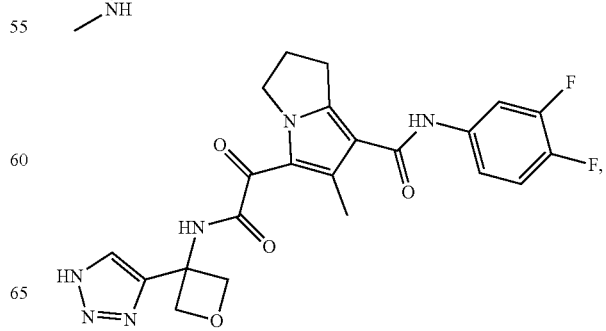

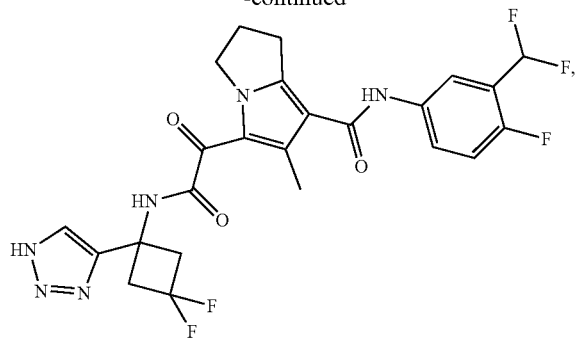
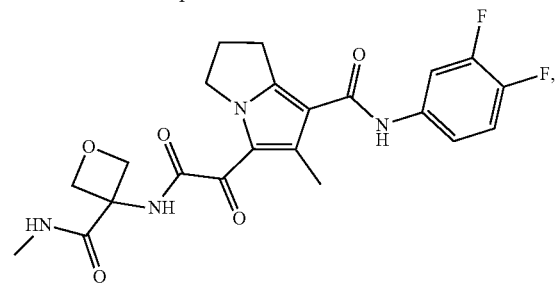
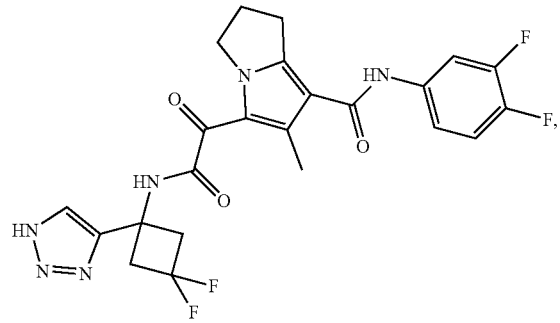
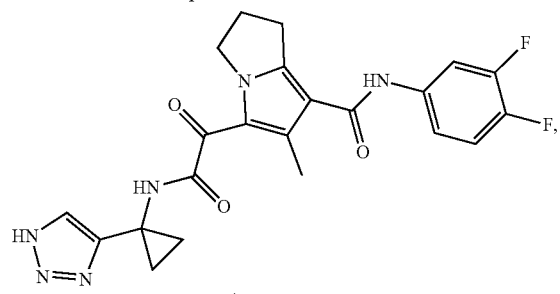
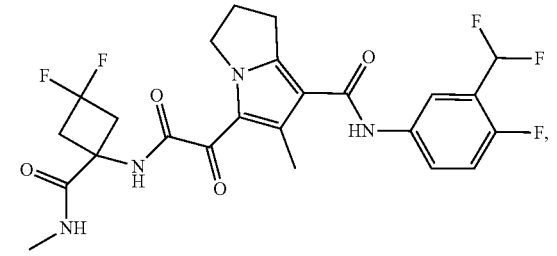
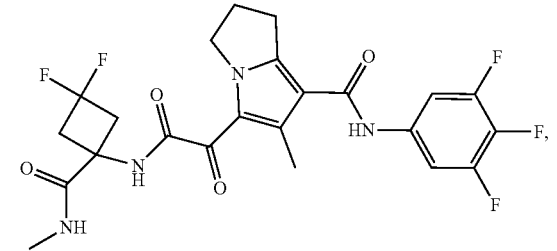
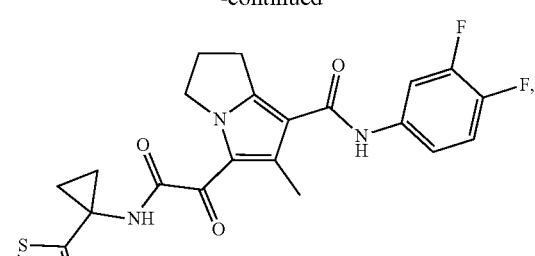
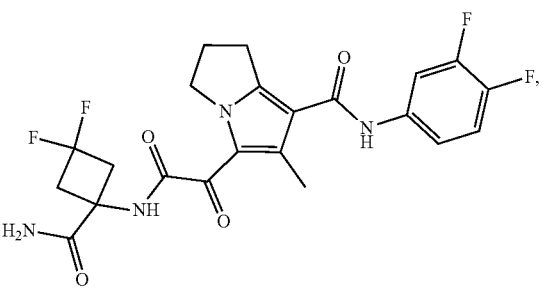
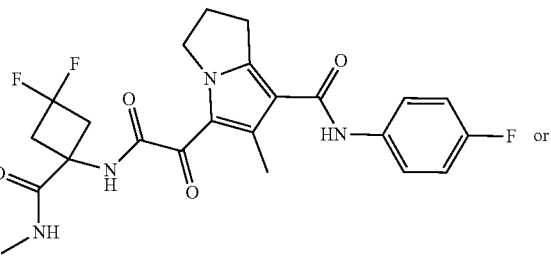
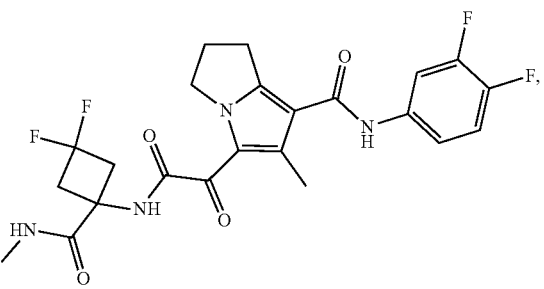
In certain embodiments a compound of Formula (I), (II) or (IV), is:
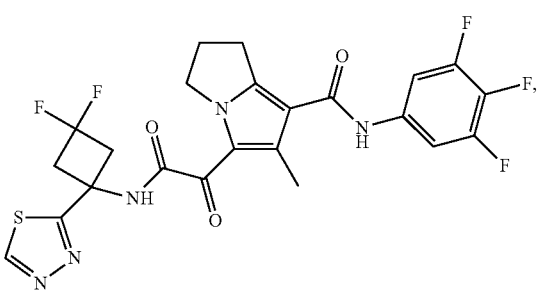

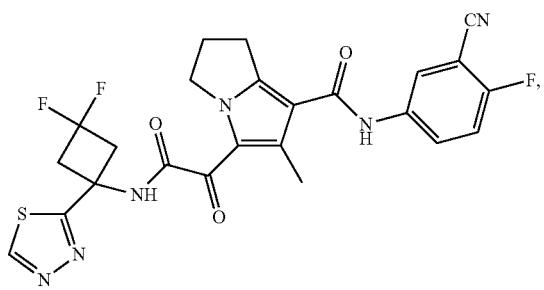
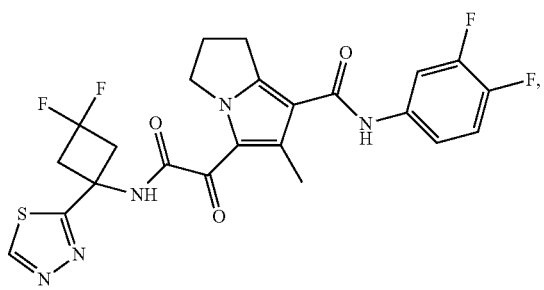
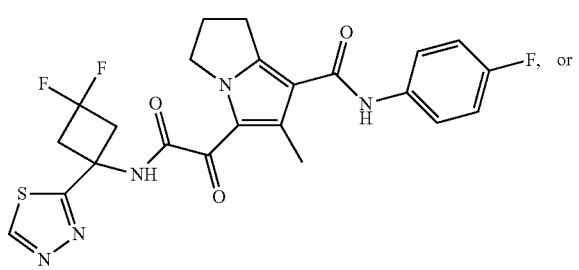
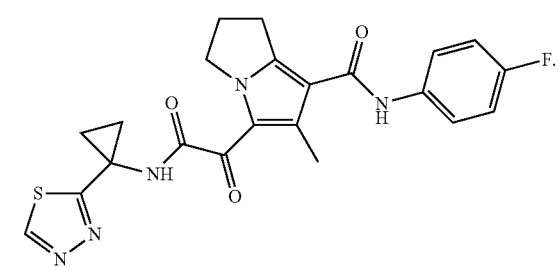
In certain embodiments a compound of Formula (I), (II) or (V), is:
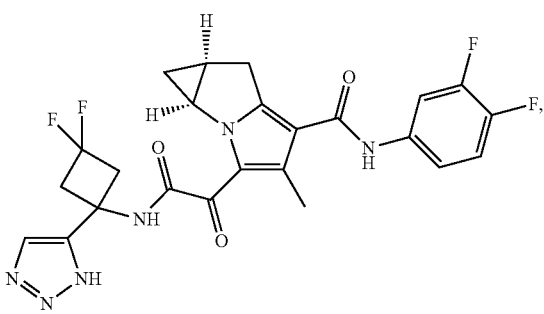
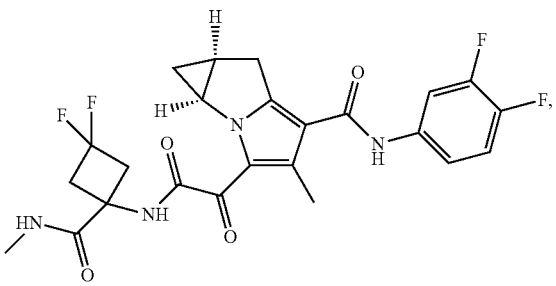
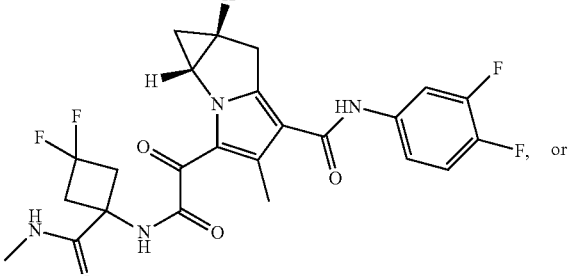
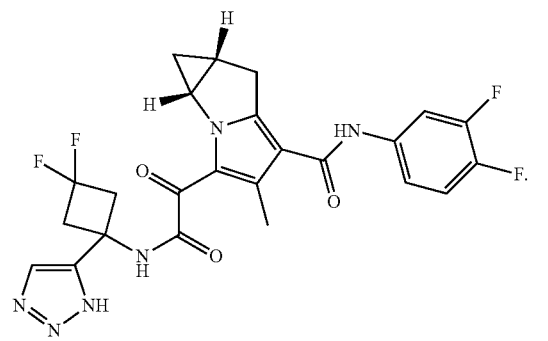
In some embodiments, the compound of Formula (I) or (II) is
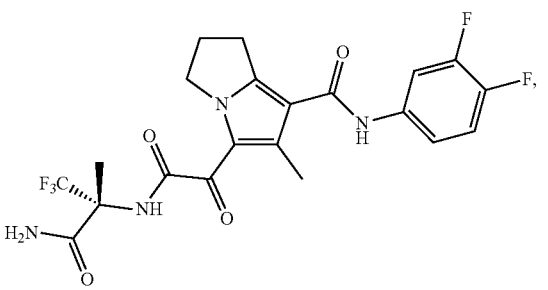
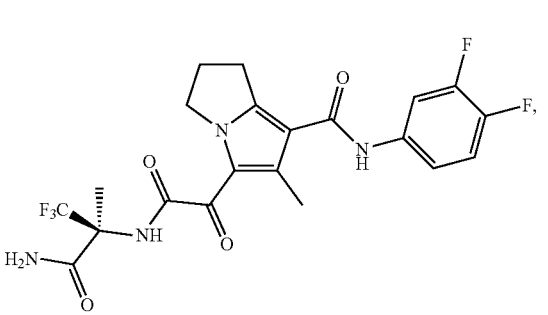

-continued

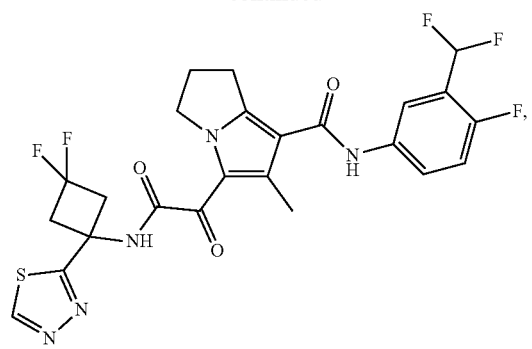

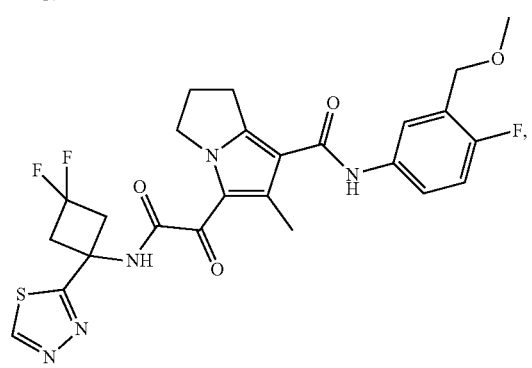

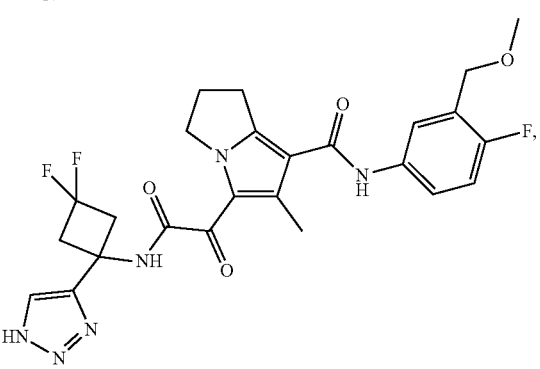

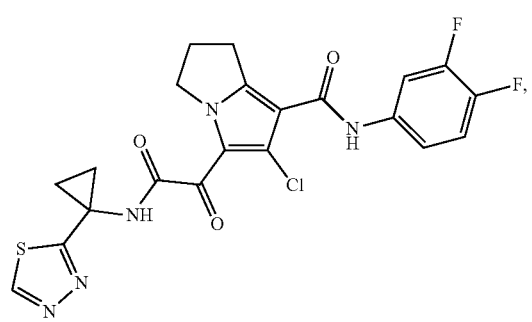

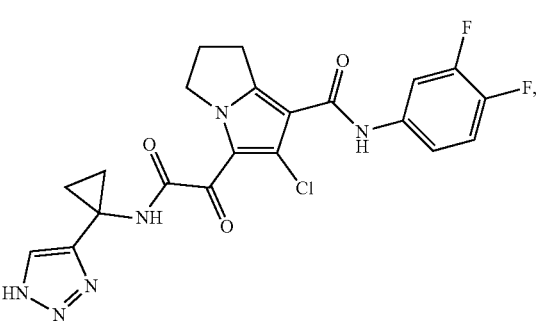

-continued

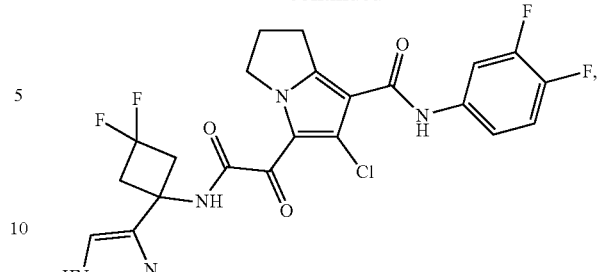

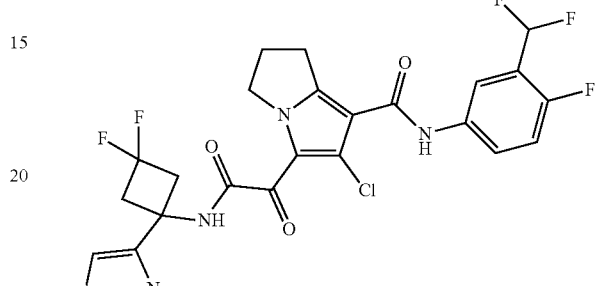

or

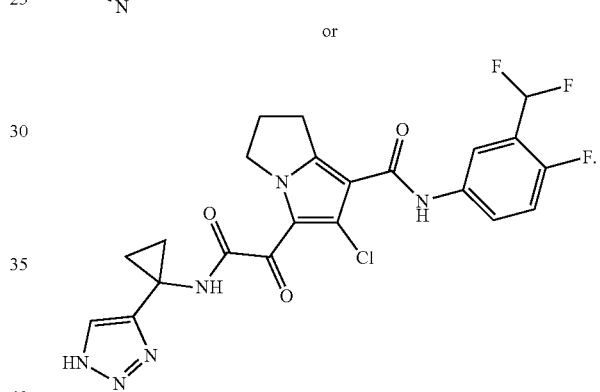

IV. Compositions

In certain embodiments, the present disclosure provides a pharmaceutical composition comprising a compound of the present disclosure (e.g. a compound of Formula (I), (II), (IIa), (IIb), (III), (IIIa), (IIIb), (IV), (V), (Va) or (Vb), or a pharmaceutically acceptable salt thereof, and a pharmaceutically acceptable excipient.

In certain embodiments, the pharmaceutical composition comprises one or more additional therapeutic agent, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 6$^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In certain embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, 21$^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient. In one embodiment, the pharmaceutical composition is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of a pharmaceutically acceptable excipient. In certain embodiments, the pharmaceutically acceptable excipient varies from about 5 to about 95% of the total compositions (weight:weight).

In certain embodiments, a composition comprising a compound of the present disclosure (e.g. a compound of Formula (I), (II), (IIa), (IIb), (III), (IIIa), (IIIb)), (IV), (V), (Va) or (Vb)), or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

V. Methods

In certain embodiments, the present disclosure provides methods for treating a HBV infection, comprising administering to an individual (e.g. a human) infected with hepatitis B virus a therapeutically effective amount a compound of the present disclosure or a pharmaceutically acceptable salt thereof. Typically, the individual is suffering from a chronic hepatitis B infection, although it is within the scope of the present disclosure to treat people who are acutely infected with HBV.

In certain embodiments, a method of inhibiting HBV replication is provided, comprising administering a compound of the present disclosure, or a pharmaceutically acceptable salt thereof, to an individual (e.g. a human).

In certain embodiments, the present disclosure provides a method for reducing the viral load associated with HBV infection, wherein the method comprises administering to an individual (e.g. a human) infected with HBV a therapeutically effective amount of a compound of the present disclosure, or a pharmaceutically acceptable salt thereof, wherein the therapeutically effective amount is sufficient to reduce the HBV viral load in the individual.

As described more fully herein, compounds of the present disclosure can be administered with one or more additional therapeutic agent(s) to an individual (e.g. a human) infected with HBV. The additional therapeutic agent(s) can be administered to the infected individual (e.g. a human) at the same time as a compound of the present disclosure or before or after administration of a compound of the present disclosure.

In certain embodiments, a compound of the present disclosure, or a pharmaceutically acceptable salt thereof, for use in treating or preventing a HBV infection is provided. In certain embodiments, a compound of the present disclosure (e.g. a compound of Formula (I)), or a pharmaceutically acceptable salt thereof, for the manufacture of a medicament for treating or preventing a HBV infection is provided. In certain embodiments, a compound of the present As described more fully herein, compounds of the present disclosure can be administered with one or more additional therapeutic agent(s) to an individual (e.g. a human) infected with HBV. Further, in certain embodiments, when used to treat or prevent HBV, a compound of the present disclosure may be administered with one or more (e.g. one, two, three, four or more) additional therapeutic agent(s) selected from the group consisting of HBV combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

VI. Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure, may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In certain embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month.

Other therapeutically effective amounts of the compound of the present disclosure are about 20, 25, 30, 35, 40, 45, 50, 55, 60, 65, 70, 75, 80, 85, 90, 95, or about 100 mg per dose.

The frequency of dosage of the compound of the present disclosure are will be determined by the needs of the individual patient and can be, for example, once per day or twice, or more times, per day. Administration of the compound continues for as long as necessary to treat the HBV infection. For example, a compound can be administered to a human being infected with HBV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

In one embodiment, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising a compound of the present disclosure, or a pharmaceutically acceptable salt thereof, in combination with one or more (e.g., one, two, three, four, one or two, one to three, or one to four) additional therapeutic agents are provided.

In certain embodiments, a compound of the present disclosure, or a pharmaceutically acceptable salt thereof, is combined with one, two, three, four or more additional therapeutic agents. In certain embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In certain embodiments, when a compound of the present disclosure is combined with one or more additional therapeutic agents as described herein, the components of the composition are administered as a simultaneous or sequential regimen. When administered sequentially, the combination may be administered in two or more administrations.

In certain embodiments, a compound of the present disclosure is combined with one or more additional therapeutic agents in a unitary dosage form for simultaneous administration to a patient, for example as a solid dosage form for oral administration.

In certain embodiments, a compound of the present disclosure is co-administered with one or more additional therapeutic agents.

VII. Combination Therapy

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when a compound disclosed herein is combined with one or more additional therapeutic agents as described above, the components of the composition are administered as a simultaneous or sequential regimen. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments a compound of Formula (I) is formulated as a tablet, which may optionally contain one or more other compounds useful for treating HBV. In certain embodiments, the tablet can contain another active ingredient for treating HBV.

In certain embodiments, such tablets are suitable for once daily dosing.

HBV Combination Therapy

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In the above embodiments, the additional therapeutic agent may be an anti-HBV agent. For example, the additional therapeutic agent may be selected from the group consisting of HBV combination drugs, other drugs for treating HBV, 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPB inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, zinc finger nucleases or synthetic nucleases (TALENs), and combinations thereof.

In certain embodiments, a compound of Formula (I) is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPB inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD', T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

In certain embodiments, a compound of the present disclosure, or a pharmaceutically acceptable salt thereof, is combined with one, two, three, four or more additional therapeutic agents selected from HBV combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucleotide reductase inhibitors, HBV E antigen inhibitors, covalently closed circular DNA (cccDNA) inhibitors, famesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

HBV Combination Drugs

Examples of combination drugs for the treatment of HBV include TRUVADA® (tenofovir disoproxil fumarate and emtricitabine); ABX-203, lamivudine, and PEG-IFNalpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPER-VAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. Further examples of HBV DNA polymerase inhibitors include filocilovir.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, AIC-649, and IR-103. Further examples of immunomodulators include JNJ-440, AB-452, CRV-431, JNJ-0535, TG-1050, ABI-H2158, GS-9688, RG-7854, and AB-506.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, GS-9688 and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, RG-7854, and the compounds disclosed in US20100143301 (Gilead Sciences), US20110098248 (Gilead Sciences), and US20090047249 (Gilead Sciences). Additional examples of TLR7 modulators include telratolimod, SP-0509, and LHC-165.

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), US20130251673 (Novira Therapeutics), U.S. Pat. No. 9,670,205, US20160289229, U.S. patent application Ser. No. 15/692,161, and U.S. patent application Ser. No. 15/692,093.

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Further examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO201804163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO201803143 (Merck), WO2016096778 (Roche), WO2017190669 (Shanghai De Novo Pharmatech), U.S. Ser. No. 09/884,866 (University of Minnesota), WO2017219931 (Sichuan Kelun Biotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), and WO2015023958 (University of Kansas).

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsA2) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRX, IONIS-HBVRX, IONIS-GSK6-LRX, GSK-3389404, RG-6004.

Short Interfering RNAs (siRNA) and ddRNAi.

Examples of siRNA include TKM-HBV (TKM-HepB), ALN-HBV, SR-008, HepB-nRNA-, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucelotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Example of farnesoid x receptor agonist such as EYP-001. Additional examples of farnesoid x receptor agonist include GS-9674, EDP-305, MET-409, Tropifexor, AKN-083, RDX-023, BWD-100, LMB-763, INV-3, NTX-023-1, EP-024297 and GS-8670.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies such as HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience)

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include AB-423, AT-130, GLS4, NVR-1221, NVR-3778, BAY 41-4109, morphothiadine mesilate, JNJ-379, RG-7907, ABI-H0731, ABI-H2158 and DVR-23. Further examples of nucleoprotein modulators include GS-4882, AL-3778, ARB-168786, ARB-880, HEC-72702, AB-506, and JNJ-440.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche). Additional examples of capsid inhibitors include the compounds disclosed in WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), and US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Retinoic Acid-Inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-Dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include nivolumab, pembrolizumab, pidilizumab, BGB-108, SHR-1210, PDR-001, PF-06801591, IBI-308, GB-226, STI-1110, and mDX-400. Additional examples of PD-1 inhibitors include cemiplimab, STI-A1014, JNJ-63723283, CA-170, durvalumab, atezolizumab, JS-001, camrelizumab, sintilimab, sintilimab, tislelizumab, BCD-100, BGB-A333 JNJ-63723283, GLS-010 (WBP-3055), CX-072, AGEN-2034, GNS-1480 (epidermal growth factor receptor antagonist; programmed cell death ligand 1 inhibitor), CS-1001, M-7824 (PD-L1/TGF-β bifunctional fusion protein), Genolimzumab, and BMS-936559.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PD-L, STI-A1014, CX-072, and BMS-936559. Additional examples of PD-L1 inhibitors include GS-4224.

Further examples of PD-1/PD-L1 inhibitors include the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (BristolMyers Squibb Co), WO20161266460 (BristolMyers Squibb Co), WO2017087678 (BristolMyers Squibb Co), WO2016149351 (BristolMyers Squibb Co), WO2015033299 (Aurigene Discovery Technologies Ltd), WO2015179615 (Eisai Co Ltd; Eisai Research Institute), WO2017066227 (BristolMyers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), and WO2018026971 (Arising International).

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), and GSK-2879552, RG-6016, ORY-2001.

STING Agonists

Examples of STING agonists include SB-11285, AdVCA0848, and STINGVAX. Further Examples of STING agonists include the compounds disclosed in WO 2018065360 (Biolog Life Science Institute Forschungslabor and Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkiline), WO 2017075477 (Aduro Biotech), US 20170044206 (Merck), WO 2014179760 (University of California), WO2018098203 (Janssn), WO2018118665 (Merck), WO2018118664 (Merck), WO2018100558 (Takeda), WO2018067423 (Merck), and WO2018060323 (Boehringer).

Non-Nucleoside Reverse Transcriptase Inhibitors (NNRTIs)

Examples of NNRTI include the compounds disclosed in WO2018118826 (Merck), WO2018080903 (Merck), WO2018119013 (Merck), WO2017100108 (Idenix), WO2017027434 (Merck), WO2017007701 (Merck), and WO2008005555 (Gilead).

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Gene Editors

The genome editing system is selected from the group consisting of: a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreS1, PreS2, S, P or SP gene refers to (1) reducing or eliminating PreC, C, X, PreS1, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreS1, PreS2, S, P and/or SP gene(s) is performed by targeting the gene(s) within HBV cccDNA and/or integrated HBV DNA.

CAR-T Cell Therapy

A population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

T cells expressing HBV-specific T cell receptors. TCR-T cells are engineered to target HBV derived peptides presented on the surface of virus-infected cells.

T-Cells expressing HBV surface antigen (HBsAg)-specific TCR.

TCR-T therapy directed to treatment of HBV, such as LTCR-H2-1.

HBV Combination Therapy

In a particular embodiment, a compound disclosed herein, or a pharmaceutically acceptable salt thereof, is combined with one, two, three, or four additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents and a pharmaceutically acceptable carrier, diluent, or excipient are provided.

HBV DNA Polymerase Inhibitor Combination Therapy

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Ax1, modulators of Mer, modulators of Tyro, gene modifiers or editors such as CRISPR (including CRISPR Cas9), zinc finger nucleases or synthetic nucleases (TALENs), IAPB inhibitors, SMAC mimetics, KDM5 inhibitors, IDO inhibitors, and hepatitis B virus replication inhibitors.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

HBV Drug Combination Therapy

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambda, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Ax1, modulators of Mer, modulators of Tyro, gene modifiers or editors such as CRISPR (including CRISPR Cas9), zinc finger nucleases or synthetic nucleases (TALENs), IAPB inhibitors, SMAC mimetics, KDM5 inhibitors, and hepatitis B virus replication inhibitors.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPIVIR-HBV®) and at least a second additional therapeutic agent selected from the group consisting of peginterferon alfa-2b (PEG-INTRON®), MULTIFERON®, interferon alpha 1b (HAPGEN®), interferon alpha-2b (INTRON A®), pegylated interferon alpha-2a (PEGASYS®), interferon alfa-n1 (HUMOFERON®), ribavirin, interferon beta-1a (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Religeron, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, Arginase inhibitors, PI3K inhibitors, PD-1 inhibitors, PD-L1 inhibitors, IDO inhibitors, and stimulators of NOD2.

In a particular embodiment, a compound disclosed herein, or a pharmaceutically acceptable salt thereof, is combined with a first additional therapeutic agent selected from the group consisting of: adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, a compound as disclosed herein (e.g., any compound of Formula I) may be combined with one or more (e.g., one, two, three, four, one or two, one to three, or one to four) additional therapeutic agents in any dosage amount of the compound of Formula I (e.g., from 10 mg to 1000 mg of compound).

In certain embodiments, a compound disclosed herein, or a pharmaceutically acceptable salt thereof, is combined with inarigivir.

In a particular embodiment, a compound of the present disclosure, or a pharmaceutically acceptable salt thereof is combined with a PD-1 inhibitor. In a particular embodiment, a compound of the present disclosure, or a pharmaceutically acceptable salt thereof is combined with a PD-L1 inhibitor. In a particular embodiment, a compound of the present disclosure, or a pharmaceutically acceptable salt thereof is combined with an IDO inhibitor. In a particular embodiment, a compound of the present disclosure, or a pharmaceutically acceptable salt thereof is combined with an IDO inhibitor and a PD-1 inhibitor. In a particular embodiment, a compound of the present disclosure, or a pharmaceutically acceptable salt thereof, is combined with an IDO inhibitor and a PD-L1 inhibitor. In a particular embodiment, a compound of the present disclosure, or a pharmaceutically acceptable salt thereof is combined with an IDO inhibitor, a TLR8 agonist, and a PD-1 inhibitor. In a particular embodiment, a compound of the present disclosure, or a pharmaceutically acceptable salt thereof, is combined with an IDO inhibitor, a TLR8 agonist, and a PD-L1 inhibitor. In a particular embodiment, a compound of the present disclosure, or a pharmaceutically acceptable salt thereof, is combined with a TLR7 modulator, such as GS-9620. In a particular embodiment, a compound of the present disclosure, or a pharmaceutically acceptable salt thereof, is combined with a TLR8 modulator, such as GS-9688.

In a particular embodiment, a compound of the present disclosure, or a pharmaceutically acceptable salt thereof, is combined with a TLR8 modulator and an IDO inhibitor. In a particular embodiment, a compound of the present disclosure, or a pharmaceutically acceptable salt thereof, is combined with a TLR8 modulator such as GS-9688 and an IDO inhibitor such as epacadostat.

In certain embodiments of the combinations recited herein, the TLR8 modulator is an TLR8 agonist disclosed in U.S. Pat. No. 9,670,205, which is incorporated herein by reference in its entirety and specifically with respect to the compounds disclosed (such as, but not limited to, compounds of Examples 59, 61, 62, 63, 65, 66, 80 and 98 or a pharmaceutically acceptable salt thereof) and methods of making and using the same. In some embodiments, the Toll-like receptor 8 (TLR8) agonist is selected from the group consisting of:

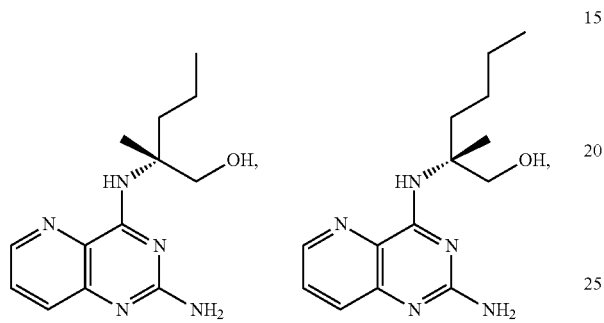

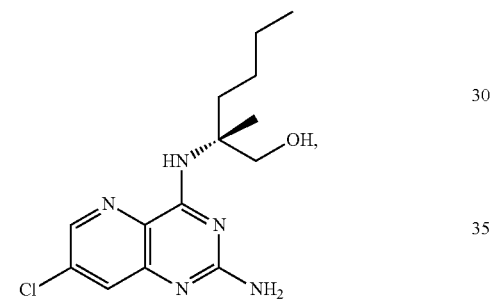

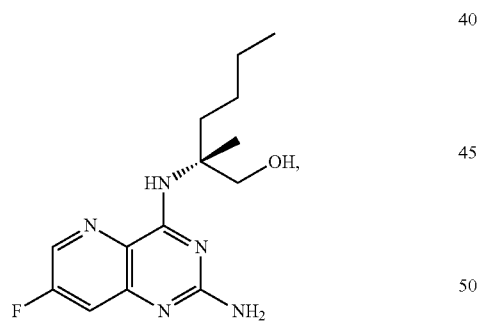

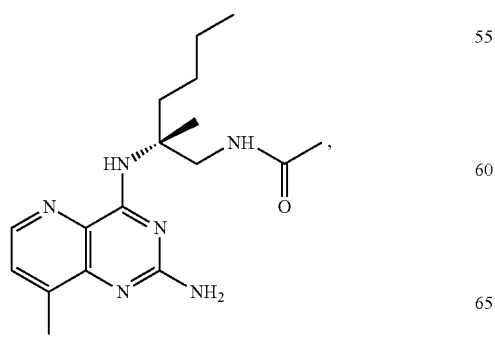

-continued

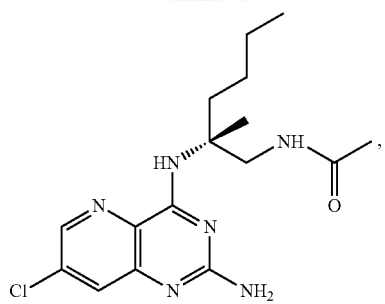

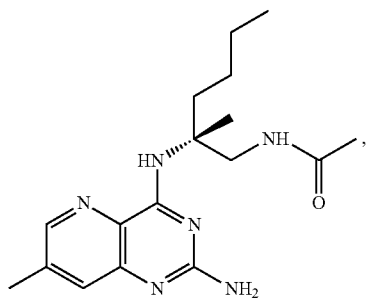

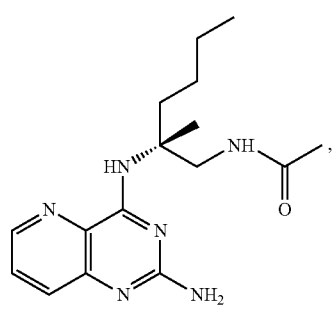

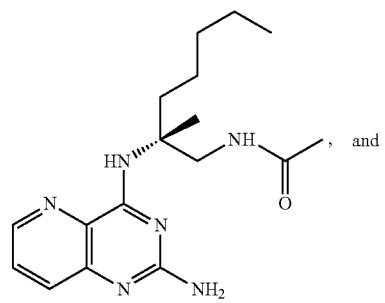, and

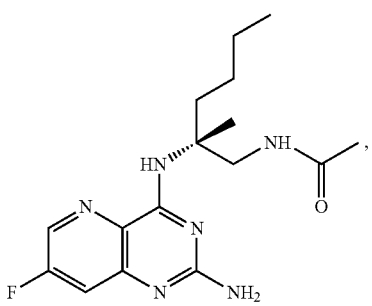

or a pharmaceutically acceptable salt thereof. In some embodiments, the TLR8 agonist is selected from the group consisting of:

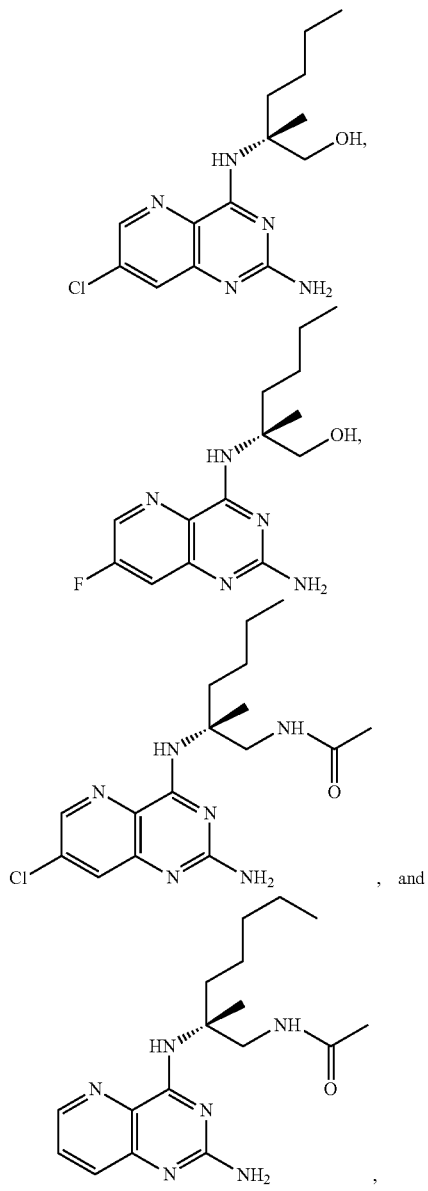

, and or a pharmaceutically acceptable salt thereof.

In certain embodiments of the combinations recited herein the PD-1 inhibitor is selected from the group consisting of nivolumab, lambrolizumab, pembrolizumab, pidilizumab, PDR001, and TSR-001, or a pharmaceutically acceptable salt thereof. In some embodiments, the PD-L1 inhibitor is selected from the group consisting of atezolizumab, durvalumab, or avelumab, or a pharmaceutically acceptable salt thereof.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

VIII. Kits

The present disclosure provides a kit comprising a compound of the present disclosure or a pharmaceutically acceptable salt thereof. The kit may further comprise instructions for use, e.g., for use in treating a HBV infection. The instructions for use are generally written instructions, although electronic storage media (e.g., magnetic diskette or optical disk) containing instructions are also acceptable.

The present disclosure also provides a pharmaceutical kit comprising one or more containers comprising a compound of the present disclosure or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Also provided are articles of manufacture comprising a unit dosage of a compound of the present disclosure or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

IX. Examples

The embodiments are also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, 7$^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

The methods of the present invention generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in schemes below, and the particular examples that follow.

Example 1. 5-(2-((3,3-difluoro-1-(1,3,4-thiadiazol-2-yl)cyclobutyl)amino)-2-oxoacetyl)-6-methyl-N-(3,4,5-trifluorophenyl)-2,3-dihydro-1H-pyrrolizine-7-carboxamide

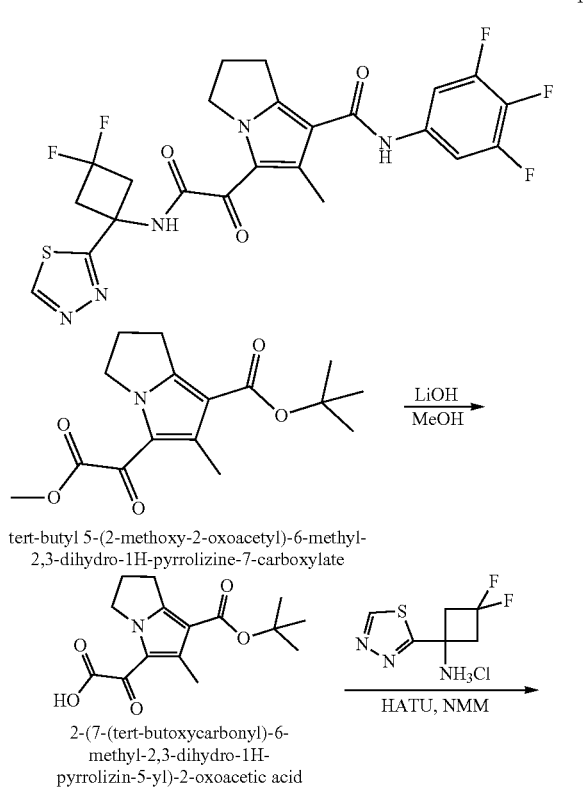

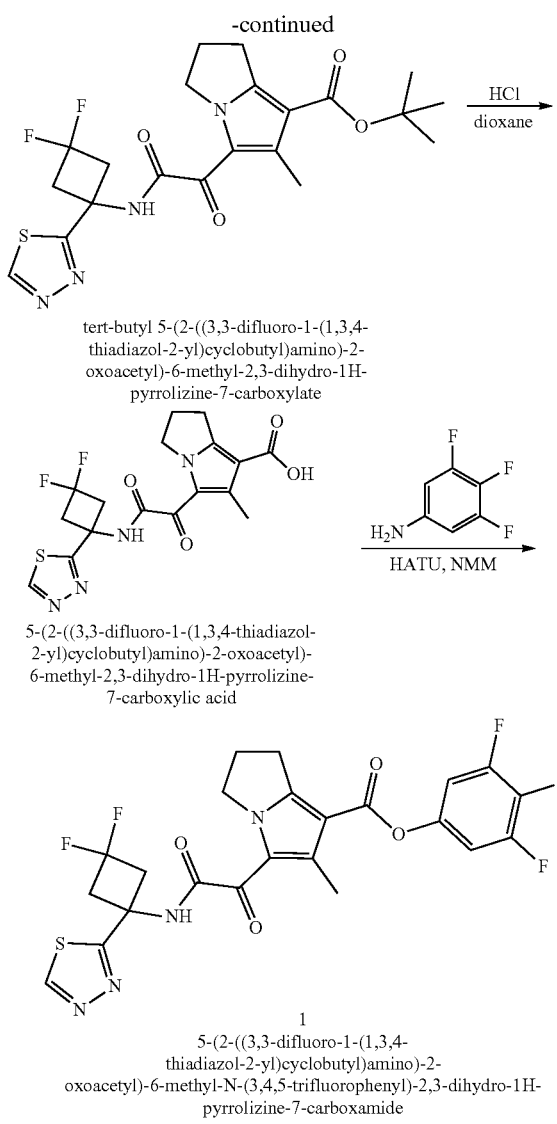

tert-butyl 5-(2-((3,3-difluoro-1-(1,3,4-thiadiazol-2-yl)cyclobutyl)amino)-2-oxoacetyl)-6-methyl-2,3-dihydro-1H-pyrrolizine-7-carboxylate 5-(2-((3,3-difluoro-1-(1,3,4-thiadiazol-2-yl)cyclobutyl)amino)-2-oxoacetyl)-6-methyl-2,3-dihydro-1H-pyrrolizine-7-carboxylic acid 1
5-(2-((3,3-difluoro-1-(1,3,4-thiadiazol-2-yl)cyclobutyl)amino)-2-oxoacetyl)-6-methyl-N-(3,4,5-trifluorophenyl)-2,3-dihydro-1H-pyrrolizine-7-carboxamide To a solution of tert-butyl 5-(2-methoxy-2-oxoacetyl)-6-methyl-2,3-dihydro-1H-pyrrolizine-7-carboxylate (619 mg, 2.01 mmol) in methanol (16 mL) was added a 2N solution of aqueous lithium hydroxide (3 mL). The reaction mixture was stirred for 90 minutes at which point it was diluted with water, acidified with aqueous hydrogen chloride, and extracted into ethyl acetate. The combined organics were dried over sodium sulfate, filtered, and concentrated under reduced pressure to afford 2-(7-(tert-butoxycarbonyl)-6-methyl-2,3-dihydro-1H-pyrrolizin-5-yl)-2-oxoacetic acid which was carried on without further purification.

A solution of 2-(7-(tert-butoxycarbonyl)-6-methyl-2,3-dihydro-1H-pyrrolizin-5-yl)-2-oxoacetic acid (503 mg, 2.21 mmol), 3,3-difluoro-1-(1,3,4-thiadiazol-2-yl)cyclobutan-1-amine hydrogen chloride (503 mg, 2.21 mmol), N-methylmorpholine (0.75 mL, 6.8 mmol), and (1-[bis(dimethylamino)methylene]-1H-1,2,3-triazolo[4,5-b]pyridinium 3-oxid hexafluorophosphate) (985 mg, 2.59 mmol) in N-methyl-2-pyrrolidone (8 mL) was stirred at room temperature for 30 minutes at which point the reaction mixture was diluted with ethyl acetate and sequentially washed with 1M aqueous hydrogen chloride, 5% aqueous sodium bicarbonate, 5% aqueous lithium chloride, and saturated aqueous sodium chloride. The organic phase was then dried over sodium sulfate, filtered, and concentrated under reduced pressure to afford tert-butyl 5-(2-((3,3-difluoro-1-(1,3,4-thiadiazol-2-yl)cyclobutyl)amino)-2-oxoacetyl)-6-methyl-2,3-dihydro-1H-pyrrolizine-7-carboxylate which was carried forward without further purification. $^1$H NMR (400 MHz, Chloroform-d) δ 9.11 (s, 1H), 7.53 (s, 1H), 4.24 (t, J=7.4 Hz, 2H), 3.67 (dd, J=14.1, 12.0 Hz, 2H), 3.33 (dd, J=13.0, 7.8 Hz, 2H), 3.07 (t, J=7.6 Hz, 2H), 2.49 (d, J=13.9 Hz, 5H), 1.54 (s, 9H).

A solution of tert-butyl 5-(2-((3,3-difluoro-1-(1,3,4-thiadiazol-2-yl)cyclobutyl)amino)-2-oxoacetyl)-6-methyl-2,3-dihydro-1H-pyrrolizine-7-carboxylate (0.94 g, 2.0 mmol) in 4M hydrogen chloride in dioxane (10 mL) was stirred at 40° C. for 3.5 h at which point the reaction mixture was cooled to room temperature and diethyl ether added to initiate precipitation. The resultant precipitate was collected by filtration with ethereal trituration to afford 5-(2-((3,3-difluoro-1-(1,3,4-thiadiazol-2-yl)cyclobutyl)amino)-2-oxoacetyl)-6-methyl-2,3-dihydro-1H-pyrrolizine-7-carboxylic acid which was carried forward without further purification. $^1$H NMR (400 MHz, DMSO-d6) δ 10.26 (s, 1H), 9.57 (s, 1H), 4.18 (t, J=7.3 Hz, 2H), 3.58-3.50 (m, 2H), 3.31 (dd, J=14.1, 8.0 Hz, 2H), 2.98 (t, J=7.6 Hz, 2H), 2.41 (t, J=7.3 Hz, 2H), 2.34 (s, 3H).

A solution of 5-(2-((3,3-difluoro-1-(1,3,4-thiadiazol-2-yl)cyclobutyl)amino)-2-oxoacetyl)-6-methyl-2,3-dihydro-1H-pyrrolizine-7-carboxylic acid (40.6 mg, 0.1 mmol), 3,4,5-trifluoroaniline (96 mg, 0.65 mmol), N-methylmorpholine (0.05 mL, 0.45 mmol), and (1-[Bis(dimethylamino)methylene]-1H-1,2,3-triazolo[4,5-b]pyridinium 3-oxid hexafluorophosphate) (59 mg, 0.16 mmol) in N-methyl-2-pyrrolidone (0.5 mL) was stirred at 100° C. 24 h at which point the reaction mixture was cooled to room temperature, passed through a syringe filter, and purified by preparative hplc (10-100% acetonitrile in water, 0.1% TFA buffer) to afford 5-(2-((3,3-difluoro-1-(1,3,4-thiadiazol-2-yl)cyclobutyl)amino)-2-oxoacetyl)-6-methyl-N-(3,4,5-trifluorophenyl)-2,3-dihydro-1H-pyrrolizine-7-carboxamide (1).

Synthesis of tert-butyl 5-(2-methoxy-2-oxoacetyl)-6-methyl-2,3-dihydro-1H-pyrrolizine-7-carboxylate

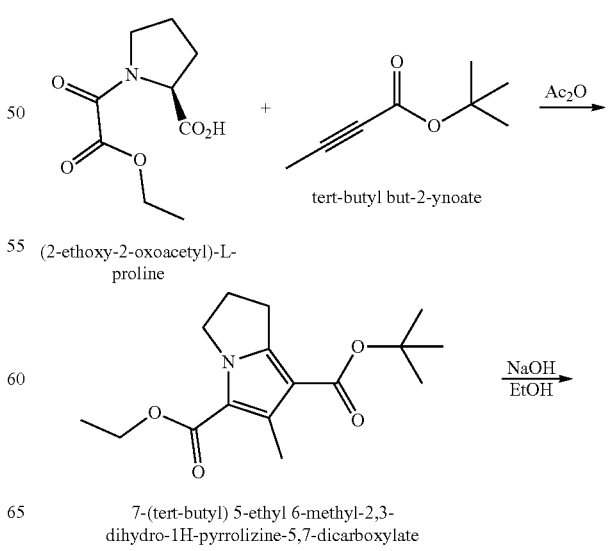

(2-ethoxy-2-oxoacetyl)-L-proline tert-butyl but-2-ynoate 7-(tert-butyl) 5-ethyl 6-methyl-2,3-dihydro-1H-pyrrolizine-5,7-dicarboxylate -continued

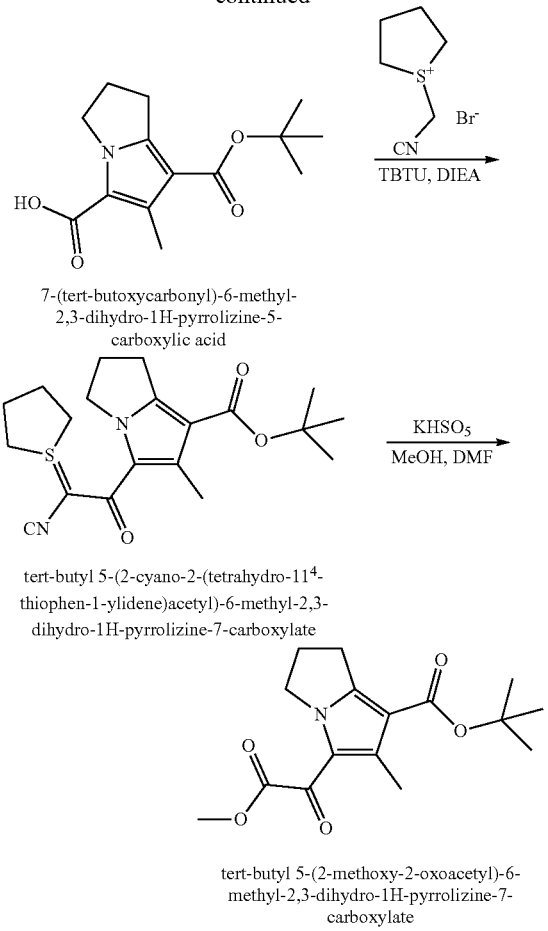

7-(tert-butoxycarbonyl)-6-methyl-2,3-dihydro-1H-pyrrolizine-5-carboxylic acid tert-butyl 5-(2-cyano-2-(tetrahydro-1λ⁴-thiophen-1-ylidene)acetyl)-6-methyl-2,3-dihydro-1H-pyrrolizine-7-carboxylate tert-butyl 5-(2-methoxy-2-oxoacetyl)-6-methyl-2,3-dihydro-1H-pyrrolizine-7-carboxylate (2-ethoxy-2-oxoacetyl)-L-proline (30.5 g, 142 mmol) and tert-butyl but-2-ynoate (22.5 g, 161 mmol) were stirred in acetic anhydride (150 mL, 1.6 mol) at a of 120° C. for 18 h. The majority of acetic anhydride was removed under reduced pressure, adsorbing crude reaction material onto silica gel. The desired cycloaddition regioisomer, 7-(tert-butyl) 5-ethyl 6-methyl-2,3-dihydro-1H-pyrrolizine-5,7-dicarboxylate, was isolated as the major product upon purification by silica gel chromatography (0-15% ethyl acetate: hexanes). ¹H NMR (400 MHz, Chloroform-d) δ 4.32-4.16 (m, 4H), 3.10-2.97 (m, 2H), 2.57 (s, 3H), 2.43 (dq, J=8.5, 7.4 Hz, 2H), 1.56 (s, 9H), 1.32 (t, J=7.1 Hz, 3H).

7-(tert-butyl) 5-ethyl 6-methyl-2,3-dihydro-1H-pyrrolizine-5,7-dicarboxylate (11.7 g, 39.9 mmol) was dissolved in ethanol (130 mL) and treated with 4N aqueous sodium hydroxide (20 mL). The reaction mixture was stirred at 60° C. for 18 h and reaction volume concentrated by half under reduced pressure. This mixture was then cooled to 0° C. and acidified with dilute aqueous hydrochloric acid. Resultant precipitate was collected by filtration, triturating sequentially with water, ethanol, and diethyl ether to afford 7-(tert-butoxycarbonyl)-6-methyl-2,3-dihydro-1H-pyrrolizine-5-carboxylic acid. ¹H NMR (400 MHz, DMSO-d6) δ 4.14 (t, J=7.3 Hz, 2H), 2.92 (t, J=7.6 Hz, 2H), 2.44 (s, 3H), 2.42-2.28 (m, 2H), 1.45 (s, 9H).

To a suspension of 7-(tert-butoxycarbonyl)-6-methyl-2,3-dihydro-1H-pyrrolizine-5-carboxylic acid (10.6 g, 39.9 mmol) in dichloromethane (340 mL) was added 2-(1H-benzotriazole-1-yl)-1,1,3,3-tetramethylaminium tetrafluoroborate (15.0 g, 50 mmol), N,N-diisopropylethylamine (25 mL, 144 mmol), and 1-(cyanomethyl)tetrahydro-1H-thiophen-1-ium bromide (10.2 g, 49.0 mmol). An additional 3.3 g 1-(cyanomethyl)tetrahydro-1H-thiophen-1-ium bromide and 13 mL N,N-diisopropylethylamine was added after 2 h, after which the reaction mixture was partitioned between dichloromethane and saturated aqueous ammonium chloride. The aqueous phase was thrice extracted to dichloromethane, the combined organic phases dried over sodium sulfate, filtered, and concentrated under reduced pressure. Silica gel column chromatography (0-10% methanol:dichloromethane) afforded tert-butyl 5-(2-cyano-2-(tetrahydro-1λ4-thiophen-1-ylidene)acetyl)-6-methyl-2,3-dihydro-1H-pyrrolizine-7-carboxylate. ¹H NMR (400 MHz, Chloroform-d) δ 4.08 (t, J=7.2 Hz, 2H), 3.47 (q, J=6.3 Hz, 2H), 3.38 (dt, J=13.1, 6.7 Hz, 2H), 3.00 (dd, J=13.8, 6.4 Hz, 2H), 2.66-2.52 (m, 2H), 2.46 (s, 3H), 2.41 (t, J=7.3 Hz, 2H), 2.18-2.01 (m, 2H), 1.52 (s, 9H).

To a solution of tert-butyl 5-(2-cyano-2-(tetrahydro-1λ4-thiophen-1-ylidene)acetyl)-6-methyl-2,3-dihydro-1H-pyrrolizine-7-carboxylate (15.0 g, 39.9 mmol) in 1:1 N,N-dimethylformamide:methanol (340 mL) was added potassium peroxymonosulfate (61.4 g, 100 mmol) and stirred for 2 h. The reaction mixture was partially concentrated under reduced pressure then partitioned between 5% aqueous sodium bicarbonate and ethyl acetate. The aqueous phase was thrice extracted to ethyl acetate and the combined organics washed with 5% aqueous lithium chloride then brine. The organic phase was then dried over sodium sulfate, filtered, and concentrated under reduced pressure. Purification by silica gel column chromatography (20-100% dichloromethane:hexanes) afforded tert-butyl 5-(2-methoxy-2-oxoacetyl)-6-methyl-2,3-dihydro-1H-pyrrolizine-7-carboxylate. ¹H NMR (400 MHz, Chloroform-d) δ 4.37-4.26 (m, 2H), 3.93 (s, 3H), 3.06 (t, J=7.7 Hz, 2H), 2.55-2.45 (m, 2H), 2.42 (s, 3H), 1.54 (s, 9H).

Synthesis of 3,3-difluoro-1-(1,3,4-thiadiazol-2-yl)cyclobutan-1-amine hydrogen chloride

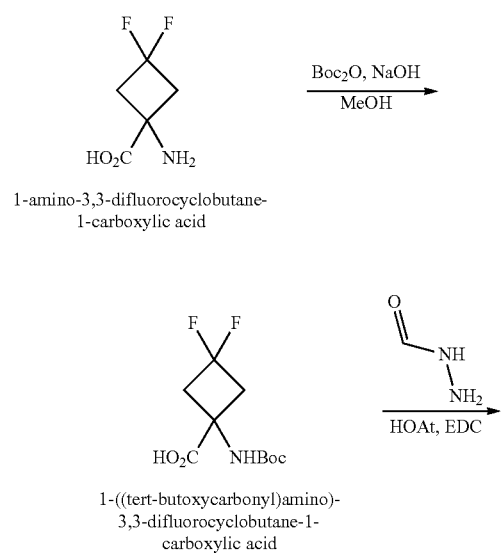

1-amino-3,3-difluorocyclobutane-1-carboxylic acid 1-((tert-butoxycarbonyl)amino)-3,3-difluorocyclobutane-1-carboxylic acid

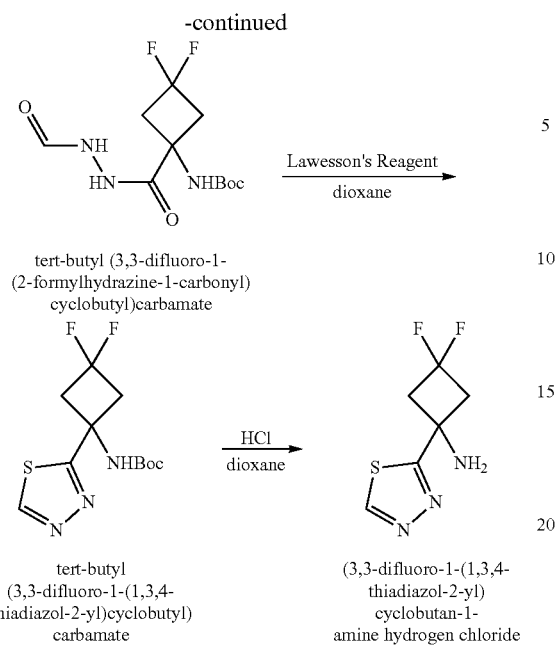

tert-butyl (3,3-difluoro-1-(2-formylhydrazine-1-carbonyl)cyclobutyl)carbamate tert-butyl (3,3-difluoro-1-(1,3,4-thiadiazol-2-yl)cyclobutyl)carbamate (3,3-difluoro-1-(1,3,4-thiadiazol-2-yl)cyclobutan-1-amine hydrogen chloride To a 0° C. solution of 1-amino-3,3-difluorocyclobutane-1-carboxylic acid (990 mg, 6.55 mmol) in methanol (8 mL) was added a 1M aqueous solution of sodium hydroxide (7 mL, 7 mmol) followed by di-tert-butyl dicarbonate (1.8 g, 8.2 g). The reaction mixture was warmed to ambient temperature was stirred for 14 h, acidified with dilute aqueous hydrogen chloride, and extracted to diethyl ether. The ethereal phase was washed with 1:1 water:brine, dried over sodium sulfate, filtered, and concentrated under reduced pressure to afford 1-((tert-butoxycarbonyl)amino)-3,3-difluorocyclobutane-1-carboxylic acid which was carried forward without further purification.

To a solution of 1-((tert-butoxycarbonyl)amino)-3,3-difluorocyclobutane-1-carboxylic acid (1.95 g, 7.75 mmol), formohydrazide (1.26 g, 20.1 mmol), and 1-hydroxybenzotriazole (1.06 g, 7.81 mmol) in dichloromethane (60 mL) was added 1-ethyl-3-(3-dimethylaminopropyl)carbodiimide (3.69 g, 19.2 mmol). The reaction mixture was stirred at room temperature for 60 h at which point it was diluted with ethyl acetate, filtered through a pad of celite, and the organic phase sequentially washed with 1M aqueous hydrogen chloride, saturated aqueous sodium bicarbonate, and saturated aqueous sodium chloride to afford tert-butyl (3,3-difluoro-1-(2-formylhydrazine-1-carbonyl)cyclobutyl)carbamate which was carried forward without further purification.

To a solution of tert-butyl (3,3-difluoro-1-(2-formylhydrazine-1-carbonyl)cyclobutyl)carbamate (1.87 g, 6.36 mmol) in dioxane (80 mL) was added Lawesson's reagent (2.65 g, 6.55 mmol). The reaction mixture was heated to 85° C. for 2 h at which point it was cooled to room temperature, diluted with ethyl acetate, and sequentially washed with a 1:1 solution of saturated sodium carbonate:water then brine. The organic phase was then dried over sodium sulfate, filtered, concentrated under reduced pressure, and purified by silica gel column chromatography (0-60% ethyl acetate:hexanes) to afford tert-butyl (3,3-difluoro-1-(1,3,4-thiadiazol-2-yl)cyclobutyl)carbamate.

A solution of tert-butyl (3,3-difluoro-1-(1,3,4-thiadiazol-2-yl)cyclobutyl)carbamate (1.1 g, 3.8 mmol) in 4M hydrogen chloride in dioxane (20 mL) was stirred at 60° C. for 1 h at which point the reaction mixture was concentrated under reduced pressure and resultant solids collected by filtration with ethereal trituration to afford 3,3-difluoro-1-(1,3,4-thiadiazol-2-yl)cyclobutan-1-amine hydrogen chloride. $^1$H NMR (400 MHz, DMSO-d6) δ 9.74 (s, 1H), 3.65-3.41 (m, 4H).

Example 2. N-(3-cyano-4-fluorophenyl)-5-(2-((3,3-difluoro-1-(1,3,4-thiadiazol-2-yl)cyclobutyl)amino)-2-oxoacetyl)-6-methyl-2,3-dihydro-1H-pyrrolizine-7-carboxamide (2)

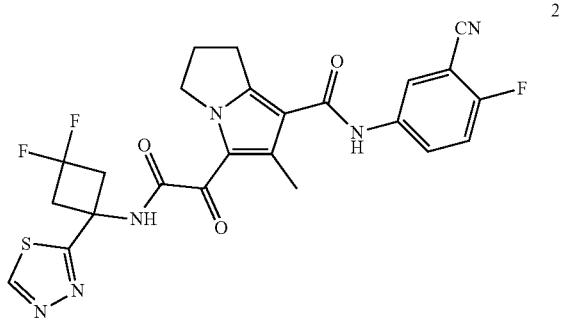 [SMILES: Cc1c(C(=O)Nc2ccc(F)c(C#N)c2)c2n(c1C(=O)C(=O)NC1(c3nncs3)CC(F)(F)C1)CCC2]

The product was synthesized in a manner similar to Example 1 using 3-cyano-4-fluoroaniline in place of 3,4,5-trifluoroaniline.

Example 3. 5-(2-((3,3-difluoro-1-(1,3,4-thiadiazol-2-yl)cyclobutyl)amino)-2-oxoacetyl)-N-(3,4-difluorophenyl)-6-methyl-2,3-dihydro-1H-pyrrolizine-7-carboxamide (3)

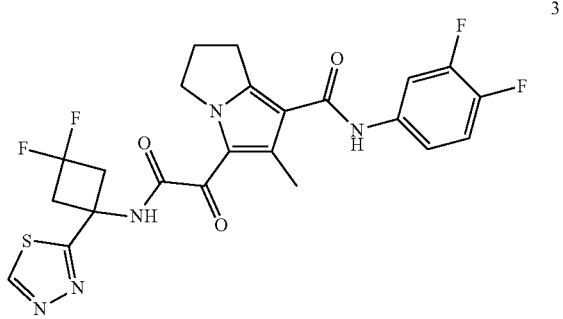 [SMILES: Cc1c(C(=O)Nc2ccc(F)c(F)c2)c2n(c1C(=O)C(=O)NC1(c3nncs3)CC(F)(F)C1)CCC2]

The product was synthesized in a manner similar to Example 1 using 3,4-difluoroaniline in place of 3,4,5-trifluoroaniline.

Example 4. 5-(2-((3,3-difluoro-1-(1-methyl-1H-1,2,3-triazol-4-yl)cyclobutyl)amino)-2-oxoacetyl)-6-methyl-N-(3,4,5-trifluorophenyl)-2,3-dihydro-1H-pyrrolizine-7-carboxamide (4)

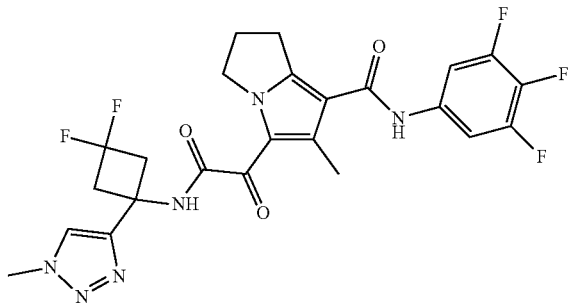

The product was synthesized in a manner similar to Example 1 using 3,3-difluoro-1-(1-methyl-1H-1,2,3-triazol-4-yl)cyclobutan-1-amine bis(hydrogen chloride) in place of 3,3-difluoro-1-(1,3,4-thiadiazol-2-yl)cyclobutan-1-amine hydrogen chloride.

Synthesis of 3,3-difluoro-1-(1-methyl-1H-1,2,3-triazol-4-yl)cyclobutan-1-amine bis(hydrogen chloride)

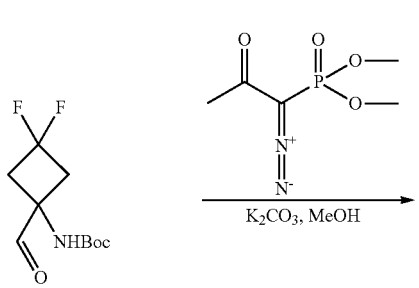

tert-butyl (3,3-difluoro-1-formylcyclobutyl)carbamate

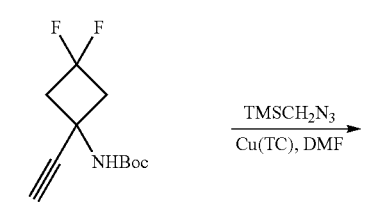

tert-butyl (1-ethynyl-3,3-difluorocyclobutyl)carbamate

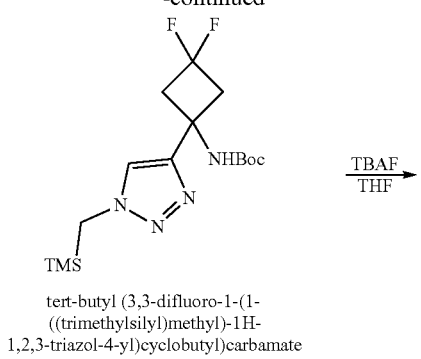

tert-butyl (3,3-difluoro-1-(1-((trimethylsilyl)methyl)-1H-1,2,3-triazol-4-yl)cyclobutyl)carbamate

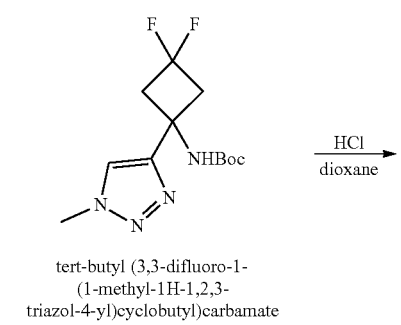

tert-butyl (3,3-difluoro-1-(1-methyl-1H-1,2,3-triazol-4-yl)cyclobutyl)carbamate 3,3-difluoro-1-(1-methyl-1H-1,2,3-triazol-4-yl)cyclobutan-1-amine To a solution of tert-butyl (3,3-difluoro-1-formylcyclobutyl)carbamate (1.66 g, 7.04 mmol) in methanol (50 mL) was added potassium carbonate (3.12 g, 22.6 mmol) followed by dimethyl (1-diazo-2-oxopropyl)phosphonate (1.6 mL, 10.7 mmol) dropwise. The reaction mixture was stirred at room temperature for 18 h at which point it was passed through a pad of celite, concentrated under reduced pressure, and purified by silica gel column chromatography (0-10% ethyl acetate:hexanes) to afford tert-butyl (1-ethynyl-3,3-difluorocyclobutyl)carbamate. $^1$H NMR (400 MHz, Chloroform-d) δ 3.06 (t, J=11.1 Hz, 4H), 2.44 (s, 1H), 1.46 (s, 9H).

A solution of tert-butyl (1-ethynyl-3,3-difluorocyclobutyl)carbamate (739 mg, 3.2 mmol), (trimethylsilyl)methyl azide (0.7 mL, 4.7 mmol), and copper(I) thiophene-2-carboxylate (610 mg, 3.2 mmol) in N,N-dimethylformamide (20 mL) was stirred at 80° C. for 45 minutes at which point it was cooled to room temperature, passed through a pad of celite, and sequentially washed with 5% aqueous lithium chloride then saturated aqueous sodium chloride to afford tert-butyl (3,3-difluoro-1-(1-(((trimethylsilyl)methyl)-1H-1,2,3-triazol-4-yl)cyclobutyl)carbamate which was carried forward without further purification. ¹H NMR (400 MHz, Chloroform-d) δ 7.48 (d, J=28.7 Hz, 1H), 3.89 (s, 2H), 3.22 (s, 4H), 1.41 (s, 9H), 0.13 (s, 9H).

To a solution of tert-butyl (3,3-difluoro-1-(1-((trimethylsilyl)methyl)-1H-1,2,3-triazol-4-yl)cyclobutyl)carbamate (1.11 g, 3.09 mmol) in tetrahydrofuran (40 mL) was added a 1M solution of tetra-N-butylammonium fluoride in tetrahydrofuran (4 mL). The reaction mixture was stirred for 40 minutes at which point it was partitioned between ethyl acetate and water and the aqueous phase extracted to ethyl acetate. The combined organic phases were washed with saturated aqueous sodium chloride, dried over sodium sulfate, filtered, and concentrated under reduced pressure to afford tert-butyl (3,3-difluoro-1-(1-methyl-1H-1,2,3-triazol-4-yl)cyclobutyl)carbamate which was carried forward without further purification. ¹H NMR (400 MHz, Chloroform-d) δ 7.54 (s, 1H), 4.08 (s, 3H), 3.20 (t, J=11.8 Hz, 4H), 1.42 (s, 9H).

A solution of tert-butyl (3,3-difluoro-1-(1-methyl-1H-1,2,3-triazol-4-yl)cyclobutyl)carbamate (892 mg, 3.09 mmol) in dioxane (6 mL) was treated with 4M hydrogen chloride in dioxane (8 mL) and stirred at room temperature for 18 h at which point the reaction mixture was concentrated under reduced pressure and resultant solids collected by filtration with ethereal trituration to afford 3,3-difluoro-1-(1-methyl-1H-1,2,3-triazol-4-yl)cyclobutan-1-amine bis(hydrogen chloride). ¹H NMR (400 MHz, DMSO-d6) δ 9.17 (s, 3H), 8.34 (s, 1H), 4.08 (s, 3H), 3.48-3.33 (m, 2H), 3.25 (td, J=15.6, 14.5, 4.2 Hz, 2H).

Example 5. N-(3-cyano-4-fluorophenyl)-5-(2-((3,3-difluoro-1-(1-methyl-1H-1,2,3-triazol-4-yl)cyclobutyl)amino)-2-oxoacetyl)-6-methyl-2,3-dihydro-1H-pyrrolizine-7-carboxamide (5)

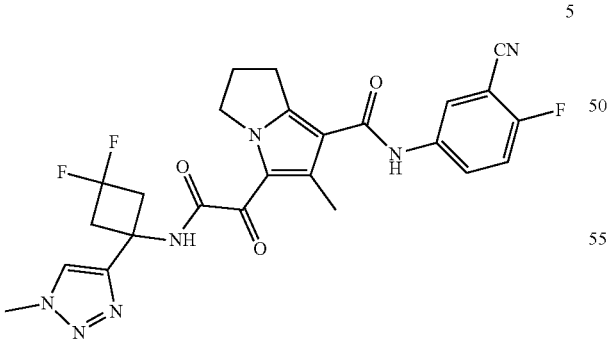

The product was synthesized in a manner similar to Example 4 using 3-cyano-4-fluoroaniline in place of 3,4,5-trifluoroaniline.

Example 6. 5-(2-((3,3-difluoro-1-(1-methyl-1H-1,2,3-triazol-4-yl)cyclobutyl)amino)-2-oxoacetyl)-N-(3,4-difluorophenyl)-6-methyl-2,3-dihydro-1H-pyrrolizine-7-carboxamide (6)

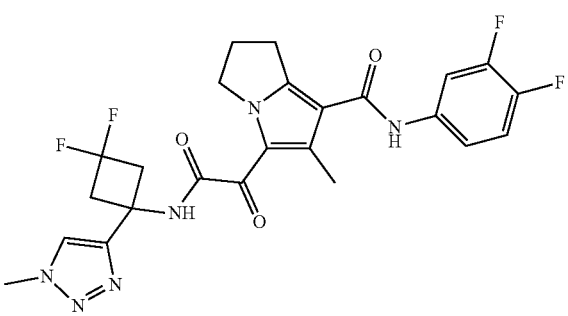

The product was synthesized in a manner similar to Example 4 using 3,4-difluoroaniline in place of 3,4,5-trifluoroaniline.

Example 7. 5-(2-((3,3-difluoro-1-(1-methyl-1H-1,2,3-triazol-5-yl)cyclobutyl)amino)-2-oxoacetyl)-N-(4-fluorophenyl)-6-methyl-2,3-dihydro-1H-pyrrolizine-7-carboxamide (7)

Example 9. 5-(2-((3,3-difluoro-1-(2-methyl-2H-1,2,3-triazol-4-yl)cyclobutyl)amino)-2-oxoacetyl)-N-(4-fluorophenyl)-6-methyl-2,3-dihydro-1H-pyrrolizine-7-carboxamide (9)

Example 10. 5-(2-((3,3-difluoro-1-(1-methyl-1H-1,2,3-triazol-4-yl)cyclobutyl)amino)-2-oxoacetyl)-N-(4-fluorophenyl)-6-methyl-2,3-dihydro-1H-pyrrolizine-7-carboxamide (10)

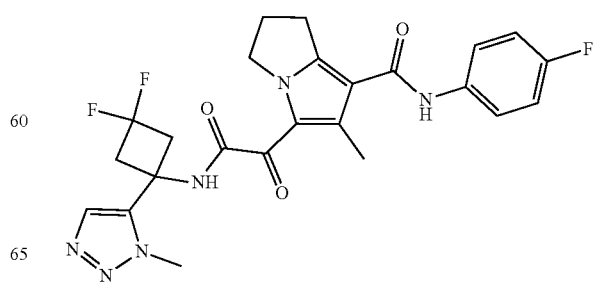

9

5-(2-((3,3-difluoro-1-(2-methyl-2H-1,2,3-triazol-4-yl)cyclobutyl)amino)-2-oxoacetyl)-N-(4-fluorophenyl)-6-methyl-2,3-dihydro-1H-pyrrolizine-7-carboxamide

10

5-(2-((3,3-difluoro-1-(1-methyl-1H-1,2,3-triazol-4-yl)cyclobutyl)amino)-2-oxoacetyl)-N-(4-fluorophenyl)-6-methyl-2,3-dihydro-1H-pyrrolizine-7-carboxamide

17

5-(2-((3,3-difluoro-1-(1H-1,2,3-triazol-5-yl)cyclobutyl)amino)-2-oxoacetyl)-N-(4-fluorophenyl)-6-methyl-2,3-dihydro-1H-pyrrolizine-7-carboxamide

7

5-(2-((3,3-difluoro-1-(1-methyl-1H-1,2,3-triazol-5-yl)cyclobutyl)amino)-2-oxoacetyl)-N-(4-fluorophenyl)-6-methyl-2,3-dihydro-1H-pyrrolizine-7-carboxamide A solution of 5-(2-((3,3-difluoro-1-(1H-1,2,3-triazol-5-yl)cyclobutyl)amino)-2-oxoacetyl)-N-(4-fluorophenyl)-6-methyl-2,3-dihydro-1H-pyrrolizine-7-carboxamide (Example 17) (29.7 mg, 0.06 mmol) in N,N-dimethylformamide (1 mL) was treated with potassium carbonate (12 mg, 0.09 mmol) followed by iodomethane (0.05 mL, 0.8 mmol) and stirred at room temperature for 48 h, at which point the reaction mixture was pass through a syringe filtered and purified by preparative hplc (10-100% acetonitrile in water, 0.1% TFA buffer) to afford a peak mixture of 5-(2-((3,3-difluoro-1-(1-methyl-1H-1,2,3-triazol-5-yl)cyclobutyl)amino)-2-oxoacetyl)-N-(4-fluorophenyl)-6-methyl-2,3-dihydro-1H-pyrrolizine-7-carboxamide (7) and 5-(2-((3,3-difluoro-1-(1-methyl-1H-1,2,3-triazol-4-yl)cyclobutyl)amino)-2-oxoacetyl)-N-(4-fluorophenyl)-6-methyl-2,3-dihydro-1H-pyrrolizine-7-carboxamide (Example 10) (elutes first) and a pure peak of 5-(2-((3,3-difluoro-1-(2-methyl-2H-1,2,3-triazol-4-yl)cyclobutyl)amino)-2-oxoacetyl)-N-(4-fluorophenyl)-6-methyl-2,3-dihydro-1H-pyrrolizine-7-carboxamide (Example 9) (elutes second). Compounds 7 and 10 were further separated from one another by supercritical fluid chromatography (30% methanol:CO$_2$ IC-5 um-4.6×100 mm column) with 5-(2-((3,3-difluoro-1-(1-methyl-1H-1,2,3-triazol-4-yl)cyclobutyl)amino)-2-oxoacetyl)-N-(4-fluorophenyl)-6-methyl-2,3-dihydro-1H-pyrrolizine-7-carboxamide (Example 10) eluting first as the major product and 5-(2-((3,3-difluoro-1-(1-methyl-1H-1,2,3-triazol-5-yl)cyclobutyl)amino)-2-oxoacetyl)-N-(4-fluorophenyl)-6-methyl-2,3-dihydro-1H-pyrrolizine-7-carboxamide (Example 7) eluting second as the mirror product.

Example 8. 5-(2-(((3,3-difluoro-1-(1,3,4-thiadiazol-2-yl)cyclobutyl)amino)-2-oxoacetyl)-N-(4-fluorophenyl)-6-methyl-2,3-dihydro-1H-pyrrolizine-7-carboxamide (8)

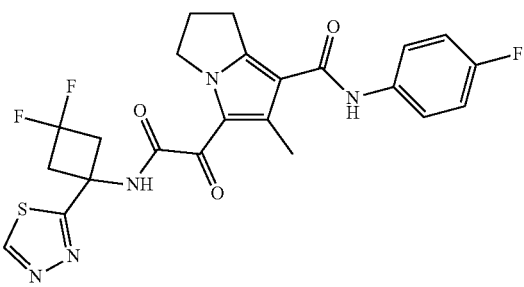

The product was synthesized in a manner similar to Example 1 using 4-fluoroaniline in place of 3,4,5-trifluoroaniline.

Example 11. N-(3,4-difluorophenyl)-6-methyl-5-(2-((1-(1-methyl-1H-1,2,3-triazol-4-yl)cyclopropyl)amino)-2-oxoacetyl)-2,3-dihydro-1H-pyrrolizine-7-carboxamide (11)

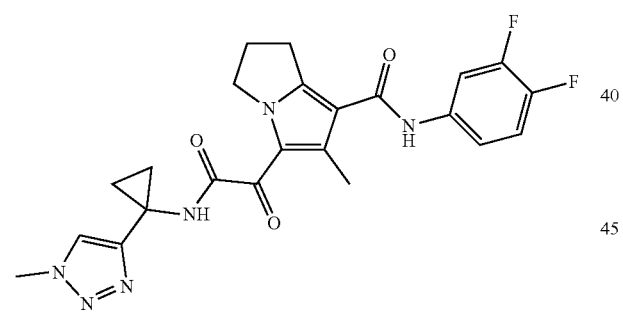

11

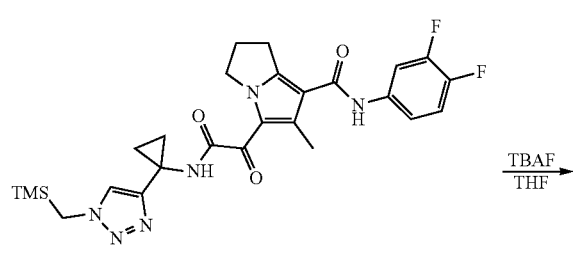

12

N-(3,4-difluorophenyl)-6-methyl-5-(2-oxo-2-((1-(1-((trimethylsilyl)methyl)-1H-1,2,3-triazol-4-yl)cyclopropyl)amino)acetyl)-2,3-dihydro-1H-pyrrolizine-7-carboxamide

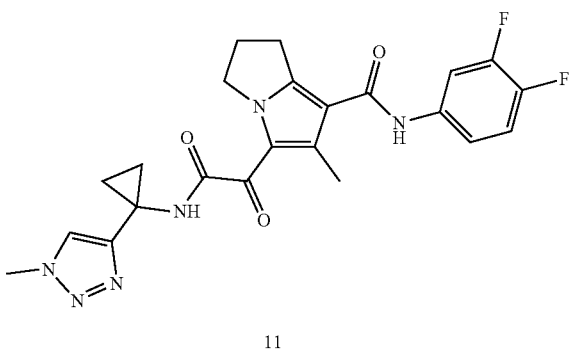

11

N-(3,4-difluorophenyl)-6-methyl-5-(2-((1-(1-methyl-1H-1,2,3-triazol-4-yl)cyclopropyl)amino)-2-oxoacetyl)-2,3-dihydro-1H-pyrrolizine-7-carboxamide To a solution of N-(3,4-difluorophenyl)-6-methyl-5-(2-oxo-2-((1-(1-((trimethylsilyl)methyl)-1H-1,2,3-triazol-4-yl)cyclopropyl)amino)acetyl)-2,3-dihydro-1H-pyrrolizine-7-carboxamide (Example 12) (28.8 mg, 0.05 mmol) in tetrahydrofuran (1.8 mL) was added a 1M solution of tetra-N-butylammonium fluoride in tetrahydrofuran (0.2 mL). The reaction mixture was stirred for 20 minutes at which point it was concentrated under reduced pressure, dissolved in N,N-dimethylformamide, passed through a syringe filter and purified by preparative hplc (10-100% acetonitrile in water, 0.1% TFA buffer) to afford the product.

Example 12. N-(3,4-difluorophenyl)-6-methyl-5-(2-oxo-2-((1-(1-((trimethylsilyl)methyl)-1H-1,2,3-triazol-4-yl)cyclopropyl)amino)acetyl)-2,3-dihydro-1H-pyrrolizine-7-carboxamide (12)

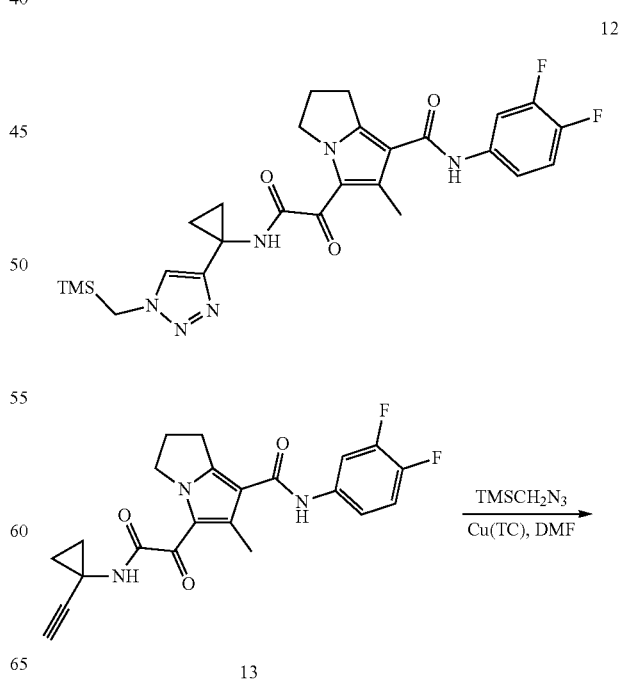

-continued

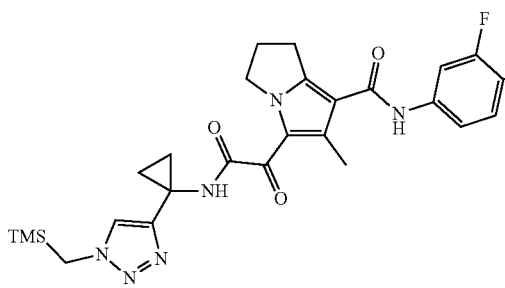

12
N-(3,4-difluorophenyl)-6-methyl-5-(2-oxo-2-((1-(1-(((trimethylsilyl)methyl)-1H-1,2,3-triazol-4-yl)cyclopropyl)amino)acetyl)-2,3-dihydro-1H-pyrrolizine-7-carboxamide A solution of N-(3,4-difluorophenyl)-5-(2-((1-ethynylcyclopropyl)amino)-2-oxoacetyl)-6-methyl-2,3-dihydro-1H-pyrrolizine-7-carboxamide (Example 13) (55.8 mg, 0.14 mmol), (trimethylsilyl)methyl azide (0.03 mL, 0.2 mmol), and copper(I) thiophene-2-carboxylate (26.4 mg, 0.14 mmol) in N,N-dimethylformamide (2 mL) was stirred at 80° C. for 40 minutes at which point it was cooled to room temperature and partitioned between water and ethyl acetate. The organic phase was sequentially washed with 5% aqueous lithium chloride then saturated aqueous sodium chloride, dried over sodium sulfate, filtered, concentrated under reduced pressure, and purified by silica gel column chromatography (0-7% methanol:dichloromethane) to afford the product.

Example 13. N-(3,4-difluorophenyl)-5-(2-((1-ethynylcyclopropyl)amino)-2-oxoacetyl)-6-methyl-2,3-dihydro-1H-pyrrolizine-7-carboxamide (13)

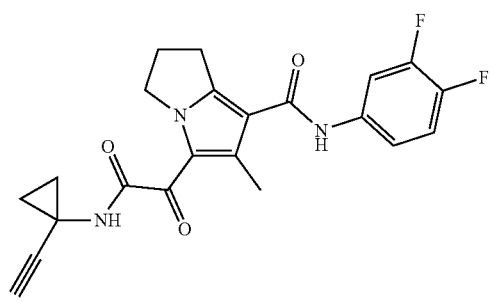

13

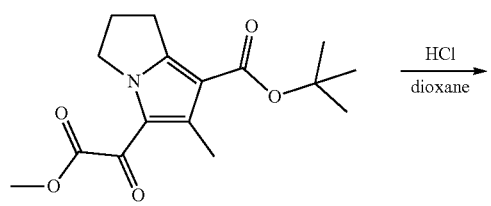

tert-butyl 5-(2-methoxy-2-oxoacetyl)-6-methyl-2,3-dihydro-1H-pyrrolizine-7-carboxylate

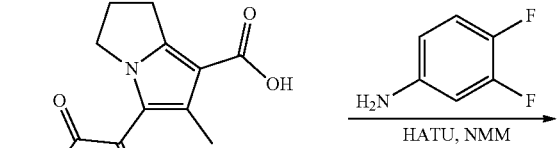

5-(2-methoxy-2-oxoacetyl)-6-methyl-2,3-dihydro-1H-pyrrolizine-7-carboxylic acid

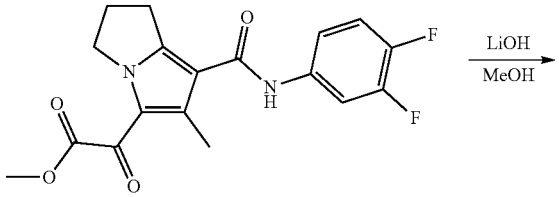

methyl 2-(7-((3,4-difluorophenyl)carbamoyl)-6-methyl-2,3-dihydro-1H-pyrrolizin-5-yl)-2-oxoacetate

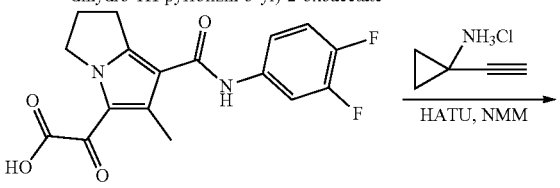

2-(7-((3,4-difluorophenyl)carbamoyl)-6-methyl-2,3-dihydro-1H-pyrrolizin-5-yl)-2-oxoacetic acid

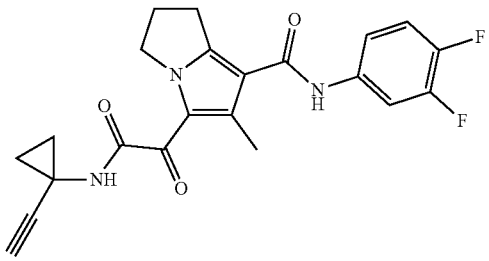

13
N-(3,4-difluorophenyl)-5-(2-((1-ethynylcyclopropyl)amino)-2-oxoacetyl)-6-methyl-2,3-dihydro-1H-pyrrolizine-7-carboxamide A solution of tert-butyl 5-(2-methoxy-2-oxoacetyl)-6-methyl-2,3-dihydro-1H-pyrrolizine-7-carboxylate (763 mg, 2.48 mmol) in 4M hydrogen chloride in dioxane (20 mL) was stirred at 40° C. for 2.5 h at which point the reaction mixture was concentrated under reduced pressure to provide 5-(2-methoxy-2-oxoacetyl)-6-methyl-2,3-dihydro-1H-pyrrolizine-7-carboxylic acid which was carried forward without further purification.

A solution of 5-(2-methoxy-2-oxoacetyl)-6-methyl-2,3-dihydro-1H-pyrrolizine-7-carboxylic acid (624 mg, 2.48 mmol), 3,4-difluoroaniline (1.5 mL, 15.1 mmol), N-methylmorpholine (1.2 mL, 10.9 mmol), and (1-[Bis(dimethylamino)methylene]-1H-1,2,3-triazolo[4,5-b]pyridinium 3-oxid hexafluorophosphate) (1.10 g, 2.89 mmol) in N-methyl-2-pyrrolidone (1.5 mL) was stirred at 100° C. 1 h at which point the reaction mixture was cooled to room temperature, diluted with ethyl acetate, and sequentially washed with 1N aqueous hydrogen chloride, 5% aqueous lithium chloride, and brine, then dried over sodium sulfate, filtered, and concentrated under reduced pressure. The resultant residue was purified by silica gel column chromatography (0-100% ethyl acetate:hexanes) to afford methyl 2-(7-((3,4-difluorophenyl)carbamoyl)-6-methyl-2,3-dihydro-1H-pyrrolizin-5-yl)-2-oxoacetate.

To a solution of methyl 2-(7-((3,4-difluorophenyl)carbamoyl)-6-methyl-2,3-dihydro-1H-pyrrolizin-5-yl)-2-oxoacetate (751 mg, 2.07 mmol) in methanol (16 mL) was added a 2N solution of aqueous lithium hydroxide (2.6 mL). The reaction mixture was stirred for 15 minutes at which point it was diluted with water, acidified with aqueous hydrogen chloride, and product extracted into dichloromethane. The combined organics were dried over sodium sulfate, filtered, and concentrated under reduced pressure to afford 2-(7-((3,4-difluorophenyl)carbamoyl)-6-methyl-2,3-dihydro-1H-pyrrolizin-5-yl)-2-oxoacetic acid which was carried on without further purification.

A solution of 2-(7-((3,4-difluorophenyl)carbamoyl)-6-methyl-2,3-dihydro-1H-pyrrolizin-5-yl)-2-oxoacetic acid (85.6 mg, 0.25 mmol), ethynylcyclopropylamine hydrogen chloride (62 mg, 0.53 mmol), N-methylmorpholine (0.1 mL, 0.91 mmol), and (1-[Bis(dimethylamino)methylene]-1H-1,2,3-triazolo[4,5-b]pyridinium 3-oxid hexafluorophosphate) (123 mg, 0.32 mmol) in N-methyl-2-pyrrolidone (1 mL) was stirred at room temperature for 10 minutes at which point the reaction mixture was diluted with ethyl acetate and sequentially washed with 1M aqueous hydrogen chloride, 5% aqueous sodium bicarbonate, 5% aqueous lithium chloride, and saturated aqueous sodium chloride. The organic phase was then dried over sodium sulfate, filtered, and concentrated under reduced pressure. The resultant residue was purified by silica gel column chromatography (0-100% ethyl acetate:hexanes) to afford N-(3,4-difluorophenyl)-5-(2-((1-ethynylcyclopropyl)amino)-2-oxoacetyl)-6-methyl-2,3-dihydro-1H-pyrrolizine-7-carboxamide (13).

Example 14. (1aS,6bR)-4-(2-((3,3-difluoro-1-(1H-1,2,3-triazol-4-yl)cyclobutyl)amino)-2-oxoacetyl)-N-(4-fluorophenyl)-5-methyl-1,1a,2,6b-tetrahydrocyclopropa[a]pyrrolizine-6-carboxamide (14)

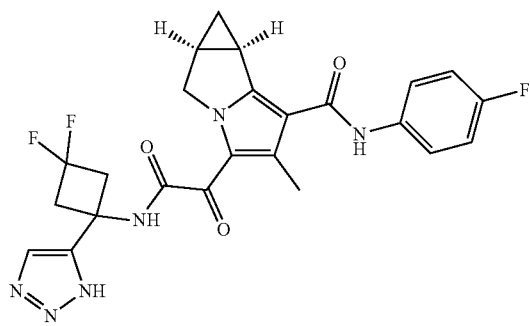

14

The product was synthesized in a manner similar to Example 34 using (1R,2S,5S)-3-azabicyclo[3.1.0]hexane-2-carboxylic acid in place of (1R,3S,5R)-3-(hydroxy(oxo)-λ5-methyl)-2-azabicyclo[3.1.0]hexane and 4-fluoroaniline in place of 3,4-difluoroaniline.

Example 15. N-(3-cyano-4-fluorophenyl)-5-(2-((3,3-difluoro-1-(1H-1,2,3-triazol-4-yl)cyclobutyl)amino)-2-oxoacetyl)-6-methyl-2,3-dihydro-1H-pyrrolizine-7-carboxamide (15)

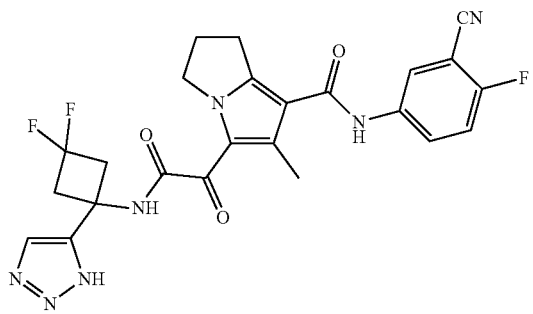

15

The product was synthesized in a manner similar to Example 1 using 3,3-difluoro-1-(1H-1,2,3-triazol-5-yl)cyclobutan-1-amine hydrogen chloride in place of 3,3-difluoro-1-(1,3,4-thiadiazol-2-yl)cyclobutan-1-amine hydrogen chloride and 3-cyano-4-fluoroaniline in place of 3,4,5-trifluoroaniline.

Synthesis of 3,3-difluoro-1-(1H-1,2,3-triazol-4-yl)cyclobutan-1-aminium chloride

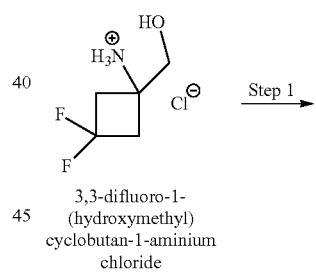

3,3-difluoro-1-(hydroxymethyl)cyclobutan-1-aminium chloride

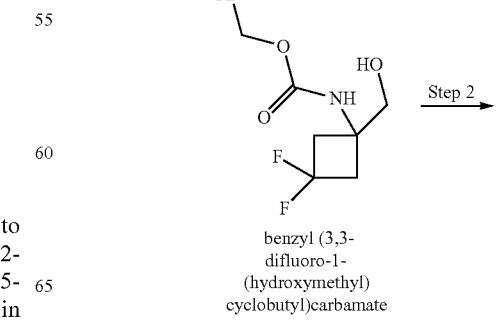

benzyl (3,3-difluoro-1-(hydroxymethyl)cyclobutyl)carbamate

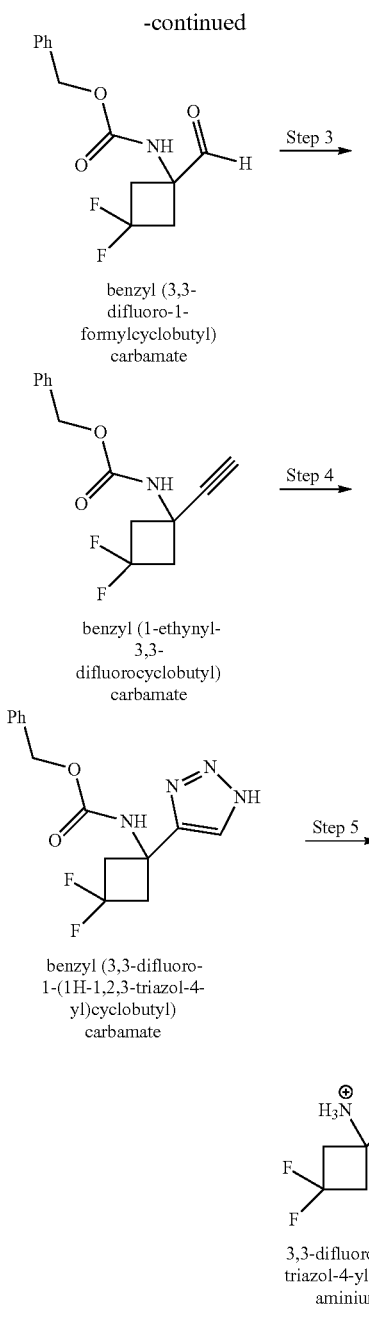

benzyl (3,3-difluoro-1-formylcyclobutyl)carbamate benzyl (1-ethynyl-3,3-difluorocyclobutyl)carbamate benzyl (3,3-difluoro-1-(1H-1,2,3-triazol-4-yl)cyclobutyl)carbamate 3,3-difluoro-1-(1H-1,2,3-triazol-4-yl)cyclobutan-1-aminium chloride Benzyl (2,5-dioxopyrrolidin-1-yl) carbonate (696 mg, 2.79 mmol) was added as a solid to a stirred mixture of 3,3-difluoro-1-(hydroxymethyl)cyclobutan-1-aminium chloride (485 mg, 2.79 mmol) and N-ethyl-N-isopropylpropan-2-amine (1.22 mL, 6.99 mmol) in dichloromethane (20 mL) at ambient temperature. After 19 h, water (5 mL) and diethyl ether (100 mL) were added sequentially. The organic layer was washed with aqueous hydrogen chloride solution (2×70 mL) and water (70 mL), was dried over anhydrous magnesium sulfate, was filtered, and was concentrated under reduced pressure. The residue was dissolved in dichloromethane (20 mL), and the resulting solution was stirred at ambient temperature. Dess-Martin periodinane (1.78 g, 4.19 mmol) was added as a solid. After 4 h, aqueous sodium thiosulfate solution (1.0 M, 25 mL) and diethyl ether (100 mL) were added sequentially. The organic layer was washed with saturated aqueous sodium bicarbonate solution (2×100 mL) and water (100 mL), was dried over anhydrous magnesium sulfate, was filtered, and was concentrated under reduced pressure. The residue was dissolved in methanol (20 mL), potassium carbonate (1.16 g, 8.38 mmol) was added as a solid, and the resulting heterogeneous mixture was stirred at 0° C. Dimethyl (1-diazo-2-oxopropyl)phosphonate (629 µL, 4.19 mmol) was added via syringe. After 5 min, the reaction mixture was warmed to ambient temperature. After 15 h, the reaction mixture was filtered through celite, and the filter cake was extracted with ethyl acetate (80 mL). The filtrate was concentrated under reduced pressure, and the residue was dissolved in diethyl ether (100 mL). The organic layer was washed with water (50 mL), was dried over anhydrous magnesium sulfate, was filtered, and was concentrated under reduced pressure. The residue was purified by flash column chromatography on silica gel (0 to 10% ethyl acetate in hexanes) to give benzyl (1-ethynyl-3,3-difluorocyclobutyl)carbamate.

Azidotrimethylsilane (344 µL, 2.59 mmol) was added via syringe to a stirred mixture of benzyl (1-ethynyl-3,3-difluorocyclobutyl)carbamate (491 mg, 1.85 mmol) and copper(I) iodide (17.6 mg, 92.5 µmol) in N,N-dimethylformamide (3.5 mL) and methanol (0.4 mL) at ambient temperature, and the resulting mixture was heated to 100° C. After 6 h, the reaction mixture was cooled to ambient temperature, and diethyl ether (130 mL) was added. The organic layer was washed sequentially with a mixture of brine and water (1:1, 100 mL) and water (100 mL), was dried over anhydrous magnesium sulfate, was filtered, and was concentrated under reduced pressure. The residue was purified by flash column chromatography on silica gel (0 to 40% ethyl acetate in hexanes) to give benzyl (3,3-difluoro-1-(1H-1,2,3-triazol-4-yl)cyclobutyl)carbamate.

A heterogeneous mixture of benzyl (3,3-difluoro-1-(1H-1,2,3-triazol-4-yl)cyclobutyl)carbamate (307 mg, 0.995 mmol) and palladium on activated carbon (10% wt/wt, 248 mg, 23.3 µmol) in ethanol (10 mL) at ambient temperature was placed under 1 atm of hydrogen gas and stirred vigorously. After 1.5 h, the reaction mixture was filtered through celite, and the filter cake was extracted with ethyl acetate (80 mL). Hydrogen chloride solution (4 M in 1,4-dioxane, 0.5 mL) was added via syringe to the filtrate, and the resulting mixture was swirled vigorously for 1 min and then concentrated under reduced pressure to give 3,3-difluoro-1-(1H-1,2,3-triazol-4-yl)cyclobutan-1-aminium chloride.

Example 16. N-(3-chloro-4-fluorophenyl)-5-(2-((3,3-difluoro-1-(1H-1,2,3-triazol-4-yl)cyclobutyl)amino)-2-oxoacetyl)-6-methyl-2,3-dihydro-1H-pyrrolizine-7-carboxamide (16)

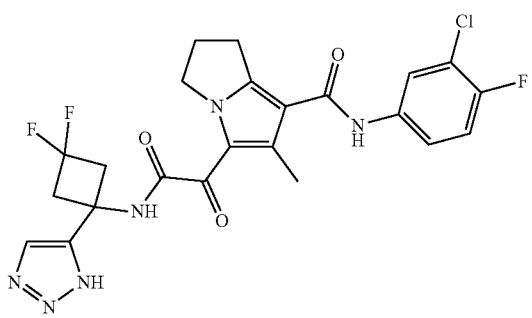

16

The product was synthesized in a manner similar to Example 15 using 3-chloro-4-fluoroaniline in place of 3-cyano-4-fluoroaniline.

Example 17. 5-(2-((3,3-difluoro-1-(1H-1,2,3-triazol-4-yl)cyclobutyl)amino)-2-oxoacetyl)-N-(4-fluorophenyl)-6-methyl-2,3-dihydro-1H-pyrrolizine-7-carboxamide (17)

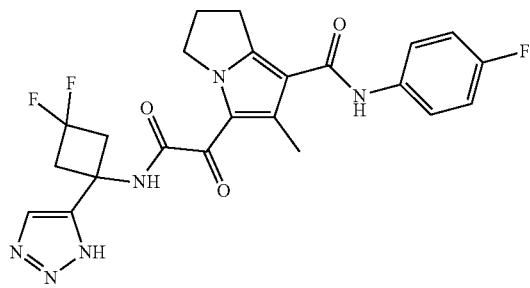

The product was synthesized in a manner similar to Example 15 using 4-fluoroaniline in place of 3-cyano-4-fluoroaniline.

Example 18. 5-(2-((3,3-difluoro-1-(1H-1,2,3-triazol-4-yl)cyclobutyl)amino)-2-oxoacetyl)-6-methyl-N-(3,4,5-trifluorophenyl)-2,3-dihydro-1H-pyrrolizine-7-carboxamide (18)

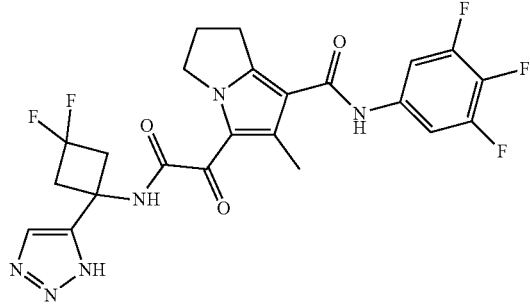

The product was synthesized in a manner similar to Example 15 using 3,4,5-trifluoroaniline in place of 3-cyano-4-fluoroaniline.

Example 19. 5-(2-((3,3-difluoro-1-(hydroxymethyl)cyclobutyl)amino)-2-oxoacetyl)-N-(3,4-difluorophenyl)-6-methyl-2,3-dihydro-1H-pyrrolizine-7-carboxamide

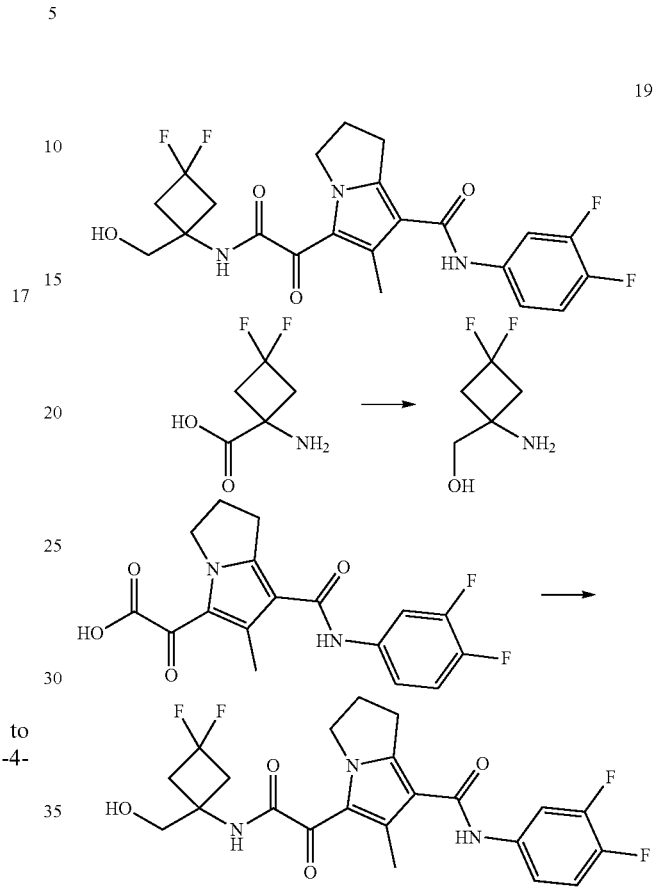

A flame dried microwave vial was charged with 1-amino-3,3-difluorocyclobutane-1-carboxylic acid (250 mg 1.65 mmol) and then purged with nitrogen and dissolved in anhydrous THF and cooled to 0° C. Then lithium aluminum hydride (1M in THF, 0.8 mL) was added. The mixture stirred in an ice bath and after the addition is complete the ice bath is removed, and the reaction mixture is warmed to room temperature and then heated to 50° C. overnight. The reaction mixture is then cooled again and diluted with THF. The reaction is quenched over a 30-min period with water, aqueous 15% sodium hydroxide and water. The solution is stirred for 30 min and the white precipitate is filtered. The filter cake is washed with ethyl ether (3×150 mL) and the organic filtrates are combined, and the filtrate was concentrated using ACN to azeotrope the water. The crude product material was then used in the next reaction.

2-(7-((3,4-difluorophenyl)carbamoyl)-6-methyl-2,3-dihydro-1H-pyrrolizin-5-yl)-2-oxoacetic acid (40 mg 0.072 mmol) HATU (20 mg 0.086 mmol) were dissolved in 0.5 mL of DMF then NMM (0.05 mL 44 mg 0.431 mmol) was added. (1-amino-3,3-difluorocyclobutyl)methanol (40 mg 0.287 mmol) was dissolved in 0.25 mL of DMF and added to the reaction mixture. This was stirred at rt for 3 h, until no further reaction by LCMS. The reaction was diluted in EtOAc, washed with 1N (aq) HCl, (3×), NaHCO₃ (3×) and brine (1×), the organic layer was dried over MgSO4 filtered then concentrated. The crude material was then purified on prep HPLC to yield 5-(2-((3,3-difluoro-1-(hydroxymethyl)

cyclobutyl)amino)-2-oxoacetyl)-N-(3,4-difluorophenyl)-6-methyl-2,3-dihydro-1H-pyrrolizine-7-carboxamide (15 mg 28%). ES/MS m/z: calculated for C22H21F4N3O4+H: 468.1541, found: M+H 468.18. $^1$H NMR (400 MHz, Acetonitrile-$d_3$) δ 8.10 (s, 1H), 7.78 (ddd, J=13.2, 7.4, 2.5 Hz, 1H), 7.42 (s, 1H), 7.31 (d, J=8.8 Hz, 1H), 7.28-7.18 (m, 1H), 4.31-4.19 (m, 2H), 3.73 (d, J=1.0 Hz, 2H), 3.10 (t, J=7.5 Hz, 3H), 3.02-2.75 (m, 5H), 2.54 (q, J=7.4 Hz, 2H), 2.48 (s, 3H).

Example 20. 5-(2-((3,3-difluoro-1-(methylcarbamoyl)cyclobutyl)amino)-2-oxoacetyl)-N-(2-(difluoromethyl)-3-fluoropyridin-4-yl)-6-methyl-2,3-dihydro-1H-pyrrolizine-7-carboxamide

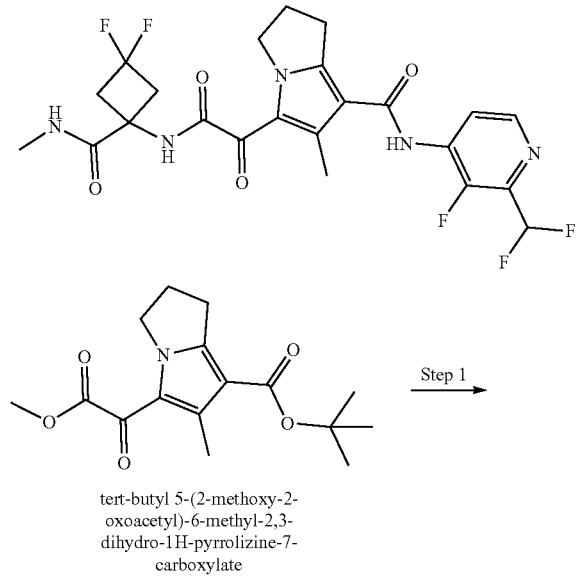

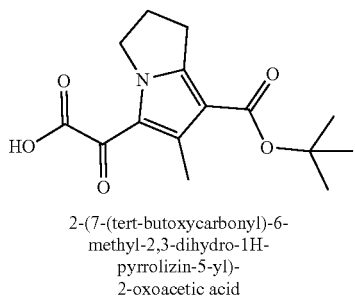

2-(7-(tert-butoxycarbonyl)-6-methyl-2,3-dihydro-1H-pyrrolizin-5-yl)-2-oxoacetic acid

+

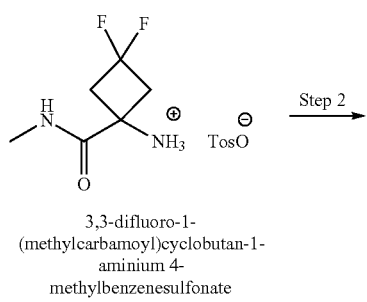

3,3-difluoro-1-(methylcarbamoyl)cyclobutan-1-aminium 4-methylbenzenesulfonate

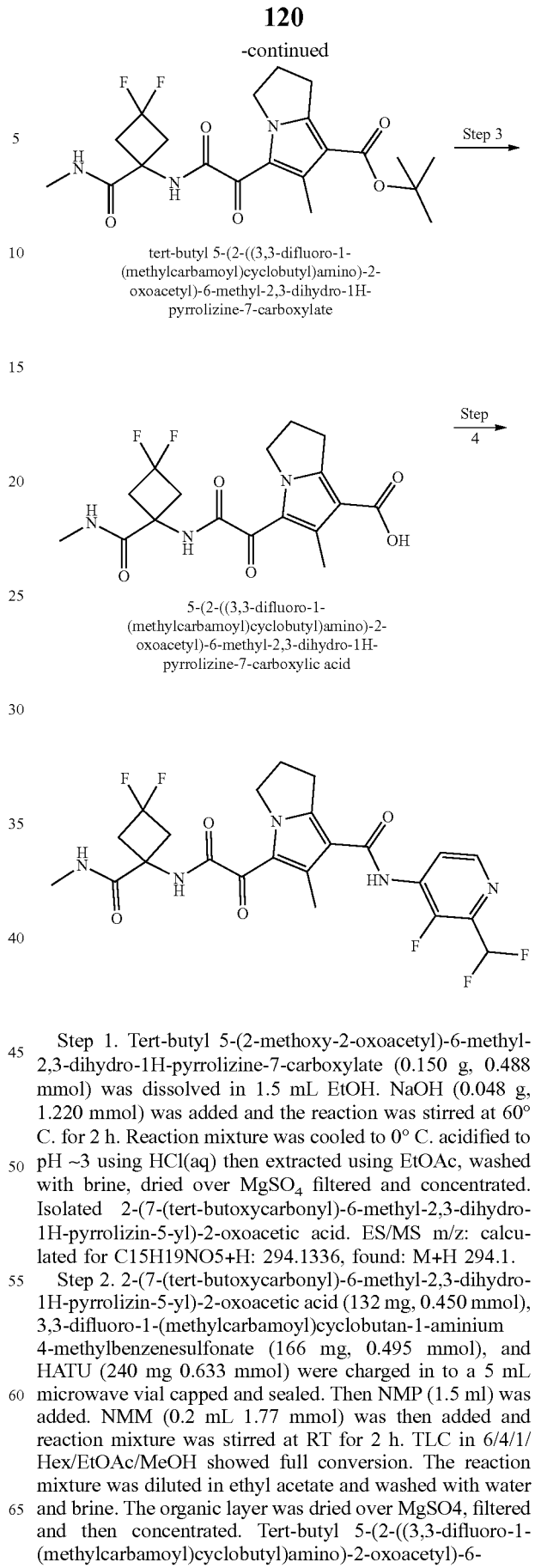

Step 1. Tert-butyl 5-(2-methoxy-2-oxoacetyl)-6-methyl-2,3-dihydro-1H-pyrrolizine-7-carboxylate (0.150 g, 0.488 mmol) was dissolved in 1.5 mL EtOH. NaOH (0.048 g, 1.220 mmol) was added and the reaction was stirred at 60° C. for 2 h. Reaction mixture was cooled to 0° C. acidified to pH ~3 using HCl(aq) then extracted using EtOAc, washed with brine, dried over MgSO$_4$ filtered and concentrated. Isolated 2-(7-(tert-butoxycarbonyl)-6-methyl-2,3-dihydro-1H-pyrrolizin-5-yl)-2-oxoacetic acid. ES/MS m/z: calculated for C15H19NO5+H: 294.1336, found: M+H 294.1.

Step 2. 2-(7-(tert-butoxycarbonyl)-6-methyl-2,3-dihydro-1H-pyrrolizin-5-yl)-2-oxoacetic acid (132 mg, 0.450 mmol), 3,3-difluoro-1-(methylcarbamoyl)cyclobutan-1-aminium 4-methylbenzenesulfonate (166 mg, 0.495 mmol), and HATU (240 mg 0.633 mmol) were charged in to a 5 mL microwave vial capped and sealed. Then NMP (1.5 ml) was added. NMM (0.2 mL 1.77 mmol) was then added and reaction mixture was stirred at RT for 2 h. TLC in 6/4/1/ Hex/EtOAc/MeOH showed full conversion. The reaction mixture was diluted in ethyl acetate and washed with water and brine. The organic layer was dried over MgSO4, filtered and then concentrated. Tert-butyl 5-(2-((3,3-difluoro-1-(methylcarbamoyl)cyclobutyl)amino)-2-oxoacetyl)-6- methyl-2,3-dihydro-1H-pyrrolizine-7-carboxylate was recovered and carried forward as crude. ES/MS m/z: calculated for C21H27F2N3O5+H: 440.1992, found: M+H 440.2.

Step 3. tert-butyl 5-(2-((3,3-difluoro-1-(methylcarbamoyl)cyclobutyl)amino)-2-oxoacetyl)-6-methyl-2,3-dihydro-1H-pyrrolizine-7-carboxylate (274 mg, 0.623 mmol) was dissolved in DCM (2 mL) and the reaction was cooled to 0° C. Then TFA (0.3 mL) was added and the reaction was stirred for 2 h. TLC 1/1 Hex/EtOAc showed no SM. Reaction mixture was concentrated to yield 5-(2-((3,3-difluoro-1-(methylcarbamoyl)cyclobutyl)amino)-2-oxoacetyl)-6-methyl-2,3-dihydro-1H-pyrrolizine-7-carboxylic acid. ES/MS m/z: calculated for C17H19F2N3O5+Na: 406.1185, found: M+H 406.21.

Step 4. 5-(2-((3,3-difluoro-1-(methylcarbamoyl)cyclobutyl)amino)-2-oxoacetyl)-6-methyl-2,3-dihydro-1H-pyrrolizine-7-carboxylic acid (75 mg, 0.196 mmol) 2-(difluoromethyl)-3-fluoropyridin-4-aminium chloride (213 mg, 1.07 mmol) and 1-Propanephosphonic anhydride solution (74.7 mg, 0.23 mmol) 50 wt % in EtOAc (140 mg, 0.274 mmol) was charged into microwave vial, and dissolved in DMF 1 mL. Then NMM was added 0.2 mL and the reaction was stirred at 100° C. for 5 h. No starting material detected by LCMS. The reaction was diluted with EtOAc, and washed with 1N HCl (2×) and NaHCO₃ (2×) and brine (1×). The organic layer was dried over MgSO4, filtered then concentrated and purified by prep HPLC to yield the desired product. ES/MS m/z: calculated for C23H22F5N5O4+Na: 528.1665, found: M+H 528.11. 1H NMR (400 MHz, Acetone-d6) δ 8.88 (s, 1H), 8.77 (s, 1H), 8.59 (t, J=5.7 Hz, 1H), 8.40 (d, J=5.4 Hz, 1H), 6.93 (t, J=53.6 Hz, 1H), 4.31 (t, J=7.3 Hz, 2H), 3.38 (td, J=15.4, 11.6 Hz, 2H), 3.27 (t, J=7.5 Hz, 2H), 3.00 (td, J=14.7, 6.6 Hz, 2H), 2.77 (d, J=4.7 Hz, 3H), 2.65-2.57 (m, 2H), 2.55 (s, 3H).

Example 21. (1aR,6bS)-4-(2-((3,3-difluoro-1-(1H-1,2,3-triazol-5-yl)cyclobutyl)amino)-2-oxoacetyl)-N-(3,4-difluorophenyl)-5-methyl-1,1a,2,6b-tetrahydrocyclopropa[a]pyrrolizine-6-carboxamide (21)

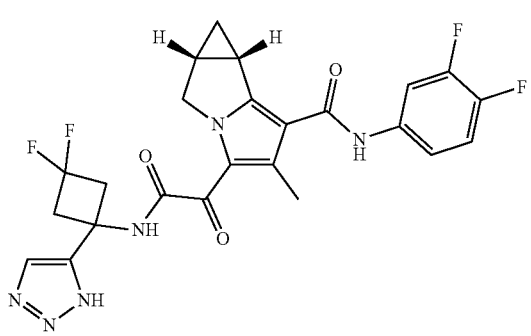

The product was synthesized in a manner similar to Example 34 using (1S,2S,5R)-3-azabicyclo[3.1.0]hexane-2-carboxylic acid in place of (1R,3S,5R)-3-(hydroxy(oxo)-λ5-methyl)-2-azabicyclo[3.1.0]hexane.

Example 22. (1aR,6bS)-4-(2-((3,3-difluoro-1-(methylcarbamoyl)cyclobutyl)amino)-2-oxoacetyl)-N-(3,4-difluorophenyl)-5-methyl-1,1a,2,6b-tetrahydrocyclopropa[a]pyrrolizine-6-carboxamide (22)

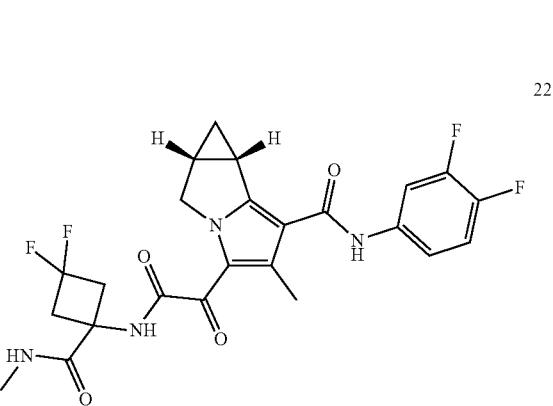 [SMILES: CNC(=O)C1(NC(=O)C(=O)c2c(C)c(C(=O)Nc3ccc(F)c(F)c3)c3n2C[C@@H]2C[C@H]32)CC(F)(F)C1]

The product was synthesized in a manner similar to Example 21 using 1-amino-3,3-difluoro-N-methylcyclobutane-1-carboxamide hydrochloride in place of 3,3-difluoro-1-(1H-1,2,3-triazol-4-yl)cyclobutan-1-aminium chloride.

Synthesis of 1-amino-3,3-difluoro-N-methylcyclobutane-1-carboxamide hydrochloride

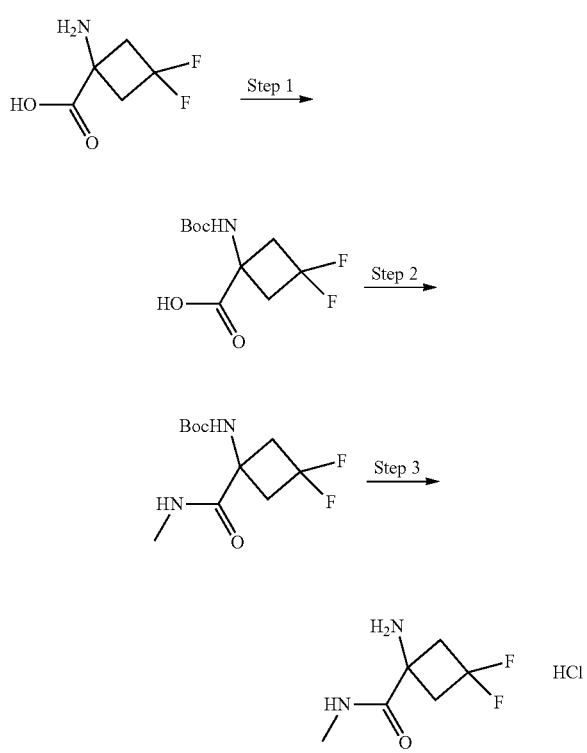

To a 0° C. solution of 1-amino-3,3-difluorocyclobutane-1-carboxylic acid (990 mg, 6.55 mmol) in methanol (8 mL) was added a 1M aqueous solution of sodium hydroxide (7 mL, 7 mmol) followed by di-tert-butyl dicarbonate (1.8 g, 8.2 g). The reaction mixture was warmed to ambient temperature was stirred for 14 h, acidified with dilute aqueous hydrogen chloride, and extracted to diethyl ether. The ethereal phase was washed with 1:1 water:brine, dried over sodium sulfate, filtered, and concentrated under reduced pressure to afford 1-((tert-butoxycarbonyl)amino)-3,3-difluorocyclobutane-1-carboxylic acid which was carried forward without further purification.

To a 0° C. solution of 1-((tert-butoxycarbonyl)amino)-3,3-difluorocyclobutane-1-carboxylic acid (1.65 g, 6.6 mmol), methanamine hydrochloride (2.28 g, 33.8 mmol), and triethylamine (7.4 mL, 53 mmol) in N,N-dimethylformamide (24 mL) was added 1-[Bis(dimethylamino)methylene]-1H-1,2,3-triazolo[4,5-b]pyridinium 3-oxid hexafluorophosphate (3.75 g, 9.86 mmol). The reaction was warmed to ambient temperature and stirred for 20 h, at which point the reaction mixture was diluted with diethyl ether, washed with a saturate aqueous solution of sodium bicarbonate, a 5% aqueous solution of lithium chloride, and brine. The ethereal phase was then dried over sodium sulfate, filtered, and concentrated under reduced pressure to afford tert-butyl (3,3-difluoro-1-(methylcarbamoyl)cyclobutyl)carbamate which was carried forward without further purification.

Tert-butyl (3,3-difluoro-1-(methylcarbamoyl)cyclobutyl) carbamate (1.3 g, 4.92 mmol) was dissolved in a 4M solution of hydrogen chloride in dioxane (20 mL, 80 mmol) and stirred at 90° C. for 90 minutes. Solvent was removed under reduced pressure, twice azeotroping with toluene, and the resultant material dried under high vacuum to afford 1-amino-3,3-difluoro-N-methylcyclobutane-1-carboxamide hydrochloride: 1H NMR (400 MHz, DMSO-d6) δ 8.86 (s, 3H), 8.44 (s, 1H), 3.27 (dd, J=13.3, 7.5 Hz, 2H), 3.05 (q, J=14.3 Hz, 2H), 2.69 (d, J=4.5 Hz, 3H).

Example 23. (1aS,6aS)-3-(2-((3,3-difluoro-1-(1H-1,2,3-triazol-5-yl)cyclobutyl)amino)-2-oxoacetyl)-N-(3,4-difluorophenyl)-4-methyl-1,1a,6,6a-tetrahydrocyclopropa[b]pyrrolizine-5-carboxamide (23)

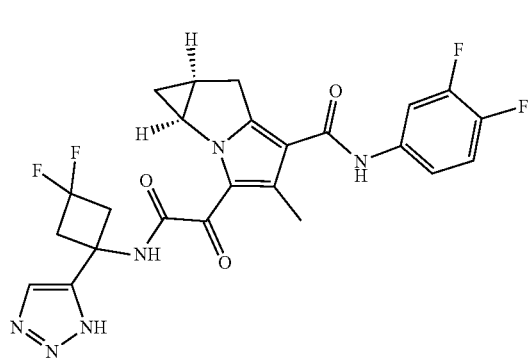

23

The product was synthesized in a manner similar to Example 34 using (1S,3S,5S)-2-azabicyclo[3.1.0]hexane-3-carboxylic acid in place of (1R,3S,5R)-3-(hydroxy(oxo)-λ5-methyl)-2-azabicyclo[3.1.0]hexane.

Example 24. (1aS,6aS)-3-(2-((3,3-difluoro-1-(methylcarbamoyl)cyclobutyl)amino)-2-oxoacetyl)-N-(3,4-difluorophenyl)-4-methyl-1,1a,6,6a-tetrahydrocyclopropa[b]pyrrolizine-5-carboxamide (24)

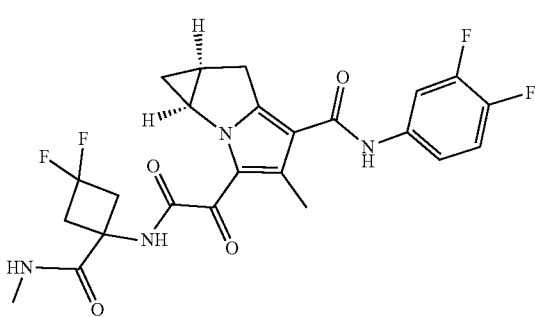

24

The product was synthesized in a manner similar to Example 23 using 1-amino-3,3-difluoro-N-methylcyclobutane-1-carboxamide hydrochloride in place of 3,3-difluoro-1-(1H-1,2,3-triazol-4-yl)cyclobutan-1-aminium chloride.

Example 25. (1aS,6bR)-4-(2-((3,3-difluoro-1-(1H-1,2,3-triazol-5-yl)cyclobutyl)amino)-2-oxoacetyl)-N-(3,4-difluorophenyl)-5-methyl-1,1a,2,6b-tetrahydrocyclopropa[a]pyrrolizine-6-carboxamide (25)

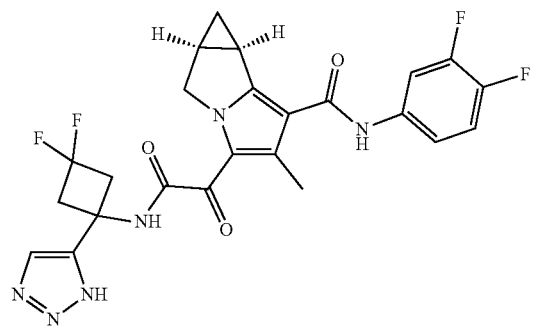

25

The product was synthesized in a manner similar to Example 14 using 3,4-difluoroaniline in place of 4-fluoroaniline.

125

Example 26. (1aS,6bR)-4-(2-((3,3-difluoro-1-(methylcarbamoyl)cyclobutyl)amino)-2-oxoacetyl)-N-(3,4-difluorophenyl)-5-methyl-1,1a,2,6b-tetrahydrocyclopropa[a]pyrrolizine-6-carboxamide (26)

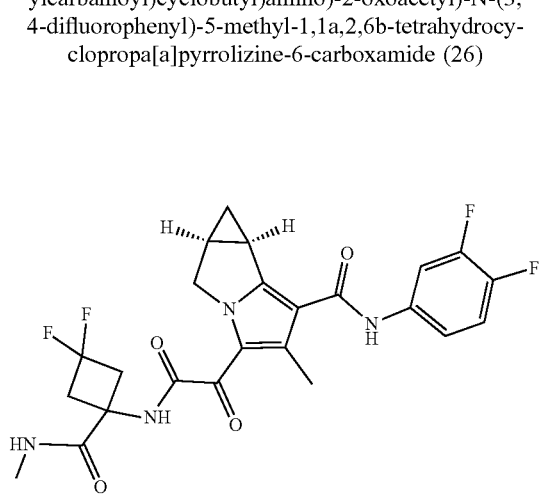

26

The product was synthesized in a manner similar to Example 25 using 1-amino-3,3-difluoro-N-methylcyclobutane-1-carboxamide hydrochloride in place of 3,3-difluoro-1-(1H-1,2,3-triazol-5-yl)cyclobutan-1-amine hydrogen chloride.

Example 27. 5-(2-((1-(1H-1,2,3-triazol-4-yl)cyclopropyl)amino)-2-oxoacetyl)-N-(3-(difluoromethyl)-4-fluorophenyl)-6-methyl-2,3-dihydro-1H-pyrrolizine-7-carboxamide

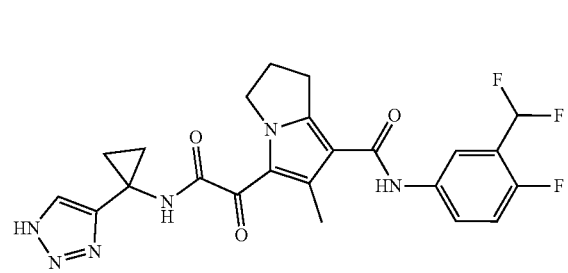

27
5-(2-methoxy-2-oxoacetyl)-6-methyl-2,3-dihydro-1H-pyrrolizine-7-carboxylic acid

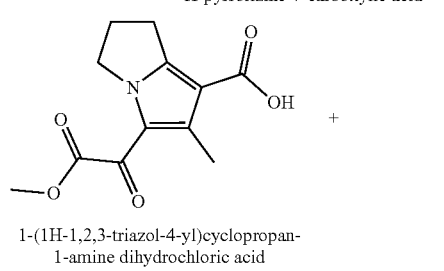

1-(1H-1,2,3-triazol-4-yl)cyclopropan-1-amine dihydrochloric acid

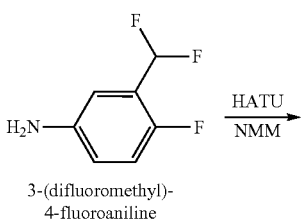

3-(difluoromethyl)-4-fluoroaniline

126

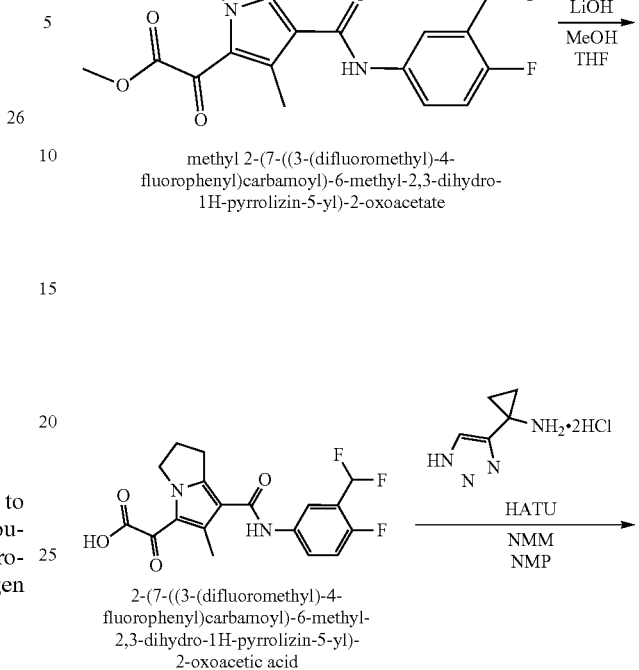

Methyl 2-(7-((3-(difluoromethyl)-4-fluorophenyl)carbamoyl)-6-methyl-2,3-dihydro-1H-pyrrolizin-5-yl)-2-oxoacetate was prepared as described in Example 1 using 3-(difluoromethyl)-4-fluoroaniline in place of 3,4,5-trifluoroaniline. ES/MS m/z: calculated for C19H18F3N2O4: 395.11, found: 395.42.

2-(7-(3-(Difluoromethyl)-4-fluorophenyl)carbamoyl)-6-methyl-2,3-dihydro-1H-pyrrolizin-5-yl)-2-oxoacetic acid was prepared as described in example 1. ES/MS m/z: calculated for C18H16F3N2O4: 381.10, found: 381.36.

The product was prepared as described in Example 1 using 1-(1H-1,2,3-triazol-4-yl)cyclopropan-1-amine dihydrochloric acid in place of 3,3-difluoro-1-(1,3,4-thiadiazol-2-yl)cyclobutan-1-amine. $^1$H NMR (400 MHz, Acetone-d6) δ 8.88 (s, 1H), 8.57 (s, 1H), 8.08 (d, J=6.4 Hz, 1H), 7.90 (s, 1H), 7.68 (s, 1H), 7.27 (t, J=9.4 Hz, 1H), 7.10 (t, J=54.5 Hz, 1H), 4.27 (t, J=7.5 Hz, 2H), 3.18 (t, J=7.5 Hz, 2H), 2.55 (quin, J=7.5 Hz, 2H), 2.46 (s, 3H), 1.50-1.28 (m, 4H). ES/MS m/z: calculated for C23H22F3N6O3: 487.16, found: 487.54.

Synthesis of 1-(1H-1,2,3-triazol-4-yl)cyclopropan-1-amine dihydrochloric acid

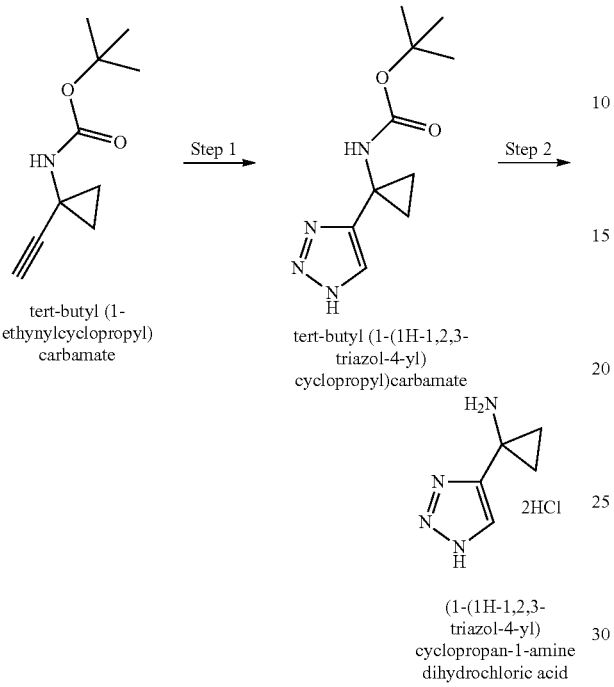

tert-butyl (1-ethynylcyclopropyl) carbamate tert-butyl (1-(1H-1,2,3-triazol-4-yl) cyclopropyl)carbamate (1-(1H-1,2,3-triazol-4-yl) cyclopropan-1-amine dihydrochloric acid Step 1. tert-Butyl (1-ethynylcyclopropyl)carbamate (200.0 mg, 1.104 mmol) was treated with azidotrimethylsilane (508.6 mg, 4.414 mmol, 4 equiv.) in the presence of copper iodide (21.0 mg, 0.11 mmol) in N,N-dimethylformamide (1 mL) and methanol (1 mL) and stirred at 110° C. for 2 h. After cooling, purification by prep HPLC gave tert-butyl (1-(1H-1,2,3-triazol-4-yl)cyclopropyl)carbamate. LCMS-ESI+ (m/z): [M+H]+ calculated for $C_{10}H_{17}N_4O_2$: 225.1; found: 225.1.

Step 2. tert-Butyl (1-(1H-1,2,3-triazol-4-yl)cyclopropyl) carbamate (243.2 mg, 1.084 mmol) was treated with hydrogen chloride (4N in 1,4-dioxane, 4 mL) in methanol (2 mL) and stirred at 110° C. for 1 h. The organic solvent was removed under a reduced pressure to give 1-(1H-1,2,3-triazol-4-yl)cyclopropan-1-amine dihydrochloric acid. LCMS-ESI+ (m/z): [M+H]+ calculated for $C_5H_9N_4$: 125.1; found: 125.1.

Example 28. N-(3-cyano-4-fluorophenyl)-5-(2-((3,3-difluoro-1-(methylcarbamoyl)cyclobutyl)amino)-2-oxoacetyl)-6-methyl-2,3-dihydro-1H-pyrrolizine-7-carboxamide

28

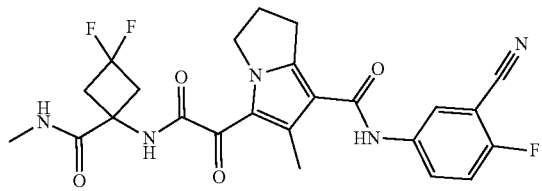

5-(2-((3,3-difluoro-1-(methylcarbamoyl)cyclobutyl) amino)-2-oxoacetyl)-6-methyl-2,3-dihydro-1H-pyrrolizine-7-carboxylic acid (75 mg, 0.196 mmol) 5-amino-2-fluorobenzonitrile (146 mg, 1.07 mmol) and HATU (64 mg, 0.274 mmol) were charged into microwave vial, and dissolved in DMF 1 mL. Then NMM was added 0.2 mL and the reaction was stirred at 100° C. for 5 h. No starting material detected by LCMS. The reaction was diluted with EtOAc, and washed with 1N HCl (2×) and NaHCO₃ (2×) and brine (1×). The organic layer was dried over MgSO4, filtered then concentrated and purified by prep HPLC to yield the desired product. ES/MS m/z: calculated for C24H22F3N5O4+Na: 524.1516, found: M+H 524.1. 1H NMR (400 MHz, Acetonitrile-d3) δ 8.16 (s, 1H), 8.04 (dd, J=5.7, 2.7 Hz, 1H), 7.97 (s, 1H), 7.87-7.79 (m, 1H), 7.28 (t, J=9.0 Hz, 1H), 4.22 (t, J=7.3 Hz, 2H), 3.35-3.23 (m, 2H), 3.07 (t, J=7.5 Hz, 2H), 2.88 (dd, J=14.8, 7.3 Hz, 2H), 2.68 (d, J=4.7 Hz, 3H), 2.50 (q, J=7.2 Hz, 2H), 2.42 (s, 3H).

Example 29. 5-(2-((1-(1,3,4-thiadiazol-2-yl)cyclopropyl)amino)-2-oxoacetyl)-6-methyl-N-(3,4,5-trifluorophenyl)-2,3-dihydro-1H-pyrrolizine-7-carboxamide (29)

29

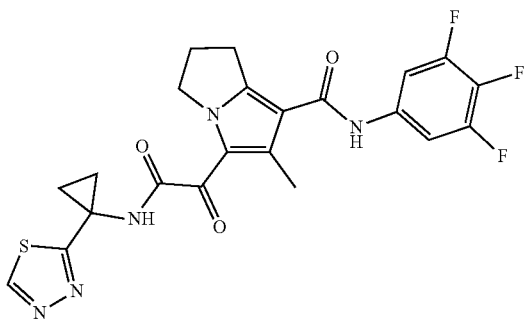

The product was synthesized in a manner similar to Example 1 using 1-(1,3,4-thiadiazol-2-yl)cyclopropan-1-amine in place of 3,3-difluoro-1-(1,3,4-thiadiazol-2-yl)cyclobutan-1-amine hydrogen chloride.

Example 30. 5-(2-((1-(1,3,4-thiadiazol-2-yl)cyclopropyl)amino)-2-oxoacetyl)-N-(4-fluorophenyl)-6-methyl-2,3-dihydro-1H-pyrrolizine-7-carboxamide (30)

30

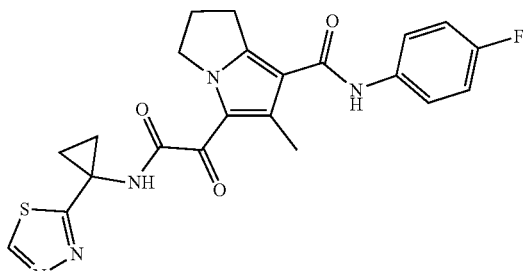

The product was synthesized in a manner similar to Example 29 using 4-fluoroaniline in place of 3,4,5-trifluoroaniline.

Example 31. 5-(2-((1-(1,3,4-thiadiazol-2-0)cyclopropyl)amino)-2-oxoacetyl)-N-(3-(difluoromethyl)-4-fluorophenyl)-6-methyl-2,3-dihydro-1H-pyrrolizine-7-carboxamide (31)

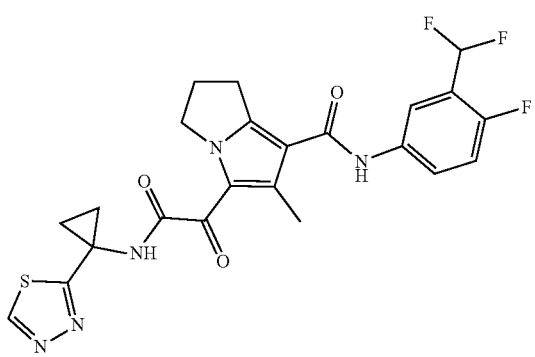

The product was synthesized in a manner similar to Example 29 using 3-(difluoromethyl)-4-fluoroaniline in place of 3,4,5-trifluoroaniline.

Example 32. 5-(2-((1-carbamoyl-3,3-difluorocyclobutyl)amino)-2-oxoacetyl)-N-(3-(difluoromethyl)-4-fluorophenyl)-6-methyl-2,3-dihydro-1H-pyrrolizine-7-carboxamide (32)

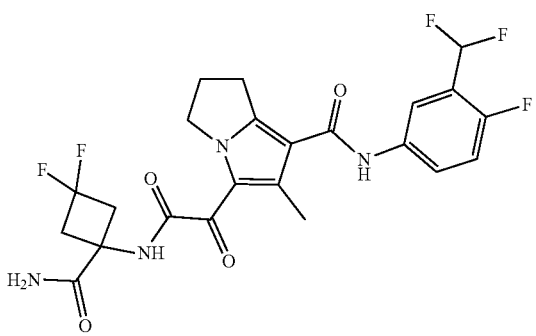

The product was synthesized in a manner similar to Example 1 using 3-(difluoromethyl)-4-fluoroaniline in place of 3,4,5-trifluoroaniline and 1-amino-3,3-difluorocyclobutane-1-carboxamide in place of 3,3-difluoro-1-(1,3,4-thiadiazol-2-yl)cyclobutan-1-amine hydrogen chloride.

Synthesis of
1-amino-3,3-difluorocyclobutane-1-carboxamide

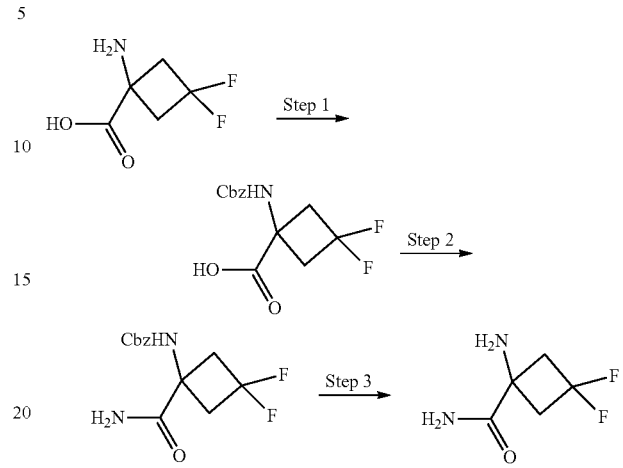

To solution of 1-amino-3,3-difluorocyclobutane-1-carboxylic acid (5.09 g, 33.7 mmol) and N,N-diisopropylethylamine (14 mL) in dichloromethane (100 mL) was added N-(benzyloxycarbonyloxy)succinimide (7.1 mL, 34.1 mmol) and the reaction mixture allowed to stir at room temperature for 2 h at which point the reaction volume was concentrated by two thirds under reduced pressure. This solution was then diluted with diethyl ether and washed with 1M aqueous hydrogen chloride then water, dried over sodium sulfate, filtered, and concentrated under reduced pressure to afford 1-(((benzyloxy)carbonyl)amino)-3,3-difluorocyclobutane-1-carboxylic acid which was carrier on without further purification.

To a 0° C. solution of 1-(((benzyloxy)carbonyl)amino)-3,3-difluorocyclobutane-1-carboxylic acid (9.61 g, 35.4 mmol), ammonium chloride (9.52 g, 178 mmol), and triethylamine (40 mL, 287 mmol) in N,N-dimethylformamide (100 mL) was added 1-[Bis(dimethylamino)methylene]-1H-1,2,3-triazolo[4,5-b]pyridinium 3-oxid hexafluorophosphate (20.4 g, 53.8 mmol). The reaction was warmed to ambient temperature and stirred for 3 h, at which point the reaction mixture was partially concentrated under reduced pressure, diluted with diethyl ether, washed sequentially with 0.25M aqueous hydrogen chloride, 5% aqueous sodium bicarbonate, 5% aqueous lithium chloride, and saturated aqueous sodium chloride solutions resulting in precipitation of product in the organic phase. This precipitate was collected by filtration to afford benzyl (1-carbamoyl-3,3-difluorocyclobutyl)carbamate which was carried forward without further purification.

To a solution of benzyl (1-carbamoyl-3,3-difluorocyclobutyl)carbamate (1.2 g, 4.44 mmol) in ethanol (20 mL) was added 10% palladium on carbon (510 mg, 0.48 mmol). This reaction mixture was place under one atmosphere hydrogen and stirred for 2 h. The reaction mixture was then filtered through celite and the resultant filtrate concentrated under reduced pressure to afford 1-amino-3,3-difluorocyclobutane-1-carboxamide which was carried on without further purification. $^1$H NMR (400 MHz, DMSO-d6) δ 7.40 (s, 1H), 7.15 (s, 1H), 3.06-2.91 (m, 2H), 2.54 (s, 2H), 2.44-2.27 (m, 2H).

Example 33. (1aR,6aR)-3-(2-((3,3-difluoro-1-(methylcarbamoyl)cyclobutyl)amino)-2-oxoacetyl)-N-(3,4-difluorophenyl)-4-methyl-1,1a,6,6a-tetrahydrocyclopropa[b]pyrrolizine-5-carboxamide

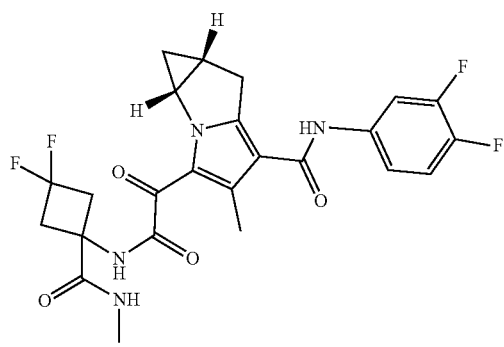 [SMILES: CNC(=O)C1(NC(=O)C(=O)c2c(C)c(C(=O)Nc3ccc(F)c(F)c3)c3n2[C@@H]2C[C@@H]2C3)CC(F)(F)C1]

The compound was synthesized in a similar manner to Example 34 except 1-amino-3,3-difluoro-N-methylcyclobutane-1-carboxamide 4-methylbenzenesulfonate was used in place of 3,3-difluoro-1-(1H-1,2,3-triazol-4-yl)cyclobutan-1-amine dihydrochloride. 1H NMR (400 MHz, DMSO-d6) δ 9.67 (d, J=19.2 Hz, 2H), 7.85-7.74 (m, 2H), 7.44-7.32 (m, 2H), 4.34 (d, J=6.2 Hz, 1H), 3.54 (s, 3H), 3.36 (dd, J=18.1, 6.8 Hz, 1H), 3.21 (t, J=14.1 Hz, 2H), 3.10 (d, J=18.2 Hz, 1H), 2.59 (d, J=4.5 Hz, 3H), 2.29 (s, 3H), 2.14 (d, J=7.6 Hz, 1H), 1.14-1.04 (m, 1H), 0.23 (d, J=4.7 Hz, 1H). LCMS-ESI+ (m/z): [M+H]+: 507.13

Example 34. (1aR,6aR)-3-(2-((3,3-difluoro-1-(1H-1,2,3-triazol-5-yl)cyclobutyl)amino)-2-oxoacetyl)-N-(3,4-difluorophenyl)-4-methyl-1,1a,6,6a-tetrahydrocyclopropa[b]pyrrolizine-5-carboxamide

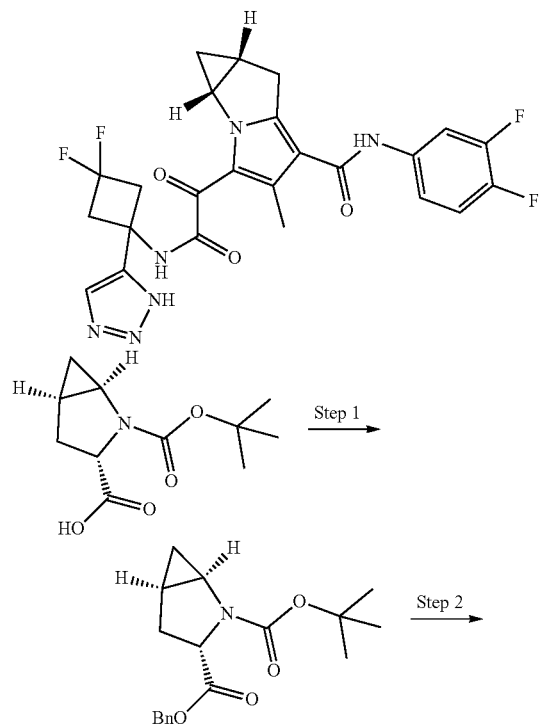

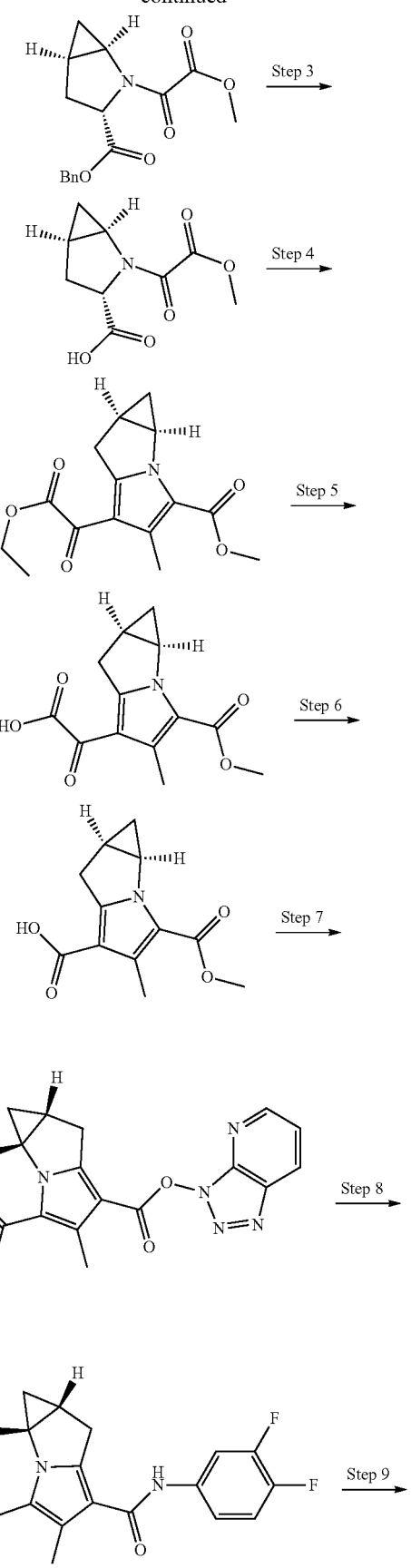

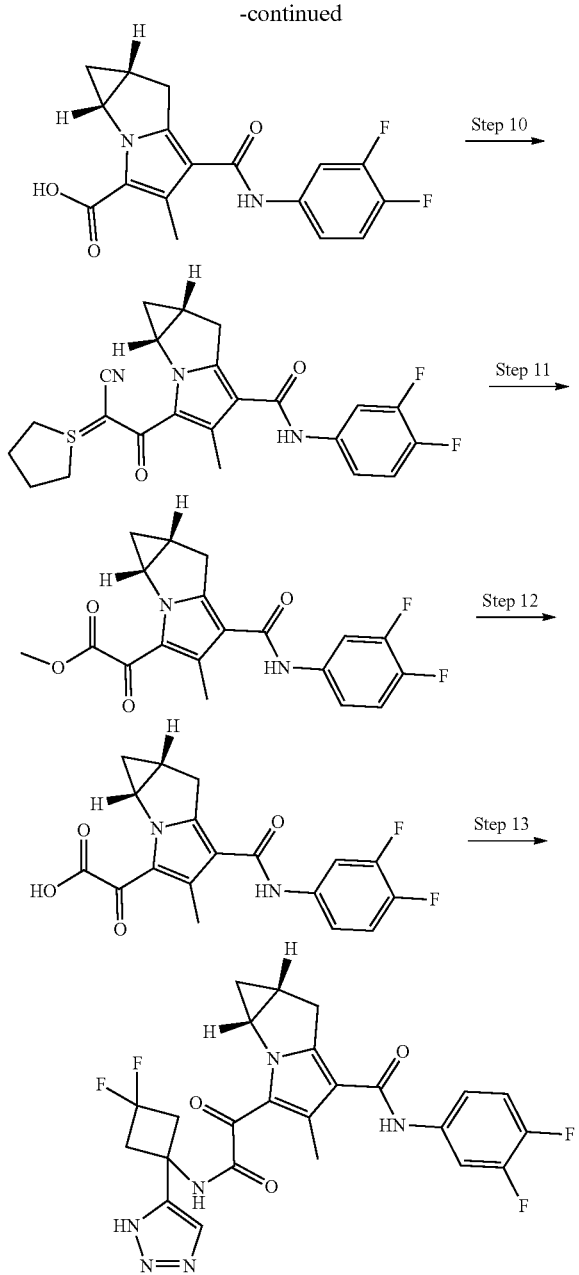

Step 1. To a solution of (1R,3S,5R)-2-(tert-butoxycarbonyl)-2-azabicyclo[3.1.0]hexane-3-carboxylic acid (10 g, 44 mmol) and cesium carbonate (21.5 g, 66 mmol) in DMF (100 mL) was added benzyl bromide (6.4 mL, 53.7 mmol). The mixture was stirred for 10 h at ambient temperature. The reaction was then partitioned with ethyl acetate (500 mL) and water (500 mL). The aqueous was then taken and extracted with ethyl acetate (300 mL) the organic was then dried over magnesium sulfate and then purified via normal phase chromatography 0-40% ethyl acetate/hexanes to give 3-benzyl 2-(tert-butyl) (1R,3S,5R)-2-azabicyclo[3.1.0]hexane-2,3-dicarboxylate.

Step 2. 3-benzyl 2-(tert-butyl) (1R,3S,5R)-2-azabicyclo[3.1.0]hexane-2,3-dicarboxylate (13.7 g, 43.1 mmol) was dissolved in DCM (120 mL). To this was added TFA (26 mL, 345 mmol) This was allowed to stir for 1 h at ambient temperature. The reaction was then condensed and coevaporated with toluene (100 mL) twice to give benzyl (1R,3S,5R)-2-(2-methoxy-2-oxoacetyl)-2-azabicyclo[3.1.0]hexane-3-carboxylate which was used crude for the next step.

Step 3. Benzyl (1R,3S,5R)-2-(2-methoxy-2-oxoacetyl)-2-azabicyclo[3.1.0]hexane-3-carboxylate was dissolved in DCM (120 mL) and to it was added DIPEA (53 mL, 304 mmol). The reaction was cooled to 0° C. in an ice bath. Then methyl oxalyl chloride (4.3 mL, 47 mmol) was added dropwise over 30 minutes. The reaction was stirred for 1 h. The reaction was then diluted with water (300 mL) and the organic phase was separated. The reaction was washed with ethyl acetate (200 mL) and the organics were combined and dried with magnesium sulfate then condensed to an oil. The oil was purified via normal phase chromatography 0-60% ethyl acetate/hexanes which was condensed to an oil. This material was then treated with 10 wt % palladium on carbon (~50% water, 1 g, 1.5 mmol) in ethanol (250 mL) was stirred under one atmosphere hydrogen for 2 h. Upon completion of reaction the crude mixture was filtered through celite with ethanol rinses and concentrated under reduced pressure to provide (1R,3S,5R)-2-(2-methoxy-2-oxoacetyl)-2-azabicyclo[3.1.0]hexane-3-carboxylic acid which was carried forward without further purification.

Step 4. To a solution of oxalyl chloride (16.4 mL, 192 mmol) and 1% DMF in toluene (0.5 mL) in toluene (60 mL) was added (1R,3S,5R)-2-(2-methoxy-2-oxoacetyl)-2-azabicyclo[3.1.0]hexane-3-carboxylic acid (37.2 mmol) in dichloromethane (80 mL) dropwise. The resulting solution was stirred at ambient temperature for 1 h. The solution was concentrated and the residue was co-evaporated with toluene (100 mL). The resulting residue was dried in vacuo for 30 min to give crude methyl 2-((1R,3S,5R)-3-(chlorocarbonyl)-2-azabicyclo[3.1.0]hexan-2-yl)-2-oxoacetate After the above crude methyl 2-((1R,3S,5R)-3-(chlorocarbonyl)-2-azabicyclo[3.1.0]hexan-2-yl)-2-oxoacetate was dissolved in acetonitrile (50 mL), 2,6-di-tert-butylpyridine (12.7 mL, 57 mmol) followed by ethyl 2-oxopent-3-ynoate (10.8 mL, 84 mmol) were added. The resulting solution was stirred at ambient temperature for 2 h. The mixture was concentrated and the residue was purified by silica gel column chromatography eluting with 0-50% ethyl acetate in hexanes to give methyl (1aR,6aR)-5-(2-ethoxy-2-oxoacetyl)-4-methyl-1,1a,6,6a-tetrahydrocyclopropa[b]pyrrolizine-3-carboxylate. LCMS-ESI+ (m/z): [M+H]+: 291.98

Step 5. methyl (1aR,6aR)-5-(2-ethoxy-2-oxo acetyl)-4-methyl-1,1a,6,6a-tetrahydrocyclopropa[b]pyrrolizine-3-carboxylate, (7.7 g, 26.5 mmol) was dissolved in (1:1) MeOH/THF (40 mL), this was chilled to 0° C. and 1N LiOH (40 mL) was added the reaction was stirred for 30 mins till complete, reaction was condensed down and evaporated twice with toluene to give 2-((1aR,6aR)-3-(methoxycarbonyl)-4-methyl-1,1a,6,6a-tetrahydrocyclopropa[b]pyrrolizin-5-yl)-2-oxoacetic acid which was carried forward without further purification. LCMS-ESI+ (m/z): [M+H]+: 264.00

Step 6. 2-((1 aR,6aR)-3-(methoxy carbonyl)-4-methyl-1,1a,6,6a-tetrahydrocyclopropa[b]pyrrolizin-5-yl)-2-oxoacetic acid (2 g, 7.6 mmol) was dissolved in EtOAc (100 mL) to this was added TBAI (0.14 g, 0.38 mmol), followed by addition of 5.0-6.0M tert-butyl hydroperoxide (1.7 mL, 8.4 mmol) The reaction was heated to 80° C. for 38 h. The reaction was cooled to ambient temperature then condensed to ~40 mL of volume and cooled to 0° C. material was filtered to give (1aR,6aR)-3-(methoxycarbonyl)-4-methyl-1,1a,6,6a-tetrahydrocyclopropa[b]pyrrolizine-5-carboxylic acid which was used in the next step without further purification. LCMS-ESI+ (m/z): [M+H]+: 236.07

Step 7. (1aR,6aR)-3-(methoxycarbonyl)-4-methyl-1,1a,6,6a-tetrahydrocyclopropa[b]pyrrolizine-5-carboxylic acid (1.2 g, 5.1 mmol) was dissolved in DMF (15 mL) to this was added HATU (2.3 g, 6.1 mmol) and DIPEA (3.6 mL, 20.4 mmol). The reaction was stirred at rt for 30 m and then diluted with EtOAc (200 mL), washed with saturated ammonium chloride (50 mL) twice, saturated sodium bicarbonate (50 mL) twice and saturated sodium chloride (50 mL). Organics were dried with magnesium sulfate and concentrated. The resulting oil was purified via normal phase chromatography EtOAc/Hexanes (0-70%) to give 5-(3H-[1,2,3]triazolo[4,5-b]pyridin-3-yl) 3-methyl (1aR,6aR)-4-methyl-1,1a,6,6a-tetrahydrocyclopropa[b]pyrrolizine-3,5-dicarboxylate which was used in the next step without further purification.

Step 8. 5-(3H-[1,2,3]triazolo[4,5-b]pyridin-3-yl) 3-methyl (1aR,6aR)-4-methyl-1,1a,6,6a-tetrahydrocyclopropa[b]pyrrolizine-3,5-dicarboxylate (350 mg, 0.99 mmol), 3,4-difluoroaniline (0.3 mL, 3 mmol), 2,6-lutidine (0.45 mL, 3.9 mmol) were dissolved in dioxane (2 mL) in a sealed vial. This was then heated for 32 h at 100° C. the reaction was then diluted with DCM (5 mL) and purified via normal phase chromatography EtOAc/Hexanes (0-80%) to give methyl (1aR,6aR)-5-((3,4-difluorophenyl)carbamoyl)-4-methyl-1,1a,6,6a-tetrahydrocyclopropa[b]pyrrolizine-3-carboxylate 1H NMR (400 MHz, DMSO-d6) δ 9.52 (s, 1H), 7.83-7.72 (m, 1H), 7.41-7.27 (m, 2H), 4.31 (s, 1H), 3.37 (d, J=6.8 Hz, 1H), 3.33 (d, J=6.8 Hz, 1H), 3.06 (d, J=17.7 Hz, 1H), 2.39 (s, 3H), 2.11 (s, 1H), 1.08 (dt, J=8.5, 5.8 Hz, 1H), 0.21 (td, J=5.3, 2.1 Hz, 1H). LCMS-ESI+ (m/z): [M+H]$^+$: 347.14

Step 9. Methyl (1aR,6aR)-5-((3,4-difluorophenyl)carbamoyl)-4-methyl-1,1a,6,6a-tetrahydrocyclopropa[b]pyrrolizine-3-carboxylate (300 mg, 0.87 mmol) was dissolved in (1:1) MeOH/THF (6 mL) to this was added 1N LiOH (2.6 mL, 2.6 mmol). The reaction was heated for 11 h at 60° C. The reaction was then neutralized with 1N HCl (2.6 mL) and condensed down to give (1aR,6aR)-5-((3,4-difluorophenyl)carbamoyl)-4-methyl-1,1a,6,6a-tetrahydrocyclopropa[b]pyrrolizine-3-carboxylic acid which was used in the next step without further purification.

Step 10. (1 aR,6aR)-5-((3,4-difluorophenyl)carbamoyl)-4-methyl-1,1a,6,6a-tetrahydrocyclopropa[b]pyrrolizine-3-carboxylic acid (258 mg, 0.78 mmol) was dissolved in DMF (3 mL) to this was added 1-(cyanomethyl)tetrahydro-1H-thiophen-1-ium bromide (210 mg, 1.0 mmol), DIPEA (0.96 mL, 5.5 mmol) and HBTU (330 mg, 0.85 mmol). Reaction was stirred on at ambient temperature, then filtered to give a (1aR,6aR)-3-(2-cyano-2-(tetrahydro-1l4-thiophen-1-ylidene)acetyl)-N-(3,4-difluorophenyl)-4-methyl-1,1a,6,6a-tetrahydrocyclopropa[b]pyrrolizine-5-carboxamide which was used in the next step without further purification.

Step 11: (1aR,6aR)-3-(2-cyano-2-(tetrahydro-1l4-thiophen-1-ylidene)acetyl)-N-(3,4-difluorophenyl)-4-methyl-1,1a,6,6a-tetrahydrocyclopropa[b]pyrrolizine-5-carboxamide (340 mg, 0.77 mmol) and OXONE (1.0 g, 1.7 mmol) were suspended in DMF (4 mL) and MeOH (4 mL) and stirred at ambient temperature for 1 h. The reaction was diluted with DCM (25 mL) and washed with saturated sodium bicarbonate (20 mL) and the organic was then dried with magnesium sulfate and concentrated to an oil. The oil was then purified via normal phase chromatography EtOAc/Hexanes (0-70%) to give methyl 2-((1aR,6aR)-5-((3,4-difluorophenyl)carbamoyl)-4-methyl-1,1a,6,6a-tetrahydrocyclopropa[b]pyrrolizin-3-yl)-2-oxoacetate.

Step 12. Methyl 2-((1aR,6aR)-5-((3,4-difluorophenyl)carbamoyl)-4-methyl-1,1a,6,6a-tetrahydrocyclopropa[b]pyrrolizin-3-yl)-2-oxoacetate (199 mg, 0.5 mmol) was dissolved in (1:1) MeOH/THF (4 mL) to this was added 1N LiOH (1.0 mL). This was stirred at ambient temperature for 30 m. To this was added 1N HCl (1.0 mL). and the reaction was condensed down to give 2-((1aR,6aR)-5-((3,4-difluorophenyl)carbamoyl)-4-methyl-1,1a,6,6a-tetrahydrocyclopropa[b]pyrrolizin-3-yl)-2-oxoacetic acid, which was used in the next step without further purification. LCMS-ESI+ (m/z): [M+1-1]$^+$: 361.09

Step 13. 2-((1aR,6aR)-5-((3,4-difluorophenyl)carbamoyl)-4-methyl-1,1a,6,6a-tetrahydrocyclopropa[b]pyrrolizin-3-yl)-2-oxoacetic acid (95 mg, 0.26 mmol) and 3,3-difluoro-1-(1H-1,2,3-triazol-4-yl)cyclobutan-1-amine dihydrochloride (65 mg, 0.26 mmol) were dissolved in DMF (10 mL) to this was added HATU (200 mg, 0.52 mmol) and DIPEA (0.32 mL, 20 mmol). The reaction was stirred for 1 h at ambient temperature then purified via reverse phase HPLC to give (1aR,6aR)-3-(2-((3,3-difluoro-1-(1H-1,2,3-triazol-5-yl)cyclobutyl)amino)-2-oxoacetyl)-N-(3,4-difluorophenyl)-4-methyl-1,1a,6,6a-tetrahydrocyclopropa[b]pyrrolizine-5-carboxamide. 1H NMR (400 MHz, DMSO-d6) δ 9.87 (s, 1H), 9.69 (s, 1H), 7.84-7.72 (m, 2H), 7.44-7.27 (m, 2H), 4.28 (s, 1H), 3.27 (d, J=9.9 Hz, 4H), 3.11 (s, 1H), 3.06 (s, 1H), 2.17 (s, 4H), 1.13-0.99 (m, 1H), 0.23 (d, J=4.7 Hz, 1H). LCMS-ESI+ (m/z): [M+H]$^+$: 517.17

Example 35. N-(3-chloro-4-fluorophenyl)-5-(2-((3,3-difluoro-1-(methylcarbamoyl)cyclobutyl)amino)-2-oxoacetyl)-6-methyl-2,3-dihydro-1H-pyrrolizine-7-carboxamide

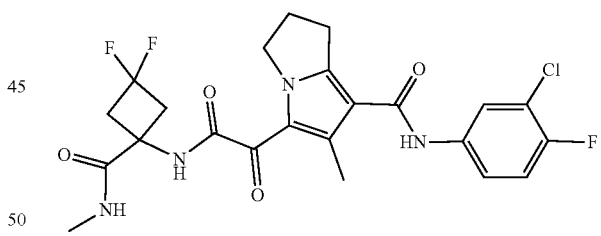

The product was prepared as described in Example 16 using 1-amino-3,3-difluoro-N-methylcyclobutane-1-carboxamide in place of 3,3-difluoro-1-(1H-1,2,3-triazol-5-yl)cyclobutan-1-amine. $^1$H NMR (400 MHz, Acetone-d6) δ 8.85 (s, 1H), 8.69 (s, 1H), 8.05 (ddd, J=6.8, 2.6, 1.7 Hz, 1H), 7.64 (dddd, J=8.5, 4.2, 2.7, 1.4 Hz, 1H), 7.40 (m, 1H), 7.26 (t, J=9.0 Hz, 1H), 4.27 (t, J=7.3 Hz, 2H), 3.38 (td, J=15.2, 11.5 Hz, 2H), 3.17 (t, J=7.5 Hz, 2H), 3.00 (td, J=14.7, 6.6 Hz, 2H), 2.77 (d, J=4.2 Hz, 3H), 2.54 (quin, J=7.5 Hz, 2H), 2.47 (s, 3H). ES/MS m/z: calculated for C23H23ClF3N4O4: 511.13, found: 511.1.

Example 36. 5-(2-((3-(1H-1,2,3-triazol-4-yl)oxetan-3-yl)amino)-2-oxoacetyl)-N-(3,4-difluorophenyl)-6-methyl-2,3-dihydro-1H-pyrrolizine-7-carboxamide

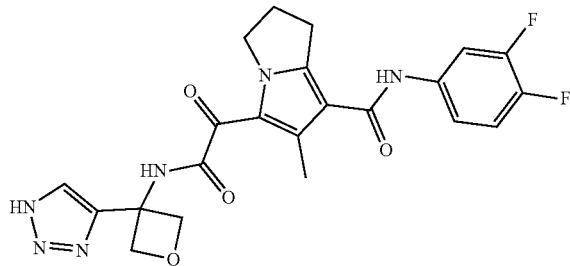

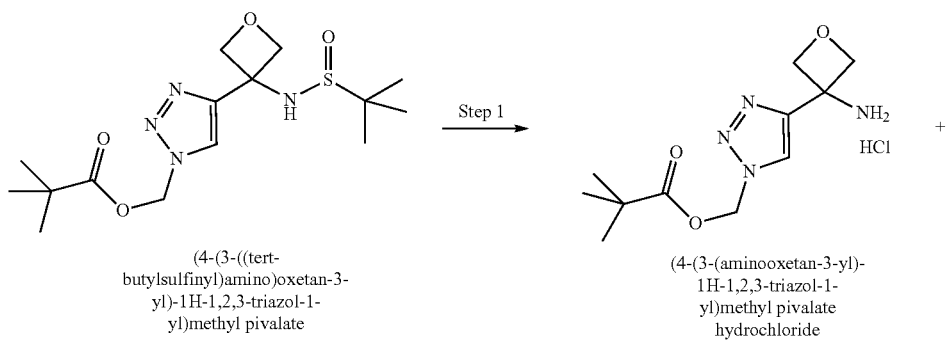

(4-(3-((tert-butylsulfinyl)amino)oxetan-3-yl)-1H-1,2,3-triazol-1-yl)methyl pivalate (4-(3-(aminooxetan-3-yl)-1H-1,2,3-triazol-1-yl)methyl pivalate hydrochloride

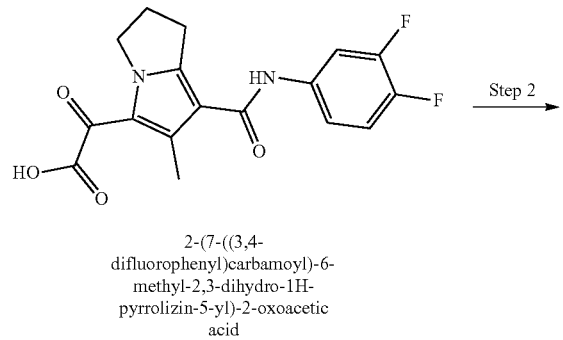

2-(7-((3,4-difluorophenyl)carbamoyl)-6-methyl-2,3-dihydro-1H-pyrrolizin-5-yl)-2-oxoacetic acid

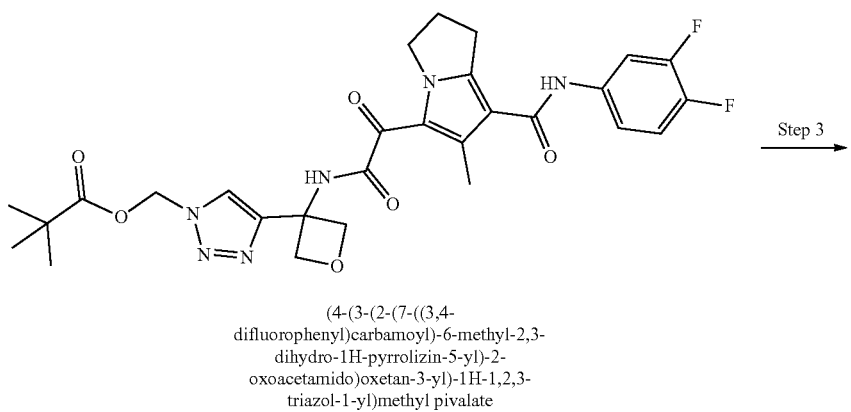

(4-(3-(2-(7-((3,4-difluorophenyl)carbamoyl)-6-methyl-2,3-dihydro-1H-pyrrolizin-5-yl)-2-oxoacetamido)oxetan-3-yl)-1H-1,2,3-triazol-1-yl)methyl pivalate

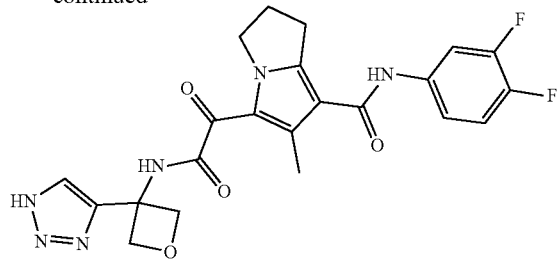

Step 1 (4-(3-((tert-butylsulfinyl)amino)oxetan-3-yl)-1H-1,2,3-triazol-1-yl)methyl pivalate (69.7 mg, 0.194 mmol) in methanol (0.7 mL) was stirred at 0° C. as 4 N hydrochloric acid in dioxane (0.3 mL, 1.20 mmol) was added down the side of the flask. After ~3 min, the mixture was concentrated without heating. The residue was treated with ethyl ether and then concentrated again and dried in vacuum overnight to give crude (4-(3-aminooxetan-3-yl)-1H-1,2,3-triazol-1-yl)methyl pivalate hydrochloride.

Step 2 A solution of 2-(7-((3,4-difluorophenyl)carbamoyl)-6-methyl-2,3-dihydro-1H-pyrrolizin-5-yl)-2-oxoacetic acid (62 mg, 0.18 mmol), the above (4-(3-aminooxetan-3-yl)-1H-1,2,3-triazol-1-yl)methyl pivalate hydrochloride (0.19 mmol), and 1-[bis(dimethylamino)methylene]-1H-1,2,3-triazolo[4,5-b]pyridinium 3-oxide hexafluorophosphate (82 mg, 0.21 mmol) in dimethylformamide (1.5 mL) was stirred at ambient temperature as N,N-diisopropylethylamine (0.2 mL, 1.148 mmol) was added. After 30 min at rt, the reaction mixture was diluted with ethyl acetate (30 mL), washed with aqueous ammonium chloride (×2), aqueous NaHCO₃ (×2), and brine (×1). After the aqueous fractions were extracted with ethyl acetate (×1), the organic fractions were combined, dried (MgSO4), and concentrated. The residue was purified by preparative HPLC (column, Gemini 10 u C18 110A, AXI/; 250×21.2 mm) eluting 10-70% acetonitrile (0.1% TFA) in water (0.1% TFA) to give (4-(3-(2-(7-((3,4-difluorophenyl)carbamoyl)-6-methyl-2,3-dihydro-1H-pyrrolizin-5-yl)-2-oxoacetamido)oxetan-3-yl)-1H-1,2,3-triazol-1-yl)methyl pivalate: $^1$H NMR (400 MHz, Chloroform-d) δ 8.24 (s, 1H), 7.98 (s, 1H), 7.70-7.58 (m, 2H), 7.17-7.01 (m, 2H), 6.22 (s, 2H), 5.10 (d, J=6.9 Hz, 2H), 5.03 (d, J=6.9 Hz, 2H), 4.20 (t, J=7.3 Hz, 2H), 3.05 (t, J=7.5 Hz, 2H), 2.49 (p, J=7.5 Hz, 2H), 2.36 (s, 3H), 1.18 (s, 9H). $^{19}$F NMR (376 MHz, Chloroform-d) δ−136.19 (ddd, J=21.9, 12.2, 7.7 Hz), −141.81-144.80 (m). ES/MS m/z: calculated for $C_{28}H_{31}F_2N_6O_6$ (M+H): 585.23, found: 585.27.

Step 3 A solution of (4-(3-(2-(7-((3,4-difluorophenyl)carbamoyl)-6-methyl-2,3-dihydro-1H-pyrrolizin-5-yl)-2-oxoacetamido)oxetan-3-yl)-1H-1,2,3-triazol-1-yl)methyl pivalate (73 mg, 0.13 mmol) in methanol (2 mL) was stirred at rt as added 2M sodium hydroxide (0.2 mL, 0.4 mmol) was added. After 30 min, the mixture was acidified with 1 N hydrochloric acid (~0.08 mL) and the resulting mixture was concentrated. The resulting residue was purified by preparative HPLC (Synergi 4 u Polar-RP 80A, Axia; 10% aq. acetonitrile-60% aq. acetonitrile with 0.1% TFA, over 30 min. gradient) followed by an additional preparative HPLC without trifluoroacetic acid modifier and freeze-dried to give 5-(2-((3-(1H-1,2,3-triazol-4-yl)oxetan-3-yl)amino)-2-oxoacetyl)-N-(3,4-difluorophenyl)-6-methyl-2,3-dihydro-1H-pyrrolizine-7-carboxamide: $^1$H NMR (400 MHz, Acetonitrile-d₃) δ 8.17 (s, 1H), 8.10 (s, 1H), 7.78 (s, 1H), 7.79-7.70 (m, 1H), 7.33-7.26 (m, 1H), 7.22 (dt, J=10.6, 8.8 Hz, 1H), 5.02 (d, J=6.7 Hz, 2H), 4.96 (d, J=6.7 Hz, 2H), 4.23 (t, J=7.2 Hz, 2H), 3.07 (t, J=7.5 Hz, 2H), 2.50 (p, J=7.4 Hz, 2H), 2.39 (s, 3H). $^{19}$F NMR (376 MHz, Acetonitrile-d₃) δ−139.21 (ddd, J=21.5, 13.2, 8.8 Hz), −146.32-146.83 (m). ES/MS m/z: calculated for $C_{22}H_{21}F_2N_6O_4$ (M+H): 471.16, found: 471.22.

Example 37. 5-(2-((3-(1H-1,2,3-triazol-4-yl)oxetan-3-yl)amino)-2-oxoacetyl)-N-(3,4-difluorophenyl)-6-methyl-2,3-dihydro-1H-pyrrolizine-7-carboxamide

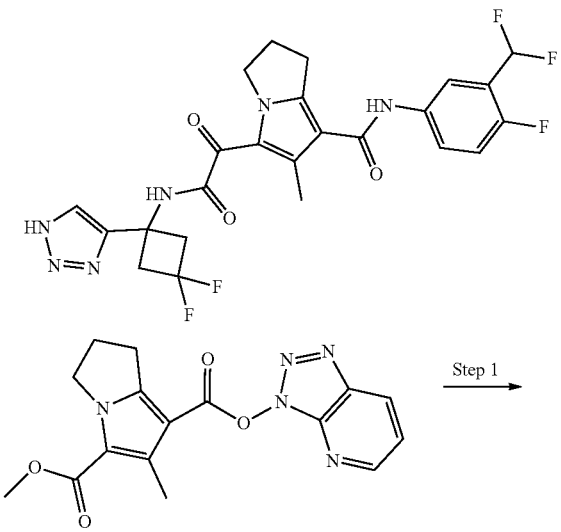

7-(3H-[1,2,3]triazolo[4,5-b]pyridin-3-yl) 5-methyl 6-methyl-2,3-dihydro-1H-pyrrolizine-5,7-dicarboxylate

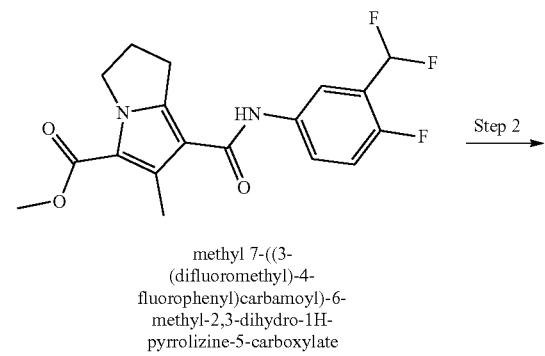

methyl 7-((3-(difluoromethyl)-4-fluorophenyl)carbamoyl)-6-methyl-2,3-dihydro-1H-pyrrolizine-5-carboxylate

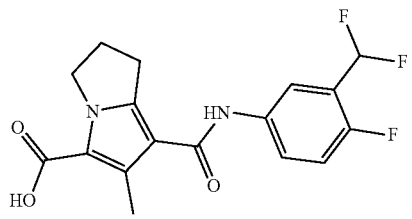

7-((3-(difluoromethyl)-4-fluorophenyl)carbamoyl)-6-methyl-2,3-dihydro-1H-pyrrolizine-5-carboxylic acid

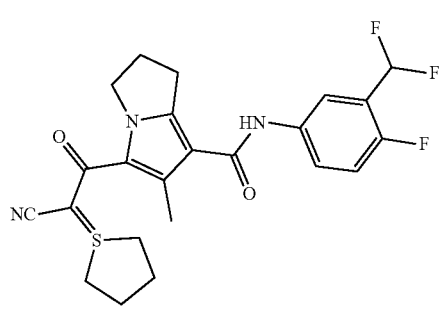

5-(2-cyano-2-(tetrahydro-1l$^4$-thiophen-1-ylidene)acetyl)-N-(3-(difluoromethyl)-4-fluorophenyl)-6-methyl-2,3-dihydro-1H-pyrrolizine-7-carboxamide

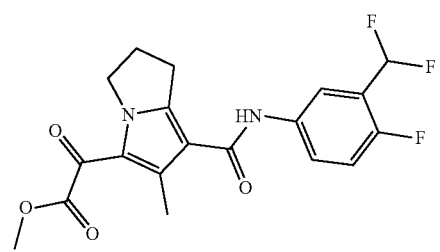

methyl 2-(7-((3-(difluoromethyl)-4-fluorophenyl)carbamoyl)-6-methyl-2,3-dihydro-1H-pyrrolizin-5-yl)-2-oxoacetate

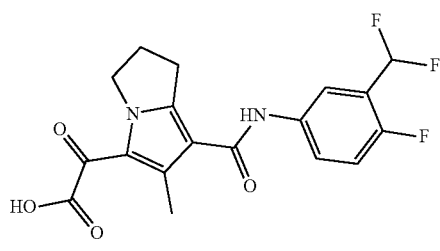

2-(7-((3-(difluoromethyl)-4-fluorophenyl)carbamoyl)-6-methyl-2,3-dihydro-1H-pyrrolizin-5-yl)-2-oxoacetic acid

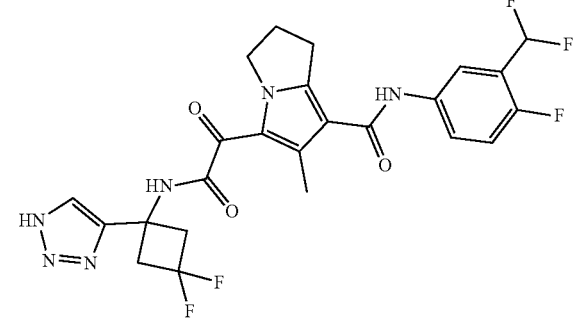

Step 1 Methyl 7-((3-(difluoromethyl)-4-fluorophenyl)carbamoyl)-6-methyl-2,3-dihydro-1H-pyrrolizine-5-carboxylate was synthesized in a manner similar to Example 40, step 4, using 3-(difluoromethyl)-4-fluoroaniline in place of 3,4-difluoroaniline: $^1$H NMR (400 MHz, Chloroform-d) δ 7.82-7.75 (m, 1H), 7.68 (dd, J=6.0, 2.7 Hz, 1H), 7.35 (s, 1H), 7.15-7.08 (m, 1H), 6.88 (t, J=54.9 Hz, 1H), 4.30 (dd, J=8.1, 6.5 Hz, 2H), 3.86 (s, 3H), 3.15 (dd, J=8.0, 7.1 Hz, 2H), 2.68 (s, 3H), 2.54 (ddd, J=14.9, 8.0, 6.8 Hz, 2H). $^{19}$F NMR (376 MHz, Chloroform-d) δ−114.59 (d, J=55.4 Hz, 2F), −125.61-125.98 (m, 1F). ES/MS m/z: calculated for $C_{18}H_{18}F_3N_2O_3$ (M+H): 367.13, found: 367.16.

Step 2 7-((3-(Difluoromethyl)-4-fluorophenyl)carbamoyl)-6-methyl-2,3-dihydro-1H-pyrrolizine-5-carboxylic acid was synthesized in a manner similar to Example 40, step 5 using methyl 7-((3-(difluoromethyl)-4-fluorophenyl)carbamoyl)-6-methyl-2,3-dihydro-1H-pyrrolizine-5-carboxylate.

Step 3 5-(2-Cyano-2-(tetrahydro-1l4-thiophen-1-ylidene)acetyl)-N-(3-(difluoromethyl)-4-fluorophenyl)-6-methyl-2,3-dihydro-1H-pyrrolizine-7-carboxamide was synthesized in a manner similar to Example 40, step 6, using 7-((3-(Difluoromethyl)-4-fluorophenyl)carbamoyl)-6-methyl-2,3-dihydro-1H-pyrrolizine-5-carboxylic acid: ES/MS m/z: calculated for $C_{23}H_{23}F_3N_3O_2S$ (M+H): 462.15, found: 462.27.

Step 4 Methyl 2-(7-(3-(difluoromethyl)-4-fluorophenyl)carbamoyl)-6-methyl-2,3-dihydro-1H-pyrrolizin-5-yl)-2-oxoacetate was synthesized in a manner similar to Example 40, step 7, using 5-(2-cyano-2-(tetrahydro-1l4-thiophen-1-ylidene)acetyl)-N-(3-(difluoromethyl)-4-fluorophenyl)-6-methyl-2,3-dihydro-1H-pyrrolizine-7-carboxamide: $^1$H NMR (400 MHz, Chloroform-d) δ 7.82-7.73 (m, 1H), 7.68 (dd, J=6.0, 2.7 Hz, 1H), 7.44 (s, 1H), 7.17-7.07 (m, 1H), 6.88 (t, J=54.9 Hz, 1H), 4.33 (t, J=7.3 Hz, 2H), 3.94 (s, 3H), 3.13 (t, J=7.6 Hz, 2H), 2.58 (p, J=7.6 Hz, 2H), 2.44 (s, 3H). $^{19}$F NMR (376 MHz, Chloroform-d) δ-114.72 (d, J=55.0 Hz), −125.27 (dt, J=10.3, 5.2 Hz). ES/MS m/z: calculated for $C_{19}H_{18}F_3N_2O_4$ (M+H): 395.12, found: 395.20.

Step 5 2-(7-((3-(difluoromethyl)-4-fluorophenyl)carbamoyl)-6-methyl-2,3-dihydro-1H-pyrrolizin-5-yl)-2-oxoacetic acid was synthesized in a manner similar to Example 40, step 8, using methyl 2-(7-(3-(difluoromethyl)-4-fluorophenyl)carbamoyl)-6-methyl-2,3-dihydro-1H-pyrrolizin-5-yl)-2-oxoacetate: ES/MS m/z: calculated for $C_{18}H_{16}F_3N_2O_4$ (M+H): 381.11, found: 381.06.

Step 6 5-(2-((3,3-Difluoro-1-(1H-1,2,3-triazol-4-yl)cyclobutyl)amino)-2-oxoacetyl)-N-(3-(difluoromethyl)-4-fluorophenyl)-6-methyl-2,3-dihydro-1H-pyrrolizine-7-carboxamide (21) was synthesized in a manner similar to Example 40, step 9, using 3,3-difluoro-1-(1H-1,2,3-triazol-4-yl)cyclobutan-1-amine dihydrochloride in place of 1-(1H-1,2,3-triazol-4-yl)cyclopropan-1-amine dihydrochloride and 2-(7-(3-(difluoromethyl)-4-fluorophenyl)carbamoyl)-6-methyl-2,3-dihydro-1H-pyrrolizin-5-yl)-2-oxoacetic acid: $^1$H NMR (400 MHz, Chloroform-d) δ 7.82-7.73 (m, 1H), 7.68 (dd, J=6.0, 2.7 Hz, 1H), 7.44 (s, 1H), 7.17-7.07 (m, 1H), 6.88 (t, J=54.9 Hz, 1H), 4.33 (t, J=7.3 Hz, 2H), 3.94 (s, 3H), 3.13 (t, J=7.6 Hz, 2H), 2.58 (p, J=7.6 Hz, 2H), 2.44 (s, 3H). $^{19}$F NMR (376 MHz, Chloroform-d) δ−114.72 (d, J=55.0 Hz), −125.27 (dt, J=10.3, 5.2 Hz). ES/MS m/z: calculated for $C_{24}H_{22}F_5N_6O_3$ (M+H): 537.17, found: 537.13.

Example 38. N-(3,4-difluorophenyl)-6-methyl-5-(2-((3-(methylcarbamoyl)oxetan-3-yl)amino)-2-oxoacetyl)-2,3-dihydro-1H-pyrrolizine-7-carboxamide (38)

38

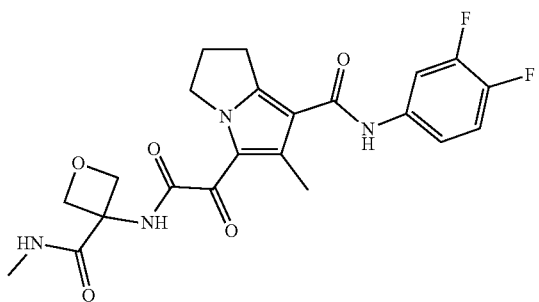

The product was synthesized in a manner similar to Example 13 using 3-amino-N-methyloxetane-3-carboxamide in place of ethynylcyclopropylamine hydrogen chloride.

Synthesis of 3-amino-N-methyloxetane-3-carboxamide

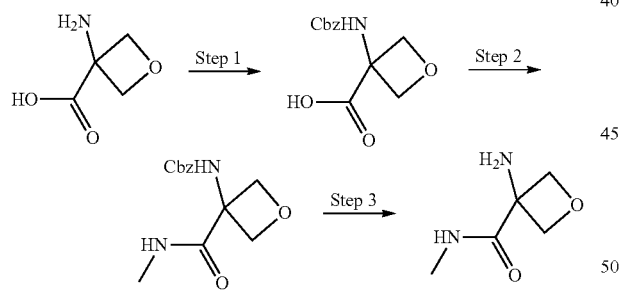

To solution of 3-aminooxetane-3-carboxylic acid (4.99 g, 42.6 mmol) and N,N-diisopropylethylamine (18 mL) in dichloromethane (120 mL) was added N-(benzyloxycarbonyloxy)succinimide (9.21 mL, 34.1 mmol) and the reaction mixture allowed to stir at room temperature for 24 h at which point the reaction volume was concentrated by two thirds under reduced pressure. This solution was then diluted with diethyl ether and washed with 1M aqueous hydrogen chloride then water, dried over sodium sulfate, filtered, and concentrated under reduced pressure to afford 3-(((benzyloxy)carbonyl)amino)oxetane-3-carboxylic acid which was carrier on without further purification.

To a solution of 3-(((benzyloxy)carbonyl)amino)oxetane-3-carboxylic acid (9.2 g, 36.6 mmol), methylamine hydrochloride (12.9 g, 191.5 mmol), and N-methylmorpholine (25 mL, 230 mmol) in N,N-dimethylformamide (100 mL) was added 1-[Bis(dimethylamino)methylene]-1H-1,2,3-triazolo[4,5-b]pyridinium 3-oxid hexafluorophosphate (21.4 g, 56.3 mmol). The reaction mixture was stirred for 18 h, at which point the majority of N,N-dimethylformamide was removed under reduced pressure, the remaining material diluted with diethyl ether, washed sequentially with 1M aqueous hydrogen chloride, 5% aqueous sodium bicarbonate, 5% aqueous lithium chloride, and saturated aqueous sodium chloride solutions, dried over sodium sulfate, filtered, and concentrated under reduced pressure. The resulting residue was purified by silica gel column chromatography (0-10% methanol:dichloromethane) to afford benzyl (3-(methylcarbamoyl)oxetan-3-yl)carbamate.

To a solution of benzyl (3-(methylcarbamoyl)oxetan-3-yl)carbamate (4.9 g, 18.5 mmol) in ethanol (80 mL) was added 10% palladium on carbon (1.95 g, 0.92 mmol). This reaction mixture was place under one atmosphere hydrogen and stirred for 3 h. The reaction mixture was then filtered through celite and the resultant filtrate concentrated under reduced pressure to afford 3-amino-N-methyloxetane-3-carboxamide. $^1$H NMR (400 MHz, DMSO-d6) δ 7.82 (s, 1H), 4.70 (d, J=5.8 Hz, 2H), 4.26 (d, J=5.7 Hz, 2H), 2.61 (d, J=4.7 Hz, 3H).

Example 39. 5-(2-((3,3-difluoro-1-(1H-1,2,3-triazol-4-yl)cyclobutyl)amino)-2-oxoacetyl)-N-(3,4-difluorophenyl)-6-methyl-2,3-dihydro-1H-pyrrolizine-7-carboxamide

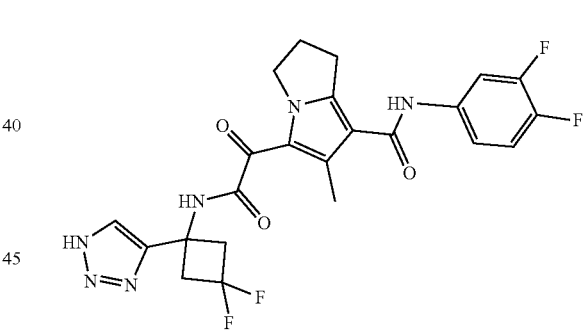

The product was synthesized in a manner similar to Example 1, step 9, using 3,3-difluoro-1-(1H-1,2,3-triazol-4-yl)cyclobutan-1-amine dihydrochloride in place of 1-(1H-1,2,3-triazol-4-yl)cyclopropan-1-amine dihydrochloride: $^1$H NMR (400 MHz, Acetonitrile-d3) δ 8.08 (s, 1H), 7.97 (s, 1H), 7.76 (s, 1H), 7.75 (ddd, J=12.8, 7.5, 2.6 Hz, 1H), 7.28 (dddd, J=9.0, 4.2, 2.6, 1.3 Hz, 1H), 7.22 (dt, J=10.5, 8.8 Hz, 1H), 4.25-4.17 (m, 2H), 3.42-3.21 (m, 4H), 3.07 (t, J=7.5 Hz, 2H), 2.49 (p, J=7.5 Hz, 2H), 2.34 (s, 3H). $^{19}$F NMR (376 MHz, Acetonitrile-d3) δ−77.32 (d, J=15.1 Hz), −90.19-90.89 (m, 1F), −90.98-91.69 (m, 1F), −139.21 (ddd, J=21.6, 13.2, 8.5 Hz, 1F), −146.56 (ddd, J=14.9, 10.9, 7.3 Hz, 1F). ES/MS m/z: calculated for $C_{23}H_{21}F_4N_6O_3$ (M+H): 505.16, found: 505.19.

Example 40. 5-(2-((1-(1H-1,2,3-triazol-4-yl)cyclopropyl)amino)-2-oxoacetyl)-N-(3,4-difluorophenyl)-6-methyl-2,3-dihydro-1H-pyrrolizine-7-carboxamide

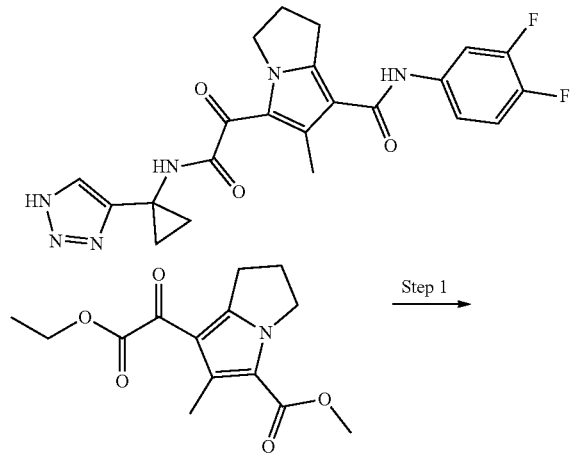

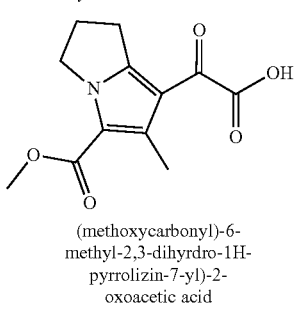

methyl 7-(2-ethoxy-2-oxoacetyl)-6-methyl-2,3-dihydro-1H-pyrrolizine-5-carboxylate Step 1 →

5-(methoxycarbonyl)-6-methyl-2,3-dihydro-1H-pyrrolizin-7-yl)-2-oxoacetic acid

Step 2 →

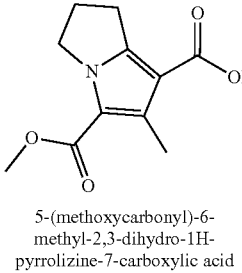

5-(methoxycarbonyl)-6-methyl-2,3-dihydro-1H-pyrrolizine-7-carboxylic acid

Step 3 →

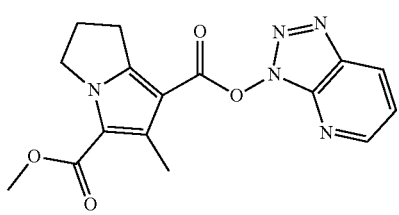

7-(3H-[1,2,3]triazolo[4,5-b]pyridin-3-yl) 5-methyl 6-methyl-2,3-dihydro-1H-pyrrolizine-5,7-dicarboxylate Step 4 →

-continued

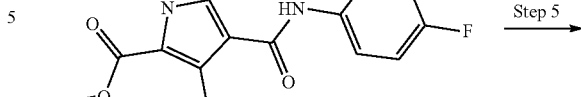

methyl 7-((3,4-difluorophenyl)carbamoyl)-6-methyl-2,3-dihydro-1H-pyrrolizine-5-carboxylate Step 5 →

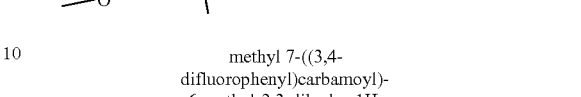

7-((3,4-difluorophenyl)carbamoyl)-6-methyl-2,3-dihydro-1H-pyrrolizine-5-carboxylic acid Step 6 →

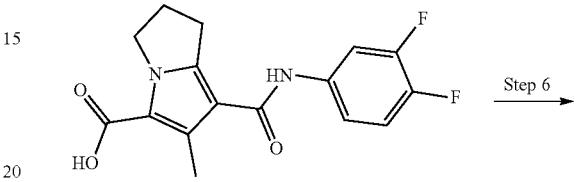

5-(2-cyano-2-(tetrahydro-1$1^4$-thiophen-1-ylidene)acetyl)-N-(3,4-difluorophenyl)-6-methyl-2,3,-dihydro-1H-pyrrolizine-7-carboxamide Step 7 →

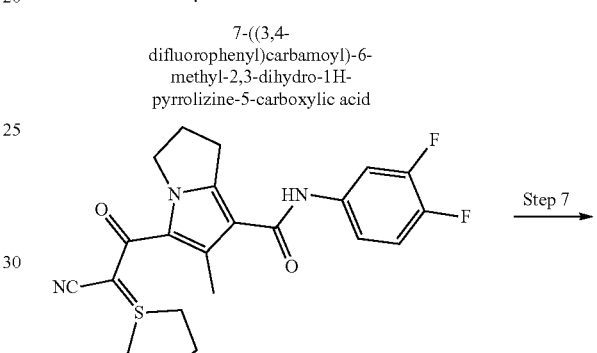

methyl 2-(7-((3,4-difluorophenyl)carbamoyl)-6-methyl-2,3-dihydro-1H-pyrrolizin-5-yl)-2-oxoacetate Step 8 →

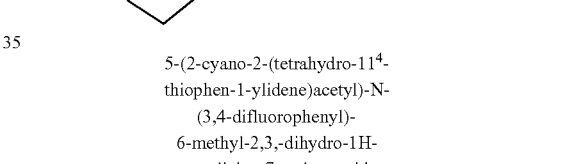

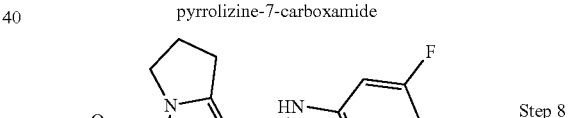

2-(7-((3,4-difluorophenyl)carbamoyl)-6-methyl-2,3-dihydro-1H-pyrrolizin-5-yl)-2-oxoacetic acid Step 9 →

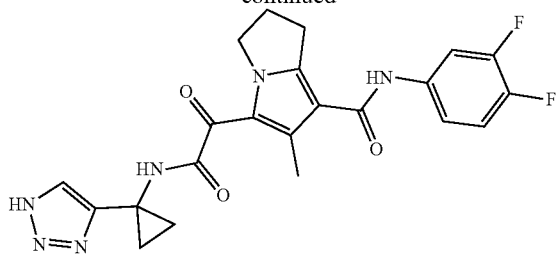

40

Step 1 A solution of methyl 7-(2-ethoxy-2-oxoacetyl)-6-methyl-2,3-dihydro-1H-pyrrolizine-5-carboxylate (10.4126 g, 37.28 mmol) in tetrahydrofuran (20 mL) and methanol (20 mL) was stirred at 0° C. as 1 N lithium hydroxide (56 mL) was added. After stirring for 45 min at 0° C., the reaction mixture was washed with ethyl ether (200 mL×1), acidified with 1 N hydrochloric acid, and the product was extracted with ethyl acetate (100 mL×2). The combined extracts were dried (MgSO4) and concentrated to give 2-(5-(methoxycarbonyl)-6-methyl-2,3-dihydro-1H-pyrrolizin-7-yl)-2-oxoacetic acid: ES/MS m/z: calculated for $C_{12}H_{14}NO_5$ (M+H)=252.09, found: 251.97.

Step 2 To a mixture of 2-(5-(methoxycarbonyl)-6-methyl-2,3-dihydro-1H-pyrrolizin-7-yl)-2-oxoacetic acid (300 mg, 1.2 mmol) and tetrabutylammonium iodide (44 mg, 0.12 mmol) in ethyl acetate (12 mL) was added 5.0-6.0 M tert-butyl hydroperoxide in decane (0.27 mL, 1.350-1.620 mmol) at rt. The reaction mixture was stirred at 80° C. bath for 16 h. The solids in the reaction mixture was dissolved by addition of ethyl acetate (~40 mL) and heating, and the resulting solution was washed with water (~50 mL), acidified with 1 N hydrochloric acid, and the two fractions were separated. After the aqueous fraction was extracted with ethyl acetate (~30 mL), the two organic fractions were washed with water (with 1~2 drops of 1 N hydrochloric acid), combined, dried (MgSO4), and concentrated to give a crude 5-(methoxycarbonyl)-6-methyl-2,3-dihydro-1H-pyrrolizine-7-carboxylic acid: ES/MS m/z: calculated for $C_{11}H_{14}NO_4$ (M+H)=224.09, found: 224.03.

Step 3 The above crude acid and 1-[bis(dimethylamino)methylene]-1H-1,2,3-triazolo[4,5-b]pyridinium 3-oxide hexafluorophosphate (546 mg, 1.44 mmol) in dimethylformamide (3 mL) was stirred at 0° C. bath as N,N-diisopropylethylamine (0.9 mL, 5.2 mmol) was added. After 1 h at 0° C., the reaction mixture was diluted with ethyl acetate (~40 mL), washed with saturated NH4Cl solution (×2), saturated NaHCO3 solution (×2), and brine (×1). After the aqueous fractions were extracted with ethyl acetate (~30 mL×1), the organic fractions were combined, dried (MgSO4), and concentrated. The residue was purified by CombiFlash (40 g column) eluting 0-100% ethyl acetate in hexane to give 7-(3H-[1,2,3]triazolo[4,5-b]pyridin-3-yl) 5-methyl 6-methyl-2,3-dihydro-1H-pyrrolizine-5,7-dicarboxylate: $^1$H NMR (400 MHz, Chloroform-d) δ 8.72 (dd, J=4.5, 1.4 Hz, 1H), 8.43 (dd, J=8.4, 1.4 Hz, 1H), 7.43 (dd, J=8.4, 4.5 Hz, 1H), 4.45-4.33 (m, 2H), 3.88 (s, 3H), 3.35 (t, J=7.6 Hz, 2H), 2.64-2.54 (m, 2H), 2.61 (s, 3H). ES/MS m/z: calculated for C16H16N5O4 (M+H): 342.12, found: 341.77.

Step 4 7-(3H-[1,2,3]triazolo[4,5-b]pyridin-3-yl) 5-methyl 6-methyl-2,3-dihydro-1H-pyrrolizine-5,7-dicarboxylate (230 mg, 0.67 mmol), 3,4-difluoroaniline (0.2 mL 2.0 mmol), 2,6-lutidine (0.3 mL, 2.6 mmol), and 1,2-dichloroethane (0.5 mL) were mixed in a flask and stirred at 70° C. bath for 24 h. The reaction mixture was purified by CombiFlash (40 g column) eluting with 0-85% ethyl acetate in hexane twice and further purified by preparative HPLC (Synergi 4 u Polar-RP 80A, Axia; 10% aq. acetonitrile-70% aq. acetonitrile with 0.1% TFA, over 30 min. gradient). The major UV peak containing fractions were combined, concentrated to remove most of acetonitrile, neutralized by adding some saturated NaHCO3 solution, and the product was extracted with ethyl acetate (×2). After the organic fractions were washed with water (×1), combined and concentrated, the residue was dried in vacuum over the weekend to give methyl 7-((3,4-difluorophenyl)carbamoyl)-6-methyl-2,3-dihydro-1H-pyrrolizine-5-carboxylate: $^1$H NMR (400 MHz, Chloroform-d) δ 7.77-7.62 (m, 1H), 7.29 (s, 1H), 7.15-7.05 (m, 2H), 4.39-4.21 (m, 2H), 3.86 (s, 3H), 3.13 (t, J=7.5 Hz, 2H), 2.66 (s, 3H), 2.53 (p, J=7.3 Hz, 2H). $^{19}$F NMR (376 MHz, Chloroform-d) δ −136.09-136.53 (m), −143.53-143.94 (m). ES/MS m/z: calculated for $C_{17}H_{17}F_2N_2O_3$ (M+H): 335.12, found: 335.10.

Step 5 To a suspension of methyl 7-((3,4-difluorophenyl)carbamoyl)-6-methyl-2,3-dihydro-1H-pyrrolizine-5-carboxylate (252 mg, 0.754 mmol) in methanol (3 mL) and tetrahydrofuran (3 mL) was added 1 N LiOH (2.25 mL) and the resulting suspension was stirred at 60° C. for 12 h. The reaction mixture was acidified by addition of 1 N hydrochloric acid (~2.3 mL), concentrated to remove organic solvents, diluted with water (4050 mL), and the residual aqueous suspension was filtered, washed with water, and dried in vacuum to give crude 7-((3,4-difluorophenyl)carbamoyl)-6-methyl-2,3-dihydro-1H-pyrrolizine-5-carboxylic acid.

Step 6 A suspension of the above crude acid, O-(benzotriazol-1-yl)-N,N,N',N'-tetramethyluronium hexafluorophosphate (317 mg, 0.84 mmol), and 1-(cyanomethyl)tetrahydro-1H-thiophen-1-ium bromide (209 mg, 1.0 mmol) in dimethylformamide (3 mL) was stirred at ambient temperature as N,N-diisopropylethylamine (0.94 mL, 5.4 mmol) was added. The reaction mixture was stirred ~17 h and diluted with water (30 mL) and some saturated NH4Cl solution. The remaining solids were filtered, and the collected solids were washed with water, and then dichloromethane. The resulting solids were collected and dried for 1 h in vacuum to give 5-(2-cyano-2-(tetrahydro-1l4-thiophen-1-ylidene)acetyl)-N-(3,4-difluorophenyl)-6-methyl-2,3-dihydro-1H-pyrrolizine-7-carboxamide: $^1$H NMR (400 MHz, DMSO-d$_6$) δ 9.39 (s, 1H), 7.91-7.73 (m, 1H), 7.43-7.26 (m, 2H), 4.01 (t, J=7.2 Hz, 2H), 3.74-3.55 (m, 2H), 3.19 (dt, J=12.5, 6.3 Hz, 2H), 3.02 (t, J=7.4 Hz, 2H), 2.40 (p, J=7.4 Hz, 2H), 2.33 (m, 2H), 2.30 (s, 3H), 2.07 (m, 2H). $^{19}$F NMR (376 MHz, DMSO-d6) δ−138.09-138.58 (m), −146.15-146.66 (m). ES/MS m/z: calculated for $C_{22}H_{22}F_2N_3O_2S$ (M+H): 430.14, found: 430.16.

Step 7 A suspension of 5-(2-cyano-2-(tetrahydro-1l4-thiophen-1-ylidene)acetyl)-N-(3,4-difluorophenyl)-6-methyl-2,3-dihydro-1H-pyrrolizine-7-carboxamide (250 mg, 0.58 mmol) and OXONE, monopersulfate compound (2KHSO$_5$—KHSO$_4$—K$_2$SO$_4$, 724 mg, 1.2 mmol) in dimethylformamide (2 mL) and methanol (2 mL) was stirred at rt. After 15 min, additional solvents, dimethylformamide (2 mL) and methanol (2 mL) were added. After 22 h, the reaction mixture was diluted with ethyl acetate (~15 mL), dichloromethane (~30 mL) and saturated NaHCO$_3$ solution. After the two layers were separated, the organic fraction was washed with 5 LiCl solution (×1), and brine (×1). After aqueous fractions were extracted with dichloromethane (~20 mL×1), the two organic fractions were combined, dried (MgSO4), and concentrated. The residue was purified by CombiFlash (24 g column) eluting 0-70% ethyl acetate in hexane to give methyl 2-(7-((3,4-difluorophenyl)carbamoyl)-6-methyl-2,3-dihydro-1H-pyrrolizin-5-yl)-2-oxoacetate: $^1$H NMR (400 MHz, Chloroform-d) δ 7.66 (ddd, J=12.0, 7.2, 2.4 Hz, 1H), 7.18 (s, 1H), 7.16-7.02 (m, 2H), 4.36 (t, J=7.4 Hz, 2H), 3.95 (s, 3H), 3.13 (t, J=7.6 Hz, 2H), 2.59 (p, J=7.5 Hz, 2H), 2.47 (s, 3H). $^{19}$F NMR (376 MHz, Chloroform-d) δ−135.74-136.19 (m), −142.87-143.19 (m). ES/MS m/z: calculated for C$_{18}$H$_{17}$F$_2$N$_2$O$_4$ (M+H): 363.12, found: 363.15.

Step 8 A solution of methyl 2-(7-((3,4-difluorophenyl)carbamoyl)-6-methyl-2,3-dihydro-1H-pyrrolizin-5-yl)-2-oxoacetate (181 mg, 0.50 mmol) in tetrahydrofuran (1 mL) and MeOH (1 mL) was stirred at ambient temperature as 1 N LiOH (1.0 mL) was added. After 30 min at ambient temperature, the reaction mixture was concentrated to remove most of the organic solvent, diluted with water, acidified, and the product was extracted with ethyl acetate (×2). The combined extracts were dried (MgSO4) and concentrated to give crude 2-(7-((3,4-difluorophenyl)carbamoyl)-6-methyl-2,3-dihydro-1H-pyrrolizin-5-yl)-2-oxoacetic acid: ES/MS m/z: calculated for C$_{17}$H$_{15}$F$_2$N$_2$O$_4$ (M+H): 349.10, found: 349.11.

Step 9 A solution of the crude 2-(7-((3,4-difluorophenyl)carbamoyl)-6-methyl-2,3-dihydro-1H-pyrrolizin-5-yl)-2-oxoacetic acid (49 mg, 0.14 mmol), 1-(1H-1,2,3-triazol-4-yl)cyclopropan-1-amine dihydrochloride (40 mg, 0.20 mmol), and 1-[bis(dimethylamino)methylene]-1H-1,2,3-triazolo[4,5-b]pyridinium 3-oxide hexafluorophosphate (150 mg, 0.39 mmol) in dimethylformamide (1.2 mL) was stirred at ambient temperature as N,N-diisopropylethylamine (0.2 mL, 1.15 mmol) was added. After 30 min at rt, methanol (1 mL) was added to the reaction mixture and stirred at ambient temperature for 2 h. The reaction mixture was diluted with ethyl acetate (20 mL), washed with aqueous ammonium chloride (×2), aqueous NaHCO$_3$ (×2), and brine (×1). After the aqueous fractions were extracted with ethyl acetate (×1), the organic fractions were combined, dried (MgSO4), and concentrated. The residue was purified by preparative HPLC (column, Gemini 10 u C18 110A, AXI/; 250×21.2 mm) eluting 10-80% acetonitrle (0.1% TFA) in water (0.1% TFA) and freeze-dried to give 5-(2-((1-(1H-1,2,3-triazol-4-yl)cyclopropyl)amino)-2-oxoacetyl)-N-(3,4-difluorophenyl)-6-methyl-2,3-dihydro-1H-pyrrolizine-7-carboxamide: $^1$H NMR (400 MHz, Acetonitrile-d$_3$) δ 8.08 (s, 1H), 7.87 (s, 1H), 7.76 (ddd, J=13.2, 7.5, 2.5 Hz, 1H), 7.59 (s, 1H), 7.33-7.26 (m, 1H), 7.22 (dt, J=10.5, 8.8 Hz, 1H), 4.30-4.19 (m, 2H), 3.07 (t, J=7.5 Hz, 2H), 2.50 (p, J=7.5 Hz, 2H), 2.39 (s, 3H), 1.43-1.34 (m, 2H), 1.34-1.25 (m, 2H). $^{19}$F NMR (376 MHz, Acetonitrile-d$_3$) δ−77.34 (s, 3F), −139.21 (ddd, J=21.3, 12.9, 8.6 Hz, 1F), −146.26-147.01 (m, 1F). ES/MS m/z: calculated for C$_{22}$H$_{21}$F$_2$N$_6$O$_3$ (M+H): 455.16, found: 455.13.

Example 41. 5-(2-((3,3-difluoro-1-(methylcarbamoyl)cyclobutyl)amino)-2-oxoacetyl)-N-(3-(difluoromethyl)-4-fluorophenyl)-6-methyl-2,3-dihydro-1H-pyrrolizine-7-carboxamide

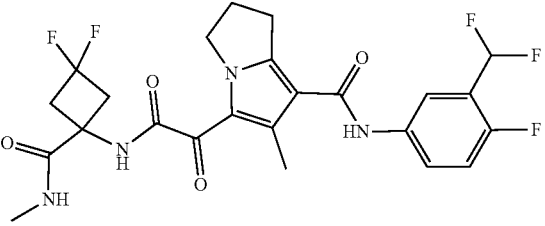

41

The product was prepared as described in Example 27 using 1-amino-3,3-difluoro-N-methylcyclobutane-1-carboxamide in place of 1-(1H-1,2,3-triazol-4-yl)cyclopropan-1-amine dihydrochloric acid. $^1$H NMR (400 MHz, DMSO-d$_6$) δ 9.79 (br s, 1H), 9.62 (br s, 1H), 8.01 (dd, J=6.6, 2.6 Hz, 1H), 8.75-8.82 (m, 1H), 7.38-7.29 (m, 1H), 7.22 (t, J=54.3 Hz, 1H), 4.21 (t, J=7.3 Hz, 2H), 3.24 (q, J=14.1 Hz, 2H), 3.08 (t, J=7.5 Hz, 2H), 3.01-2.82 (m, 2H), 2.62 (d, J=4.5 Hz, 3H), 2.45 (quin, J=7.4 Hz, 1H), 2.36 (s, 3H). ES/MS m/z: calculated for C24H24F5N4O4: 527.16, found: 527.1.

Example 42. 5-(2-((3,3-difluoro-1-(methylcarbamoyl)cyclobutyl)amino)-2-oxoacetyl)-6-methyl-N-(3,4,5-trifluorophenyl)-2,3-dihydro-1H-pyrrolizine-7-carboxamide

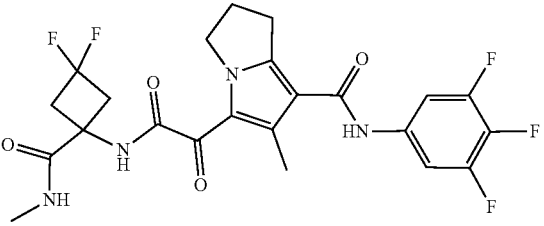

42

The product was prepared as described in Example 1 using 1-amino-3,3-difluoro-N-methylcyclobutane-1-carboxamide in place of 3,3-difluoro-1-(1,3,4-thiadiazol-2-yl)cyclobutan-1-amine. $^1$H NMR (400 MHz, Acetone-d$_6$) δ 8.99 (br s, 1H), 8.73 (br s, 1H), 7.62 (s, 2H), 7.39 (br s, 1H), 4.26 (br s, 2H), 3.37 (br s, 2H), 3.16 (br s, 2H), 2.99 (br s, 2H), 2.76 (s, 3H), 2.50 (br s, 2H), 2.48 (s, 3H). ES/MS m/z: calculated for C23H22F5N4O4: 513.15, found: 513.1.

Example 43. 5-(2-((1-(1,3,4-thiadiazol-2-yl)cyclopropyl)amino)-2-oxoacetyl)-N-(3,4-difluorophenyl)-6-methyl-2,3-dihydro-1H-pyrrolizine-7-carboxamide (43)

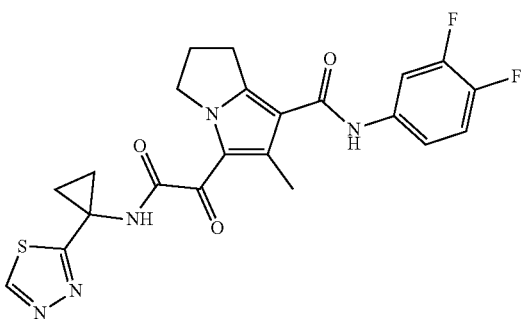

43

The product was synthesized in a manner similar to Example 29 using 3,4-difluoroaniline in place of 3,4,5-trifluoroaniline.

Example 44. 5-(2-((1-carbamoyl-3,3-difluorocyclobutyl)amino)-2-oxoacetyl)-N-(3,4-difluorophenyl)-6-methyl-2,3-dihydro-1H-pyrrolizine-7-carboxamide (44)

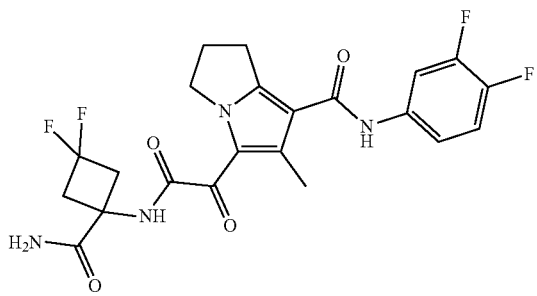

44

The product was synthesized in a manner similar to Example 32 using 3,4-difluoroaniline in place of 3-(difluoromethyl)-4-fluoroaniline.

Example 45. 5-(2-((3,3-difluoro-1-(methylcarbamoyl)cyclobutyl)amino)-2-oxoacetyl)-N-(4-fluorophenyl)-6-methyl-2,3-dihydro-1H-pyrrolizine-7-carboxamide

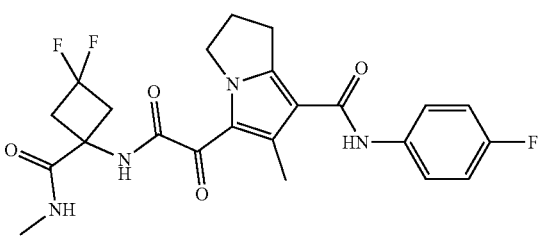

45

The product was prepared as described in Example 7 using 1-amino-3,3-difluoro-N-methylcyclobutane-1-carboxamide in place of 3,3-difluoro-1-(1-methyl-1H-1,2,3-triazol-5-yl)cyclobutan-1-amine. $^1$H NMR (400 MHz, DMSO-$d_6$) δ 9.18 (s, 1H), 9.16 (s, 1H), 7.32 (q, J=4.6 Hz, 1H), 7.28-7.12 (m, 2H), 6.70 (t, J=7.0 Hz, 2H), 3.75 (t, J=7.3 Hz, 2H), 2.79 (q, J=14.1 Hz, 2H), 2.61 (t, J=7.3 Hz, 2H), 2.46 (td, J=14.5, 7.7 Hz, 2H), 2.16 (d, J=4.6 Hz, 1H), 2.00 (quin, J=7.5 Hz, 2H), 1.89 (s, 3H). ES/MS m/z: calculated for C23H24F3N4O4: 477.17, found: 477.1.

Example 46. 5-(2-((3,3-difluoro-1-(methylcarbamoyl)cyclobutyl)amino)-2-oxoacetyl)-N-(3,4-difluorophenyl)-6-methyl-2,3-dihydro-1H-pyrrolizine-7-carboxamide (46)

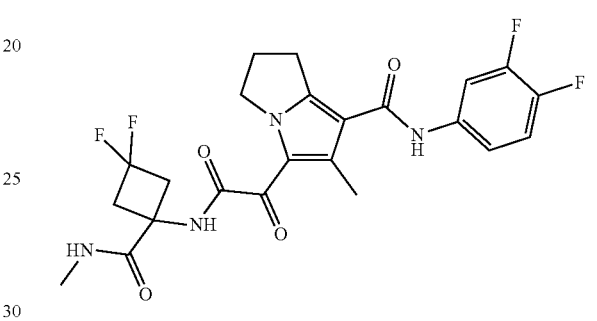

46

The product was synthesized in a manner similar to Example 1 using 1-amino-3,3-difluoro-N-methylcyclobutane-1-carboxamide hydrochloride in place of 3,3-difluoro-1-(1,3,4-thiadiazol-2-yl)cyclobutan-1-amine hydrogen chloride and 3,4-difluoroaniline in place of 3,4,5-trifluoroaniline.

Example 47. (R)-5-(2-((3-amino-1,1,1-trifluoro-2-methyl-3-oxopropan-2-0)amino)-2-oxoacetyl)-N-(3,4-difluorophenyl)-6-methyl-2,3-dihydro-1H-pyrrolizine-7-carboxamide (47)

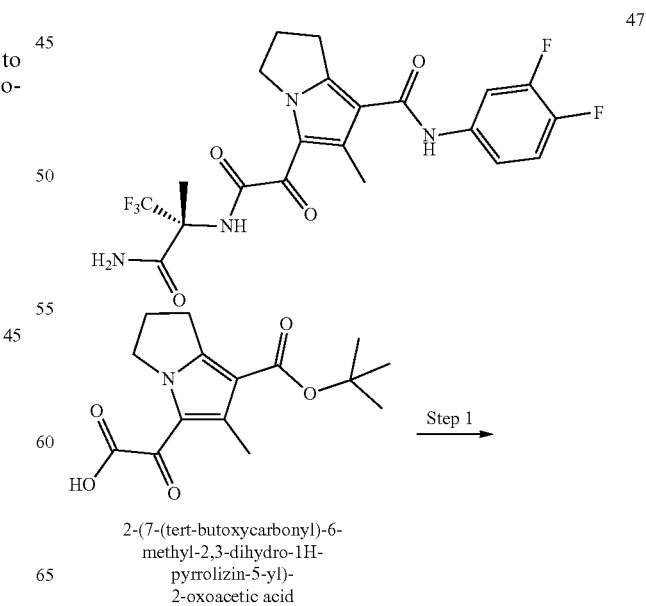

47

2-(7-(tert-butoxycarbonyl)-6-methyl-2,3-dihydro-1H-pyrrolizin-5-yl)-2-oxoacetic acid Step 1

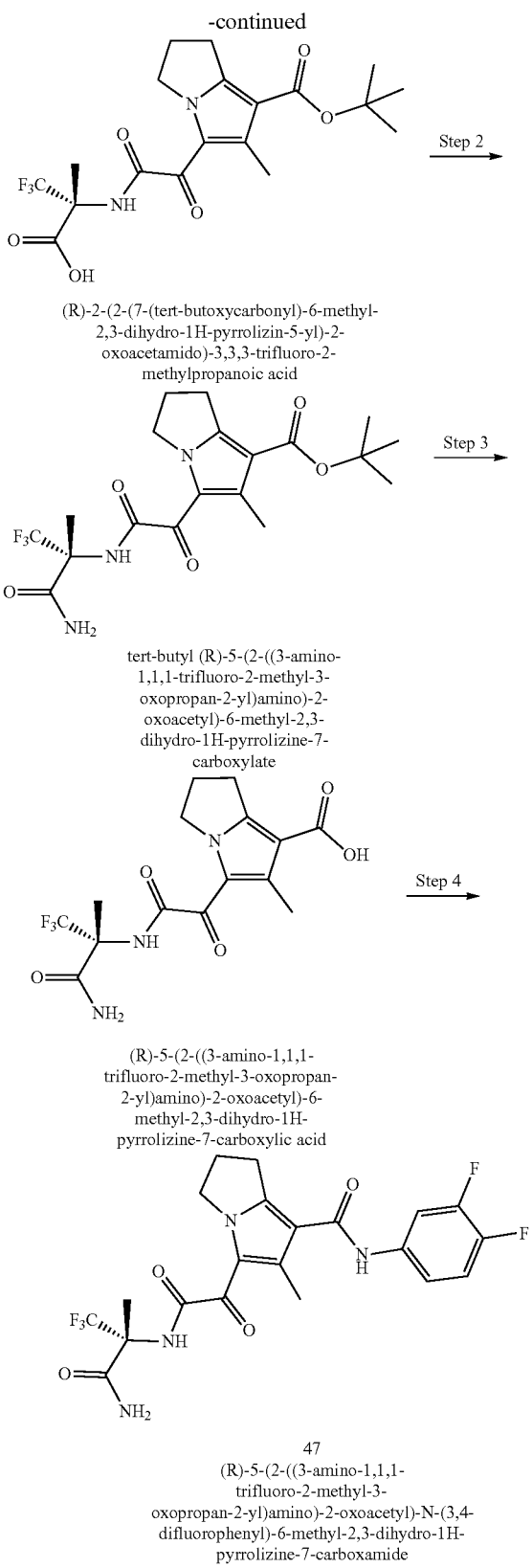

(R)-2-(2-(7-(tert-butoxycarbonyl)-6-methyl-
2,3-dihydro-1H-pyrrolizin-5-yl)-2-
oxoacetamido)-3,3,3-trifluoro-2-
methylpropanoic acid tert-butyl (R)-5-(2-((3-amino-
1,1,1-trifluoro-2-methyl-3-
oxopropan-2-yl)amino)-2-
oxoacetyl)-6-methyl-2,3-
dihydro-1H-pyrrolizine-7-
carboxylate (R)-5-(2-((3-amino-1,1,1-
trifluoro-2-methyl-3-oxopropan-
2-yl)amino)-2-oxoacetyl)-6-
methyl-2,3-dihydro-1H-
pyrrolizine-7-carboxylic acid 47
(R)-5-(2-((3-amino-1,1,1-
trifluoro-2-methyl-3-
oxopropan-2-yl)amino)-2-oxoacetyl)-N-(3,4-
difluorophenyl)-6-methyl-2,3-dihydro-1H-
pyrrolizine-7-carboxamide Step 1 A solution of (R)-2-amino-3,3,3-trifluoro-2-methylpropanoic acid hydrochloride (116 mg, 0.60 mmol) in dichloromethane (5 mL) was treated with trimethylamine (0.2 mL, 1.47 mmol) and concentrated under reduced pres-sure. The resultant residue was redissolved in N-methyl-2-pyrrolidone (2 mL), treated with trimethylsilylchloride (0.1 mL, 0.8 mmol), and stirred for 20 minutes. This mixture was then added to a premixed solution of 2-(7-(tert-butoxycar-bonyl)-6-methyl-2,3-dihydro-1H-pyrrolizin-5-yl)-2-oxoacetic acid (102 mg, 0.35 mmol), trimethylamine (0.20 mL, 1.5 mmol), and HATU (1-[bis(dimethylamino)methyl-ene]-1H-1,2,3-triazolo[4,5-b]pyridinium 3-oxide hexafluo-rophosphate) (159 mg, 0.42 mmol) in N-methyl-2-pyrroli-done (1 mL) and then stirred at room temperature for 60 minutes at which point the reaction mixture was diluted with ethyl acetate and sequentially washed with 1 M aqueous hydrogen chloride, 5% aqueous lithium chloride, and satu-rated aqueous sodium chloride. The organic phase was then dried over sodium sulfate, filtered, and concentrated under reduced pressure, then purified by silica gel chromatography (0-20% ethanol:dichloromethane) and preparative HPLC (10-100% acetonitrile in water, 0.1% TFA buffer) to afford (R)-2-(2-(7-(tert-butoxycarbonyl)-6-methyl-2,3-dihydro-1H-pyrrolizin-5-yl)-2-oxoacetamido)-3,3,3-trifluoro-2-methylpropanoic acid.

Step 2 A solution of (R)-2-(2-(7-(tert-butoxycarbonyl)-6-methyl-2,3-dihydro-1H-pyrrolizin-5-yl)-2-oxoacetamido)-3,3,3-trifluoro-2-methylpropanoic acid (33 mg, 0.08 mmol), ammonium chloride (23 mg, 0.43 mmol), N-methylmorpho-line (0.10 mL, 0.91 mmol), 4-dimethylaminopyridine (11 mg, 0.09 mmol), and HATU (1-[bis(dimethylamino)meth-ylene]-1H-1,2,3-triazolo[4,5-b]pyridinium 3-oxide hexafluorophosphate) (94 mg, 0.25 mmol) in N-methyl-2-pyrrolidone (1 mL) was stirred at room temperature for 20 minutes at which point the reaction mixture was diluted with ethyl acetate and sequentially washed with 1 M aqueous hydrogen chloride, 5% aqueous sodium bicarbonate, 5% aqueous lithium chloride, and saturated aqueous sodium chloride. The organic phase was then dried over sodium sulfate, filtered, and concentrated under reduced pressure to afford tert-butyl (R)-5-(2-((3-amino-1,1,1-trifluoro-2-methyl-3-oxopropan-2-yl)amino)-2-oxoacetyl)-6-methyl-2,3-dihydro-1H-pyrrolizine-7-carboxylate which was carried forward without further purification.

Step 3 A solution of tert-butyl (R)-5-(2-((3-amino-1,1,1-trifluoro-2-methyl-3-oxopropan-2-yl)amino)-2-oxoacetyl)-6-methyl-2,3-dihydro-1H-pyrrolizine-7-carboxylate (33 mg, 0.08 mmol) in 4 M hydrogen chloride in dioxane (1 mL) was stirred at 40° C. for 45 minutes at which point the reaction mixture was cooled to room temperature and solvent removed under reduced pressure to afford (R)-5-(2-((3-amino-1,1,1-trifluoro-2-methyl-3-oxopropan-2-yl)amino)-2-oxoacetyl)-6-methyl-2,3-dihydro-1H-pyrrolizine-7-car-boxylic acid which was carried forward without further purification.

Step 4 A solution of (R)-5-(2-((3-amino-1,1,1-trifluoro-2-methyl-3-oxopropan-2-yl)amino)-2-oxoacetyl)-6-methyl-2,3-dihydro-1H-pyrrolizine-7-carboxylic acid (29 mg, 0.08 mmol), 3,4-difluoroaniline (0.1 mL, 1.0 mmol), N-methyl-morpholine (0.05 mL, 0.45 mmol), and HATU (1-[Bis (dimethylamino)methylene]-1H-1,2,3-triazolo[4,5-b]pyri-dinium 3-oxide hexafluorophosphate) (41 mg, 0.11 mmol) in N-methyl-2-pyrrolidone (1 mL) was stirred at 100° C. for 3 h at which point the reaction mixture was cooled to room temperature, passed through a syringe filter, and purified by preparative HPLC (10-100% acetonitrile in water, 0.1% TFA buffer) to afford (R)-5-(2-((3-amino-1,1,1-trifluoro-2-methyl-3-oxopropan-2-yl)amino)-2-oxoacetyl)-N-(3,4-dif-luorophenyl)-6-methyl-2,3-dihydro-1H-pyrrolizine-7-car-boxamide (47).

Example 48. (S)-5-(2-((3-amino-1,1,1-trifluoro-2-methyl-3-oxopropan-2-yl)amino)-2-oxoacetyl)-N-(3,4-difluorophenyl)-6-methyl-2,3-dihydro-1H-pyrrolizine-7-carboxamide (48)

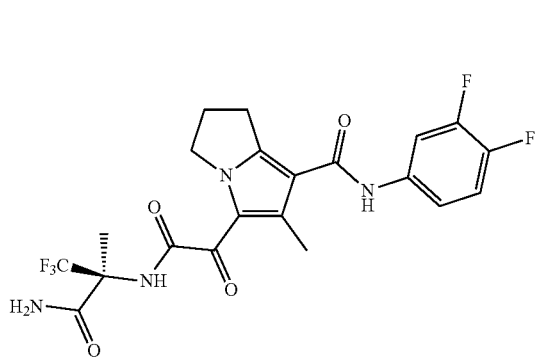

The product was synthesized in a manner similar to Example 47 using (S)-2-amino-3,3,3-trifluoro-2-methylpropanoic acid hydrochloride in place of (R)-2-amino-3,3,3-trifluoro-2-methylpropanoic acid hydrochloride.

Example 49. 5-(2-((3,3-difluoro-1-(1,3,4-thiadiazol-2-yl)cyclobutyl)amino)-2-oxoacetyl)-N-(3-(difluoromethyl)-4-fluorophenyl)-6-methyl-2,3-dihydro-1H-pyrrolizine-7-carboxamide (49)

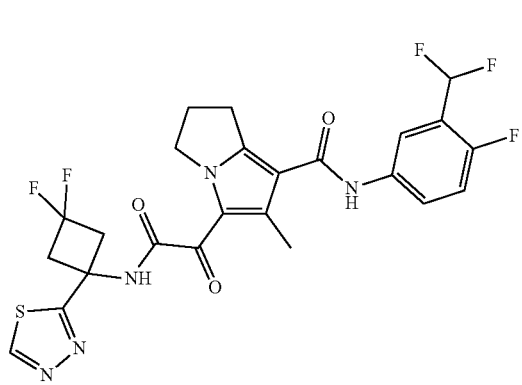

The product was synthesized in a manner similar to Example 1 using 3-(difluoromethyl)-4-fluoroaniline in place of 3,4,5-trifluoroaniline.

Example 50. 5-(2-((3,3-difluoro-1-(1,3,4-thiadiazol-2-yl)cyclobutyl)amino)-2-oxoacetyl)-N-(4-fluoro-3-(methoxymethyl)phenyl)-6-methyl-2,3-dihydro-1H-pyrrolizine-7-carboxamide (50)

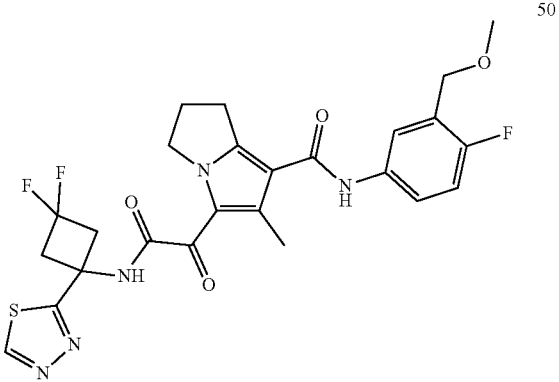 [SMILES: COCc1cc(NC(=O)c2c(C)c(C(=O)C(=O)NC3(c4nncs4)CC(F)(F)C3)n3c2CCC3)ccc1F]

The product was synthesized in a manner similar to Example 1 using 4-fluoro-3-(methoxymethyl)aniline in place of 3,4,5-trifluoroaniline.

Example 51. 5-(2-((3,3-difluoro-1-(1H-1,2,3-triazol-4-yl)cyclobutyl)amino)-2-oxoacetyl)-N-(4-fluoro-3-(methoxymethyl)phenyl)-6-methyl-2,3-dihydro-1H-pyrrolizine-7-carboxamide (51)

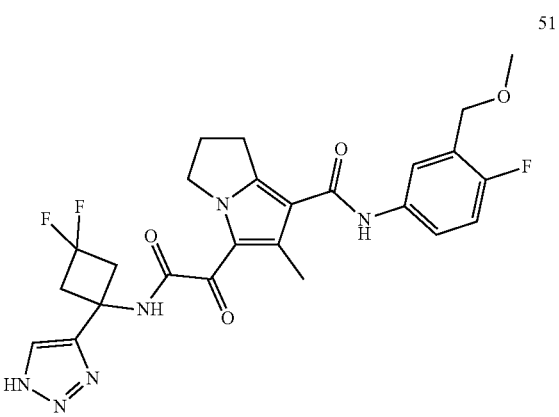 [SMILES: COCc1cc(NC(=O)c2c(C)c(C(=O)C(=O)NC3(c4c[nH]nn4)CC(F)(F)C3)n3c2CCC3)ccc1F]

The product was synthesized in a manner similar to Example 15 using 4-fluoro-3-(methoxymethyl)aniline in place of 3-cyano-4-fluoroaniline.

Example 52. 5-(2-(((1-(1,3,4-thiadiazol-2-yl)cyclopropyl)amino)-2-oxoacetyl)-6-chloro-N-(3,4-difluorophenyl)-2,3-dihydro-1H-pyrrolizine-7-carboxamide (52)

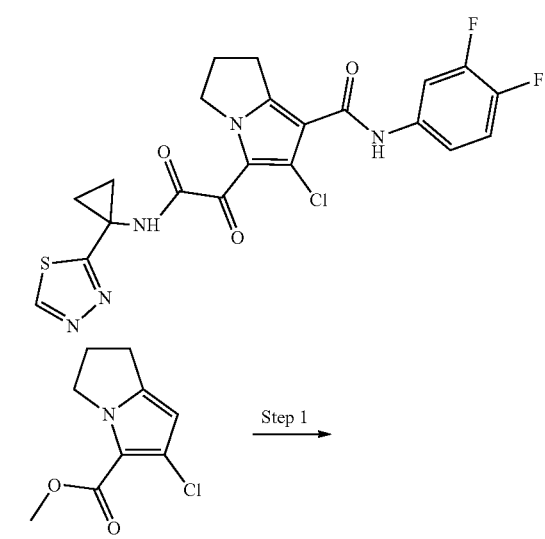

52 methyl 6-chloro-2,3-dihydro-1H-pyrrolizine-5-carboxylate

Step 1 methyl 6-chloro-7-(2,2,2-trichloroacetyl)-2,3-dihydro-1H-pyrrolizine-5-carboxylate Step 2 dimethyl 6-chloro-2,3-dihydro-1H-pyrrolizine-5,7-dicarboxylate

Step 3

6-chloro-7-(methoxycarbonyl)-2,3-dihydro-1H-pyrrolizine-5-carboxylic acid

Step 4

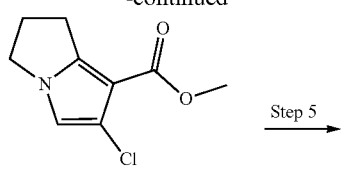

methyl 6-chloro-2,3-dihydro-1H-pyrrolizine-7-carboxylate

Step 5

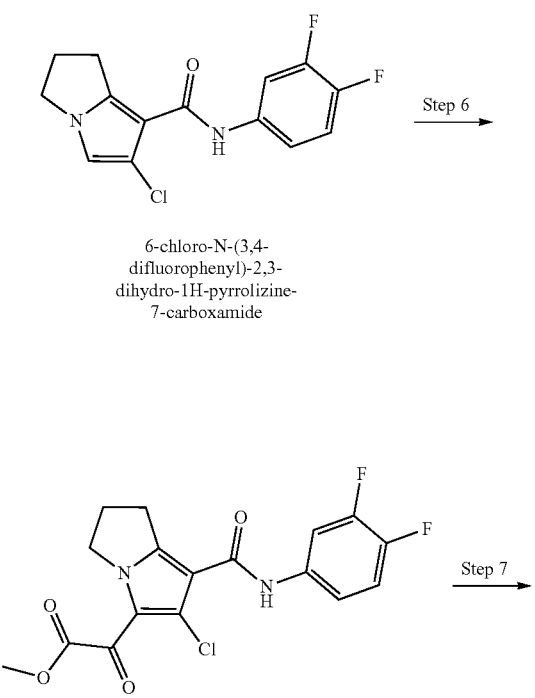

6-chloro-N-(3,4-difluorophenyl)-2,3-dihydro-1H-pyrrolizine-7-carboxamide

Step 6 methyl 2-(6-chloro-7-((3,4-difluorophenyl)carbamoyl)-2,3-dihydro-1H-pyrrolizin-5-yl)-2-oxoacetate Step 7

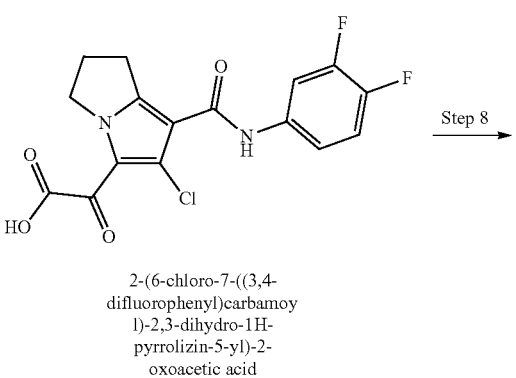

2-(6-chloro-7-((3,4-difluorophenyl)carbamoyl)-2,3-dihydro-1H-pyrrolizin-5-yl)-2-oxoacetic acid Step 8

-continued

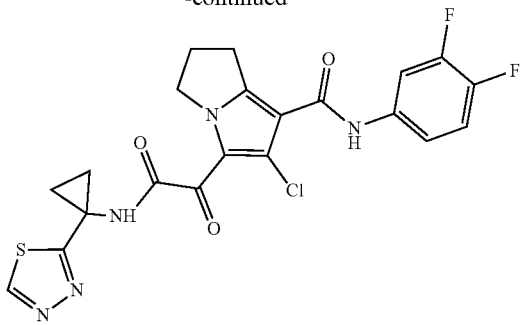

52
5-(2-((1-(1,3,4-thiadiazol-2-yl)cyclopropyl)amino)-2-oxoacetyl)-6-chloro-N-(3,4-difluorophenyl)-2,3-dihydro-1H-pyrrolizine-7-carboxamide Step 1 To a 0° C. solution of aluminum chloride (557 mg, 4.2 mmol) in dichloromethane (16 mL) was added methyl 6-chloro-2,3-dihydro-1H-pyrrolizine-5-carboxylate (395 mg, 2.0 mmol) followed by trichloroacetyl chloride (0.5 mL, 4.5 mmol). The reaction solution was then warmed to room temperature and stirred for 18 h at which point it was passed partitioned between dichloromethane and ice water. The aqueous phase was thrice extracted to dichloromethane and the combined organic phases were dried over sodium sulfate, filtered, concentrated under reduced pressure, and purified by silica gel column chromatography (0-10% ethyl acetate:hexanes) to afford methyl 6-chloro-7-(2,2,2-trichloroacetyl)-2,3-dihydro-1H-pyrrolizine-5-carboxylate. $^1$H NMR (400 MHz, Chloroform-d) δ 4.48-4.35 (m, 2H), 3.94 (s, 3H), 3.33 (t, J=7.6 Hz, 2H), 2.54 (p, J=7.5 Hz, 2H).

Step 2 Methyl 6-chloro-7-(2,2,2-trichloroacetyl)-2,3-dihydro-1H-pyrrolizine-5-carboxylate (358 mg, 1.0 mmol) was dissolved in a mixture of methanol (24 mL) and tetrahydrofuran (16 mL) then treated with 4 N aqueous sodium hydroxide (1 mL). The reaction mixture was stirred at room temperature for 1 h, acidified with dilute aqueous hydrochloric acid. The aqueous mixture was extracted to ethyl acetate and the combined organic phases washed with water, dried over sodium sulfate, filtered, and concentrated under reduced pressure to afford dimethyl 6-chloro-2,3-dihydro-1H-pyrrolizine-5,7-dicarboxylate which was carried forward without further purification. $^1$H NMR (400 MHz, Chloroform-d) δ 4.41-4.28 (m, 2H), 3.91 (s, 3H), 3.86 (s, 3H), 3.20-3.07 (m, 2H), 2.55-2.44 (m, 2H).

Step 3 Dimethyl 6-chloro-2,3-dihydro-1H-pyrrolizine-5,7-dicarboxylate (260 mg, 1.0 mmol) was dissolved in methanol (6 mL) and treated with 4 N aqueous sodium hydroxide (0.6 mL). The reaction mixture was stirred at 60° C. for 24 h, diluted with water, and acidified with dilute aqueous hydrochloric acid. The aqueous mixture was extracted to dichloromethane and the combined organic phases dried over sodium sulfate, filtered, and concentrated under reduced pressure to afford 6-chloro-7-(methoxycarbonyl)-2,3-dihydro-1H-pyrrolizine-5-carboxylic acid which was carried forward without further purification.

Step 4 To a solution of 6-chloro-7-(methoxycarbonyl)-2,3-dihydro-1H-pyrrolizine-5-carboxylic acid (160 mg, 0.62 mmol) in dichloromethane (4 mL) was added trifluoroacetic acid (0.75 mL, 9.8 mmol). The reaction mixture was stirred at 40° C. for 4 h, diluted with EtOAc and sequentially washed with water, saturated aqueous sodium bicarbonate, and saturated aqueous sodium chloride. The organic phase was then dried over sodium sulfate, filtered, concentrated under reduced pressure, and purified by silica gel column chromatography (0-30% ethyl acetate:hexanes) to afford methyl 6-chloro-2,3-dihydro-1H-pyrrolizine-7-carboxylate. $^1$H NMR (400 MHz, Chloroform-d) δ 6.61 (s, 1H), 3.97 (t, J=7.2 Hz, 2H), 3.82 (s, 3H), 3.15-2.98 (m, 2H), 2.49 (p, J=7.3 Hz, 2H).

Step 5 To a solution of methyl 6-chloro-2,3-dihydro-1H-pyrrolizine-7-carboxylate (26 mg, 0.13 mmol) and 3,4-difluoroaniline (39 mg, 0.30 mmol) in tetrahydrofuran (1 mL) was added a 1 M solution of Lithium bis(trimethylsilyl)amide in tetrahydrofuran (0.25 mL, 0.25 mmol). The reaction mixture was stirred at room temperature for 2 h, at which point it was diluted with ethyl acetate, washed sequentially with dilute aqueous hydrochloric acid then saturated aqueous sodium chloride, dried over sodium sulfate, filtered, concentrated under reduced pressure, and purified by silica gel column chromatography (0-30% ethyl acetate:hexanes) to afford 6-chloro-N-(3,4-difluorophenyl)-2,3-dihydro-1H-pyrrolizine-7-carboxamide. $^1$H NMR (400 MHz, Chloroform-d) δ 8.46 (s, 1H), 7.79 (ddd, J=12.5, 7.3, 2.5 Hz, 1H), 7.21-7.04 (m, 2H), 6.67 (s, 1H), 3.99 (t, J=7.2 Hz, 2H), 3.26-3.16 (m, 2H), 2.53 (tt, J=8.0, 6.9 Hz, 2H).

Step 6 To a solution of 6-chloro-N-(3,4-difluorophenyl)-2,3-dihydro-1H-pyrrolizine-7-carboxamide (24 mg, 0.08 mmol) in ethyl acetate (1 mL) was added methyl 2-chloro-2-oxoacetate (0.1 mL, 1.0 mmol). The reaction mixture was stirred at 40° C. for 3 h, cooled to room temperature and partitioned between ethyl acetate and saturated aqueous sodium bicarbonate. The aqueous phase was extracted to ethyl acetate and combined organic phases dried over sodium sulfate, filtered, and concentrated under reduced pressure to afford methyl 2-(6-chloro-7-((3,4-difluorophenyl)carbamoyl)-2,3-dihydro-1H-pyrrolizin-5-yl)-2-oxoacetate which was carried forward without further purification.

Step 7 A solution of methyl 2-(6-chloro-7-((3,4-difluorophenyl)carbamoyl)-2,3-dihydro-1H-pyrrolizin-5-yl)-2-oxoacetate (30 mg, 0.08 mmol) in methanol (1 mL) was treated with a 2 M solution of lithium hydroxide (0.1 mL, 0.2 mmol). After stirring for 40 min at room temperature, the reaction mixture was diluted with water, acidified with dilute aqueous hydrochloric acid and thrice extracted to ethyl acetate. The combined organic phase was dried over sodium sulfate, filtered, and concentrated under reduced pressure to afford 2-(6-chloro-7-((3,4-difluorophenyl)carbamoyl)-2,3-dihydro-1H-pyrrolizin-5-yl)-2-oxoacetic acid which was carried forward without further purification.

Step 8 A solution of 2-(6-chloro-7-((3,4-difluorophenyl)carbamoyl)-2,3-dihydro-1H-pyrrolizin-5-yl)-2-oxoacetic acid (20 mg, 0.09 mmol), 1-(1,3,4-thiadiazol-2-yl)cyclopropan-1-amine hydrobromide (30 mg, 0.14 mmol), N-methylmorpholine (0.05 mL, 0.45 mmol), and HATU (1-[Bis(dimethylamino)methylene]-1H-1,2,3-triazolo[4,5-b]pyridinium 3-oxid hexafluorophosphate) (43 mg, 0.11 mmol) in N,N-dimethylformamide (1 mL) was stirred at room temperature for 2 h at which point the reaction mixture was passed through a syringe filter, and purified by preparative HPLC (10-100% acetonitrile in water, 0.1% TFA buffer) to afford 5-(2-((1-(1,3,4-thiadiazol-2-yl)cyclopropyl)amino)-2-oxoacetyl)-6-chloro-N-(3,4-difluorophenyl)-2,3-dihydro-1H-pyrrolizine-7-carboxamide (52).

Example 53. 5-(2-((1-(1H-1,2,3-triazol-4-yl)cyclopropyl)amino)-2-oxoacetyl)-6-chloro-N-(3,4-difluorophenyl)-2,3-dihydro-1H-pyrrolizine-7-carboxamide (53)

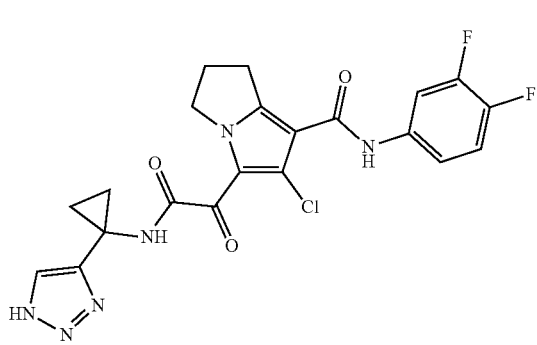

53

The product was synthesized in a manner similar to Example 52 using 1-(1H-1,2,3-triazol-4-yl)cyclopropan-1-amine bis(hydrogen chloride) in place of 1-(1,3,4-thiadiazol-2-yl)cyclopropan-1-amine hydrobromide.

Example 54. 6-chloro-5-(2-((3,3-difluoro-1-(1H-1,2,3-triazol-4-yl)cyclobutyl)amino)-2-oxoacetyl)-N-(3,4-difluorophenyl)-2,3-dihydro-1H-pyrrolizine-7-carboxamide (54)

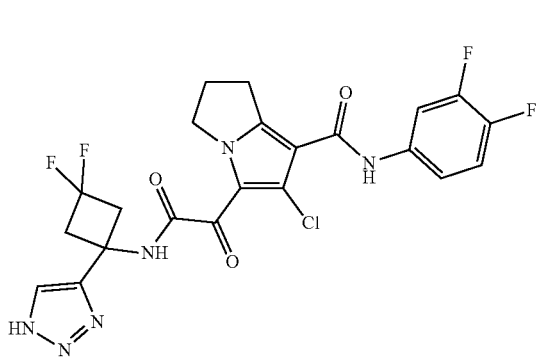

54

The product was synthesized in a manner similar to Example 52 using 3,3-difluoro-1-(1H-1,2,3-triazol-4-yl)cyclobutan-1-amine bis(hydrogen chloride) in place of 1-(1,3,4-thiadiazol-2-yl)cyclopropan-1-amine hydrobromide.

Example 55. 6-chloro-5-(2-((3,3-difluoro-1-(1H-1,2,3-triazol-4-0)cyclobutyl)amino)-2-oxoacetyl)-N-(3-(difluoromethyl)-4-fluorophenyl)-2,3-dihydro-1H-pyrrolizine-7-carboxamide (55)

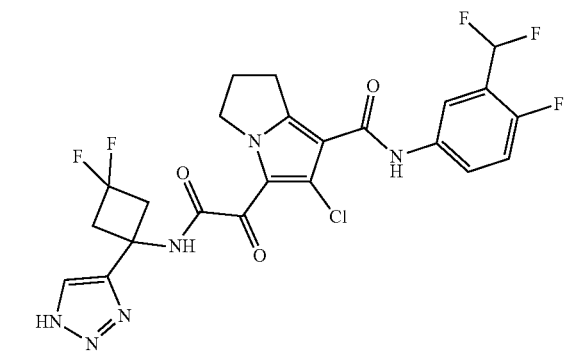

55

The product was synthesized in a manner similar to Example 54 using 3-(difluoromethyl)-4-fluoroaniline in place of 3,4-difluoroaniline.

Example 56. 5-(2-((1-(1H-1,2,3-triazol-4-yl)cyclopropyl)amino)-2-oxoacetyl)-6-chloro-N-(3-(difluoromethyl)-4-fluorophenyl)-2,3-dihydro-1H-pyrrolizine-7-carboxamide (56)

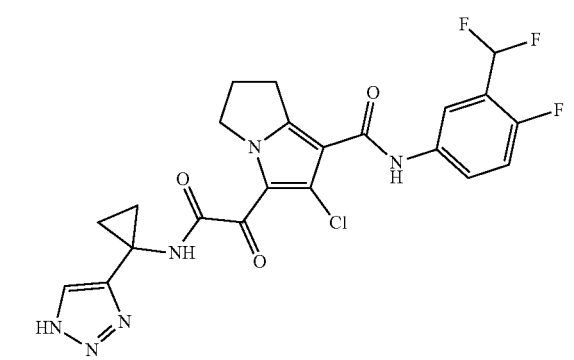

56

The product was synthesized in a manner similar to Example 53 using 3-(difluoromethyl)-4-fluoroaniline in place of 3,4-difluoroaniline.

TABLE 1

Compound Characterization Data

| Example No. | ES/MS m/z | 1H-NMR |
|---|---|---|
| 1 | [M + H]+ = 540.4 | 1H NMR (400 MHz, DMSO-d6) δ 10.30 (s, 1H), 9.90 (s, 1H), 9.57 (s, 1H), 7.56 (dd, J = 10.4, 6.5 Hz, 2H), 4.20 (t, J = 7.3 Hz, 2H), 3.63-3.47 (m, 2H), 3.31 (td, J = 14.1, 7.6 Hz, 2H), 3.04 (t, J = 7.5 Hz, 2H), 2.47-2.41 (m, 2H), 2.27 (s, 3H). |
| 2 | [M + H]+ = 529.5 | 1H NMR (400 MHz, DMSO-d6) δ 10.30 (s, 1H), 9.89 (s, 1H), 9.57 (s, 1H), 8.14 (dd, J = 5.8, 2.7 Hz, 1H), 7.92 (ddd, J = 9.3, 4.9, 2.8 Hz, 1H), 7.50 (t, J = 9.1 Hz, 1H), 4.20 (t, J = 7.3 Hz, 2H), 3.54 |

TABLE 1-continued

Compound Characterization Data

| Example No. | ES/MS m/z | 1H-NMR |
|---|---|---|
| | | (t, J = 13.7 Hz, 2H), 3.36-3.24 (m, 2H), 3.06 (t, J = 7.5 Hz, 2H), 2.47-2.40 (m, 2H), 2.28 (s, 3H). |
| 3 | [M + H]+ = 522.5 | 1H NMR (400 MHz, DMSO-d6) δ 10.29 (s, 1H), 9.79 (s, 1H), 9.57 (s, 1H), 7.80 (ddd, J = 13.2, 7.3, 2.1 Hz, 1H), 7.41-7.33 (m, 2H), 4.20 (t, J = 7.2 Hz, 2H), 3.62-3.48 (m, 2H), 3.31 (td, J = 14.2, 9.1 Hz, 2H), 3.04 (t, J = 7.5 Hz, 2H), 2.46-2.40 (m, 2H), 2.28 (s, 3H). |
| 4 | [M + H]+ = 537.5 | 1H NMR (400 MHz, DMSO-d6) δ 9.87 (s, 1H), 9.81 (s, 1H), 7.98 (s, 1H), 7.56 (dd, J = 10.5, 6.5 Hz, 2H), 4.16 (t, J = 7.3 Hz, 2H), 4.02 (s, 3H), 3.36-3.17 (m, 5H), 3.03 (t, J = 7.5 Hz, 2H), 2.43 (m, 2H), 2.20 (s, 3H). |
| 5 | [M + H]+ = 526.5 | 1H NMR (400 MHz, DMSO-d6) δ 9.86 (s, 1H), 9.80 (s, 1H), 8.13 (dd, J = 5.8, 2.7 Hz, 1H), 7.98 (s, 1H), 7.91 (ddd, J = 9.2, 4.9, 2.7 Hz, 1H), 7.49 (t, J = 9.2 Hz, 1H), 4.16 (t, J = 7.3 Hz, 2H), 4.02 (s, 3H), 3.35-3.17 (m, 4H), 3.05 (t, J = 7.5 Hz, 2H), 2.43 (m, 2H), 2.21 (s, 3H). |
| 6 | [M + H]+ = 519.6 | 1H NMR (400 MHz, DMSO-d6) δ 9.80 (s, 1H), 9.75 (s, 1H), 7.98 (s, 1H), 7.80 (ddd, J = 12.9, 7.8, 2.0 Hz, 1H), 7.41-7.31 (m, 2H), 4.15 (t, J = 7.3 Hz, 2H), 4.02 (s, 3H), 3.35-3.16 (m, 4H), 3.15 (s, 3H), 3.03 (t, J = 7.5 Hz, 2H), 2.46-2.40 (m, 2H), 2.20 (s, 3H). |
| 7 | MS: [M + H]+ = 501.5 | NMR: 1H NMR (400 MHz, Acetonitrile-d3) δ 8.27 (s, 1H), 8.02 (s, 1H), 7.74 (s, 1H), 7.65-7.58 (m, 2H), 7.10 (t, J = 8.9 Hz, 2H), 4.18 (t, J = 7.2 Hz, 2H), 4.04 (s, 3H), 3.45-3.30 (m, 4H), 3.08 (t, J = 7.5 Hz, 2H), 2.55-2.44 (m, 2H), 2.27 (s, 3H). |
| 8 | [M + H]+ = 504.5 | 1H NMR (400 MHz, DMSO-d6) δ 10.28 (s, 1H), 9.63 (s, 1H), 9.57 (s, 1H), 7.70-7.56 (m, 2H), 7.13 (t, J = 8.9 Hz, 2H), 4.20 (t, J = 7.3 Hz, 2H), 3.61-3.48 (m, 2H), 3.37-3.24 (m, 2H), 3.05 (t, J = 7.5 Hz, 2H), 2.28 (s, 3H). (one core methylene occluded by solvent signal) |
| 9 | LCMS: [M + H]+ = 501.6 | 1H NMR: 1H NMR (400 MHz, DMSO-d6) δ 9.81 (s, 1H), 9.60 (s, 1H), 7.67-7.61 (m, 3H), 7.13 (t, J = 8.9 Hz, 2H), 4.16 (t, J = 7.3 Hz, 2H), 4.11 (s, 3H), 3.24 (m, 4H), 3.03 (t, J = 7.5 Hz, 2H), 2.43 (m, 2H, partially solvent occluded), 2.22 (s, 3H). |
| 10 | LCMS: [M + H]+ = 501.6 | 1H NMR: 1H NMR (400 MHz, Acetonitrile-d3) δ 8.04 (s, 1H), 8.00 (s, 1H), 7.77 (s, 1H), 7.66-7.58 (m, 2H), 7.14-7.06 (m, 2H), 4.22 (t, J = 7.3 Hz, 2H), 4.04 (s, 3H), 3.47-3.20 (m, 4H), 3.08 (t, J = 7.5 Hz, 2H), 2.51 (p, J = 7.4 Hz, 2H), 2.37 (s, 3H). |
| 11 | [M + H]+ = 469.5 | 1H NMR (400 MHz, DMSO-d6) δ 9.74 (s, 1H), 9.52 (s, 1H), 7.85-7.73 (m, 2H), 7.40-7.32 (m, 2H), 4.17 (t, J = 7.2 Hz, 2H), 3.98 (s, 3H), 3.03 (t, J = 7.5 Hz, 2H), 2.43 (m, 2H, partially occluded by solvent signal), 2.25 (s, 3H), 1.31-1.24 (m, 2H), 1.19-1.11 (m, 2H). |
| 12 | [M + H]+ = 541.7 | 1H NMR (400 MHz, DMSO-d6) δ 9.74 (s, 1H), 9.49 (s, 1H), 7.86-7.74 (m, 1H), 7.63 (s, 1H), 7.41-7.31 (m, 2H), 4.17 (t, J = 7.2 Hz, 2H), 3.94 (s, 2H), 3.03 (t, J = 7.5 Hz, 2H), 2.43 (m, 2H, partially occluded by solvent signal), 2.24 (s, 3H), 1.26 (q, J = 4.9, 4.4 Hz, 2H), 1.14 (td, J = 8.2, 7.5, 6.1 Hz, 2H), 0.04 (s, 9H). |
| 13 | [M + H]+ = 412.4 | 1H NMR (400 MHz, DMSO-d6) δ 9.75 (s, 1H), 9.36 (s, 1H), 7.86-7.75 (m, 1H), 7.41-7.32 (m, 2H), 4.18 (t, J = 7.2 Hz, 2H), 3.07 (s, 1H), 3.03 (t, J = 7.5 Hz, 2H), 2.43 (m, 2H, partially solvent obscured), 2.31 (s, 3H), 1.20-1.13 (m, 2H), 1.06-0.97 (m, 2H). |
| 14 | LCMS: [M + H]+ = 499.5 | HNMR: 1H NMR (400 MHz, DMSO-d6) δ 9.80 (s, 1H), 9.76 (s, 1H), 7.72-7.61 (m, 2H), 7.18-7.08 (m, 2H), 4.29-4.15 (m, 1H), 3.25 (h, J = 13.1 Hz, 4H), 2.69 (d, J = 9.3 Hz, 1H), 2.42 (d, J = 6.7 Hz, 2H), 2.16 (s, 3H), 1.28 (td, J = 7.9, 4.8 Hz, 1H), 0.43 (q, J = 4.4 Hz, 1H). |
| 15 | [M + H]+ = 512.4 | 1H NMR (400 MHz, DMSO-d6) δ 9.86 (s, 1H), 9.81 (s, 1H), 8.13 (dd, J = 5.8, 2.7 Hz, 1H), 7.91 (ddd, J = 9.2, 4.9, 2.7 Hz, 1H), 7.79 (s, 1H), 7.49 (t, J = 9.1 Hz, 1H), 4.16 (t, J = 7.2 Hz, 2H), 3.26 (q, J = 12.2 Hz, 4H), 3.04 (t, J = 7.5 Hz, 2H), 2.43 (d, J = 7.2 Hz, 2H, partially obscured by solvent), 2.20 (s, 3H). |
| 16 | [M + H]+ = 521.6 | 1H NMR (400 MHz, DMSO-d6) δ 9.80 (s, 1H), 9.72 (s, 1H), 7.93 (dd, J = 6.9, 2.6 Hz, 1H), 7.80 (s, 1H), 7.55 (ddd, J = 9.0, 4.3, 2.6 Hz, 1H), 7.35 (t, J = 9.1 Hz, 1H), 4.16 (t, J = 7.2 Hz, 2H), 3.25 (dt, J = 22.9, 12.9 Hz, 4H), 3.04 (t, J = 7.5 Hz, 2H), 2.46-2.38 (m, 2H), 2.20 (s, 3H). |
| 17 | [M + H]+ = 487.5 | 1H NMR (400 MHz, DMSO-d6) δ 9.79 (s, 1H), 9.59 (s, 1H), 7.79 (s, 1H), 7.68-7.59 (m, 2H), 7.18-7.07 (m, 2H), 4.16 (t, J = 7.2 Hz, 2H), 3.26 (q, J = 12.0, 11.6 Hz, 4H), 3.03 (t, J = 7.5 Hz, 2H), 2.47-2.38 (m, 2H), 2.20 (s, 3H). |
| 18 | [M + H]+ = 523.4 | 1H NMR (400 MHz, DMSO-d6) δ 9.87 (s, 1H), 9.81 (s, 1H), 7.79 (s, 1H), 7.56 (dd, J = 10.4, 6.5 Hz, 2H), 4.16 (t, J = 7.3 Hz, 2H), 3.26 (q, J = 12.1, 11.7 Hz, 4H), 3.03 (t, J = 7.5 Hz, 2H), 2.43 (d, J = 7.2 Hz, 2H, partially obscured by solvent signal), 2.19 (s, 3H). |

TABLE 1-continued

Compound Characterization Data

| Example No. | ES/MS m/z | 1H-NMR |
|---|---|---|
| 19 | [M + H]+ = 468.18 | 1H NMR (400 MHz, Acetonitrile-d3) δ 8.10 (s, 1H), 7.78 (ddd, J = 13.2, 7.4, 2.5 Hz, 1H), 7.42 (s, 1H), 7.31 (d, J = 8.8 Hz, 1H), 7.28-7.18 (m, 1H), 4.31-4.19 (m, 2H), 3.73 (d, J = 1.0 Hz, 2H), 3.10 (t, J = 7.5 Hz, 3H), 3.02-2.75 (m, 5H), 2.54 (q, J = 7.4 Hz, 2H), 2.48 (s, 3H). |
| 20 | [M + H]+ = 528.11 | 1H NMR (400 MHz, Acetone-d6) δ 8.88 (s, 1H), 8.77 (s, 1H), 8.59 (t, J = 5.7 Hz, 1H), 8.40 (d, J = 5.4 Hz, 1H), 6.93 (t, J = 53.6 Hz, 1H), 4.31 (t, J = 7.3 Hz, 2H), 3.38 (td, J = 15.4, 11.6 Hz, 2H), 3.27 (t, J = 7.5 Hz, 2H), 3.00 (td, J = 14.7, 6.6 Hz, 2H), 2.77 (d, J = 4.7 Hz, 3H), 2.65-2.57 (m, 2H), 2.55 (s, 3H). |
| 21 | [M+H]+= 517.5 | 1H NMR (400 MHz, DMSO-d6) δ 9.96 (s, 1H), 9.77 (s, 1H), 7.88-7.73 (m, 2H), 7.45-7.30 (m, 2H), 4.30-4.16 (m, 2H), 3.25 (h, J = 13.0, 12.1 Hz, 4H), 2.75-2.66 (m, 1H), 2.41 (d, J = 6.6 Hz, 1H), 2.15 (s, 3H), 1.28 (td, J = 7.8, 4.6 Hz, 1H), 0.43 (q, J = 4.3 Hz, 1H). |
| 22 | LCMS: [M + H]+ = 507.4 | HNMR: 1H NMR (400 MHz, DMSO-d6) δ 9.97 (s, 1H), 9.56 (s, 1H), 7.84 (ddd, J = 13.4, 7.5, 2.2 Hz, 1H), 7.73 (q, J = 4.5 Hz, 1H), 7.45-7.31 (m, 2H), 4.31 (dd, J = 13.2, 5.8 Hz, 1H), 4.22 (d, J = 13.1 Hz, 1H), 3.31-3.10 (m, 2H), 2.88 (ddt, J = 22.6, 14.5, 8.0 Hz, 2H), 2.77-2.68 (m, 1H), 2.59 (d, J = 4.5 Hz, 3H), 2.46-2.36 (m, 1H), 2.29 (s, 3H), 1.28 (td, J = 7.9, 4.7 Hz, 1H), 0.42 (q, J = 4.4 Hz, 1H). |
| 23 | [M + H]+ = 517.4 | 1H NMR (400 MHz, DMSO-d6) δ 9.87 (s, 1H), 9.68 (s, 1H), 7.78 (ddd, J = 12.1, 7.0, 2.0 Hz, 2H), 7.43-7.29 (m, 2H), 4.31-4.25 (m, 1H), 3.40-3.18 (m, 5H), 3.09 (d, J = 18.1 Hz, 1H), 2.17 (s, 4H), 1.07 (dt, J = 8.5, 5.8 Hz, 1H), 0.23 (td, J = 5.4, 2.1 Hz, 1H). |
| 24 | LCMS: [M + H]+ = 507.4 | HNMR: 1H NMR (400 MHz, DMSO-d6) δ 9.69 (s, 1H), 9.64 (s, 1H), 7.85-7.69 (m, 2H), 7.44-7.29 (m, 2H), 4.33 (t, J = 6.0 Hz, 1H), 3.36 (dd, J = 18.1, 6.8 Hz, 1H), 3.23 (q, J = 13.8 Hz, 2H), 3.10 (d, J = 18.1 Hz, 1H), 2.90 (qd, J = 12.7, 11.4, 7.2 Hz, 2H), 2.59 (d, J = 4.6 Hz, 3H), 2.29 (s, 3H), 2.20-2.09 (m, 1H), 1.09 (dt, J = 8.5, 5.8 Hz, 1H), 0.23 (td, J = 5.4, 2.1 Hz, 1H). |
| 25 | [M + H]+ = 517.5 | 1H NMR (400 MHz, DMSO-d6) δ 9.96 (s, 1H), 9.77 (s, 1H), 7.89-7.72 (m, 2H), 7.44-7.31 (m, 2H), 4.31-4.16 (m, 2H), 3.25 (h, J = 13.1 Hz, 4H), 2.70 (d, J = 8.9 Hz, 1H), 2.41 (t, J = 6.3 Hz, 1H), 2.15 (s, 3H), 1.28 (td, J = 7.9, 4.7 Hz, 1H), 0.42 (q, J = 4.4 Hz, 1H). |
| 26 | [M + H]+ = 507.4 | 1H NMR (400 MHz, DMSO-d6) δ 9.98 (s, 1H), 9.56 (s, 1H), 7.84 (ddd, J = 13.4, 7.5, 2.2 Hz, 1H), 7.73 (q, J = 4.6 Hz, 1H), 7.46-7.31 (m, 2H), 4.31 (dd, J = 13.2, 5.8 Hz, 1H), 4.22 (d, J = 13.2 Hz, 1H), 3.21 (dq, J = 26.3, 13.7 Hz, 2H), 2.89 (ddd, J = 25.7, 13.7, 6.8 Hz, 2H), 2.76-2.68 (m, 1H), 2.59 (d, J = 4.5 Hz, 3H), 2.42 (td, J = 7.0, 3.5 Hz, 1H), 2.29 (s, 3H), 1.28 (td, J = 7.9, 4.7 Hz, 1H), 0.42 (q, J = 4.4 Hz, 1H). |
| 27 | [M + H]+ = 487.54 | 1H NMR (400 MHz, Acetone-d6) δ 8.88 (s, 1H), 8.57 (s, 1H), 8.08 (d, J = 6.4 Hz, 1H), 7.90 (s, 1H), 7.68 (s, 1H), 7.27 (t, J = 9.4 Hz, 1H), 7.10 (t, J = 54.5 Hz, 1H), 4.27 (t, J = 7.5 Hz, 2H), 3.18 (t, J = 7.5 Hz, 2H), 2.55 (quin, J = 7.5 Hz, 2H), 2.46 (s, 3H), 1.50-1.28 (m, 4H). |
| 28 | [M + H]+ = 524.1 | 1H NMR (400 MHz, Acetonitrile-d3) δ 8.16 (s, 1H), 8.04 (dd, J = 5.7, 2.7 Hz, 1H), 7.97 (s, 1H), 7.87-7.79 (m, 1H), 7.28 (t, J = 9.0 Hz, 1H), 4.22 (t, J = 7.3 Hz, 2H), 3.35-3.23 (m, 2H), 3.07 (t, J = 7.5 Hz, 2H), 2.88 (q, J = 14.8, 7.3 Hz, 2H), 2.68 (d, J = 4.7 Hz, 3H), 2.50 (q, J = 7.2 Hz, 2H), 2.42 (s, 3H). |
| 29 | [M + H]+ = 490.2 | 1H NMR (400 MHz, DMSO-d6) δ 10.02 (s, 1H), 9.90 (s, 1H), 9.41 (s, 1H), 7.57 (dd, J = 10.4, 6.5 Hz, 2H), 4.21 (t, J = 7.2 Hz, 2H), 3.04 (t, J = 7.6 Hz, 2H), 2.29 (s, 3H), 1.70-1.62 (m, 2H), 1.48-1.36 (m, 2H). (note: one core methylene occluded by solvent signal) |
| 30 | [M + H]+ = 454.3 | 1H NMR (400 MHz, DMSO-d6) δ 10.01 (s, 1H), 9.78 (s, 1H), 9.41 (s, 1H), 7.98 (dd, J = 6.6, 2.6 Hz, 1H), 7.77 (dd, J = 8.5, 4.5 Hz, 1H), 7.38-7.26 (m, 1H), 7.13 (d, J = 54.3 Hz, 1H), 4.21 (t, J = 7.3 Hz, 2H), 3.06 (t, J = 7.5 Hz, 2H), 2.31 (s, 3H), 1.72-1.61 (m, 2H), 1.47-1.36 (m, 2H). |
| 31 | [M + H]+ = 504.2 | 1H NMR (400 MHz, DMSO-d6) δ 10.01 (s, 1H), 9.78 (s, 1H), 9.41 (s, 1H), 7.98 (dd, J = 6.6, 2.6 Hz, 1H), 7.77 (dd, J = 8.5, 4.5 Hz, 1H), 7.38-7.26 (m, 1H), 7.13 (d, J = 54.3 Hz, 1H), 4.21 (t, J = 7.3 Hz, 2H), 3.06 (t, J = 7.5 Hz, 2H), 2.31 (s, 3H), 1.72-1.61 (m, 2H), 1.47-1.36 (m, 2H). (note: one core methylene occluded by solvent signal) |
| 32 | [M + H]+ = 513.4 | 1H NMR (400 MHz, DMSO-d6) δ 9.78 (s, 1H), 9.56 (s, 1H), 7.99 (dd, J = 6.5, 2.6 Hz, 1H), 7.81-7.71 (m, 1H), 7.41-7.26 (m, 2H), 7.23-7.02 (m, 2H), 4.20 (t, J = 7.3 Hz, 2H), 3.30-3.15 (m, 2H), 3.06 (t, J = 7.5 Hz, 2H), 2.95-2.81 (m, 2H), 2.43 (m, 1H (occluded by solvent signal)), 2.35 (s, 3H). |

TABLE 1-continued

Compound Characterization Data

| Example No. | ES/MS m/z | 1H-NMR |
|---|---|---|
| 33 | [M + H]+ = 507.13 | 1H NMR (400 MHz, DMSO-d6) δ 9.67 (d, J = 19.2 Hz, 2H), 7.85-7.74 (m, 2H), 7.44-7.32 (m, 2H), 4.34 (d, J = 6.2 Hz, 1H), 3.54 (s, 3H), 3.36 (dd, J = 18.1, 6.8 Hz, 1H), 3.21 (t, J = 14.1 Hz, 1H), 3.10 (d, J = 18.2 Hz, 1H), 2.59 (d, J = 4.5 Hz, 3H), 2.29 (s, 3H), 2.14 (d, J = 7.6 Hz, 1H), 1.14-1.04 (m, 1H), 0.23 (d, J = 4.7 Hz, 1H). |
| 34 | [M + H]+ = 517.17 | 1H NMR (400 MHz, DMSO-d6) δ 9.87 (s, 1H), 9.69 (s, 1H), 7.84-7.72 (m, 2H), 7.44-7.27 (m, 2H), 4.28 (s, 1H), 3.27 (d, J = 9.9 Hz, 4H), 3.11 (s, 1H), 3.06 (s, 1H), 2.17 (s, 4H), 1.13-0.99 (m, 1H), 0.23 (d, J = 4.7 Hz, 1H). |
| 35 | [M + H]+ = 511.1 | 1H NMR (400 MHz, Acetone-d6) δ 8.85 (s, 1H), 8.69 (s, 1H), 8.05 (ddd, J = 6.8, 2.6, 1.7 Hz, 1H), 7.64 (dddd, J = 8.5, 4.2, 2.7, 1.4 Hz, 1H), 7.40 (m, 1H), 7.26 (t, J = 9.0 Hz, 1H), 4.27 (t, J = 7.3 Hz, 2H), 3.38 (td, J = 15.2, 11.5 Hz, 2H), 3.17 (t, J = 7.5 Hz, 2H), 3.00 (td, J = 14.7, 6.6 Hz, 2H), 2.77 (d, J = 4.2 Hz, 3H), 2.54 (quin, J = 7.5 Hz, 2H), 2.47 (s, 3H). |
| 36 | [M + H]+ = 471.22 | 1H NMR (400 MHz, Acetonitrile-d3) δ 8.17 (s, 1H), 8.10 (s, 1H), 7.78 (s, 1H), 7.79-7.70 (m, 1H), 7.33-7.26 (m, 1H), 7.22 (dt, J = 10.6, 8.8 Hz, 1H), 5.02 (d, J = 6.7 Hz, 2H), 4.96 (d, J = 6.7 Hz, 2H), 4.23 (t, J = 7.2 Hz, 2H), 3.07 (t, J = 7.5 Hz, 2H), 2.50 (p, J = 7.4 Hz, 2H), 2.39 (s, 3H). |
| 37 | [M + H]+ = 537.13 | 1H NMR (400 MHz, Acetonitrile-d3) δ 8.13 (s, 1H), 8.01 (s, 1H), 7.92 (dd, J = 6.3, 2.6 Hz, 1H), 7.76 (s, 1H), 7.72 (dd, J = 8.6, 4.1 Hz, 1H), 7.20 (ddd, J = 10.2, 9.1, 1.2 Hz, 1H), 6.98 (t, J = 54.7 Hz, 1H), 4.21 (t, J = 7.3 Hz, 2H), 3.44-3.22 (m, 4H), 3.08 (t, J = 7.5 Hz, 2H), 2.49 (p, J = 7.5 Hz, 2H), 2.34 (d, J = 1.0 Hz, 3H). |
| 38 | [M + H]+ = 461.4 | 1H NMR (400 MHz, DMSO-d6) δ 9.77 (s, 1H), 7.80 (dd, J = 13.2, 7.5 Hz, 1H), 7.69 (d, J = 4.9 Hz, 1H), 7.41-7.32 (m, 2H), 5.28 (t, J = 5.8 Hz, 1H), 4.61 (d, J = 8.8 Hz, 1H), 4.44 (d, J = 8.8 Hz, 1H), 4.20 (d, J = 7.6 Hz, 1H), 3.61 (ddd, J = 35.9, 11.1, 5.8 Hz, 2H), 3.05 (t, J = 7.5 Hz, 2H), 2.60 (d, J = 4.7 Hz, 3H), 2.30 (s, 3H). [NOTE: distal ring internal methylene obscured by solvent signal]; 1H NMR (400 MHz, DMSO-d6) δ 9.76 (s, 1H), 9.72 (s, 1H), 7.87-7.71 (m, 2H), 7.43-7.30 (m, 2H), 4.84 (d, J = 6.7 Hz, 2H), 4.60 (d, J = 6.7 Hz, 2H), 4.19 (t, J = 7.3 Hz, 2H), 3.04 (t, J = 7.5 Hz, 2H), 2.62 (d, J = 4.5 Hz, 3H), 2.46-2.38 (m, 2H), 2.34 (s, 3H). |
| 39 | [M + H]+ = 505.19 | 1H NMR (400 MHz, Acetonitrile-d3) δ 8.08 (s, 1H), 7.97 (s, 1H), 7.76 (s, 1H), 7.75 (ddd, J = 12.8, 7.5, 2.6 Hz, 1H), 7.28 (dddd, J = 9.0, 4.2, 2.6, 1.3 Hz, 1H), 7.22 (dt, J = 10.5, 8.8 Hz, 1H), 4.25-4.17 (m, 2H), 3.42-3.21 (m, 4H), 3.07 (t, J = 7.5 Hz, 2H), 2.49 (p, J = 7.5 Hz, 2H), 2.34 (s, 3H). |
| 40 | [M + H]+ = 455.13 | 1H NMR (400 MHz, Acetonitrile-d3) δ 8.08 (s, 1H), 7.87 (s, 1H), 7.76 (ddd, J = 13.2, 7.5, 2.5 Hz, 1H), 7.59 (s, 1H), 7.33-7.26 (m, 1H), 7.22 (dt, J = 10.5, 8.8 Hz, 1H), 4.30-4.19 (m, 2H), 3.07 (t, J = 7.5 Hz, 2H), 2.50 (p, J = 7.5 Hz, 2H), 2.39 (s, 3H), 1.43-1.34 (m, 2H), 1.34-1.25 (m, 2H). |
| 41 | [M + H]+ = 527.1 | 1H NMR (400 MHz, DMSO-d6) δ 9.79 (br s, 1H), 9.62 (br s, 1H), 8.01 (dd, J = 6.6, 2.6 Hz, 1H), 8.75-8.82 (m, 1H), 7.38-7.29 (m, 1H), 7.22 (t, J = 54.3 Hz, 1H), 4.21 (t, J = 7.3 Hz, 2H), 3.24 (q, J = 14.1 Hz, 2H), 3.08 (t, J = 7.5 Hz, 2H), 3.01-2.82 (m, 2H), 2.62 (d, J = 4.5 Hz, 3H), 2.45 (quin, J = 7.4 Hz, 1H), 2.36 (s, 3H). |
| 42 | [M + H]+ = 513.1 | 1H NMR (400 MHz, DMSO-d6) δ 9.18 (s, 1H), 9.16 (s, 1H), 7.32 (q, J = 4.6 Hz, 1H), 7.28-7.12 (m, 2H), 6.70 (t, J = 7.0 Hz, 2H), 3.75 (t, J = 7.3 Hz, 2H), 2.79 (q, J = 14.1 Hz, 2H), 2.61 (t, J = 7.3 Hz, 2H), 2.46 (td, J = 14.5, 7.7 Hz, 2H), 2.16 (d, J = 4.6 Hz, 1H), 2.00 (quin, J = 7.5 Hz, 2H), 1.89 (s, 3H). |
| 43 | [M + H]+ = 472.2 | 1H NMR (499 MHz, DMSO-d6) δ 10.00 (s, 1H), 9.77 (s, 1H), 9.41 (s, 1H), 7.81 (ddd, J = 13.3, 7.4, 2.2 Hz, 1H), 7.44-7.29 (m, 2H), 4.21 (t, J = 7.3 Hz, 2H), 3.05 (t, J = 7.6 Hz, 2H), 2.30 (s, 3H), 1.66 (q, J = 5.0 Hz, 2H), 1.43 (q, J = 5.0 Hz, 2H). [Note: one methylene signal obscured by solvent peak] |
| 44 | [M + H]+ = 481.3 | 1H NMR (499 MHz, DMSO-d6) δ 9.76 (s, 1H), 9.55 (s, 1H), 7.81 (ddd, J = 13.5, 8.1, 2.2 Hz, 1H), 7.37 (td, J = 5.4, 4.9, 3.2 Hz, 3H), 7.12 (s, 1H), 4.20 (t, J = 7.3 Hz, 2H), 3.22 (td, J = 14.8, 11.7 Hz, 2H), 3.05 (t, J = 7.5 Hz, 2H), 2.88 (td, J = 14.5, 8.1 Hz, 2H), 2.47-2.40 (m, 2H), 2.35 (s, 3H). |
| 45 | [M + H]+ = 477.1 | 1H NMR (400 MHz, DMSO-d6) δ 9.18 (s, 1H), 9.16 (s, 1H), 7.32 (q, J = 4.6 Hz, 1H), 7.28-7.12 (m, 2H), 6.70 (t, J = 7.0 Hz, 2H), 3.75 (t, J = 7.3 Hz, 2H), 2.79 (q, J = 14.1 Hz, 2H), 2.61 (t, J = 7.3 Hz, 2H), 2.46 (td, J = 14.5, 7.7 Hz, 2H), 2.16 (d, J = 4.6 Hz, 1H), 2.00 (quin, J = 7.5 Hz, 2H), 1.89 (s, 3H). |
| 46 | [M + H]+ = 495.1 | 1H NMR (400 MHz, DMSO-d6) δ 9.75 (s, 1H), 9.58 (s, 1H), 7.86-7.77 (m, 1H), 7.74 (d, J = 4.8 Hz, 1H), 7.41-7.32 (m, 2H), 4.18 (t, J = 7.3 Hz, 2H), 3.20 (dd, J = 15.0, 12.1 Hz, 2H), 3.05 (t, J = |

TABLE 1-continued

Compound Characterization Data

| Example No. | ES/MS m/z | 1H-NMR |
|---|---|---|
| | | 7.5 Hz, 2H), 2.90 (dt, J = 22.1, 7.2 Hz, 2H), 2.60 (d, J = 4.5 Hz, 3H), 2.46-2.39 (m, 2H), 2.33 (s, 3H). |
| 47 | [M + H]+ = 487.6 | $^1$H NMR (400 MHz, DMSO-d6) δ 9.76 (s, 1H), 9.18 (s, 1H), 7.87-7.73 (m, 1H), 7.60 (s, 1H), 7.50 (s, 1H), 7.37 (qd, J = 4.7, 4.0, 2.5 Hz, 2H), 4.19 (t, J = 7.4 Hz, 2H), 3.04 (t, J = 7.5 Hz, 2H), 2.47-2.39 (m, 2H), 2.34 (s, 3H), 1.72 (s, 3H). |
| 48 | [M + H]+ = 487.4 | $^1$H NMR (400 MHz, DMSO-d6) δ 9.76 (s, 1H), 9.18 (s, 1H), 7.86-7.75 (m, 1H), 7.60 (s, 1H), 7.50 (s, 1H), 7.37 (qd, J = 4.7, 4.0, 2.5 Hz, 2H), 4.24-4.14 (m, 2H), 3.04 (t, J = 7.5 Hz, 2H), 2.47-2.39 (m, 2H), 2.34 (s, 3H), 1.72 (s, 3H). |
| 49 | [M + H]+ = 553.8 | $^1$H NMR (400 MHz, DMSO-d6) δ 10.32 (s, 1H), 9.82 (s, 1H), 9.60 (s, 1H), 8.01 (dd, J = 6.5, 2.6 Hz, 1H), 7.80 (dt, J = 8.1, 3.6 Hz, 1H), 7.41-7.05 (m, 2H), 4.24 (t, J = 7.3 Hz, 2H), 3.68-3.50 (m, 2H), 3.44-3.26 (m, 2H), 3.09 (t, J = 7.5 Hz, 2H), 2.51-2.45 (m, 2H), 2.32 (s, 3H). |
| 50 | [M + H]+ = 547.9 | $^1$H NMR (400 MHz, DMSO-d6) δ 10.31 (s, 1H), 9.65 (s, 1H), 9.60 (s, 1H), 7.74 (dd, J = 6.7, 2.7 Hz, 1H), 7.61 (ddd, J = 8.9, 4.7, 2.7 Hz, 1H), 7.16 (t, J = 9.3 Hz, 1H), 4.45 (s, 2H), 4.23 (t, J = 7.3 Hz, 2H), 3.64-3.54 (m, 2H), 3.39-3.27 (m, 5H), 3.08 (t, J = 7.5 Hz, 2H), 2.47 (d, J = 8.9 Hz, 2H), 2.31 (s, 3H). |
| 51 | [M + H]+ = 531.0 | $^1$H NMR (400 MHz, DMSO-d6) δ 9.82 (s, 1H), 9.61 (s, 1H), 7.82 (s, 1H), 7.74 (dd, J = 6.7, 2.7 Hz, 1H), 7.61 (ddd, J = 8.9, 4.7, 2.8 Hz, 1H), 7.15 (t, J = 9.3 Hz, 1H), 4.45 (s, 2H), 4.19 (t, J = 7.3 Hz, 2H), 3.33 (s, 7H), 3.07 (t, J = 7.5 Hz, 2H), 2.48-2.40 (m, 2H), 2.23 (s, 3H). |
| 52 | [M + H]+ = 491.8 | $^1$H NMR (400 MHz, DMSO-d6) δ 10.04 (s, 1H), 9.99 (s, 1H), 9.44 (s, 1H), 7.90-7.77 (m, 1H), 7.48-7.34 (m, 2H), 4.31 (t, J = 7.3 Hz, 2H), 3.10 (t, J = 7.5 Hz, 2H), 1.73-1.64 (m, 2H), 1.52-1.43 (m, 2H). (One methylene signal likely occluded by solvent signal). |
| 53 | [M + H]+ = 475.0 | $^1$H NMR (400 MHz, DMSO-d6) δ 9.97 (s, 1H), 9.58 (s, 1H), 7.90-7.78 (m, 1H), 7.61 (s, 1H), 7.42 (qd, J = 4.7, 2.5 Hz, 2H), 4.29 (t, J = 7.3 Hz, 2H), 3.09 (t, J = 7.5 Hz, 2H), 2.46 (d, J = 7.4 Hz, 2H), 1.39-1.17 (m, 4H). |
| 54 | [M + H]+ = 525.0 | $^1$H NMR (400 MHz, DMSO-d6) δ 9.98 (s, 1H), 9.84 (s, 1H), 7.89-7.79 (m, 1H), 7.42 (qd, J = 4.6, 3.9, 2.5 Hz, 2H), 4.28 (t, J = 7.3 Hz, 2H), 3.31 (t, J = 12.2 Hz, 4H), 3.09 (t, J = 7.5 Hz, 2H), 2.49-2.40 (m, 2H). |
| 55 | [M + H]+ = 557.0 | $^1$H NMR (400 MHz, DMSO-d6) δ 9.99 (s, 1H), 9.84 (s, 1H), 8.02 (dd, J = 6.4, 2.6 Hz, 1H), 7.81 (dt, J = 8.0, 3.3 Hz, 2H), 7.45-6.93 (m, 2H), 4.28 (t, J = 7.3 Hz, 2H), 3.31 (t, J = 12.1 Hz, 4H), 3.10 (t, J = 7.5 Hz, 2H), 2.48-2.40 (m, 2H). |
| 56 | [M + H]+ = 507.0 | $^1$H NMR (400 MHz, DMSO-d6) δ 9.99 (s, 1H), 9.58 (s, 1H), 8.02 (dd, J = 6.5, 2.6 Hz, 1H), 7.87-7.77 (m, 1H), 7.61 (s, 1H), 7.44-7.04 (m, 2H), 4.29 (t, J = 7.3 Hz, 2H), 3.10 (t, J = 7.5 Hz, 2H), 2.50-2.40 (m, 2H), 1.35-1.19 (m, 4H). |

Example 57. HBV DNA Quantification Assay

A HepG2 cell line overexpressing the HBV virus attachment receptor sodium-taurocholate cotransporting polypeptide (NTCP) was grown to confluency in DMEM growth medium, Dulbecco's Modified Eagle Medium without sodium pyruvate (Life Technologies, Rockville, Md.) supplemented with 10% FBS (Thermo Scientific, Waltham, Md.), 1% penicillin/streptomycin (Life Technologies, Rockville, Md.) and 2 mM L-glutamine (Life Technologies, Rockville, Md.) in T175 flasks. Cells were infected with HBV AD38 viral particles (Texcell, Frederick, USA) at 4000 genome equivalents per cell. After allowing viral infection to take place for 4 days, the infected cells were harvested from the flasks by trypsinization, washed twice with OptiMEM (Life Technologies, Rockville, Md.) and re-suspended in DMEM containing 2% FBS and 1% DMSO at a density of 0.25E6 cells/ml. Infected cells were seeded on 384 well collagen coated plates (Greiner, Austria) at a density of 20,000 cells/well containing serially diluted compounds of the present disclosure or DMSO (0.5%) in a final volume of 80 μl. The assay plates were incubated for a period of 5 days and the antiviral activity of the test compounds were assayed by detecting the presence of HBV DNA in the culture supernatant using the QuantiGene™ 2.0 nucleic acid quantification kit (Affymetrix, Santa Clara, Calif.).

The culture supernatant was harvested and treated with lysis buffer containing Proteinase K (Affymetrix, Santa Clara, Calif.). The supernatant was incubated with HBV viral DNA specific probes (Affymetrix, Santa Clara, Calif.) for 30 minutes at 55° C. This was followed by addition of 0.2M NaOH for 30 minutes at room temperature to denature the DNA, followed by addition of Neutralization buffer (Affymetrix, Santa Clara, Calif.). The resulting lysed and neutralized supernatant was then added to QuantiGene™ 2.0 384 well plates coated with capture oligonucleotides and incubated overnight at 55° C. The HBV specific probe set consists of Capture Extender oligonucleotides (CE's) and blocking probes. Following the overnight incubation, the wells were incubated for one hour sequentially with a Pre-Amplifier, Amplifier and Labeled probes conjugated to alkaline phosphatase with a wash step between incubations. After the final wash step, the alkaline phosphatase substrate (Luminol APSS) was added and the resulting luminescence signal was read in an EnVision Multilabel Plate Reader (PerkinElmer, Santa Clara, Calif.). The EC50 values were calculated from the fit of the dose-response curves to a four-parameter equation. All EC50 values represent geometric mean values of a minimum of four determinations. EC50 values for certain compounds of the present disclosure are reported in the table below.

TABLE 2

Compound Activity Data

| Example No. | $EC_{50}$ (nM) |
|---|---|
| 1 | 2.5 |
| 2 | 4.8 |
| 3 | 2.3 |
| 4 | 7.5 |
| 5 | 43.6 |
| 6 | 14.0 |
| 7 | 17.9 |
| 8 | 4.7 |
| 9 | 5.8 |
| 10 | 33.2 |
| 11 | 71.2 |
| 12 | 93.6 |
| 13 | 8.5 |
| 14 | 2.6 |
| 15 | 5.2 |
| 16 | 1.8 |
| 17 | 4.1 |
| 18 | 2.4 |
| 19 | 20.2 |
| 20 | 502.9 |
| 21 | 3.9 |
| 22 | 31.5 |
| 23 | 31.8 |
| 24 | 177.3 |
| 25 | 1.9 |
| 26 | 20.6 |
| 27 | 23.0 |
| 28 | 294.4 |
| 29 | 14.3 |
| 30 | 30.6 |
| 31 | 16.5 |
| 32 | 24.2 |
| 33 | 93.6 |
| 34 | 14.4 |
| 35 | 14.2 |
| 36 | 21.4 |
| 37 | 3.6 |
| 38 | 87.2 |
| 39 | 2.9 |
| 40 | 14.7 |
| 41 | 20.8 |
| 42 | 12.7 |
| 43 | 12.8 |
| 44 | 15.2 |
| 45 | 55.9 |
| 46 | 22.5 |
| 47 | 54.1 |
| 48 | 63.9 |
| 49 | 3.2 |
| 50 | 33.4 |
| 51 | 45.0 |
| 52 | 11.0 |
| 53 | 6.9 |
| 54 | 1.6 |
| 55 | 3.0 |
| 56 | 30.2 |

Example 58. Kinetic Solubility

The 10 mM DMSO stock solution of the test compound is serially diluted into a 96-well "DMSO stock dilution plate". Then Pipette 2 µL from the DMSO stock dilution plate into the "Sample plate" and dilute with 198 L of the assay media to generate the final concentrations of the test compound ranging from 0.2 to 100 µM. The "Sample plate" is run on a BD Gentest Solubility Scanner.

Significant aqueous solubility is generally required to achieve adequate oral bioavailability in both humans and pre-clinical species. When compounds show very low solubility, absorption from solid crystalline formulations is often low.

TABLE 3

Kinetic Solubility Data

| Example No. | Kinetic Solubility at pH = 1 (µM) | Kinetic Solubility at pH = 7 (µM) |
|---|---|---|
| 1 | <1 | 1.7 |
| 2 | 7.8 | 7.4 |
| 3 | 1.5 | 1.1 |
| 4 | 43.3 | 39.9 |
| 5 | 11.3 | 20.7 |
| 6 | 46.1 | 44.8 |
| 7 | | |
| 8 | 10.5 | 3.9 |
| 9 | 2.8 | 2.3 |
| 10 | 1.4 | 52.8 |
| 11 | 48.9 | 56.3 |
| 12 | | |
| 13 | 5.0 | 6.4 |
| 14 | 57.1 | 61.4 |
| 15 | 13.5 | 13.9 |
| 16 | 16.5 | 2.8 |
| 17 | 70.2 | 77.8 |
| 18 | 50.0 | 52.7 |
| 19 | 68.7 | 62.0 |
| 20 | 26.3 | 28.0 |
| 21 | 64.7 | 57.6 |
| 22 | >100 | >100 |
| 23 | 62.0 | 49.4 |
| 24 | 99.4 | 87.1 |
| 25 | 72.6 | 65.0 |
| 26 | >100 | >100 |
| 27 | 8.4 | 2.7 |
| 28 | 55.7 | 25.3 |
| 29 | 88.7 | 4.5 |
| 30 | >100 | 13.0 |
| 31 | 23.1 | 6.3 |
| 32 | 93.1 | 89.5 |
| 33 | 92.1 | 92.3 |
| 34 | 51.7 | 52.3 |
| 35 | 9.1 | 3.4 |
| 36 | 63.0 | 59.9 |
| 37 | 7.1 | 5.2 |
| 38 | 88.7 | 86.7 |
| 39 | 66.0 | 66.8 |
| 40 | 4.9 | 2.9 |
| 41 | >100 | >100 |
| 42 | 37.5 | 29.6 |
| 43 | 77.7 | 72.8 |
| 44 | 90.3 | 49.8 |
| 45 | 99.9 | 95.3 |
| 46 | 84.4 | 88.5 |

All of the U.S. patents, U.S. patent application publications, U.S. patent applications, foreign patents, foreign patent applications and non-patent publications referred to in this specification are incorporated herein by reference, in their entirety to the extent not inconsistent with the present description.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each

What is claimed is:

1. A compound of Formula

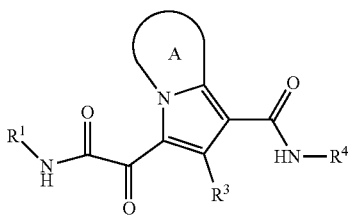

Formula I or a pharmaceutically acceptable salt thereof,
wherein:
- $R^1$ is $C_{1-6}$ alkyl optionally substituted with 1 to 3 $R^{1A}$, cyclopropyl or cyclobutyl, substituted with 1 to 3 $R^{1B}$, or oxetanyl substituted with 1 $R^{1C}$;
- each $R^{1A}$ is independently $CF_3$ or —C(O)NH$_2$;
- each $R^{1B}$ is independently F, —CH$_2$OH, —C≡CH, —C(O)NH$_2$, —C(O)NHMe, triazolyl or thiadiazolyl, wherein the triazolyl and thiadiazolyl are each optionally substituted with Me or —CH$_2$Si(Me)$_3$;
- $R^{1C}$ is —C(O)NHMe or triazolyl;
- the moiety

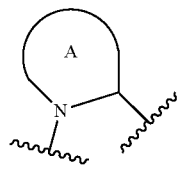

is a pyrrolidine or a 5-7 membered bicyclic heterocycle having one nitrogen, optionally substituted with 1 to 6 $R^2$ groups;
- wherein each $R^2$ is independently halogen, $C_{1-3}$ alkyl, —OH, or —OC$_{1-3}$ alkyl;
- $R^3$ is —H, halogen, or $C_{1-4}$ alkyl;
- $R^4$ is phenyl optionally substituted with 1 to 3 $R^{4A}$ groups, or pyridinyl optionally substituted with 1 to 2 $R^{4B}$ groups;
- each $R^{4A}$ group is independently F, Cl, CN, CH$_2$OCH$_3$ or CHF$_2$; and
- each $R^{4B}$ group is independently F, Cl or CHF$_2$.

2. The compound of claim 1, or a pharmaceutically acceptable salt thereof, wherein the compound is a compound of Formula (II):

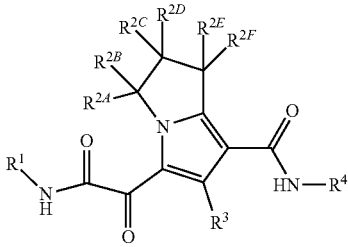

Formula II wherein
each of $R^{2A}$, $R^{2B}$, $R^{2C}$, $R^{2D}$, $R^{2E}$, and $R^{2F}$ are independently —H, halogen, $C_{1-3}$ alkyl, —OH, or —OC$_{1-3}$ alkyl, or $R^{2C}$ or $R^{2D}$ may be taken together with $R^{2A}$ or $R^{2B}$ or with $R^{2E}$ or $R^{2F}$ to form a cyclopropyl group; and
$R^3$ is halogen or methyl.

3. The compound of claim 1, or a pharmaceutically acceptable salt thereof, wherein the compound is a compound of Formula (II):

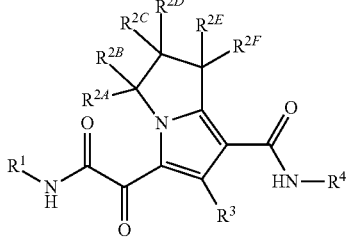

Formula II wherein
each of $R^{2A}$, $R^{2B}$, $R^{2C}$, $R^{2D}$, $R^{2E}$, and $R^{2F}$ are —H, or $R^{2C}$ or $R^{2D}$ may be taken together with $R^{2A}$ or $R^{2B}$ or with $R^{2E}$ or $R^{2F}$ to form a cyclopropyl group; and
$R^3$ is methyl.

4. The compound of claim 3, or a pharmaceutically acceptable salt thereof, wherein the compound is a compound of Formula (III):

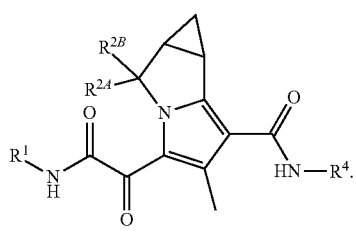

Formula III

5. The compound of claim 4, or a pharmaceutically acceptable salt thereof, wherein the compound is a compound of Formula (IIIa):

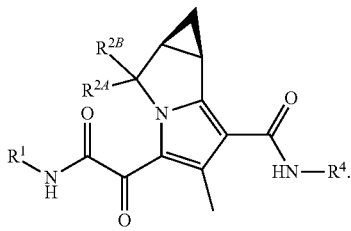

Formula IIIa

6. The compound of claim 4, or a pharmaceutically acceptable salt thereof, wherein the compound is a compound of Formula (IIIb):

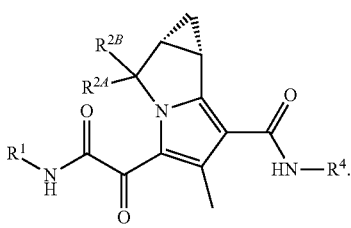

Formula IIIb

7. The compound of claim 3, or a pharmaceutically acceptable salt thereof, wherein the compound is a compound of Formula (IV):

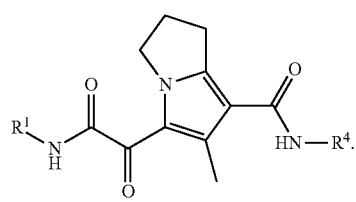

Formula IV

8. The compound of claim 3, or a pharmaceutically acceptable salt thereof, wherein the compound is a compound of Formula (V):

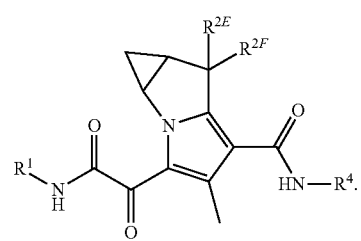

Formula V

9. The compound of claim 8, or a pharmaceutically acceptable salt thereof, wherein the compound is a compound of Formula (Va):

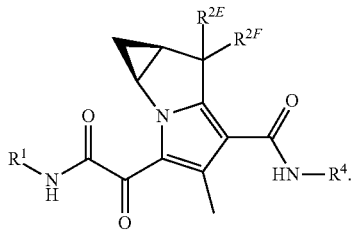

Formula Va

10. The compound of claim 8, or a pharmaceutically acceptable salt thereof, wherein the compound is a compound of Formula (Vb):

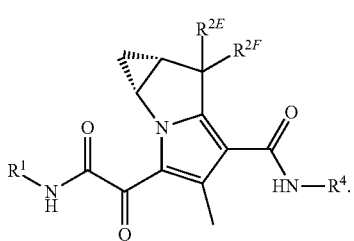

Formula Vb

11. The compound of claim 1, or a pharmaceutically acceptable salt thereof, wherein $R^1$ is cyclopropyl or cyclobutyl, substituted with 1 to 3 $R^{1B}$.

12. The compound of claim 11, or a pharmaceutically acceptable salt thereof, wherein 2 $R^{1B}$ are optionally F, and 1 $R^{1B}$ is —CH$_2$OH, —C≡CH, —C(O)NH$_2$, —C(O)NHMe, triazolyl or thiadiazolyl, wherein the triazolyl and thiadiazolyl are optionally substituted with Me or —CH$_2$Si(Me)$_3$.

13. The compound of claim 12, or a pharmaceutically acceptable salt thereof, wherein $R^1$ is cyclopropyl substituted with —C≡CH, triazolyl or thiadiazolyl, wherein the triazolyl is optionally substituted with Me or —CH$_2$Si(Me)$_3$.

14. The compound of claim 12, or a pharmaceutically acceptable salt thereof, wherein $R^1$ is cyclobutyl substituted with 2 fluoro and 1 —CH$_2$OH, —C(O)NH$_2$, —C(O)NHMe, triazolyl or thiadiazolyl, wherein the triazolyl is optionally substituted with Me.

15. The compound of claim 12, or a pharmaceutically acceptable salt thereof, wherein $R^1$ is:

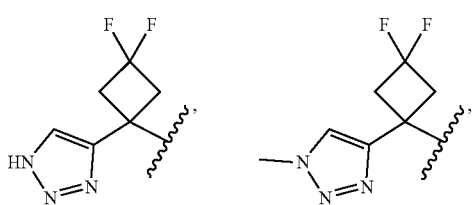

-continued

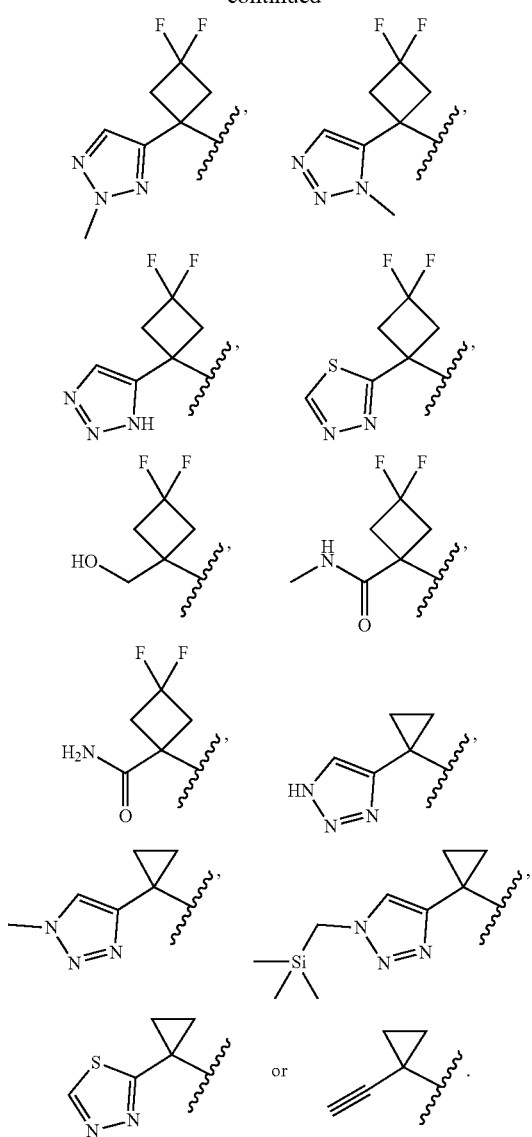

16. The compound of claim 12, or a pharmaceutically acceptable salt thereof, wherein $R^1$ is:

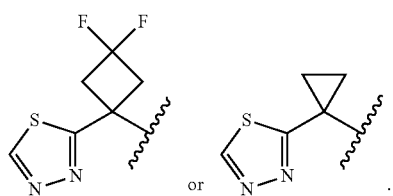 [SMILES: *C1(c2nncs2)CC(F)(F)C1 ; *C1(c2nncs2)CC1]

17. The compound of claim 1, or a pharmaceutically acceptable salt thereof, wherein $R^1$ is oxetanyl substituted with 1 $R^{1C}$.

18. The compound of claim 17, or a pharmaceutically acceptable salt thereof, wherein $R^1$ is oxetan-3-yl substituted with —C(O)NHMe or triazolyl.

19. The compound of claim 18, or a pharmaceutically acceptable salt thereof, wherein $R^1$ is

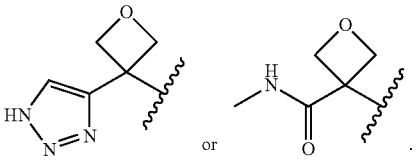

20. The compound of claim 1, or a pharmaceutically acceptable salt thereof, wherein $R^4$ is 4-F-phenyl optionally substituted with 1 to 2 $R^{4A}$ groups, or pyridin-4-yl substituted with 1 to 2 $R^{4B}$ groups.

21. The compound of claim 20, or a pharmaceutically acceptable salt thereof, wherein $R^4$ is a 4-F-phenyl optionally substituted with 1 to 2 $R^{4A}$ groups wherein each $R^{4A}$ is independently F, Cl, CN, $CH_2OCH_3$ or $CHF_2$.

22. The compound of claim 21, or a pharmaceutically acceptable salt thereof, wherein $R^4$ is selected from the group consisting of:

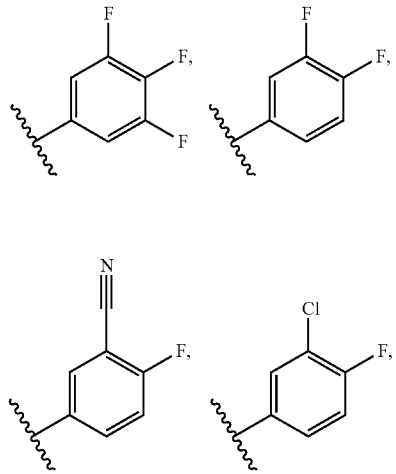

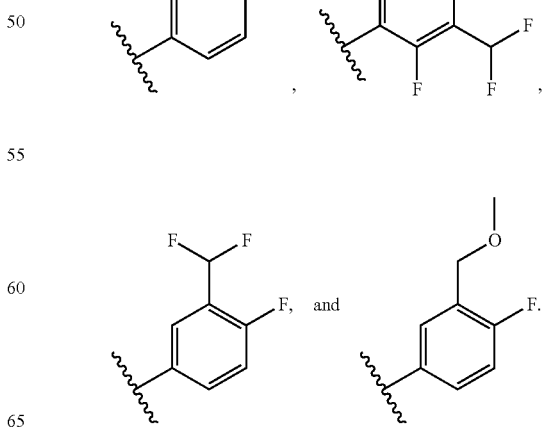

23. The compound of claim 22, or a pharmaceutically acceptable salt thereof, wherein $R^4$ is selected from the group consisting of:

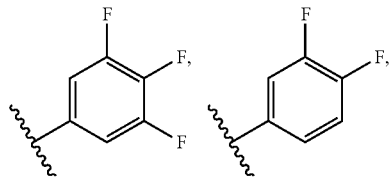

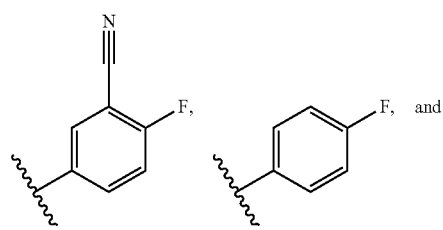

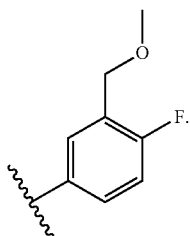 [SMILES: *c1ccc(F)c(COC)c1]

24. The compound of claim 23, or a pharmaceutically acceptable salt thereof, wherein $R^4$ is

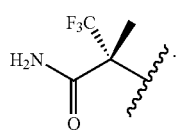

25. The compound of claim 1, or a pharmaceutically acceptable salt thereof, wherein $R^3$ is a halogen.

26. The compound of claim 25, or a pharmaceutically acceptable salt thereof, wherein $R^3$ is Cl.

27. The compound of claim 1, or a pharmaceutically acceptable salt thereof, wherein $R^1$ is

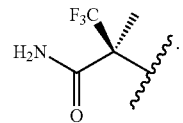

28. The compound of claim 1, or a pharmaceutically acceptable salt thereof, wherein $R^1$ is

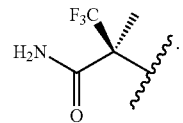

29. The compound of claim 1, or a pharmaceutically acceptable salt thereof, which is

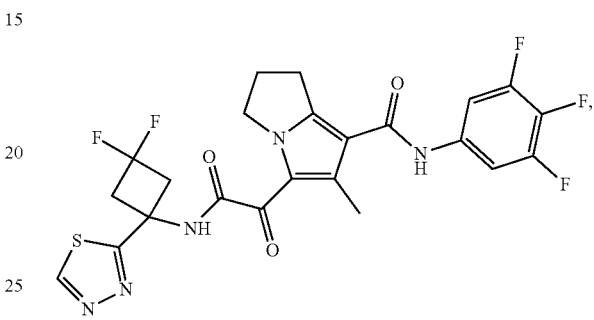

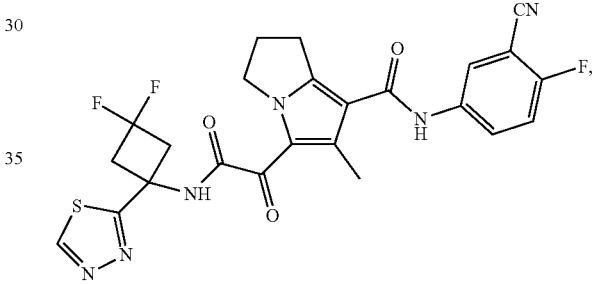

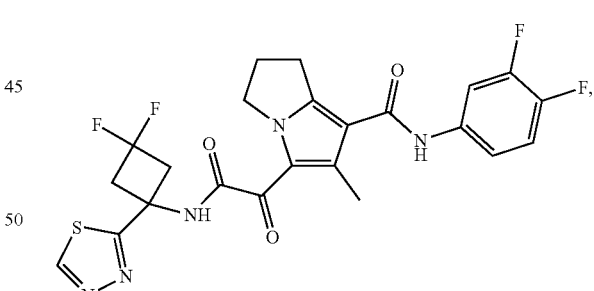

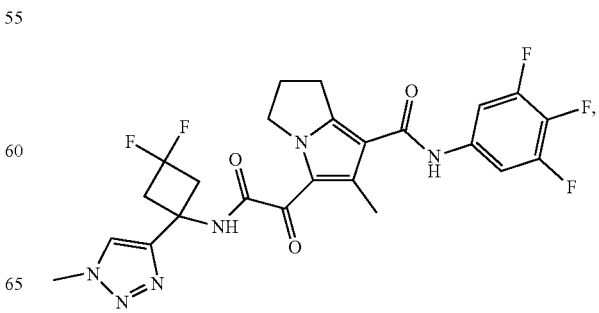

181
-continued
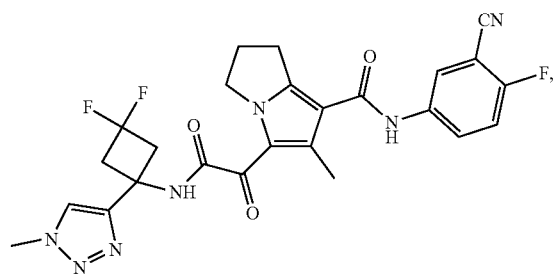
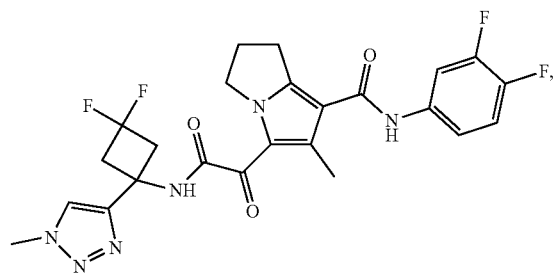
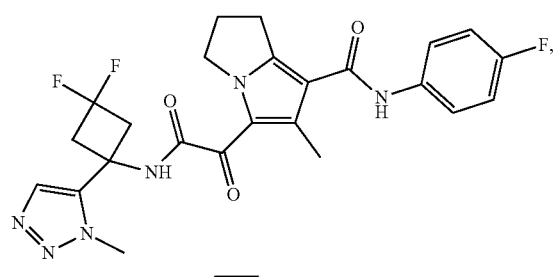
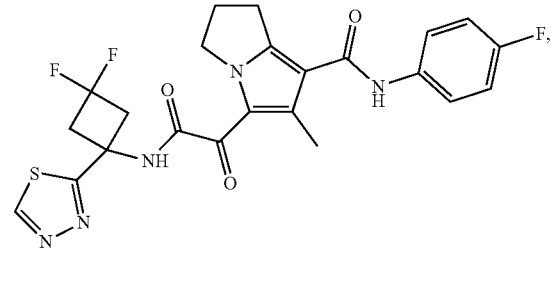
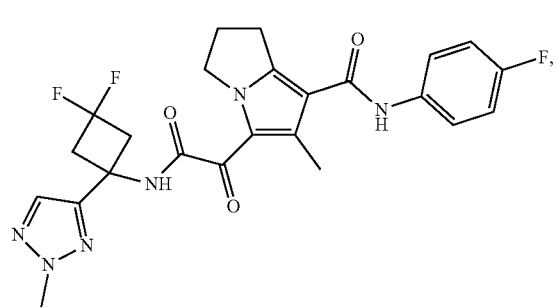
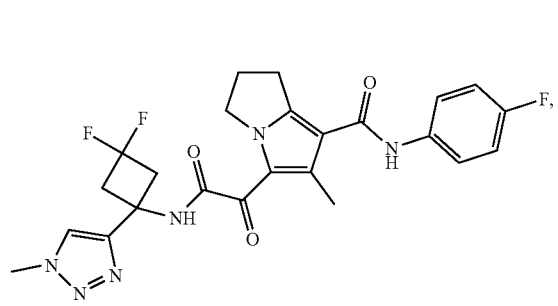
182
-continued
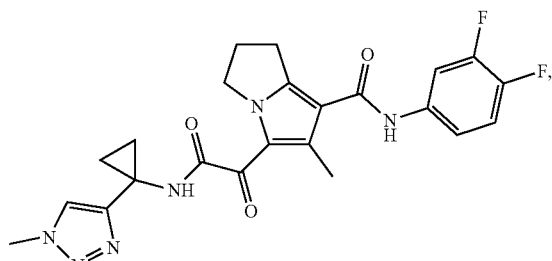
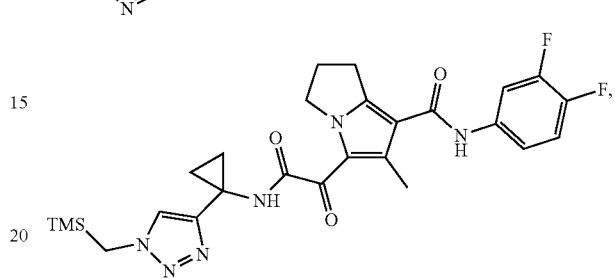
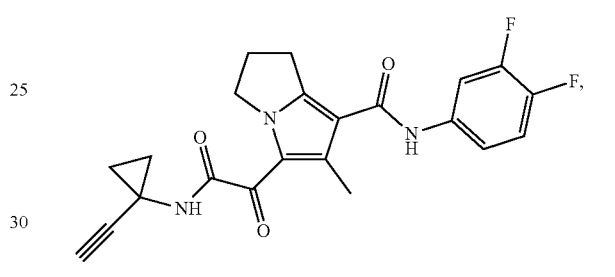
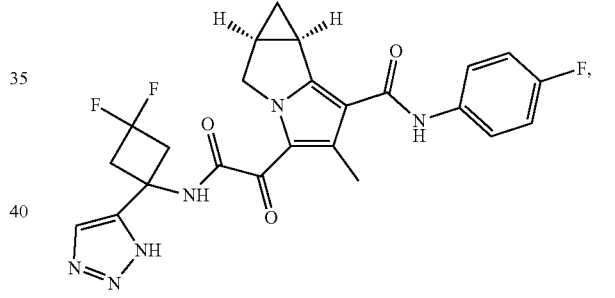
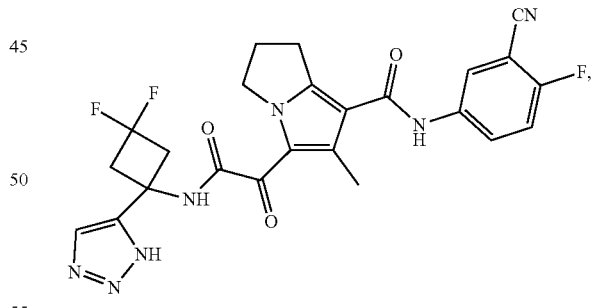
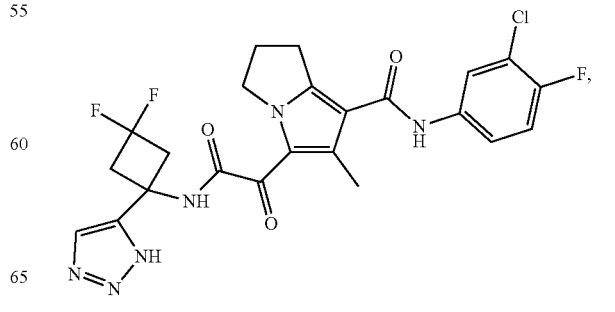

-continued
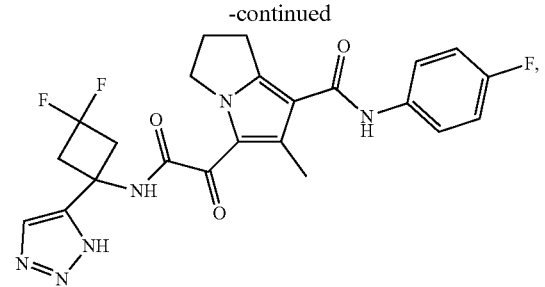
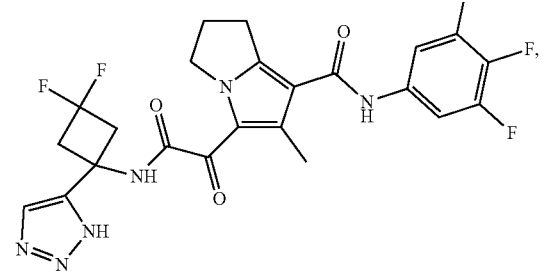
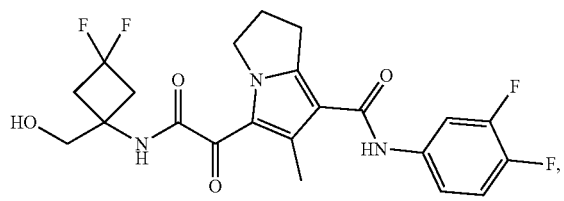
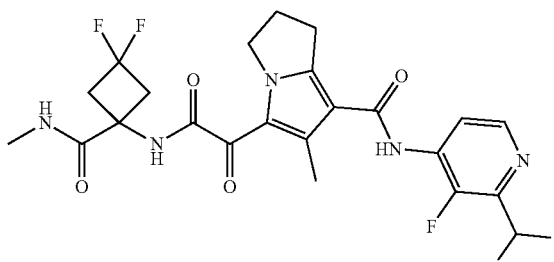
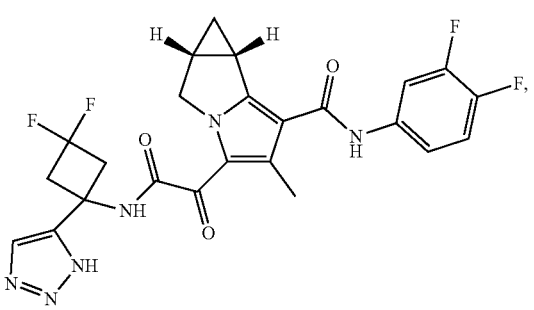
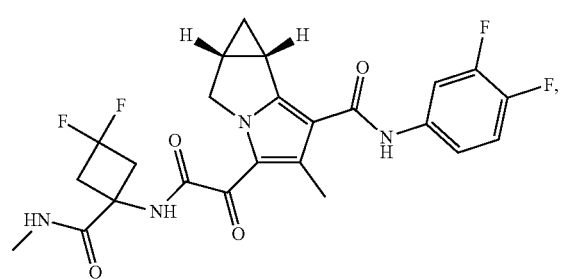
-continued
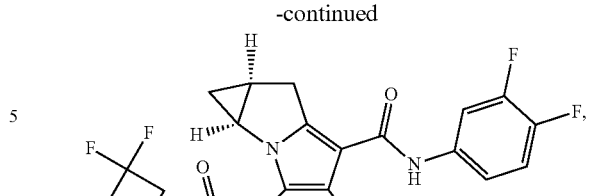
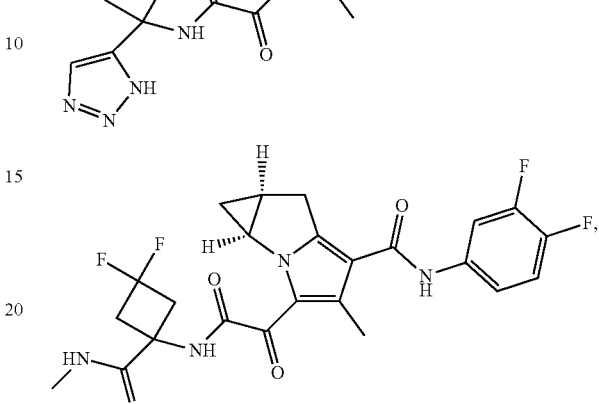
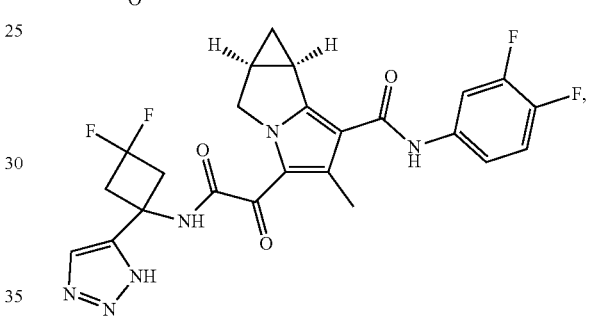
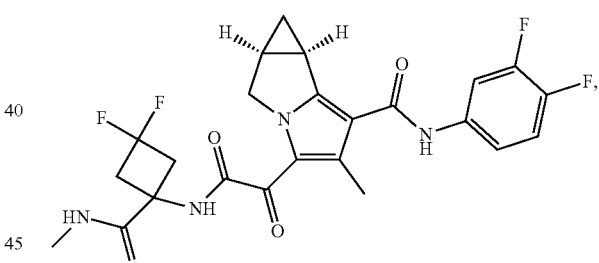
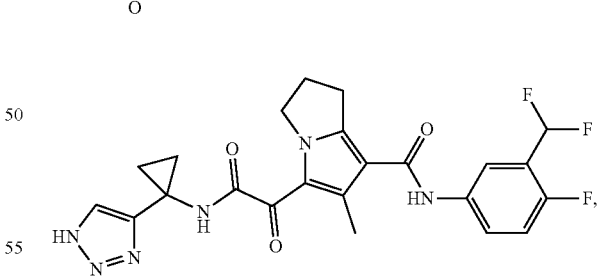
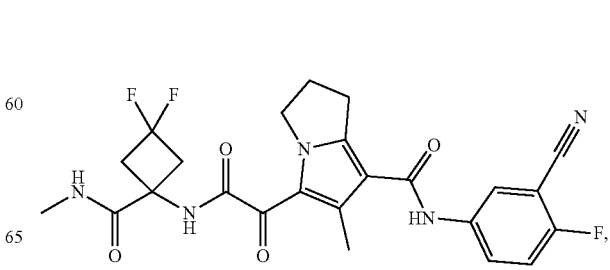

185
-continued
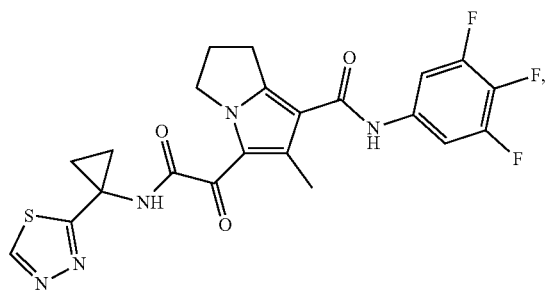
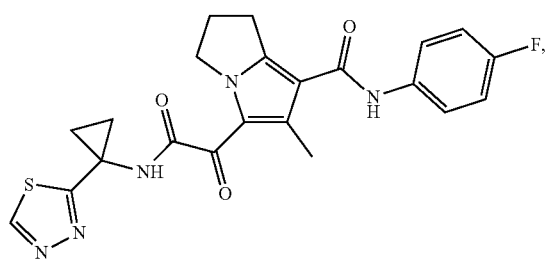
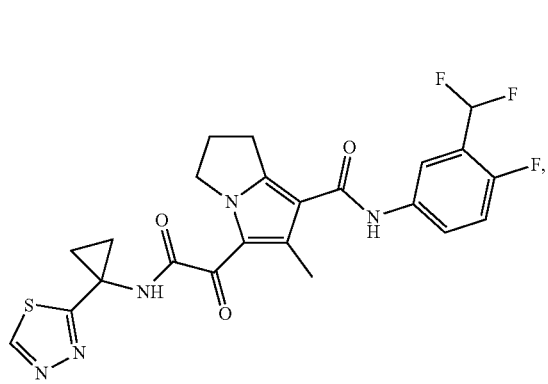
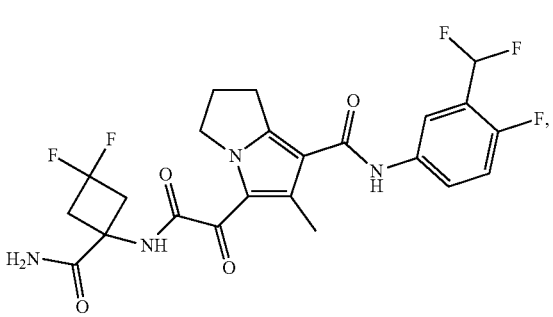
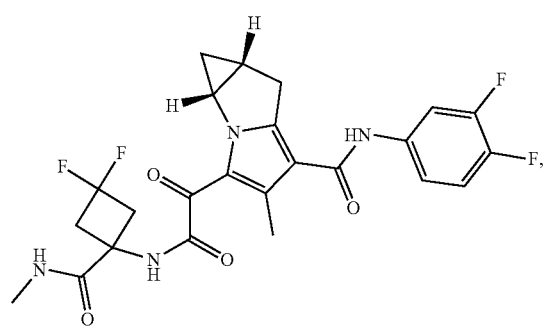
186
-continued
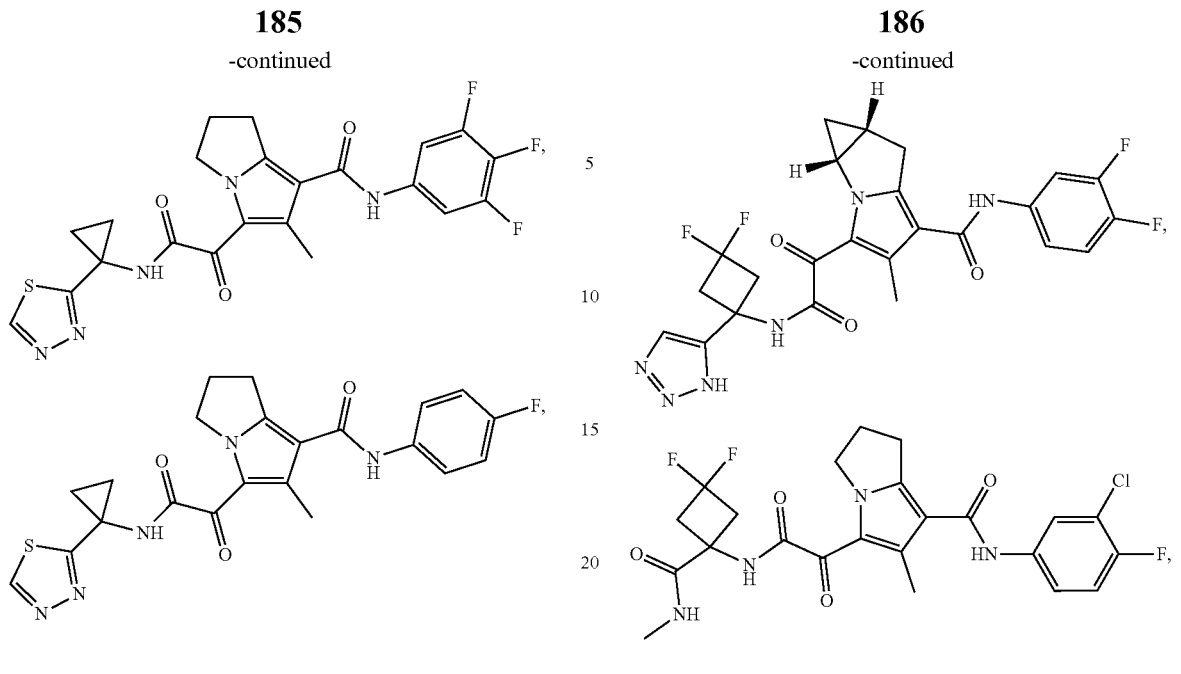
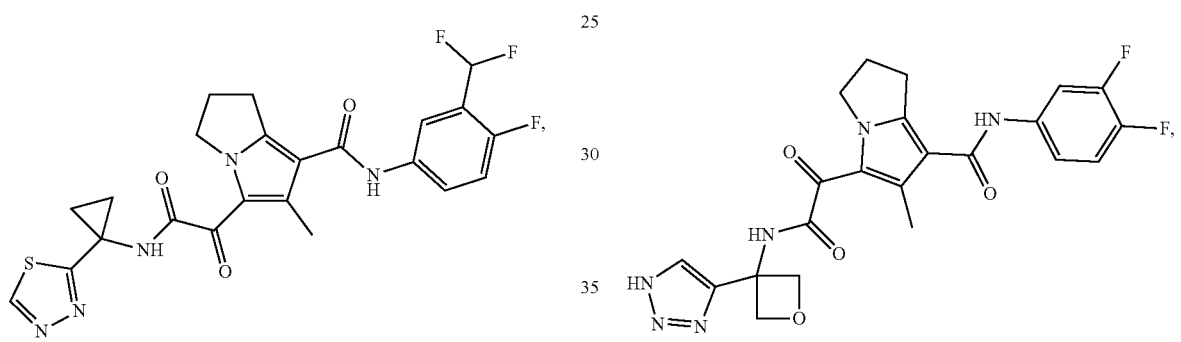
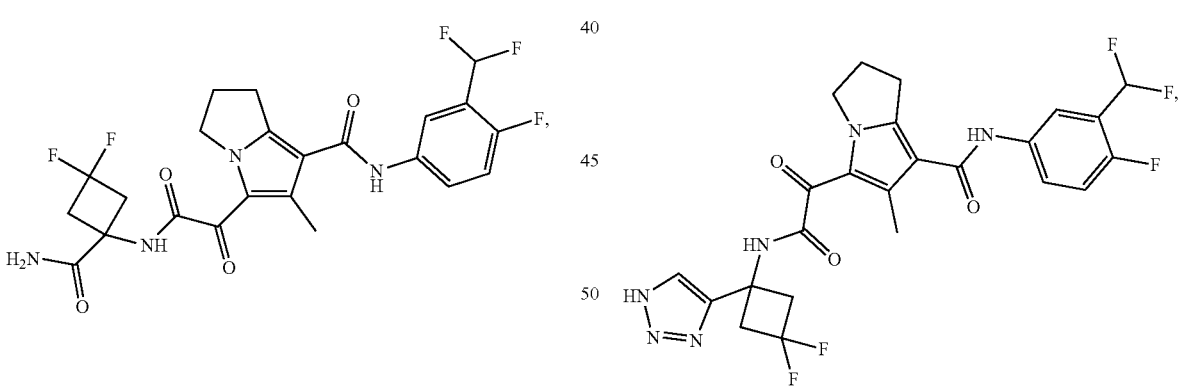
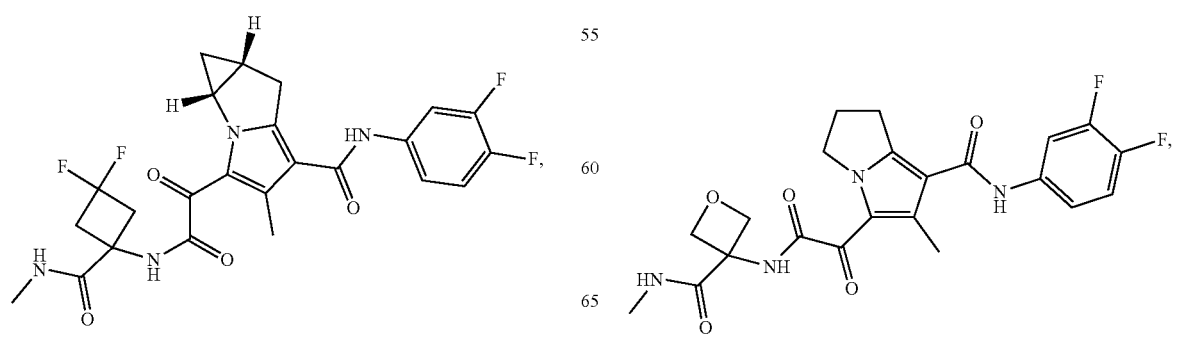

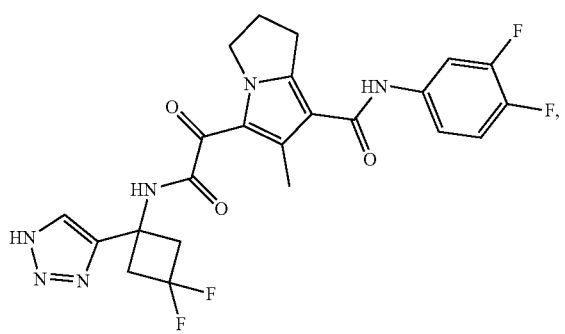
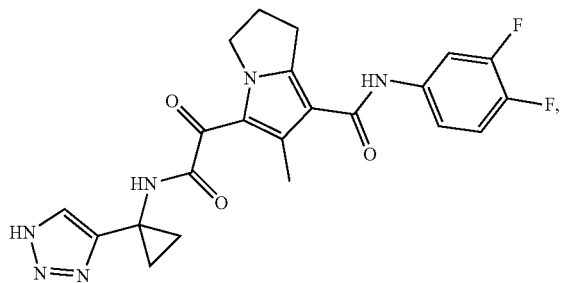
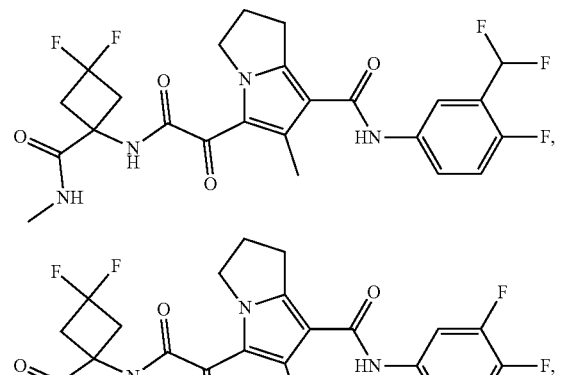
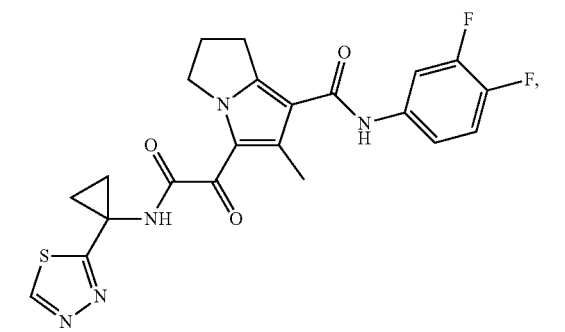
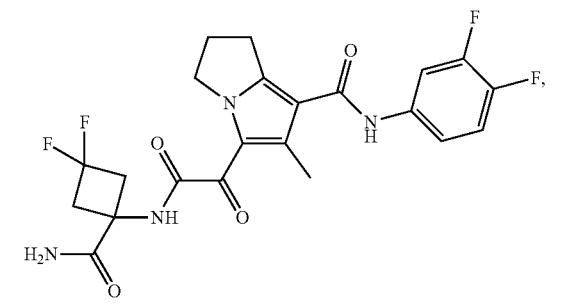
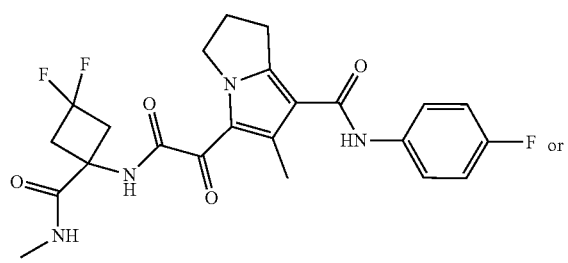
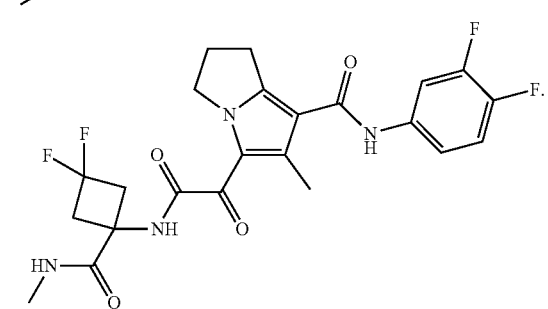
30. The compound of claim 1, or a pharmaceutically acceptable salt thereof, which is
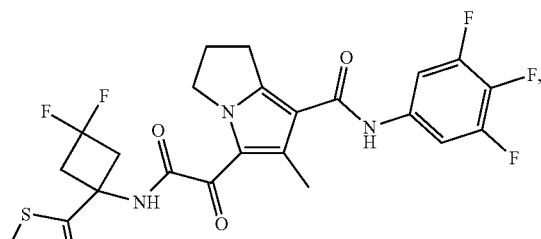
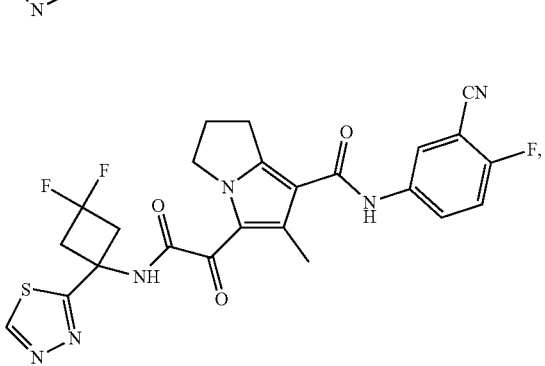
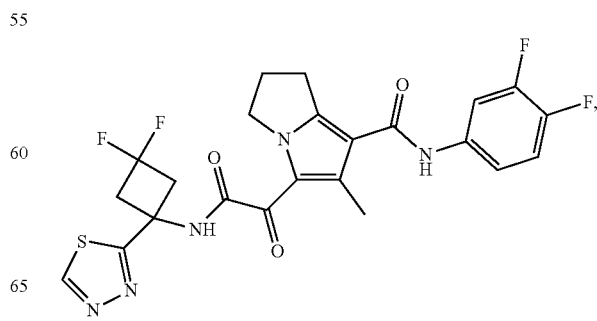

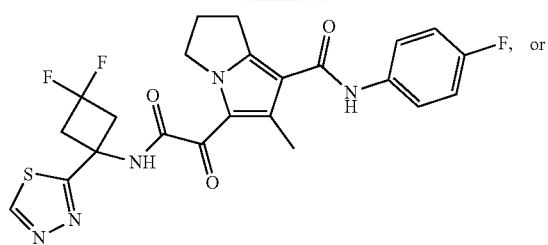
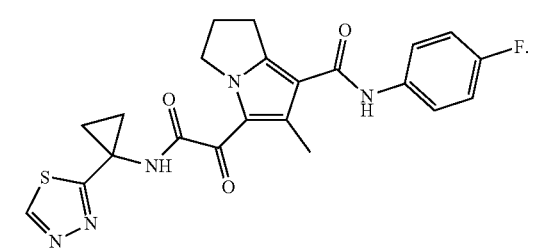
31. The compound of claim 1, or a pharmaceutically acceptable salt thereof, wherein the compound is selected from the group consisting of
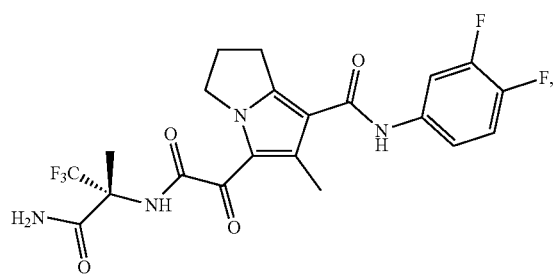
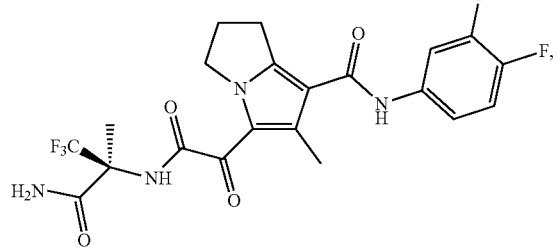
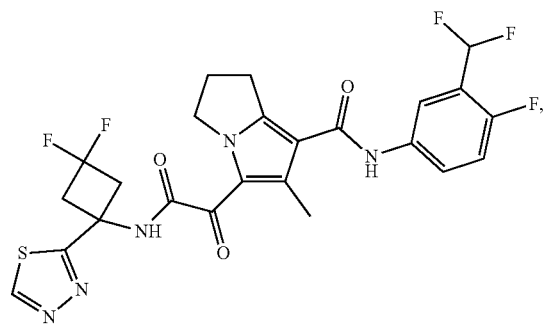
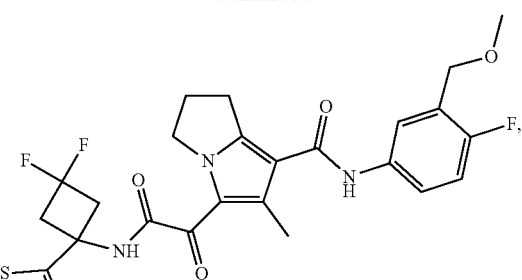
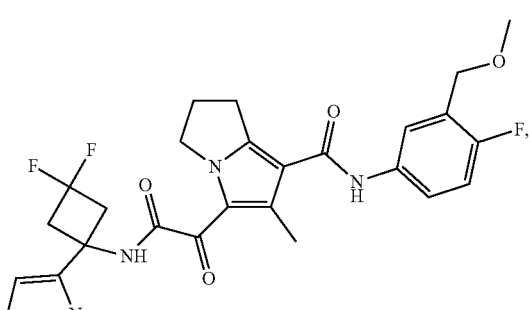
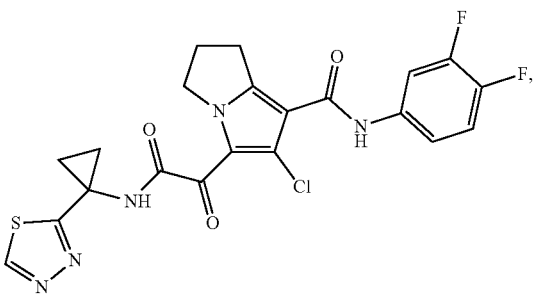
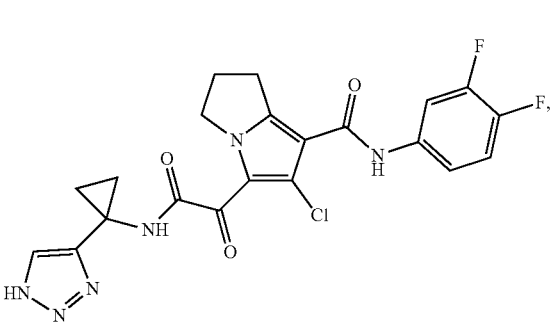

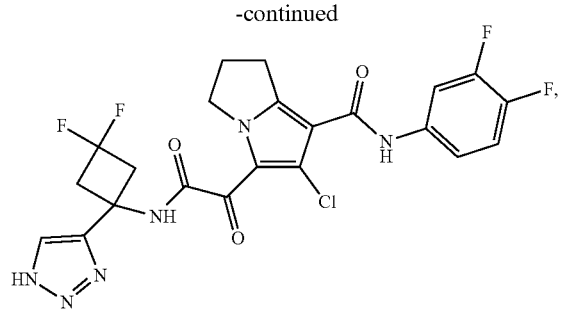

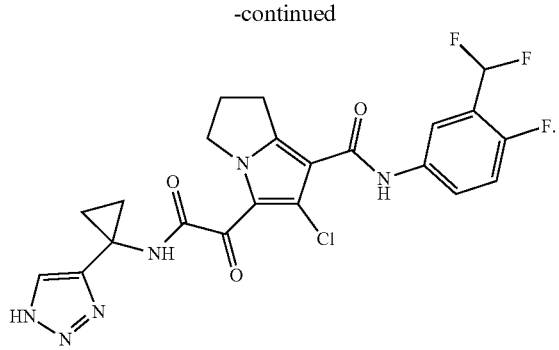

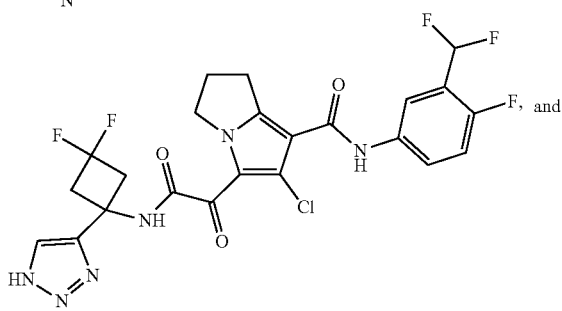

32. A pharmaceutical composition comprising a compound of claim 1, or a pharmaceutically acceptable salt thereof, and a pharmaceutically acceptable excipient.

33. A method of treating a HBV infection, comprising administering to an individual in need thereof a therapeutically effective amount of a compound of claim 1, or a pharmaceutically acceptable salt thereof.

* * * * *